(12) United States Patent
Sammons et al.

(10) Patent No.: US 11,812,738 B2
(45) Date of Patent: *Nov. 14, 2023

(54) POLYNUCLEOTIDE MOLECULES FOR GENE REGULATION IN PLANTS

(71) Applicant: Monsanto Technology LLC, St. Louis, MO (US)

(72) Inventors: Robert D Sammons, New Melle, MO (US); Sergey Ivashuta, Ballwin, MO (US); Hong Liu, St. Louis, MO (US); Dafu Wang, St. Louis, MO (US); Paul C. C. Feng, Wildwood, MO (US); Andrei Y Kouranov, Chesterfield, MO (US); Scott E Andersen, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 356 days.

This patent is subject to a terminal disclaimer.

(21) Appl. No.: 14/015,715

(22) Filed: Aug. 30, 2013

(65) Prior Publication Data

US 2014/0018241 A1  Jan. 16, 2014

Related U.S. Application Data

(62) Division of application No. 13/042,856, filed on Mar. 8, 2011, now Pat. No. 9,121,022.

(60) Provisional application No. 61/381,556, filed on Sep. 10, 2010, provisional application No. 61/349,807, filed on May 28, 2010, provisional application No. 61/311,762, filed on Mar. 8, 2010.

(51) Int. Cl.
*A01N 63/60* (2020.01)
*C12N 15/113* (2010.01)
*C12N 15/82* (2006.01)
*A01N 57/16* (2006.01)

(52) U.S. Cl.
CPC ............. *A01N 63/60* (2020.01); *A01N 57/16* (2013.01); *C12N 15/113* (2013.01); *C12N 15/1137* (2013.01); *C12N 15/8206* (2013.01); *C12N 15/8207* (2013.01); *C12N 15/8218* (2013.01)

(58) Field of Classification Search
CPC ...................................................... A01H 63/60
See application file for complete search history.

(56) References Cited

U.S. PATENT DOCUMENTS

| 3,687,808 | A | 8/1972 | Merigan et al. |
|---|---|---|---|
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,469,863 | A | 9/1984 | Ts'o et al. |
| 4,476,301 | A | 10/1984 | Imbach et al. |
| 4,535,060 | A | 8/1985 | Comai |
| 4,581,847 | A | 4/1986 | Hibberd et al. |
| 4,666,828 | A | 5/1987 | Gusella |
| 4,683,202 | A | 7/1987 | Mullis |
| 4,761,373 | A | 8/1988 | Anderson et al. |
| 4,769,061 | A | 9/1988 | Comai |
| 4,801,531 | A | 1/1989 | Frossard |
| 4,810,648 | A | 3/1989 | Stalker |
| 4,879,219 | A | 11/1989 | Wands et al. |
| 4,940,835 | A | 7/1990 | Shah et al. |
| 4,971,908 | A | 11/1990 | Kishore et al. |
| 5,004,863 | A | 4/1991 | Umbeck |
| 5,011,771 | A | 4/1991 | Bellet et al. |
| 5,013,659 | A | 5/1991 | Bedbrook et al. |
| 5,015,580 | A | 5/1991 | Christou et al. |
| 5,023,243 | A | 6/1991 | Tullis |
| 5,034,506 | A | 7/1991 | Summerton et al. |
| 5,094,945 | A | 3/1992 | Comai |
| 5,141,870 | A | 8/1992 | Bedbrook et al. |
| 5,145,783 | A | 9/1992 | Kishore et al. |
| 5,159,135 | A | 10/1992 | Umbeck |
| 5,166,315 | A | 11/1992 | Summerton et al. |
| 5,177,196 | A | 1/1993 | Meyer, Jr. et al. |

(Continued)

FOREIGN PATENT DOCUMENTS

AU   2008258254 B2   7/2014
AU   20 14262189 B2   11/2014

(Continued)

OTHER PUBLICATIONS

Wiesman et al (J. Biotechnology, 2007, 130: 85-94).*
Sun et al (Plant J, 2005, 44: 128-138).*
Chabannes et al (Plant Journal, 2001, 28(3): pp. 257-270).*
Orbovic et al (J. Amer. Soc. Hort. Sci., 2001, 126(4): 486-490).*
Andersen et al (Biomaterials, 2008, 29: 506-512).*
Liu (New Zealand Plant Protection, 2002, 55: 159-162).*
Tenllado et al (BMC Biotechnology, 2003, 3:3); IDS dated Aug. 3, 2016.*
Perez-de-Luque et al. (Pest Manga. Sci., 2009, 65: 540-545).*

(Continued)

*Primary Examiner* — David H Kruse
(74) *Attorney, Agent, or Firm* — Arnold & Porter Kaye Scholer LLP

(57) ABSTRACT

This invention provides polynucleotide molecules and methods for regulating genes in plants, e. g., by providing RNA for systemic regulation of genes. Various aspects of the invention provide polynucleotide molecules and methods for regulating endogenous genes and transgenes in a plant cell and polynucleotide molecules.

15 Claims, 42 Drawing Sheets

Specification includes a Sequence Listing.

(56) References Cited

U.S. PATENT DOCUMENTS

| | | |
|---|---|---|
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,506,599 B1 | 1/2003 | Yoon |
| 6,642,435 B1 | 11/2003 | Rafalski et al. |
| 6,644,341 B1 | 11/2003 | Chemo et al. |
| 6,645,914 B1 * | 11/2003 | Woznica .......... A01N 25/30 504/206 |
| 6,768,044 B1 | 7/2004 | Boudec et al. |
| 6,992,237 B1 | 1/2006 | Habben et al. |

(56) References Cited

U.S. PATENT DOCUMENTS

| | | |
|---|---|---|
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,119,256 B2 | 10/2006 | Shimizu et al. |
| 7,138,564 B2 | 11/2006 | Tian et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,422,557 B2 | 8/2016 | Ader |
| 9,445,603 B2 | 9/2016 | Baum et al. |
| 9,777,288 B2 | 10/2017 | Beattie et al. |
| 9,850,496 B2 | 12/2017 | Beattie et al. |
| 9,856,495 B2 | 1/2018 | Beattie et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0106653 A1 | 8/2002 | Kurane et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0235916 A1 | 12/2003 | Monahan et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0223425 A1 | 10/2005 | Clinton et al. |
| 2005/0246784 A1 | 11/2005 | Plesch et al. |
| 2005/0250647 A1 | 11/2005 | Hills et al. |
| 2005/0289664 A1 | 12/2005 | Moshiri et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0148648 A1* | 7/2006 | Crockett ............... A01N 57/20 504/128 |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0094717 A1 | 4/2009 | Troukhan et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0144848 A1 | 6/2009 | Kovalic et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |

(56) References Cited

U.S. PATENT DOCUMENTS

| | | |
|---|---|---|
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0107355 A1 | 5/2012 | Harris et al. |
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2013/0003213 A1 | 1/2013 | Kabclac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |
| 2017/0159064 A1 | 6/2017 | Carbonell et al. |
| 2017/0211085 A1 | 7/2017 | Kotchoni et al. |

FOREIGN PATENT DOCUMENTS

| | | |
|---|---|---|
| CN | 101279950 A | 10/2008 |
| CN | 101279951 A | 10/2008 |
| CN | 101892247 A | 11/2010 |
| CN | 101914540 A | 12/2010 |
| CN | 102154364 A | 8/2011 |
| CN | 102481311 A | 5/2012 |
| CN | 102822350 A | 12/2012 |
| CN | 102906263 A | 1/2013 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 10256367 A1 | 6/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 155 615 A1 | 11/2001 |
| EP | 1 157 991 A2 | 11/2001 |
| EP | 1 238 586 A1 | 9/2002 |
| EP | 1 416 049 A1 | 5/2004 |
| EP | 1 496 123 A1 | 1/2005 |
| EP | 1 889 902 A1 | 2/2008 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 473 024 A2 | 7/2012 |
| EP | 2 545 182 A1 | 1/2013 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 a | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009-508481 A | 3/2009 |
| JP | 2009067739 A | 4/2009 |
| JP | 2009114128 A | 5/2009 |
| JP | 2009126792 A | 6/2009 |
| JP | 2009137851 A | 6/2009 |
| JP | 2016-532440 A | 10/2015 |
| RU | 2 291 613 C1 | 1/2007 |
| RU | 2 337 529 C1 | 11/2008 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/14348 A1 | 3/1999 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 | 12/1999 |
| WO | WO 99/67367 A1 | 12/1999 |
| WO | WO 00/32757 A2 | 6/2000 |
| WO | WO 00/044914 A1 | 8/2000 |
| WO | WO 01/07601 A2 | 2/2001 |
| WO | WO 2001/085970 A2 | 11/2001 |
| WO | WO 02/14472 A2 | 2/2002 |
| WO | WO 02/066660 A2 | 8/2002 |
| WO | WO 03/000679 A2 | 1/2003 |
| WO | WO 03/004649 | 1/2003 |
| WO | WO 03/006422 A1 | 1/2003 |
| WO | WO 03/012052 A2 | 2/2003 |
| WO | WO 03/013247 A2 | 2/2003 |
| WO | WO 03/016308 A1 | 2/2003 |
| WO | WO 2003/014357 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |

(56) References Cited

FOREIGN PATENT DOCUMENTS

| | | |
|---|---|---|
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 03/106636 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A2 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/132270 A1 | 12/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007070389 * | 6/2007 ......... C12N 15/8279 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A1 | 10/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/029690 A1 | 3/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/060429 A2 | 5/2009 |
| WO | WO 2009/063180 A1 | 5/2009 |
| WO | WO 2009/068170 A1 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/144079 A1 | 12/2009 |
| WO | WO 2009/152995 A1 | 12/2009 |
| WO | WO 2009/153607 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/028836 A2 | 3/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/156342 A1 | 11/2012 |
| WO | WO 2012/164100 A2 | 12/2012 |
| WO | WO 2013/010691 A1 | 1/2013 |

(56) References Cited

FOREIGN PATENT DOCUMENTS

| | | |
|---|---|---|
| WO | WO 2013/025670 A1 | 2/2013 |
| WO | WO 2013/025670 A1 | 3/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2015/151255 A1 | 9/2014 |
| WO | WO 2014/164761 A1 | 10/2014 |
| WO | WO 2014/164797 A1 | 10/2014 |
| WO | WO 2014/164797 A2 | 10/2014 |
| WO | WO 2015/010026 A2 | 1/2015 |
| WO | WO 2015/200539 A1 | 12/2015 |

OTHER PUBLICATIONS

Alarcón-Reverte et al., "Resistance to ACCase-inhibiting herbicides in the weed *Lolium multiflorum*," *Comm. Appl. Biol. Sci.*, 73(4):899-902 (2008).
Amarzguioui et al., "An algorithm for selection of functional siRNA sequences," *Biochemical and Biophysical Research Communications*, 316:1050-1058 (2004).
Ambrus et al., "The Diverse Roles of RNA Helicases in RNAi," *Cell Cycle*, 8(21):3500-3505 (2009).
Anonymous, "A handbook for high-level expression and purification of 6xHis-tagged proteins," *The QUIexpressionist*, (2003).
An et al., "Transient RNAi Induction against Endogenous Genes in Arabidopsis Protoplasts Using in Vitro-Prepared Double-Stranded RNA," *Biosci Biotechnol Biochem*, 69(2):415-418 (2005).
Aoki et al., "In Vivo Transfer Efficiency of Antisense Oligonucleotides into the Myocardium Using HVJ-Liposome Method," *Biochem Biophys Res Commun*, 231:540-545 (1997).
Arpaia et al., "Production of transgenic eggplant (*Solanum melongena* L.) resistant to Colorado Potato Beetle (*Leptinotarsa decemlineata* Say)," *Theor. Appl. Genet.*, 95:329-334 (1997).
Artmymovich, "Using RNA interference to increase crop yield and decrease pest damage," *MMG 445 Basic Biotech*., 5(1):7-12 (2009).
Autralian Patent Examination report No. 1 dated Nov. 11, 2013, in Australian Application No. 2011224570.
Axtell et al., "A Two-Hit Trigger for siRNA Biogenesis in Plants," *Cell*, 127:565-577 (2006).
Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).
Baulcombe, "RNA silencing and heritable epigenetic in tomato and Arabidopsis," Abstract 13th Annual Fall Symposium, Plant Genomes to Phenomes, Donald Danforth Plant Science Center, 28-30 (2011).
Bannerjee et al., "Efficient production of transgenic potato (*S. tuberosum* L. ssp. *andigena*) plants via *Agrobacterium tumefaciens*-mediated transformation," *Plant Sci.* 170:732 738 (2006).
Bayer et al., "Programmable ligand-controlled riboregulators of eukaryotic gene expression," *Nature Biotechnol.*, 23(3):337-343 (2005).
Beal, et al., "Second Structural Motif for Recognition of DNA by Oligonucleotide-Directed Triple-Helix Formation," *Science*, 251:1360-1363 (1992).
Becker et al., "Fertile transgenic wheat from microprojectile bombardment of scutellar tissue," *The Plant Journal*, 5(2):299-307 (1994).
Bhargava et al., "Long double-stranded RNA-mediated RNA interference as a tool to achieve site-specific silencing of hypothalamic neuropeptides," *Brain Research Protocols*, 13:115-125 (2004).

Boletta et al., "High Efficient Non-Viral Gene Delivery to the Rat Kidney by Novel Polycationic Vectors," *J. Am. Soc. Nephrol.*, 7:1728 (1996).
Bolognesi et al., "Characterizing the Mechanism of Action of Double-Sranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," *FEBS Letters*, 580:789-794 (2006).
Breaker et al., "A DNA enzyme with $Mg^{2+}$-dependent RNA phosphoesterase activity," *Chemistry and Biology*, 2:655-660 (1995).
Broderson et al., "The diversity of RNA silencing pathways in plants," *Trends in Genetics*, 22(5):268-280 (2006).
Butler et al., "Priming and re-drying improve the survival of mature seeds of *Digitalis purpura* during storage," *Annals of Botany*, 103:1261-1270 (2009).
Bytebier et al., "T-DNA organization in tumor cultures and transgenic plants of the monocotyledon *Asparagus officinalis*," *Proc. Natl. Acad. Sci. U.S.A.*, 84:5345-5349 (1987).
Chabbouh et al., "Cucumber mosaic virus in artichoke," *FAO Plant Protection Bulletin*, 38:52-53 (1990).
Chakravarty et al., "Genetic Transformation in Potato: Approaches and Strategies," *Amer J Potato Res*, 84:301 311 (2007).
Chee et al., "Transformation of Soybean (*Glycene max*) by Infecting Germinating Seeds with *Agrobacterium tumefaciens*," *Plant Physiol.*, 91:1212-1218 (1989).
Chen et al., "In vitro Analysis of the Role atTic20 in Protein Import into Chloroplasts," *The Plant Cell*, 14:641-654 (2002).
Cheng et al., "Production of fertile transgenic peanut (*Arachis hypogaea* L.) plants using *Argobacterium tumefaciens*," *Plant Cell Reports*, 15:653-657 (1996).
Chi et al., "The Function of RH22, a DEAD RNA Helicase, in the Biogenesis of the 50S Ribosomal Subunits of Arabidopsis Chloroplasts," *Plant Physiology*, 158:693-707 (2012).
Chinese Office Action dated Aug. 28, 2013 in Chinese Application No. 201180012795.2.
Clough et al., "Floral dip: a simplified method for Agrobacterium-mediated transformation of *Arabidopsis thaliana*," *The Plant Journal*, 16(6):735-743 (1998).
CN101914540 Patent Diclosure, "Introduction of RNA into plant by interference," (2010).
Colombian Office Action dated Aug. 2, 2013 in Application No. 12 152898.
Colombian Office Action dated Feb. 21, 2014 in Application No. 12 152898.
Cooney et al., "Site-Specific Oligonucleotide Binding Represses Transcription of Human c-myc Gene in Vitro," *Science*,241:456-459 (1988).
Colbourne et al., "The Ecoresponsive Genome of Daphnia pulex," *Science*, 331(6017):555-561 (2011).
COST Action FA0806 progress report "Plant virus control employment RNA-based vaccines: A novel non-transgenic strategy" (2010).
Dalmay et al., "An RNA-Dependent RNA Polymerase Gene in *Arabidopsis* Is Required for Posttranscriptional Gene Silencing Mediated by a Transgene but Not by a Virus," *Cell*, 101:543-553 (2000).
Datebase EMBL CBIB Daphnia—XP-002732239 (2011).
Davidson et al., "Engineering regulatory RNAs," *TRENDS in Biotechnology*, 23(3):109-112 (2005).
De Block, et al., "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).
della-Cioppa et al., "Import of a precursor protein into chloroplasts is inhibited by the herbicide glyphosate," *The EMBO Journal*, 7(5):1299-1305 (1988).
"Devgen, The mini-Monsanto," KBC Securities (2006).
Diallo et al., "Long Endogenous dsRNAs Can Induce Complete Gene Silencing in Mammalian Cells and Primary Cultures," *Oligonucleotides*, 13:381-392 (2003).

(56) References Cited

OTHER PUBLICATIONS

Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Eurasian Office Action dated Feb. 24, 2014, in Application No. 201201264.
European Cooperatio in the field of Scientific and Technical Research—Memorandum of Understanding for COST Action FA0806 (2008).
European Supplemental Search Report dated Oct. 8, 2013 in Application No. 11753916.3.
Farooq et al., "Rice seed priming," *IPRN*, 30(2):45-48 (2005).
Fire et al., "Potent and specific genetic interference by double-stranded RNA in Caenorhabditis elegans," *Nature*, 391:806-811 (1998).
Fukuhara et al., "Enigmatic Double-Stranded RNA in Japonica Rice," *Plant Molecular Biology*, 21:1121-1130 (1993).
Fukuhara et al., "The Unusual Structure of a Novel RNA Replicon in Rice," *The Journal of Biological Chemistry*, 270(30):18147-18149 (1995).
Fukuhara et al., "The Wide distribution of endornaviruses, large double-stranded RNA replicons with plasmid-like properties," *Archives of Virology*, 151:995-1002 (2006).
Further Examination Report issued in New Zealand Patent Application No. 601784 dated May 16, 2014.
Gaines et al., "Gene amplification confers glyphosate resistance in *Amaranthus palmeri*," *Proc. Natl. Acad. Sci. USA*, 107(3):1029-1034 (2010).
Gan et al., "Bacterially expressed dsRNA protects maize against SCMV infection," *Plant Cell Rep*, 11:1261-1268 (2010).
Ge et al., "Rapid vacular sequestration: the horseweed glyphosate resistance mechanism," *Pes Management Sci.*, 66:345-348 (2010).
GenBank accession No. AY545657.1, published 2004.
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. GI:186478573, published Jan. 22, 2014.
GenEmbl FJ861243, published Feb. 3, 2010.
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solutions," Thesis submitted to Macquarie University (1983).
Hamilton et al., "Guidelines for the Indentification and Characterization of Plant Viruses," *J. gen. Virol.*, 54:223-241 (1981).
Hamilton et al., "Two classes of short interfering RNA in RNA silencing," *EMBO J.*, 21(17):4671-4679 (2002).
Han et al., "Molecular Basis for the Recognition of Primary microRNAs by the Drosha-DGCR8 Complex," *Cell*, 125(5):887-901 (2006).
Hannon, "RNA interference," *Nature*,481:244-251 (2002).
Herdegree, "Drying and storage on germination of primed grass seeds," *Journal of Range Management*, 47(3):196-199 (1994).

Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hewezi et al., "Local infiltration of high- and low-molecular-weight RNA from silenced sunflower (*Helianthus annus*L.) plants triggers post-transcriptional gene silencing in non-silenced plants," *Plant Biotechnology Journal*, 3:81-89 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).
Himber et al., "Transitivity-dependent and -independent cell-to-cell movement of RNA silencing," *The EMBO Journal*, 22(17):4523-4533 (2003).
Hirschberg et al., "Molecular Basis of Herbicide Resistance in *Amaranthus hybridus*," *Science*, 222:1346-1349 (1983).
Hoekema et al., "A binary plant vector strategy based on separation of vir- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).
Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability dated Sep. 11, 2014, in International Application No. PCT/IL13/50447.
International Search Report dated Mar. 12, 2013 in International Application No. PCT/US 12/54789.
International Search Report and the Written Opinion dated May 10, 2011, in International Application No. PCT/US 11/27528.
International Search Report and the Written Opinion dated Feb. 25, 2013, in International Application No. PCT/US 12/54883.
International Search Report and the Written Opinion dated Feb. 27, 2013, in International Application No. PCT/US 12/54814.
International Search Report and the Written Opinion dated Feb. 27, 2013, in International Application No. PCT/US 12/54842.
International Search Report and the Written Opinion dated Feb. 27, 2013, in International Application No. PCT/US 12/54862.
International Search Report and the Written Opinion dated Feb. 27, 2013, in International Application No. PCT/US 12/54894.
International Search Report and the Written Opinion dated Feb. 27, 2013, in International Application No. PCT/US 12/54974.
International Search Report and the Written Opinion dated Feb. 27, 2013, in International Application No. PCT/US 12/54980.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Isaacs et al., "Engineered riboregulators enable post-transcriptional control of gene expression," *Nature Biotechnology*, 22(7):841-847 (2004).
Ji et al., "Regulation of small RNA stability: methylation and beyond," *Cell Research*, 22:624-636 (2012).
Jones-Rhoades et al., "MicroRNAs and Their Regulatory Roles in Plants," *Annu. Rev. Plant Biol.*, 57:19-53 (2006).
Josse et al., "A DELLA is Disguise: SPATULA Restrains the Growth of the Developing Arabidopsis Seedling," *Plant Cell*, 23:1337-1351 (2011).

(56) References Cited

OTHER PUBLICATIONS

Kam et al., "Nanotube Molecular Transporters: Internalization of Carbon Nanotube—Protein Conjugates into Mammalian Cells," *J. Am. Chem. Soc.*, 126(22):6850-6851 (2004).
Katoh et al., "Specific residues at every third position of siRNA shape its efficient RNAi activity," *Nucleic Acids Res.*, 35(4): e27 (2007).
Kertbundit et al., "In vivo random β-glucuronidase gene fusions in *Arabidopsis thaliana*," *Proc. Natl. Acad. Sci. USA.*, 88:5212-5216 (1991).
Khachigian, "DNAzymes: Cutting a path to a new class of therapeutics," *Curr Opin Mol Ther* 4(2):119-121 (2002).
Khodakovskaya et al., "Carbon Nanotubes are Able to Penetrate Plant Seed Coat and Dramatically Affect Seed Germination and Plant Growth," *ACS Nano*, 3(10):3221-3227 (2009).
Kirkwood, "Use and Mode of Action of Adjuvants for Herbicides: A review of some Current Work," *Pestic Sci.*, 38:93-102 (1993).
Klahre et al., "High molecular weight RNAs and small interfering RNAs induce systemic posttranscriptional gene silencing in plants," *Proc. Natl. Acad. Sci. USA*, PNAS(18):11981-11986 (2002).
Kronenwett et al., "Oligodeoxyribonucleotide Uptake in Primary Human Hematopoietic Cells Is Enhanced by Cationic Lipids and Depends on the Hematopoietic Cell Subset," *Blood*, 91(3):852-862 (1998).
Kusaba et al., "*Low glutelin content1*: A Dominant Mutation That Suppresses the *Glutelin* Multigene Family via RNA Silencing ni Rice," *The Plant Cell*, 15(6):1455-1467 (2003).
Kusaba, "RNA interference in crop plants," *Curr Opin Biotechnol*, 15(2):139-143 (2004).
Lavigne et al., "Enhanced antisense inhibition of human immunodeficiency virus type 1 in cell cultures by DLS delivery system," *Biochem Biophys Res Commun*, 237:566-571 (1997).
Lesnik et al., "Prediction of rho-independent transcriptional terminators in *Escherichia coli*," *Nucleic Acids Research*, 29(17):3583-3594 (2001).
Li et al., "Establishment of a highly efficient transformation system for pepper (*Capsicum annuum* L.)," *Plant Cell Reports*, 21: 785-788 (2003).
Li et al., "The FAST technique: a simplified Agrobacterium-based transformation method for transient gene expression analysis in seedlings of Arabidopsis and other plant species," *Plant Methods*, 5(6):1-15 (2009).
Liu et al., "Comparative study on the interaction of DNA with three different kinds of surfactants and the formation of multilayer films," *Bioelectrochemistry*, 70:301-307 (2007).
Liu et al., "Carbon Nanotubes as Molecular Transporters for Walled Plant Cells," *Nano Letters*, 9(3):1007-1010 (2009).
Liu et al., "DNAzyme-mediated recovery of small recombinant RNAs from a 5S rRNA-derived chimera expressed in *Escherichia coli*," *BMC Biotechnology*, 10:85 (2010).
Llave et al., "Endogenous and Silencing-Associated Small RNAs in Plants," *The Plant Cell*, 14:1605-1619 (2002).
Lu et al., "RNA silencing in plants by the expression of siRNA duplexes," *Nucleic Acids Res.*, 32(21):e171 (2004).
Lu et al., "OligoWalk: an online siRNA design tool utilizing hybridization thermodynamics," *Nucleic Acids Research*, 36:W104-W108 (2008).
Luft, "Making sense out of antisense oligodeoxynucleotide delivery: getting there is half the fun," *J Mol Med*, 76:75-76 (1998).
Maas et al., "Mechanism and optimized conditions for PEG mediated DNA transfection into plant protoplasts," *Plant Cell Reports*, 8:148-149 (1989).
Maher III et al., "Inhibition of DNA binding proteins by oligonucleotide-directed triple helix formation," *Science*, 245(4919):725-730 (1989).
Makkouk et al., "Virus Diseases of Peas, Beans, and Faba Bean in the Mediterranean region," *Adv Virus Res*, 84:367-402 (2012).
Mandal et al., "Adenine riboswitches and gene activation by disruption of a transcription terminator," *Nature Struct. Mol. Biol.*, 11(1):29-35 (2004).
Mandal et al., "Gene Regulation by Riboswitches," *Nature Reviews | Molecular Cell Biology*, 5:451-463 (2004).
Masoud et al., "Constitutive expression of an inducible β-1,3-glucanase in alfalfa reduces disease severity caused by the oomycete pathogen *Phytophtora megasperma* f. sp *medicaginis*, but does not reduce disease severity of chitincontaining fungi," *Transgenic Research*, 5:313-323 (1996).
Mateeva et al., "Prediction of antisense oligonucleotide efficacy by in vitro methods," *Nature Biotechnology*, 16:1374-1375 (1998).
Meinke et al., "Identifying essential genes in *Arabidopsis thaliana*," *Trends Plants Sci.*, 13(9):483-491 (2008).
Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Misawa et al., "Functional expression of the *Erwinia uredovora* carotenoid biosynthesis gene *crtI* in transgenic plants showing an increase of β-carotene biosynthesis activity and resistance to the bleaching herbicide norflurazon," *The Plant Journal*, 4(5):833-840 (1993).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants Are Mobile and Direct Epigenetic Modification in Recipient Cells," *Science*, 328:872-875 (2010).
Moriyama et al., "Double-stranded RNA in rice: a novel RNA replicon in Plants," *Molecular & General Genetics*, 248(3):364-369 (1995).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence- specific Cleavage of Double Helical DNA by Triple Helix Formation," *Science*, 238:645-646 (1987).
Nowak et al., "A new and efficient method for inhibition of RNA viruses by DNA interference," *The FEBS Journal*, 276:4372-4380 (2009).
Office Action dated Feb. 17, 2014, in Mexican Patent Application No. MX/a/2012/010479.
Office Action dated Nov. 19, 2014, in Eurasian Patent Application No. 201201264/28.
Office Action dated Jan. 6, 2015, in Japanese Patent Application No. 2012-557165.
Ongvarrasopone et al., "A Simple and Cost Effective Method to Generate dsRNA for RNAi Studies in Invertebrates," *Science Asia*, 33:35-39 (2007).
Paddison et al., "Stable suppresion of gene expression by RNAi in mammalian cells," *Proc. Natl Acad. Sci. USA*, 99(3):1443-1448 (2002).
Palauqui et al., "Activation of systemic acquired silencing by localised introduction of DNA," *Current Biology*, 9:59-66 (1999).
Parera et al., "Dehydration Rate after Solid Matrix Priming Alters Seeds Performance of *Shrunken-2* Corn," *J. Amer. Soc. Hort. Sci.*, 119(3):629-635 (1994).
Paungfoo-Lonhienne et al., "DNA uptake by Arabidopsis induces changes in the expression of CLE peptides which control root morphology," *Plant Signaling & Behavior*, 5(9):1112-1114 (2010).
Paungfoo-Lonhienne et al., "DNA is Taken up by Root Hairs and Pollen, and Stimulates Root and Pollen Tube Growth," *Plant Physiology*, 153:799-805 (2010).
Pei et al., "On the art of identifying effective and specific siRNAs," *Nature Methods*, 3(9):670-676 (2006).
Peretz et al., "A Universal Expression/Silencing Vectors in Plants," *Plants Physiology*, 145:1251-1263 (2007).

(56) References Cited

OTHER PUBLICATIONS

Pormprom et al., "Glutamine synthetase mutation conferring target-site-based resistance to glufosinate on soybean cell selections," *Pest Manag Sci*, 2009; 65(2):216-222 (2009).
Preston et al., "Multiple effects of a Naturally occurring prolinw to threonine substitution within acetolactate synthase in two herbicide-resistant populations of *Lactuca serriola*," *Pesticide Biochem. Physiol.*, 84(3):227-235 (2006).
Qiwei,"Progress in DNA interference," *Progress in Veterinary Medicine*, 30(1):71-75 (2009).
Rajur et al., "Covalent Protein—Oligonulceotide Conjugates for Efficient Delivery of Antisense Molecules," *Bioconjug. Chem.*, 8:935-940 (1997).
Reddy et al "Organosilicone Adjuvants Increased the Efficacy of Glyphosate for Control of Weeds in Citrus (Citrus spp.)" HortScience (1992) 27(9):1003-1005.
Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix formation analyzed by a FRET assay," *BMC Biochemistry*, 3:27 (2002).
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nat Biotechnol*, 22(3):326-330 (2004).
Reynolds et al., "Rational siRNA design for RNA interference," *Nature Biotechnology*, 22:326-330 (2004).
Ryabov et al., "Cell-to-Cell, but Not Long-Distance, Spread of RNA Silencing That Is Induced in Individual Epidermal Cells," *Journal of Virology*, 78(6):3149-3154 (2004).
Ryan, "Human endogenous retroviruses in health and disease: a symbiotic perspective," *Journal of the Royal Society of Medicine*, 97:560-565 (2004).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Schwab et al., "RNA silencing amplification in plants: Sizes matters," *PNAS*, 107(34):14945-14946 (2010).
Schwember et al., "Drying Rates following Priming Affect Temperature Sensitivity of Germination and Longevity of Lettuce Seeds," *HortScience*, 40(3):778-781 (2005).
Second Chinese Office Action issued in Chinese Patent Application No. 201180012795.2, dated Jun. 10, 2014.
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa cv. Aggregatum*) and carrot (*Daucus carota*)," *Journal of Agricultural Technology*, 7(3):857-867 (2011).
Sharma et al., "A simple and efficient *Agrobacterium*-mediated procedure for transformation of tomato," *J. Biosci.*, 34(3):423 433 (2009).
Sijen et al., "On the Role RNA Amplification in dsRNA-Triggered Gene Silencing," *Cell*, 107:465-476 (2001).
Silwet L-77 Spray Adjuvant for agricultural applications, product descriptions from Momentive Performance Materials, Inc. (2003).
Singh et al., "Absorption and translocation of glyphosate with conventional and organosilicone adjuvants," *Weed Biology and Management*, 8:104-111 (2008).
Steeves et al., "Transgenic soybeans expressing siRNAs specific to a major sperm protein gene suppress *Heterodera glycines* reproductions," *Funct. Plant Biol.*, 33:991-999 (2006).
Stock et al., "Possible Mechanisms for Surfactant-Induced Foliar Uptake of Agrochemicals," *Pestic. Sci.*, 38:165-177 (1993).
Strat et al., "Specific and nontoxic silencing in mammalian cells with expressed long dsRNAs," *Nucleic Acids Research*, 34(13):3803-3810 (2006).
Sudarsan et al., "Metabolite-binding RNA domains are present in the genes of eukaryotes," *RNA*, 9:644-647 (2003).
Sun et al., "Antisense oligodeoxynucleotide inhibition as potent strategy in plant biology: identification of SUSIBA2 as a transcriptional activator in plant sugar signalling," *The Plant Journal*, 44:128-138 (2005).
Sun et al., "A Highly efficient Transformation Protocol for Micro-Tom, a Model Cultivar for Tomato Functional Genomics," *Plant Cell Physiol.*, 47(3):426-431 (2006).
Sun et al., "Sweet delivery—suger translocators as ports of entry antisense oligodeoxnucleotides in plant cells," *The Plant Journal*, 52:1192-1198 (2007).
Takasaki et al., "An Effective Method for Selecting siRNA Target Sequences in Mammalian Cells," *Cell Cycle*, 3:790-795 (2004).
Templeton et al., "Improved DNA: liposome complexes for increased systemic delivery and gene expression," *Nature Biotechnology*, 15:647-652 (1997).
Tenllado et al., "Crude extracts of bacterially expressed dsRNA can be used to protect plants against virus infection," *BMC Biotechnology*, 3(3):1-11 (2003).
Tenllado et al., "RNA interference as a new biotechnological tool for the control of virus disease in plants," *Virus Research*, 102:85-96 (2004).
Tepfer, "Risk assessment of virus resistant transgenic plants," *Annual Review of Phytopathology*, 40:467-491 (2002).
The Seed Biology Place, Website Gerhard Leubner Lab Royal Holloway, University of London, <http://www.seedbiology.de/seedtechnology.asp.
Third party Submission filed on Nov. 29, 2012 in U.S. Appl. No. 13/042,856.
Thompson, et al., "CLUSTAL W: improving the sensitivity of progressive multiple sequence alignment through sequence weighting, position-specific gap penalties and weight matrix choice," *Nucl. Acids Res.*, 22(22):4673-4680 (1994).
Timmon et al., "Specific interferences by ingested dsRNA," *Nature*, 395:854 (1998).
Tomari et al., "Perspective: machines for RNAi," *Genes & Dev.*, 19:517-529 (2005).
Töpfer et al., "Uptake and Transient Expression of Chimeric Genes in Seed-Derived Embryos," *Plant Cell*, 1:133-139 (1989).
Tran et al., "Control of specific gene expression in mammalian cells by co-expression of long complemantary RNAs," *FEBS Lett.*;573(1-3):127-134 (2004).
Turina et al., "Tospoviruses in the Mediterranean Area," *Advances in Virus Research*, 84:403-437 (2012).
Tuschl, "RNA Interference and Small Interfering RNAs," *ChemBiochem*. 2(4):239-245 (2001).
Tuschl, "Expanding small RNA interference," *Nature Biotechnol.*, 20: 446-448 (2002).
Ui-Tei et al., "Guidelines for the selection of highly effective siRNA sequences for mammalian and chick RNA interference," *Nucleic Acids Res.*, 32(3): 936-948 (2004).
Unnamalai et al., "Cationic oligopeptide-mediated delivery of dsRNA for post-transcriptional gene silencing in plant cells," *FEBS Letters*, 566:307-310 (2004).
Urayama et al., "Knock-down of *OsDCL2* in Rice Negatively Affects Maintenance of the Endogenous dsRNA Virus, *Oryza sativa* Endornavirus," *Plant and Cell Physiology*, 51(1):58-67 (2010).
van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombarbment of Regenerable Embryogenic Callus," *Bio/Technology*,10:667-674 (1992).
Vaucheret, "Post-transcriptional small RNA pathways in plants: mechanisms and regulations," *Gene Dev.*, 20:759-771 (2006).
Vencill et al., "Resistance of Weeds to Herbicides," *Herbicides and Environment*, 29:585-594 (2011).
Verma et al., "Modified oligonucleotides: synthesis and strategy for users," *Annu. Rev. Biochem.*, 67:99-134 (1998).
Vert et al., "An accurate and interpretable model for siRNA efficacy prediction," *BMC Bioinformatics*, 7:520 (2006).

(56) References Cited

OTHER PUBLICATIONS

Vionnet et al., "Systemic Spread of Sequence-Specific Transgene RNA Degradation in Plants Is Initiated by Localized Introduction of Ectopic Promoterless DNA," *Cell*, 95:177-187 (1998).
Wakelin et al., "A target-site mutation is present in a glyphosate-resistant *Lolium rigidum* population," *Weed Res. (Oxford)*, 46(5):432-440 (2006).
Walton et al., "Prediction of antisense oligonucleotide binding affinity to a structured RNA target," *Biotechnol Bioeng* 65(1):1-9 (1999).
Wan et al., "Generation of Large Numbers of Independently Transformed Fertile Barley Plants," *Plant Physiol.*, 104:37-48 (1994).
Wardell,"Floral Activity in Solutions of Deoxyribonucleic Acid Extracted from Tobacco Stems," *Plant Physiol*, 57:855-861 (1976).
Wardell, "Floral Induction of Vegetative Plants Supplied a Purified Fraction of Deoxyribonucleic Acid from Stems of Flowering Plants," *Plant Physiol*, 60:885-891 (1977).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in genes transfers systems to modulate target RNA levels," *Curr Opin Biotechnol.* 9(5):486-496 (1998).
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated May 8, 2014, in International Application No. PCT/IL2013/050447.
Written Opinion dated Sep. 1, 2014, in Singapore Patent Application No. 201206152-9.
Yin et al., "Production of double-stranded RNA for interference with TMV infection utilizing a bacterial prokaryotic expression system," *Appl. Microbiol. Biotechol.*, 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "Transgenic rice plants produced by electroporation-mediated plasmid uptake into protoplasts," *The Plant Cell Rep.*, 7:379-384 (1988).
Zhang et al., "DEG: a database of essential genes," *Nucleic Acids Res.*, 32:D271-D272 (2004).
Zhang et al., "*Agrobacterium*-mediated transformation of *Arabidopsis thaliana* using the floral dip method," *Nature Protocols*, 1(2):1-6 (2006).
Zhang et al., "Cationic lipids and polymers mediated vectors for delivery of siRNA," *Journal of Controlled Release*, 123:1-10 (2007).
Zhang et al., "A novel rice gene, NRR responds to macronutrient deficiency and regulates root growth," *Mol Plant*, 5(1):63-72 (2012).
Zhao et al., "*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing for populations of the Colorado potato beetle, *Leptinotarsa decemlineata,*" *Pest Manag Sci*, 67:175-182 (2010).
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pusruant to Article 94(3) EPC dated Mar. 18, 2016, in European Patent Application No. 12 832 160.1.
Communication pursuant to Article 94(4) EPC dated Jan. 14, 2016, in European Patent Application No. 12 832 415.9.
Database Accession No. HD315444, "Sequence 192160 from Patent EP2213738," (2010).
Extended European Search Report dated Jan. 20, 2016, in European Application No. 13 794 339.5.
First Office Action dated Feb. 2, 2016, in Chinese Patent Application No. 201380039346.6.
GenBank Accession No. GU120406, "Chrysomela tremulae ribosomal protein L7 (RpL7) mRNA, complete cds," (2009) Retrieved from the internet, U RL: <http://www.ncbi.nlm.nih.gov/nuccore/GU120406>.
GenBank Accession No. Q4GXM3_BIPLU, "Ribsomal protein L7e" (2006) [Retrieved on Feb. 5, 2016] Retrieved from the internet, URL: <http://www.ncbi.nlm.nih.gov/protein/Q4GXM3>.
Gudkov, "Minireview: The L7/L12 ribosomal domain of the ribosome: structural and functional studies," *FEBS Letters*, 407:253-256 (1997).
Heffer et al., "Rapid isolation of gene homologs across taxa: Efficient identification and isolation of gene orthologs from non-model organism genomes, a technical report," *EvoDevo Journal*, 2(7):1-5 (2011).
Knudsen, "Promoter2.0: for the recognition of Poll promoter sequences," *Bioinformatics*, 15(5):356-361 (1999).
Migge et al., "Greenhouse-grown conditionally lethal tobacco plants obtained by expression of plastidic glutamine synthetase antisense RNA may contribute to biological safety," *Plant Science* 153:107-112 (2000).
Office Action dated Apr. 13, 2016, in Chinese Patent Application No. 201280053985.3.
Patent Examination Report No. 1 dated Feb. 8, 2016, in Australian Patent Application No. 2014262189.
Promoter Prediction for SEQ ID No. 1702 from 13/612929/MK/, Promoter 2.0 Prediction Results, pp. 1-4 (2016).
Salanenka et al., "Seedcoat Permeability: Uptake and Post-germination Transport of Applied Model Tracer Compounds," *HortScience*, 46(4):622-626 (2011).
Scott et al., Botanical Insecticides for Controlling Agricultural Pests: Piperamides and the Colorado Potato Beetle *Leptinotarsa decemlineata* Say (Coleoptera: Chrysomelidae), *Archive of Insect Biochemistry and Physiology*, 54:212-225 (2003).
Second Office Action dated Mar. 4, 2016, in Chinese Patent Application No. 201280054820.8.
Second Office Action dated Feb. 25, 2016, in Chinese Patent Application No. 201280054179.8.
Shintani et al., "Antisense Expression and Overexpression of Biotin Carboxylase in Tobacco Leaves," *Plant Physiol.*, 114:881-886 (1997).
Written Opinion dated Apr. 7, 2016, in Singapore Patent Application No. 201206152-9.
Zhang et al., "Development and Validation of Endogenous Reference Genes for Expression Profiling of Medaka (*Oryzia latipes*) Exposed to Endocrine Disrupting Chemicals by Quantitative Real-Time RT-PCR," *Toxicological Sciences*, 95(2):356-368 (2007).
Agrios, *Plant Pathology* (Second Edition), 2:466-470 (1978).
Andersson et al., "A novel selection system for potato transformation using a mutated AHAS gene," *Plant Cell Reports*, 22(4):261-267 (2003).
Anonymous, "Agronomy Fact 37: Adjuvants for enhancing herbicide performance," n.p., 1-8, (Jan. 16, 2000), *Web*, (Jan. 21, 2014).
Anonymous, "Do Monsanto have the next big thing?," *Australian Herbicide Resistance Initiative(AHRI)*, (Apr. 23, 2013) Web. (Jan. 19, 2015).
Bai et al., "Naturally Occurring Broad-Spectrum Powdery Mildew Resistance in a Central American Tomato Accession Is Caused by Loss of *Mlo* Function," *MPMI*, 21(1):30-39 (2008).
Bourgeois et al., "Field and producer survey of ACCase resistant wild oat in Manitoba," *Canadian Journal of Plant Science*, 709-715 (1997).
Brugière et al., "Glutamine Synthetase in the Ploem Plays a Major Role in Controlling Proline Production," *The Plant Cell*, 11:1995-2011 (1999).

(56) References Cited

OTHER PUBLICATIONS

Busi et al., "Gene flow increases the initial frequency of herbicide resistance alleles in unselectedpopulations," *Agricultures, Ecosystems and Environments*, Elsevier, Amsterdam, NL, 142(3):403-409 (2011).
Chang et al., "Cellular Internalization of Fluorescent Proteins via Arginine-rich Intracellular Delivery Peptide in Plant Cells," *Plant Cell Physiol.*, 46(3):482-488 (2005).
Communication pursuant to Article 94(3) EPC dated Jun. 26, 2015, as received in European Patent Application No. 11 753 916.3.
Communication pursuant to Article 94(3) EPC dated Oct. 23, 2015, as received in European Patent Application No. 12 831 945.6.
Coticchia et al., "Calmodulin modulates Akt activity in human breast cancer cell lines," *Breast Cancer Res. Treat*, 115:545-560 (2009).
Desai et al., "Reduction on deformed wing virus infection in larval and adult honey bees (*Apis mellifera* L.) by double-stranded RNA ingestion," *Insect Molecular Biology*, 21(4):446-455 (2012).
Dietemann et al., "*Varroa destructor*: research avenues towards sustainable control," *Journal of Apicultural Research*, 51(1):125-132 (2012).
Emery et al., "Radial Patterning of *Arabidopsis* Shoots by Class III HD-ZIP and KANADI Genes," *Current Biology*, 13:1768-1774 (2003).
Extended European Search Report dated Feb. 2, 2015, in European Patent Application No. 12 830 932.5.
Extended European Search Report dated Feb. 27, 2015, in European Patent Application No. 12 830 160.1.
Extended European Search Report dated Feb. 3, 2015, in European Patent Application No. 12 831 945.6.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jan. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Final Office Action dated Nov. 7, 2013, in U.S. Appl. No. 13/042,856.
Gao et al., "Down-regulation of acetolactate synthase compromises 01-1-mediated resistance to powdery mildew in tomato," *BMC Plant Biology*, 14 (2014).
Gressel et al., "A strategy to provide long-term control of weedy rice while mitigating herbicide resistance transgene flow, and its potential use for other crops with related weeds," *Pest Manag Sci*, 65(7):723-731 (2009).
Harrison et al., "Does Lowering Glutamine Synthetase Activity in Nodules Modigy Nitrogen Metabolism and Growth of *Lotus japonicus?*," *Plant Physiology*, 133:253-262 (2003).
International Preliminary Report on Patentability (Chapter II) dated Jul. 24, 2015, in International Application No. PCT/US2014/047204.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated Nov. 24, 2015, in International Application No. PCT/US2015/037522.
International Search Report dated Mar. 12, 2013, in International Application No. PCT/US2012/054789.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.

Jofre-Garfia et al., "*Agrobacterium*-mediated transformation of *Amaranthus hypochondriacus*: light- and tissue-specific expression of a pea chlorophyll a/b-binding protein promoter," *Plant Cell Reports*, 16:847-852 (1997).
Khan et al., "Matriconditioning of Vegetable Seeds to Improve Stand Establishment in Early Field Plantings," *J. Amer. Soc. Hort. Sci.*, 117(1):41-47 (1992).
Kim et al., "Synthetic dsRNA Dicer substrates enhance RNAi potency and efficacy," *Nature Biotechnology*, 23(2):222-226 (2005).
Lein et al., "Target-based discovery of novel herbicides," *Current Opinion in Plant Biology*, 7:219-225 (2004).
Lermontova et al., "Reduced activity of plastid protoporphyrinogen oxidase causes attenuated photodynamic damage during high-light compared to low-light exposure," *The Plant Journal*, 48(4):499-510 (2006).
MacKenzie et al., "Transgenic *Nicotiana debneyii* expressing viral coat protein are resistant to potato virus S infection," *Journal of General Virology*, 71:2167-2170 (1990).
Maori et al., "IAPV, a bee-affecting virus associated with Colony Collapse Disorder can be silenced by dsRNA ingestion," *Insect Molecular Biology*, 18(1):55-60 (2009).
Molina et al., "Inhibition of protoporphyrinogen oxidase expression in *Arabidopsis* causes a lesion-mimic phenotype that induces systemic acquired resistance," *The Plant Journal*, 17(6):667-678 (1999).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Nord-Larsen et al., "Cloning, characterization and expression analysis of tonoplast intrinsic proteins and glutamine synthetase in ryegrass (*Lolium perenne* L.)," *Plant Cell Reports*, 28(10):1549-1562 (2009).
Notice of Allowance dated Oct. 5, 2015, in U.S. Appl. No. 13/583,302.
Office Action dated Jul. 23, 2015, in Ukrainian Patent Application No. 201211548.
Office Action dated Oct. 5, 2015, in Eurasian Patent Application No. 201201264/28.
Office Action dated Sep. 9, 2015, in Chinese Patent Application No. 201280055409.2.
Ouellet et al., "Members of the Acetohydroxyacid Synthase Muligene Family of Brassica Napus Have Divergent Patterns of Expression," *The Plant Journal*, Blackwell Scientific Publication, Oxford, GB, 2(3):321-330 (1992).
Partial Supplementary European Search Report dated Mar. 2, 2015, in European Patent Application No. 12 831 494.5.
Pratt et al., "Amaranthus rudis and A. tuberculatus, One Species or Two?," *Journal of the Torrey Botanical Society*, 128(3):282-296 (2001).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Mar. 15, 2015, in U.S. Appl. No. 13/612,948.
Restriction Requirement dated Mar. 4, 2015, in U.S. Appl. No. 13/612,941.

(56) References Cited

OTHER PUBLICATIONS

Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 21, 2014, in U.S. Appl. No. 13/583,302.
Riggins et al., "Characterization of de novo transcriptome for waterhemp (*Amaranthus tuberculatus*) using GS-FLX 454 pyrosequencing and its application for studies of herbicide targer-site genes," *Pest Manag. Sci.*, 66:1042-1052 (2010).
Rose et al., "Functional polarity is introduced by Dicer processing of short substrate RNAs," *Nucleic Acids Research*, 33(13):4140-4156 (2005).
Rothnie et al., Pararetroviruses and Retroviruses: A Comparative Review of Viral Structure and Gene Expression Strategies, *Advances in Virus Research*, 44:1-67 (1994).
Schweizer et al., "Double-stranded RNA interferes with gene function at the single-cell level in cereals," *The Plant Journal*, 24(6):895-903 (2000).
Senthil-Kumar et al., "A systemic study to determine the extent of gene silencing in Nicotiana benthamiana and other Solanaceae species when heterologous gene sequences are used for virus-induced gene silencing," *New Phytologist*, 176:782-791 (2007).
Stevens et al., "New Formulation Technology—SILWET® Organosilicone Surfactants Have Physical and Physiological Properties Which Enhance the Performance of Sprays," *Proceedings of the 9th Australian Weeds Conference*, pp. 327-331 (1990).
Street, "Why is DNA (and not RNA) a stable storage form for genetic information?," *Biochemistry Revisited*, pp. 1-4 (2008).
Sutton et al., "Activity of mesotrione on resistant weeds in maize," *Pest Manag. Sci.*, 58:981-984 (2002).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," *The Physiology of Vegetable Crops*, pp. 1-36 (1997).
Temple et al., "Can glutamine synthetase activity levels be modulated in transgenic plants by the use of recombinant DNA technology?" *Transgenic Plants and Plant Biochemistry*, 22(4):915-920 (1994).
Temple et al., "Down-regulation of specific members of the glutamine synthetase gene family in Alfalfa by antisense RNA technology," *Plant Molecular Biology*, 37:535-547 (1998).
Tranel et al., "Resistance of weeds to ALS-inhibiting herbicides: what have we learned?," *Weed Sciences*, 50:700-712 (2002).
Tsugawa et al., "Efficient transformation of rice protoplasts mediated by a synthetic polycationic amino polymer," *Theor Appl Genet*, 97:1019-1026 (1998).
Vermeulen et al., "The contributions of dsRNA structure to Dicer specificity and efficiency," *RNA*, 11(5):674-682 (2005).
Wang et al., "Foliar uptake of pesticides-Present status and future challenge," ScienceDirect, 87:1-8 (2007).
Xu et al., Characterization and Functional Analysis of the Calmodulin-Binding Domain of Rac1 GTPase, *Plos One*, 7(8)1-12:e42975 (2012).
Agricultural Chemical Usage 2006 Vegetables Summary, Agricultural Statistics Board, NASS, USDA, pp. 1-372 (2007).
Al-Kaff et al., "Plants rendered herbicide-susceptible by cauliflower mosaic virus—elicited suppression of a 35S promoter-regulated transgene," *Nature Biotechnology*, 18:995-999 (2000).
Balibrea et al., "Extracellular Invertase is an Essential Component of Cytokinin-Mediated Delay of Senescence," *The Plant Cell*, 16(5):1276-1287 (2004).
Bart et al., "A novel system for gene silencing siRNAs in rice leaf and stem-derived protoplasts," *Plant Methods*, 2(13):1-9 (2006).
Basu et al., "Weed genomics: new tools to understand weed biology," *TRENDS in Plant Science*, 9(8):391-398 (2004).
Busch et al., "RNAi for discovery of novel crop protection products," *Pflanzenschutz-Nachrichten Bayer*, 58(1):34-50 (2005).
Chen et al., "Transfection and Expression of Plasmid DNA in Plant Cells by an Arginine-Rich Intracellular Delivery Peptide without Proroplasts Preparation," *FEBS Letters 581*, pp. 1891-1897 (2007).
Colliver et al., "Differential modification of flavonoid and isoflavonoid biosynthesis with an antisense chalcone synthase construct in transgenic *Lotus corniculatus*," *Plant Molecular Biology*, 35:509-522 (1997).
Concise Descriptions of Relevance filed by a third party on Nov. 29, 2012 in U.S. Appl. No. 13/042,856.
Dawson et al., "cDNA cloning of the complete genome of tobacco mosaic virus and production of infectious transcripts," *Proc. Natl. Acad. Sci. USA*, 83:1832-1836 (1986).
Feuillet et al., "Crop genome sequencing: lessons and rationales," *Trends Plant Sci.*, 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Sep. 9, 2016, in U.S. Appl. No. 13/612,954.
Final Office Action dated Nov. 19, 2015, in U.S. Appl. No. 13/612,941.
Final Office Action dated Nov. 30, 2015, in U.S. Appl. No. 13/612,948.
Final Office Action dated Sep. 9, 2016, in U.S. Appl. No. 14/608,951.
Final Office Action dated Sep. 9, 2016, in U.S. Appl. No. 14/603,347.
Final Office Action dated Oct. 20, 2016, in U.S. Appl. No. 14/480,199.
Final Office Action dated Oct. 22, 2015, in U.S. Appl. No. 14/608,951.
Fraley et al., "Liposome-mediated delivery of tobacco mosaic virus RNA into tobacco protoplasts: A sensitive assay for monitoring liposome-protoplast interactions," *Proc Natl Acad Sci U S A.*, 79(6):1859-1863 (1982).
Gan et al., "Inhibition of Leaf Senescence by Autoregulated Production of Cytokinin," *Science*, 270:1986-1988 (1995).
Gao et al., "Nonviral Methods for siRNA Delivery," *Molecular Pharmaceutics*, 6(3):651-658 (2008).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. EW765249, "ST020010B10C12 Normalized and subtracted western corn rootworm female head cDNA library Diabrotica virgifera virgifcra cDNA clonc STO20010B10C12 5-, mRNA sequence," (2007).
GenBank Accession No. EW771198, "ST020010B10C12 Normalized and subtracted western corn rootworm female head cDNA library Diabrotica virgifera virgifera cDNA clone STO20010B10C12 5-, mRNA sequence," (2007).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. U87257.1, "Daucus carota 4-hydroxyphenylpyruvate dioxygenase mRNA, complete cds" (1997).
GenBank Accession No. XM_014456745.1, PREDICTED: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase." (2006).
Gossamer Threads, Compendium of Herbicide Adjuvants: Organo-Silicone Surfactant, p. 1-4 (1998).
Hajirezaei et al., "Impact of elevated cytosolic and apoplastic invertase activity on carbon metabolism during potato tuber development," *Journal of Experimental Botany*, 51:439-445 (2000).
Holtra et al., "Assessment of the Physiological Condition of *Salvinia Natans* L. Exposed to Copper(II) Ions," *Environ. Protect. Eng.*, 41:147-158 (2015).

(56) References Cited

OTHER PUBLICATIONS

International Preliminary Report on Patentability dated Sep. 11, 2012, in International Application No. PCT/US2011/027528.
International Rice Genome Sequencing Project, The map-based sequence of the rice genome, *Nature*, 436(11):793-800 (2005).
International Search Report and Written Opinion dated May 26, 2016, in International Application No. PCT/US2016/014344.
International Search Report and Written Opinion dated Nov. 27, 2015, in International Application No. PCT/US2015/037015.
Jin et al., "Posttranslational Elevation of Cell Wall Invertase Activity by Silencing its Inhibitor in Tomato Delays Leaf Senescence and Increases Seed Weight and Fruit Hexose Level," *The Plant Cell*, 21:2072-2089 (2009).
Kaloumenos et al., "Identification of a Johnsongrass (*Sorghum halepense*) Biotype Resistant to ACCase-Inhibiting Herbicides in Northern Greece," *Weed Technol*, 23:470-476 (2009).
Kambiranda et al., "Relationship Between Acid Invertase Activity and Sugar Content in Grape Species," *Journal of Food Biochemistry*, 35:1646-1652 (2011).
Kim et al., "Optimization of Conditions for Transient Agrobacterium-Mediated Gene Expression Assays in Arabidopsis," *Plant Cell Reports*, 28:1159-1167 (2009).
Kirkwood, "Herbicides and Plants," *Botanical Journal of Scotland*, 46(3):447-462 (1993).
Liu et al., "Identification and Application of a Rice Senescence-Associated Promoter," *Plant Physiology*, 153:1239-1249 (2010).
Mora et al., "How Many Species Are There on Earth and in the Ocean?," *PLOS Biol.*, 9(8):e100127, p. 1-8 (2011).
Mount et al., "Gene and Metabolite Regulatory Network Analysis of Early Developing Fruit Tissues Highlights New Candidate Genes for the Control of Tomato Fruit Composition and Development," *Plant Physiology*, 149:1505-1528 (2009).
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Sep. 6, 2016, in U.S. Appl. No. 14/335,135.
Non-Final Office Action dated Mar. 1, 2016, in U.S. Appl. No. 13/612,954.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Nookaraju et al., "Molecular approaches for enhancing sweetness in fruits and vegetables," *Scientia Horticulture*, 127:1-15 (2010).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Office Action dated Aug. 28, 2013, in Chinese Patent Application No. 201180012795.2.
Office Action dated Jul. 18, 2016, in Indonesian Patent Application No. W00201203610.
Office Action dated Aug. 25, 2016, in Eurasian Patent Application No. 201201264.
Office Action dated Feb. 24, 2014, in Eurasian Patent Application No. 201201264.
Office Action dated Jun. 20, 2016, in Chinese Patent Application No. 201280054819.5.
Office Action dated Jun. 24, 2016, in Chinese Patent Application No. 201280053984.9.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Nov. 11, 2013, in Australian Patent Application No. 2011224570.
Promoter Prediction for SEQ ID No. 4 from 13/612995/MK/, Promoter 2.0 Prediction Results, pp. 1-3 (2016).
Promoter Prediction for SEQ ID No. 7 from 13/612936/MK/, Promoter 2.0 Prediction Results, pp. 1-2 (2016).
Promoter Prediction for SEQ ID No. 8 from 13/612925/MK/, Promoter 2.0 Prediction Results, pp. 1-6 (2016).
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Oct. 13, 2016, in U.S. Appl. No. 14/206,707.
Restriction Requirement dated Oct. 28, 2015, in U.S. Appl. No. 14/603,347.
Restriction Requirement dated Sep. 2, 2015, in U.S. Appl. No. 14/532,596.
Roberts, "Fast-track applications: The potential for direct delivery of proteins and nucleic acids to plant cells for the discovery of gene function," *Plant Methods*, 1(12):1-3 (2005).
Robson et al., "Leaf senescence is delayed in maize expressing the Agrobacterium IPT gene under the control of a novel maize senescence-enhanced promoter," *Plant Biotechnology Journal*, 2:101-112 (2004).
Roitsch et al., "Extracellular invertase: key metabolic enzyme and PR protein," *Journal of Experimental Botany*, 54(382):513-524 (2003).
Roitsch et al., "Function and regulation of plant invertases: sweet sensations," *Trades in Plant Science*, 9(12):606-613 (2004).
Ruan et al., "Suppression of Sucrose Synthase Gene Expression Represses Cotton Fiber Cell Initiation, Elongation, and Seed Development," *The Plant Cell*, 15:952-964 (2003).
Showalter, "Structure and Function of Plant Cell Wall Proteins," *The Plant Cell*, 5:9-23 (1993).
Snead et al., "Molecular basis for improved gene silencing by Dicer substrate interfering RNA compared with other siRNA variants," *Nucleic Acids Research*, 41(12):6209-6221 (2013).
Song et al., "Herbicide," *New Heterocyclic Pesticide*, Chemical Industry Press, 354-356 (2011).
Stevens, "Organosilicone Surfactants as Adjuvants for Agrochemicals," *Journal of Pesticide Science*, 38:103-122 (1993).
Tang et al., "Efficient delivery of small interfering RNA to plant cells by a nanosecond pulsed laser-induced stress wave for post-transcriptional gene silencing," *Plant Science*, 171:375-381 (2006).
Tenllado et al., "Double-Stranded RNA-Mediated Interference with Plant Virus Infection," *Journal of Virology*, 75(24):12288-12297 (2001).
Thomas et al., "Size constraints for targeting post-transcriptional gene silencing and for RNA-directed methylation in *Nicotiana benthamiana* using a potato virus X vector," *The Plant Journal*, 25(4):417-425 (2001).

(56) References Cited

OTHER PUBLICATIONS

Tomlinson et al., "Evidence that the hexose-to-sucrose ratio does not control the switch to storage product accumulation in oilseeds: analysis of tobacco seed development and effects of overexpressing apoplastic invertase," *Journal of Experimental Botany*, 55(406):2291-2303 (2004).
Widholm et al., "Glyphosate selection of gene amplification in suspension cultures of 3 plant species," *Phyisologia Plantarum*, 112:540-545 (2001).
Zhang et al., "Chapter 10: New Characteristics of Pesticide Research & Development," *New Progress of the world agriculture chemicals*, p. 209 (2010).
Voinnet et al., "Systemic Spread of Sequence-Specific Transgene RNA Degradation in Plants Is Initiated by Localized Introduction of Ectopic Promoterless DNA," *Cell*, 95:177-187 (1998).
Bachman et al., "Characterization of the spectrum of insecticidal activity of a double-stranded RNA with targeted activity against Western Corn Rootworm (Diabrotica virgifera virgifera LeConte)," *Transgenic Res.*, pp. 1-16 (2013).
Office Action dated Mar. 16, 2017, in Chinese Patent Application No. 201280054819.5.
Written Opinion dated Mar. 6, 2017, in Singaporean Patent Application No. 2012061529.
Regalado, "The Next Great GMO Debate," *MIT Technology Review*, pp. 1-19 (2015) <http://www.technologyreview.com/s/540136/the-next-great-gmo-debate/>.
Anderson et al., "Delivery of siRNA from lyophilized polymeric surfaces," *Biomaterials*, 26:506-512 (2008).
Anonymous, "A handbook for high-level expression and purification of 6xHis-tagged proteins," *The QiaExpressionist*, (2003).
Anonymous, "Devgen, The mini-Monsanto," KBC Securities (2006).
Artymovich, "Using RNA interference to increase crop yield and decrease pest damage," *MMG 445 Basic Biotech.*, 5(1):7-12 (2009).
Brodersen et al., "The diversity of RNA silencing pathways in plants," *Trends in Genetics*, 22(5):268-280 (2006).
Campbell et al., "Gene-knockdown in the honey bee mite Varroa detructor by a non-invasive approach: studies on a glutathione S-transferase," *Parasites & Vectors*, 3(73):1-10 (2010).
Chabannes et al., "In situ analysis of lignins in transgenic tobacco reveals a differential impact of individual transformations on the spatial patterns of lignin depostition at the cellular and subcellular levels," *The Plant Journal*, 28(3):271-282 (2001).
Chupp et al., "Chapter 8: White Rust," *Vegetable Diseases and Their Control, The Ronald Press Company*, New York, pp. 267-269 (1960).
Communication pursuant to Article 94(3) EPC dated Jun. 26, 2015, in European Patent Application No. 11 753 916.3.
Communication pursuant to Article 94(3) EPC dated Oct. 23, 2015, in European Patent Application No. 12 831 945.6.
Dalakouras et al., "Induction of Silencing in Plants by High-Pressure Spraying of In vitro-Synthesized Small RNAs," *Frontiers in Plant Science*, 7(1327):1-5 (2016).
Dietermann et al., "Varroa destructor: research avenues towards sustainable control," *Journal of Apicultural Research*, 51(1):125-132 (2012).
Extended European Search Report dated Jun. 29, 2015, in European Patent Application No. 12 831 494.5.
Extended European Search Report dated Oct. 8, 2013, in European Patent Application No. 11753916.3.
Extended European Search Report dated Sep. 29, 2016, in European Patent Application No. 14778840.0.
Final Office Action dated Nov. 10, 2015, in U.S. Appl. No. 13/612,985.
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Fukunaga et al., "dsRNA with 5' overhangs v contributes to endogenous and antiviral RNA silencing pathways in plants," *The EMBO Journal*, 28(5):545-555 (2009).
Furhter Examination Report dated May 16, 2014, in New Zealand Patent Application No. 601784.
Garbian et al., "Bidirectional Transfer of RNAi between Honey Bee and Varroa destructor: Varroa Gene Silencing Reduces Varroa Population," 8(12):1-9:e1003035 (2012).
GenBank Accession No. AY545657.1 (2004).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EU024568, "Amaranthus hypochondriacus acetolactate synthase (ALS) gene" (2007).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. GU120409, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_BIPLU, "Ribosomal protein L7e" (2006).
GenEmbl Accession No. FJ861243 (2010).
Gong et al., "Silencing of Rieske iron—sulfur protein using chemically synthesised siRNA as a potential biopesticide against Plutella xylostella," *Pest Manag Sci*, 67:514-520 (2011).
Hewezi et al., "Local infiltration of high- and low-molecular-weight RNA from silenced sunflowe (*Helianthus annuus* L.) plants triggers post-transcriptional gene silencing in non-silenced plants," *Plant Biotechnology Journal*, 3:81-89 (2005).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability dated Sep. 11, 2014, in International Application No. PCT/IL2013/050447.
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated Oct. 1, 2013, in International Application No. PCT/IL2013/050447.
International Search Report and the Written Opinion dated Aug. 25, 2014, in International Application No. PCT/US2014/023503.

(56) References Cited

OTHER PUBLICATIONS

International Search Report and the Written Opinion dated Aug. 27, 2014, in International Application No. PCT/US2014/023409.
Jofre-Garfias et al., "Agrobacterium-mediated transformation of Amaranthus hypochondriacus: light- and tissue-specific expression of a pea chlorophyll a/b-binding protein promoter," *Plant Cell Reports*, 16:847-852 (1997).
Kahn et al., "Matriconditioning of Vegetable Seeds to Improve Stand Establishment in Early Field Plantings," *J. Amer. Soc. Hort. Sci.*, 117(1):41-47 (1992).
Lee et al., "Aptamer Database," *Nucleic Acids Research*, 32:D95-D100 (2004).
Leopold et al., "Chapter 4: Moisture as a Regulator of Physiological Reaction in Seeds," *Seed Moisture*, 14:51-69 (1989).
Liu et al., "DNAzyme-mediated revoery of small recombinant RNAs from a 5S rRNA-derived chimera expressed in *Escherichia coli*," *BMC Biotechnology*, 10:85 (2010).
Liu, "Influence of Sugars on the Foliar Uptake of Bentazone and Glyphosate," *New Zealand Plant Protection*, 55:159-162 (2002).
Luque et al., "Water Permeability of Isolated Cuticular Membranes: A Structural Analysis," *Archives of Biochemistry and Biophysics*, 317(2):417-422 (1995).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).
Misawa et al., "Expression of an *Erwina* phytoene desaturase gene not only confers multiple resistance to herbicides interfering with carotenoid biosynthesis but also alters xanthophyll meatbolism in transgenic plants," *The Plant Journal*, 6(4):481-489 (1994).
Miura et al., "The Balance between Protein Synthesis and Degradation in Chloroplasts Determines Leaf Variegation in *Arabidopsis yellow variegated* Mutants," *The Plant Cell*, 19:1313-1328 (2007).
Non-Final Office Action dated Nov. 9, 2016, in U.S. Appl. No. 14/907,003.
Office Action dated Sep. 5, 2016, in Ukrainian Patent Application No. a 2014 03846.
Office Action dated Nov. 15, 2016, in Mexican Patent Application No. MX/a/2014/003068.
Office Action dated Nov. 3, 2014, in Chinese Patent Application No. 201180012795.2.
Orbović et al., "Foliar-Applied Surfactants and Urea Temporarily Reduce Carbon Assimilation of Grapefruit Leaves," *J. Amer. Soc. Hort. Sci.*, 126(4):486-490 (2001).
Parera et al., "Dehydration Rate after Solid Matrix Priming Alter Seed Performance of *Shrunken-2* Corn," *J. Amer. Soc. Hort. Sci.*, 119(3):629-635 (1994).
Pornprom et al., "Glutamine synthetase mutation conferring target-site-based resistance to glufosinate in soybean cell selections," *Pest Manag Sci*, 2009; 65(2):216-222 (2009).
Preston et al., "Multiple effects of a naturally occurring proline to threonine substitution within acetolactate synthase in two herbicide-resistant populations of *Lactuca serriola*," *Pesticide Biochem. Physiol.*, 84(3):227-235 (2006).
Qiwei, "Advance in DNA interference," *Progress in Veterinary Medicine*, 30(1):71-75 (2009).
Reddy et al "Organosilicone Adjuvants Increased the Efficacy of Glyphosate for Control of Weeds in Citrus (Citrus spp.)" *HortScience* 27(9):1003-1005 (1992).
Schönherr, "Water Permeability of Isolated Cuticular Membranes: The Effect of pH and Cations on Diffusion, Hydrodynamic Permeability and Size of Polar Pores in the Cutin Matrix," *Planta*, 128:113-126 (1976).
Shaoquan, "The action target of herbicide and the innovation of a new variety," *Chemical Industry Press*, 23-24 (2001).
Second Chinese Office Action dated Jun. 10, 2014, in Chinese Patent Application No. 201180012795.2.
Unniraman et al., "Alternate Paradigm for Intrinsic Transcription Termination in Eubacteria," *The Journal of Biological Chemistry*, 276(45)(9):41850-41855 (2001).
Wiesman et al., "Novel cationic vesicle platform derived from vernonia oil for efficient delivery of DNA through plant cuticle membranes," *Journal of Biotechnology*, 130:85-94 (2007).
Anderson et al., "Delivery of siRNA from lyophilized polymeric surfaces," Biomaterials, 29:506-512 (2008).
Ascencio-Ibanez et al., "DNA abrasion onto plants is an effective method for geminivirus infection and virus-induced gene silencing," Journal of Virological Methods, 142:198-203 (2007).
Campbell et al., "Gene-knockdown in the honey bee mite Varroa destructor by a non-invasive approach: studies on a glutathionw S-transferase," Parasites & Vectors, 3(1):73, pp. 1-10 (2010).
Chen et al., "Exploring MicroRNA-Like Small RNAs in the Filamentous Fungus Fusarium oxysporum," PLOS One, 9(8):e104956:1-10 (2014).
Di Stilio et al., "Virus-Induced Gene Silencing as a Tool Comparative Functional Studies in Thalictrum,"PLoS One, 5(8):e12064 (2010).
Gan et al., "Bacterially expressed dsRNA protects maize against SCMV infection," Plant Cell Rep, 29(11):1261-1268 (2010).
Gaksin et al., "Novel organosillicone adjuvants to reduce agrochemical spray volumes on row crops," New Zealand Plant Protection, 53:350-354 (2000).
Jang et al., "Resistance to herbicides caused by single amino acid mutations in acetyl-CoA carboxylase in resistant populations of grassy weeds," New Phytologist, 197(4):1110-1116 (2013).
Leopold et al., "Chapter 4: Moisture as Regulator of Physiological Reaction in Seeds," Seed Moisture, CSSA Special Publication No. 14, pp. 51-69 (1989).
Li et al., "A Simplified Seed Transformation Method for Obtaining Transgenic *Brassica napus* Plants," Agricultural Sciences in China, 8(6):658-663 (2009).
Office Action dated Dec. 27, 2016, in Ukrainian Patent Application No. a 2014 11548.
Powles et al., "Evolution in Action: Plants Resistant to Herbicides," Annual Review of Plant Biology, 61(1):317-347 (2010).
Regaldo, "The Next Great GMO Debate," MIT Technology Review,pp. 1-19 (2015) <https://www.technologyreview.com/s/540136/the-next-great-gmo-debate/>.
Richardson et al., "Targeting and assembly of components of the TOC protein import complex at the chloroplast outer envelope membrane," Frontier in Plant Science, 5:1-14 (2014).
Small, "RNAi for revealing and engineering plant gene functions," Current Opinion in Biotechnology, 18:148-153 (2007).
Stevens, "Formulations of Sprays to Improve the Efficacy of Foliar Fertilisers," New Zealand Journal of Forestry Science, 24(1):27-34 (1994).
Stevens, "Organosilicone Surfactants as Adjuvants for Agrochemicals," New Zealand Journal of Forestry Science, 24:27-34 (1994).
Voinnet, "Origin Biogenesis, and Activity of Plant MircroRNAs," Cell, 136:669-687 (2009).
Declaration of Jerzy Zabkiewicz executed Nov. 28, 2017, as filed by Opponent in Australian Patent Application No. 2014262189, pp. 1-73.
Kirkwood, "Recent developments in our understanding of the plant cuticle as a barrier to the foliar uptake of pesticides," Pestic Sci, 55:69-77 (1999).
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Lucas et al., "Plasmodesmata—bridging the gap between neighboring plant cells," Trends in Cell Biology, 19:495-503 (2009).
Baulcombe, RNA silencing in plants, Nature, 431:356-363 (2004).
Dietzgen et al., "Transgenic gene silencing strategies for virus control," Australian Plant Pathology, 35:605-618 (2006).
Zabkiewicz, "Adjuvants and herbicidal efficacy—present status and future prospects," Weed Research, 40:139-149 (2000).
Declaration of Neena Mitter executed Nov. 30, 2017, as filed by Opponent in Australian Patent Application No. 2014262189, pp. 1-25.

(56) References Cited

OTHER PUBLICATIONS

Anonymous, "Resistant Weeds Spur Research Into New Technologies," Grains Research & Development Corporation, 2013.
Anonymous, "Agronomy Facts 37: Adjuvants for enhancing herbicide performance," n.p., 1-8, (Jan. 26, 2000), Web, (Jan. 21, 2014).
Ascensio-Ibanez et al., "DNA abrasion onto plants is an effective method for geminivirus infection and virus-induced gene silencing," Journal of Virological Methods, 142:198-203 (2007).
Bauer et al., "The major protein import receptor of plastids is essential for chloroplast biogenesis," Nature, 403:203-207 (2000).
Baum et al., "Progress Towards RNAi-Mediated Insect Pest Management," Advances in Insect Physiology, 47:249-295 (2014).
Bedell et al., "Sorghum Genome Sequencing by Methylation Filtration," PLOS Biology, 3(1):E13/104-115 (2005).
Burgos et al., "Review: Confirmation of Resistance to Herbicides and Evaluation of Resistance Levels," Weed Science, 61 (1):4-20 (2013).
Burleigh, "Relative quantitative RT-PCR to study the expression of plant nutrient transporters in arbuscular mycorrizas," Plant Science, 160:899-904 (2001).
Campbell et al., "Gene-knockdown in the honey bee mite Varroa destructor by a non-invasive approach: studies on a glutathione S-transferase," Parasites & Vectors, 3(1):73, pp. 1-10 (2010).
Chen et al., "Exploring MicroRNA-Like Small RNAs in the Filamentous Fungis Fusarium oxysporum," PLOS One, 9(8):e104956:1-10 (2014).
Cheng et al., "Transient Expression of Minimum Linear Gene Cassettes in Onion Epidermal Cells via Direct Transformation," Appl Biochem Biotechnol, 159:739-749 (2009).
Christiaens et al., "The challenge of RNAi-mediated control of hemipterans," Current Opinion in Insect Science, 6:15-21 (2014).
Communication Pursuant to Article 94(3) EPC dated Sep. 5, 2018, in European Patent Application No. 17152830.0.
Constan et al., "An outer envelope membrane component of the plastid protein import apparatus plays an essential role in Arabidopsis," The Plant Journal, 38:93-106 (2004).
Danka et al., "Field Test of Resistance to Acarapis woodi (Acari: Tarsonemidae) and of Colony Production by the Four Stocks of Honey Bees (Hymenoptera: Apidae)" Journal of Economic Entomology, 88(3):584-591 (1995).
Database EMBL XP-002781749(BG442539) dated Mar. 20, 2001.
Delye et al., "Variation in the gene encoding acetolactate-synthase in Lolium species and proactive detection of mutant, herbicide-resistant alleles," Weed Research, 49:326-336 (2009).
Di Stilio et al., "Virus-Induced Gene Silencing as a Tool for Comparative Functional Studies in Thalictrum," PLoS One, 5(8):e12064 (2010).
Dilpreet et al., "Glyphosate Rsistance in a Johnsongrass (Sorghum halepense) Biotype from Arkansas," Weed Science, 59(3):299-304 (2011).
Duhoux et al., "Reference Genes to Study Herbicide Stress Response in Lolium sp.: Up-Regulation of P3450 Genes in Plants Resistant to Acetolactate-Synthase Inhibitors," PLOS One, 8(5):e63576 (2013).
Eamens et al., "RNA Silencing in Plants: Yesterday, Today, and Tomorrow," Plant Physiology, 147(2):456-468 (2008).
Egli et al., "A Maize Acetyl-Coenzyme A Carboxylase cDNA Sequence," Plant Physiol., 108: 1299-1300 (1995).
Eudes et al., "Cell-penetrating peptides," Plant Signaling & Behavior, 3(8):549-5550 (2008).
European Search Report dated Sep. 7, 2017, in European Patent Application No. 17152830.0.
Examination Report dated Mar. 1, 2018, in Australian Patent Application No. 2013264742.
Extended European Search Report dated Nov. 16, 2018, in European Patent Application No. 18182238.8.
Extended European Search Report dated Nov. 21, 2018, in European Patent Application No. 18175809.5.
Extended European Search Report dated Nov. 7, 2017, in European Patent Application No. 15811092.4.
Extended European Search Report dated Nov. 8, 2017, in European Patent Application No. 15737282.2.
Extended European Search Report dated Sep. 28, 2018, in European Patent Application No. 16740770.9.
Extended European Search Report dated Apr. 13, 2018, in European Patent Application No. 15812530.0.
Extended European Search Report dated Mar. 15, 2018, in European Patent Application No. 17181861.0.
Fassler, BLAST Glossary, National Center for Biotechnology Information (2011).
Fernandez et al., "Uptake of Hydrophilic Solutes Through Plant Leaves: Current State of Knowledge and Perspectives of Foliar Fertilization," Critical Reviews in Plants Sciences, 28:36-38 (2009).
Final Office Action dated Nov. 10, 2016, in U.S. Appl. No. 13/583,302.
Friedberg, "Automated protein function prediction—the genomic challenge," Briefings in Bioinformatics, 7(3):225-242 (2006).
Funke et al., "Molecular basis for herbicide resistance in Roundup Ready crops," PNAS, 103:13010-13015 (2006).
Gallie et al., "Identification of the motifs within the tobacco mosaic virus 5'-leader responsible for enhancing translation," Nucleic Acids Res., 20(17):4631-4638 (1992).
Gan et al., "Baterially expressed dsRNA protects maize against SCMV infection," Plant Cell Rep, 29(11):1261-1268 (2010).
Gaskin et al., "Novel organosillicone adjuvants to reduce agrochemical spray volumes on row crops," New Zealand Plant Protection, 53:350-354 (2000).
Gasser et al., "Structure, Expression, and Evolution of the 5-Enolpyruvylshikimate-3-phosphate Synthase Genes of Petunia and Tomato," J. Biol. Chem., 263: 4280-4287 (1988).
GenBank Accession No. EF143582 (2007).
Gomez-Zurita et al., "Recalibrated Tree of Leaf Beetles (Chysomelidae) Indicated Independent Diversification of Angiosperms and Their Insect Herbivores," PLoS One, 4(e360):1-8 (2007).
Hagio, "Chapter 25: Direct Gene Transfer into Plant Mature Seeds via Electroporation After Vacuum Treatment, Electroporation and Sonoporation in Developmental Biology," p. 285-293 (2009).
Hess, "Surfactants and Additives," 1999 Proceedings of the California Weed Science Society, 51:156-172 (1999).
Hu et al., "High efficiency transport of quantum dots into plant roots with the aid of silwet L-77," Plant Physiology and Biochemistry, 48:703-709 (2010).
Huang et al., "In Vivo Analyses of the Roles of Essential Omp85-Related Proteins in the Chloroplast Outer Envelope Membrane," Plant Physiol., 157:147-159 (2011).
Huggett et al., "Real-time RT-PCR normalisation; strategies and considerations," Genes and Immunity, 6:279-284 (2005).
Inaba et al., "Arabidopsis Tic110 Is Essential for the Assembly and Function of the Protein Import Machinery of Plastids," The Plant Cell, 17:1482-1495 (2005).
International Search Report and the Written Opinion dated May 10, 2011, in International Application No. PCT/US2011/027528.
Ivanova et al., "Members of the Toc159 Import Receptor Family Represent Distinct Pathways for Protein Targeting to Plastids," Molecular Biology of the Cell, 15:3379-3392 (2004).
Jacque et al., "Modulation of HIV-1 replication by RNA interference," Nature, 418, 435-438 (2002).
Jang et al., "Resistance to herbicides caused by single amino acids mutations in acetyl-CoA carboxylase in resistant populations of grassy weeds," New Phytologist, 197(4):1110-1116 (2013).
Jarvis et al, "An arabidopsis mutant defective in the plastid general protein import apparatus," Science, 282:100-103 (1998).
Kikkert et al., "Stable Transformation of Plant Cells by Particle Bombardment/Biolistics," Methods in Molecular Biology, 286:61-78 (2005).
Kovacheva et al., "Further in vivo studies on the role of the molecular chaperone, Hsp93, in plastid protein import," The Plant Journal, 50:364-379 (2007).
Kovachena et al., "In vivo studies on the roles of Tic100, Tic40 and Hsp93 during chloroplast protein import," The Plant Journal, 41:412-428 (2005).
Kumar et al., "Sequencing, De Novo Assembly and Annotation of the Colorade Potato Beetle, Leptinotarsa decemlineata,Transcriptome," PLoS One, 9(1):e86012 (2014).

(56) References Cited

OTHER PUBLICATIONS

Leopold et al., "Chapter 4: Moisture as a Regulator of Physiological Reaction in Seeds," Seed Moisture, CSSA Special Publication No. 14, pp. 51-69 (1989).
Li et al., "A simplified Seed Transformation Method Obtaining Transgenic *Brassica Napus* Plants," Agricultural Sciences in China, 8(6):658-663 (2009).
Liu et al., "The Helicase and RNaseIIIa Domains of Arabidopsis Dicer-Like1 Modulate Catalytic Parameters during MicroRNA Biogenesis," Plant Physiology, 159:748-758 (2012).
Liu, "Calmodulin and Cell Cycle," Foreign Medical Sciences Section of Pathophysiology and Clinical Medicine, 18(4):322-324 (1998).
Liu, "Confocal laser scanning microscopy—an attractive tool for studying the uptake of xenobiotics into plant foliage," Journal of Microscopy, 213(Pt 2):87-93 (2004).
Liu, "The Transformation of Nucleic Acid Degradants in Plants," China Organic Fertilizers, Agriculture Press, ISBN: 7-1091634 (1991) (with English translation).
Lodish et al., Molecular Cell Biology, Fourth Edition, p. 210 (2000).
McGinnis, "RNAi for functional genomics in plants," Brief Funct Genomics, 9(2):111-7 (2010).
Morozov et al., "Evaluation of Preemergence Herbicides for Control of Diclofop-resistant Italian Ryegrass (Lolium multiflorum) in Virginia," Virginia Polytechnic Institute and State University, pp. 43-71 (2004).
Nemeth, "Virus, mycoplasma and rickettsia diseases of fruit trees," Martinus Nijhoff Publishers, 197-204 (1986).
Non-Final Office Action dated Mar. 21, 2018, in U.S. Appl. No. 13/619,980.
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Aug. 9, 2018, in Canadian Patent Application No. 2,848,371.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03849.
Office Action dated Dec. 15, 2016, in Ukrainian Patent Application No. a 2014 03852.
Office Action dated Dec. 27, 2016, in Ukrainian Patent Application No. a 2012 11548.
Office Action dated Dec. 5, 2017, in Japanese Patent Application No. 2016-502033.
Office Action dated Feb. 21, 2018, in Mexican Patent Application No. MX/a/2015/012632 (with English translation).
Office Action dated Jul. 11, 2017, in Mexican Patent Application No. MX/a/2015/013118 (with English translation).
Office Action dated Jul. 3, 2017, in Mexican Patent Application No. MX/a/2015/012632 (with English translation).
Office Action dated Jul. 30, 2018, in Canadian Patent Application No. 2,848,576.
Office Action dated Jul. 6, 2017, in Mexican Patent Application No. MX/a/2015/013103 (with English translation).
Office Action dated Mar. 8, 2018, (with English translation), in Chilean Patent Application No. 201403192.
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 20, 2018, in Chilean Patent Application No. 201601440 (with English translation).
Office Action dated Sep. 6, 2017, in Chinese Patent Application No. 2014800154012 (with English translation).
Paddison et al., "Stable suppression of gene expression by RNAi in mammalian cells," Proc. Natl Acad. Sci. USA, 99(3):1443-1448 (2002).
Partial European Search Report dated Jun. 29, 2018, in European Patent Application No. 18157745.3.
Partial European Search Report date Dec. 6, 2017, in European Patent Application No. 17181861.0.
Partial Supplementary European Search Report dated Jan. 11, 2018, in European Patent Application No. 15812530.2.
Partial Supplementary European Search Report dated Jan. 11, 2018, in European Patent Application No. 15812530.0.
Patent Examination Report No. 1 dated Jun. 8, 2017, in Australian Patent Application No. 2012308686.
Powles et al., "Evolution in Action: Plants Resistant to Herbicide," Annual Review of Plant Biology, 61(1):317-347 (2010).
Pratt et al., "Sorghum Expressed Sequence Tags Identify Signature Genes for Drought, Pathogenesis, and Skotomorphogenesis from a Milestone Set of 16,801 Unique Transcripts," Plant Pathologym 139:869-884 (2005).
Qichuan et al., Seed Science, China Agriculture Press, pp. 101-103, Tables 2-37 (2001).
Rakoczy-Trojanowska, "Alternative Methods of Plant Transformation—a short review," Cellular & Molecular Biology Letters, 7:849-858 (2002).
Reverdatto et al., "A Multisubunit Acetyl Coenzyme A Carboxylase from Soybean," Plant Physiol., 119: 961-978 (1999).
Richardson et al., "Targeting and assembly of components of the TOC protein import complex at the chloroplast outer envelope membrane," Frontiers in the Plant Science, 5:1-14 (2014).
Schönherr et al., "Size Selectivity of aqueous pores in astomatous cuticular membranes isolated from Populus canescens (Aiton) Sm. Leaves," Planta, 219:405-411 (2004).
Search Report dated Jul. 24, 2017, in Chinese Patent Application No. 201480014392.5 (with English translation).
Search Report dated Oct. 20, 2017, in Chinese Patent Application No. 201380039346.6.
Small, "RNAi for revealing and engineerinh plant gene functions," Current Opinion in Biotechnology, 18:148-153 (2007).
Statement of Grounds and Particulars dated Sep. 1, 2017, in Australian Patent No. 2014262189.
Stevens, "Formulation of Sprays to Improve the Efficacy of Foliar Fertilisers," New Zealand Journal of Forestry Science, 24(1):27-34 (1994).
Stevens, "Formulations of Sprays to Improve the Efficacy of Foliar Fertilisers," New Zealand Journal of Forestry Science, pp. 24(1):27-34 (1994).
Stevens, "Organosilicone Surfactants as Adjuvants for Agrochemicals," Pestic. Sci., 38:103-122 (1993).
Summons to Attend Oral Proceedings Pursuant to Rule 115(1) EPC, dated Aug. 7, 2017, in European Patent Application No. 12832160.1.
Teng et al., "Tic21 Is an Essential Translocon Component for Protein Translocation across Chloroplast Inner Envelope Inner Envelope Membrane," The Plant Cell, 18:2247-2257 (2006).
Tice, "Selecting the right compounds for screening: does Lipinski's Rule of 5 for pharamaceuticals apply to agrochemicals?" Pest Management Science, 57(1):3-16 (2001).
Toriyama et al., "Transgenic Rice Plants After Direct Gene Transfer Into Protoplasts," Bio/Technology, 6:1072-1074 (1988).
Trucco et al., "Amaranthus hybridus can be pollinated frequently by A. tuberculatus under filed conditions," Heredity, 94:64-70 (2005).
Ulrich et al., "Large scale RNAi screen in Tribolium reveals novel target genes for pest control and the proteasome as prime target," BMC genomics, 16(1):671 (2015).

(56) References Cited

OTHER PUBLICATIONS

Unniraman et al., "Conserved Economics of Transcription Termination in Eubacteria," Nucleic Acids Research, 30(3):675-684 (2002).
Voinnet, "Origin, Biogenesis, and Activity of Plant MicroRNAs," Cell, 136:669-687 (2009).
Wool et al., "Structure and evolution of mammalian ribosomal proteins," Biochem. Cell Biol., 73:933-947 (1995).
Xu et al., "Characterization and Functional Analysis of the Calmodulin-Binding Domain of Rac1 GTPase," PLoS One, 7(8):e42975 (2012).
Yu et al., "Diversity of Acetyl-Coenzyme A Carboxylase Mutations in Resistant Lolium Populations: Evaluation Using Clethodim," Plant Physiology, 145:547-558 (2007).
Yu et al., "Glyphosate, paraquat and ACCase multiple herbicide resistance evolved in a Lolium rigidum biotype," Planta, 225:499-513 (2007).
Zaiman et al., Chapter III Seeds and Seedlings, Botany, Northwest A&F University Press, pp. 87-92 (2009).
Zhang et al., "Development and Validation of Endogenous Reference Genes for Expression Profiling of Medaka (Oryzias latipes) Exposed to Endocrine Disrupting Chemicals by Quantitative Real-Time RT-PCR," Toxicological Sciences, 95(2):356-368 (2007).
Zhang et al., "Progress in research of honey bee mite Varro destructor," Journal of Environmental Entomology, 34(3):345-353 (2012).
Zhang, "Artificial trans-acting small interfering RNA: a tool for plant biology study and crop improvements," Planta, 239:1139-1146 (2014).
Zhang, Chapter 10: New Characteristics of Pesticide Research & Development, p. 209 (2010).
Zhong et al., "A forward genetic screen to explore chloroplast protein import in vivo identifies Moco sulfurase, pivotal for ABA and IAA biosynthesis and purine turnover," The Plant Journal, 63:44-59 (2010).
Zhong et al., "A pea antisense for the chloroplast stromal processing peptidase yields seedling lethals in Arabidopsis: survivors show defective GFP import in vivo," The Plant Journal, 34:802-812 (2003).
Zotti et al., "RNAi technology for insect management and protection of beneficial insects from diseases: lessons, challenges and risk assessments," Neotropical Entomology, 44(3):197-213 (2015).
Andersen et al., "Delivery of siRNA from lyophilized polymeric surfaces," Biomaterials, 29:506-512 (2008).
Baker, "Chlorophyll Fluorescence: A Probe of Photosynthesis In Vivo," Annu. Rev. Plant Biol., 59:89-113 (2008).
Brugiere et al., "Glutamine Synthetase in the Phloem Plays a Major Role in Controlling Proline Production," The Plant Cell, 11:195-2011 (1999).
Burleigh, "Relative quantitative RT-PCR to study the expression of plant nutrient transporter in arbuscular mycorrhizas," Plant Science, 160:899-904 (2001).
Chang et al., "Dual-Target gene silencing by using long, synthetic siRNA duplexes without triggering antiviral responses," Molecules and Cells, 27(6):689-695 (2009).
Communication pursuant to Article 94(3) EPC dated Mar. 16, 2020, in European Patent Application No. 17194281.6.
Communicaton pursuant to Article 94(3) EPC dated Mar. 27, 2020, in European Patent Application No. 15811092.4.
Danka et al., "Field Test of Resistance to Acarapis woodi (Acari: Tarsonemidae) and of Colony Production by Four Stocks on Honey Bees (Hymenoptera: Apidae)" Journal of Economic Entomology, 88(3):584-591 (1995).
Decision to Grant daed Feb. 24, 2020, in Ukrainian Patent Application No. a 2016 08743 (with English language translation).
Declaration of Professor Robert James Henry executed Mar. 1, 2018, as filed by Applicant in Australian Patent Application No. 2014262189, pp. 1-119.
Downey et al., "Single and dual parasitic mite infestations on the honey bee, Apis mellifera L., " Insectes Sociaux, 47(2):171-176 (2000).
Drobyazko R. V., "Reliable and environmentally friendly insecticide," Protection and quarantine of plants, 2012 (pp. 52, 53) (with English translation).
Extended European Search Report dated Mar. 25, 2020, in European Patent Application No. 19192942.1.
Gilmer et al., "Latent Viruses of Apple I. Detection with Woody Indicators," Plant Pathology, 1(10):1-9 (1971).
Hörmann et al., "Tic32, as Essential Component in Chloroplast Biogenesis," The Journal of Biological Chemistry, 279(33):34756-34762 (2004).
Hwa et al., "Fixation of hybrid vigor in rice: opportunities and challenges," Euphytica, 160:287-293 (2008).
Jasieniuk et al., "Glyphosate-Resistant Italian Ryegrass (Lolium multiflorum) in California: Distribution, Response to Glyphosate, and Molecular Evidence for an Altered Target Enzyme," Weed Science, 56(4):496-502 (2008).
Khanbekova et al., The defeat of the honey bee apis melifera caucasica Gorb. By viruses and parasites, and condition of bee colonies in different ecogeographical conditions of Greater Caucasus, Agricultural Biology. 2013 (p. 43) (in Russian).
Li et al., "Long dsRNA but not siRNA initiates RNAi in western corn rootworm larvae and adults," Journal of Applied Entomology, 139(6):432-445 (2015).
Nemeth, "Virus, mycoplasma and rickettsia diseases of fruit tress," Martinus Nijhoff Publishers, 197-204 (1986).
N-TER Nanoparticle siRNA, Sigma Aldrich TM website, Web. Nov. 20, 2018 <https://www.sigmaaldrich.com/life-science/custom-oligos/sirna-oligo/n-ter-nanoparticle.html>.
Office Action dated Feb. 20, 2020, in Canadian Patent Application No. 2,905,104.
Office Action dated Feb. 25, 2020, in Japanese Patent Application No. 2017-538699 (with English language translation).
Ossowski et al., "Gene silencing in plant using artificial microRNAs and other small RNAs," The Plant Journal, 53:674-690 (2008).
Partial European Search Report dated Dec. 4, 2019, in European Patent Application No. 19185431.4.
Prado et al., "Design and Optimization of degenerated universal primers for the cloning of the plant acetolactate synthase conserved domains," Weed Science, 52:487-491 (2004).
Regalado, "The Next Great GMO Debate," MIT Technology Review, pp. 1-19 (2015) <https://www.technologyreview.com/s/540136/the-next-great-gmo-debate/>.
Sammataro et al., "Some Volatile Plant Oils as Potential Control Agents for Varroa Mites (Acari: Varroidae) in Honey Bee Colonies (Hymenoptera: Apidae)," American Bee Journal, 138(9):681-685 (1998).
Subramoni et al., "Lipases as Pathogenicity Factors of Plant Pathogens,"Handbook of Hydrocarbon and Lipid Microbiology, 3269-3277 (2010).
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Tenllado et al., "Crude extracts of bacterially expressed dsRNA can be used to protect plants against virus infections," BMC Biotechnology, 3:1-11 (2003).
Tice, "Selecting the right compounds for screening: does Lipinski's Rule of 5 for pharmaceuticals apply to agrochemicals?" Pest Management Science, 57(1):3-16 (2001).
TransIT-TKO® Transfection Reagent, Frequently Asked Questions, Web. 2019 <https://www.mirusbio.com/tech-resources/faqs/transit-tko-faqs>.
Walton, "Deconstructing the Cell Wall," Plant Physiol., 104:1113-1118 I1994).
Wang et al., "Principle and technology of genetic engineering in plants," in Plant genetic engineering principles and techniques, Beijing: Science Press, pp. 313-315 (1998).
Watson et al., "RNA silencing platforms in plants," FEBS Letters, 579:5982-5987 (2005).
Wild Carrot, Noxious Weed Control Board (NWCB) of Washington State (2010) <www.nwcb.wa.gov/detail.asp?weed=46>.

(56) References Cited

OTHER PUBLICATIONS

Yibrah et al., "Antisense RNA inhibition of uidA gene expression in transgenic plants: Evidence for interaction between first and second transformation events," *Hereditas*, 118:273-280 (1993).
Zhao et al., "Vegetable Statdardized Production Technology," *Hangzhou: Zhejiang Science and Technology Press*, p. 19 (2008).
Waterhouse et al., "Exploring Plant Genomes by RNA-Induced Gene Silencing," *Nature Reviews Genetics*, 4(1), pp. 29-38 (2003).

\* cited by examiner

Figure 1

ATGGCTCAAGCTACTACCATCAACAATGGTGTCCATACTGGTCAATTGCACCATACTTTACCCAAAA
CCCAGTTACCCAAATCTTCAAAAACTCTTAATTTTGGATCAAACTTGAGAATTTCTCCAAAGTTCAT
GTCTTTAACCAATAAAAGAGTTGGTGGGCAATCATCAATTGTTCCCAAGATTCAAGCTTCTGTTGCT
GCTGCAGCTGAGAAACCTTCATCTGTCCCAGAAATTGTGTTACAACCCATCAAAGAGATCTCTGGTA
CTGTTCAATTGCCTGGGTCAAAGTCTTTATCCAATCGAATCCTTCTTTTAGCTGCTTTGTCTGAGGG
CACAACAGTGGTCGACAACTTGCTGTATAGTGATGATATTCTTTATATGTTGGACGCTCTCAGAACT
CTTGGTTTAAAAGTGGAGGATGATAGTACAGCCAAAAGGGCAGTCGTAGAGGGTTGTGGTGGTCTGT
TTCCTGTTGGTAAAGATGGAAAGGAAGAGATTCAACTTTTCCTTGGTAATGCAGGAACAGCGATGCG
CCCATTGACAGCTGCGGTTGCCGTTGCTGGAGGAAATTCAAGTTATGTGCTTGATGGAGTACCAAGA
ATGAGGGAGCGCCCCATTGGGGATCTGGTAGCAGGTCTAAAGCAACTTGGTTCAGATGTAGATTGTT
TTCTTGGCACAAATTGCCCTCCTGTTCGGGTCAATGCTAAAGGAGGCCTTCCAGGGGGCAAGGTCAA
GCTCTCTGGATCGGTTAGTAGCCAATATTTAACTGCACTTCTCATGGCTACTCCTTTGGGTCTTGGA
GACGTGGAGATTGAGATAGTTGATAAATTGATTTCTGTACCGTATGTTGAAATGACAATAAAGTTGA
TGGAACGCTTTGGAGTATCCGTAGAACATAGTGATAGTTGGGACAGGTTCTACATTCGAGGTGGTCA
GAAATACAAATCTCCTGGAAAGGCATATGTTGAGGGTGATGCTTCAAGTGCTAGCTACTTCCTAGCC
GGAGCCGCCGTCACTGGTGGGACTGTCACTGTCAAGGGTTGTGGAACAAGCAGTTTACAGGGTGATG
TAAAATTTGCCGAAGTTCTTGAGAAGATGGGTTGCAAGGTCACCTGGACAGAGAATAGTGTAACTGT
TACTGGACCACCCAGGGATTCATCTGGAAAGAAACATCTGCGTGCTATCGACGTCAACATGAACAAA
ATGCCAGATGTTGCTATGACTCTTGCAGTTGTTGCCTTGTATGCAGATGGGCCCACCGCCATCAGAG
ATGTGGCTAGCTGGAGAGTGAAGGAAACCGAACGGATGATTGCCATTTGCACAGAACTGAGAAAGCT
TGGGGCAACAGTTGAGGAAGGATCTGATTACTGTGTGATCACTCCGCCTGAAAAGCTAAACCCCACC
GCCATTGAAACTTATGACGATCACCGAATGGCCATGGCATTCTCTCTTGCTGCCTGTGCAGATGTTC
CCGTCACTATCCTTGATCCGGGATGCACCCGTAAAACCTTCCCGGACTACTTTGATGTTTTAGAAAA
GTTCGCCAAGCATTGA

SEQ ID NO:1

Figure 2

GGGCCCATAGGCCTTTTTCTAAAATAGGCCCATTTAAGCTATTAACAATCTTCAAAAGTACCACATCG
CTTAGGTAAAGAAAGCAGCTGAGTTTATATATGGTTAGAGACGAAGTAGTGATTG*CGACGAGCGACG*
*TCTCGCCCTCATCGCAATCCACGCCATTGAGCTTGAGGCCATTGGCGACGGCCGAGAGGCGGTCGCT*
*T*AAGATTAGCATG*TCCTTGACGCGGAGTTCTTCCAGACCGTTCATCACGGTCGCCCCTTCCGCGAAG*
*GCGGCGGCGACAGCGAGAATCGGATATTCGTCGATCATCGAAGGCGCGCGGTCTTCCGGCACCGTG*A
CGCATAAAcacggtgccggaagaccgcgcgccttcgatgatcgacgaatatccgattctcgctgtcg
ccgccgccttcgcggaaggggcgaccgtgatgaacggtctggaagaactccgcgtcaaggaaagcga
ccgcctctcggccgtcgccaatggcctcaagctcaatggcgtggattgcgatgagggcgagacgtcg
ctcgtcgTTTTTTTTGGCAAAAA

SEQ ID NO:3

Figure 3
3A
3B
3C

Figure 5

ATGCCCCAAATCGGACTTGTATCTGCTGTTAATTTGAGAGTCCAAGGTAATTCAGCTTATCTTTGGA
GCTCGAGGTCTTCGTTGGGAACTGAAAGTCAAGATGTTTGCTTGCAAAGGAATTTGTTATGTTTTGG
TAGTAGCGACTCCATGGGGCATAAGTTAAGGATTCGTACTCCAAGTGCCACGACCCGAAGATTGACA
AAGGACTTTAATCCTTTAAAGGTAGTCTGCATTGATTATCCAAGACCAGAGCTAGACAATACAGTTA
ACTATTTGGAGGCGGCGTTATTATCATCATCGTTTCGTACTTCCTCACGCCCAACTAAACCATTGGA
GATTGTTATTGCTGGTGCAGGTTTGGGTGGTTTGTCTACAGCAAAATATCTGGCAGATGCTGGTCAC
AAACCGATATTGCTGGAGGCAAGAGATGTCCTAGGTGGGAAGGTAGCTGCATGGAAAGATGATGATG
GAGATTGGTACGAGACTGGGTTGCACATATTCTTTGGGGCTTACCCAAATATGCAGAACCTGTTTGG
AGAACTAGGGATTGATGATCGGTTGCAGTGGAAGGAACATTCAATGATATTTGCGATGCCTAACAAG
CCAGGGGAGTTCAGCCGCTTTGATTTTCCTGAAGCTCTTCCTGCGCCATTAAATGGAATTTTGGCCA
TACTAAAGAACAACGAAATGCTTACGTGGCCCGAGAAAGTCAAATTTGCTATTGGACTCTTGCCAGC
AATGCTTGGAGGGCAATCTTATGTTGAAGCTCAAGACGGTTTAAGTGTTAAGGACTGGATGAGAAAG
CAAGGTGTGCCTGATAGGGTGACAGATGAGGTGTTCATTGCCATGTCAAAGGCACTTAACTTCATAA
ACCCTGACGAGCTTTCGATGCAGTGCATTTTGATTGCTTTGAACAGATTTCTTCAGGAGAAACATGG
TTCAAAAATGGCCTTTTTAGATGGTAACCCTCCTGAGAGACTTTGCATGCCGATTGTGGAACATATT
GAGTCAAAAGGTGGCCAAGTCAGACTAAACTCACGAATAAAAAAGATCGAGCTGAATGAGGATGGAA
GTGTCAAATGTTTTATACTGAATAATGGCAGTACAATTAAAGGAGATGCTTTTGTGTTTGCCACTCC
AGTGGATATCTTGAAGCTTCTTTTGCCTGAAGACTGGAAAGAGATCCCATATTTCCAAAAGTTGGAG
AAGCTAGTGGGAGTTCCTGTGATAAATGTCCATATATGGTTTGACAGAAACTGAAGAACACATCTG
ATAATCTGCTCTTCAGCAGAAGCCCGTTGCTCAGTGTGTACGCTGACATGTCTGTTACATGTAAGGA
ATATTACAACCCCAATCAGTCTATGTTGGAATTGGTATTTGCACCCGCAGAAGAGTGGATAAATCGT
AGTGACTCAGAAATTATTGATGCTACAATGAAGGAACTAGCGAAGCTTTTCCCTGATGAAATTTCGG
CAGATCAGAGCAAAGCAAAATATTGAAGTATCATGTTGTCAAAACCCCAAGGTCTGTTTATAAAAC
TGTGCCAGGTTGTGAACCCTGTCGGCCCTTGCAAAGATCCCCTATAGAGGGTTTTTATTTAGCTGGT
GACTACACGAAACAGAAGTACTTGGCTTCAATGGAAGGTGCTGTCTTATCAGGAAAGCTTTGTGCAC
AAGCTATTGTACAGGATTACGAGTTACTTCTTGGCCGGAGCCAGAAGATGTTGGCAGAAGCAAGCGT
AGTTAGCATAGTGAACTAA

SEQ ID NO:2

Figure 10

>gi|93117609|gb|DQ469932.1| Nicotiana benthamiana
phytoene desaturase mRNA, complete cds
ATGCCCCAAATCGGACTTGTATCTGCTGTTAATTTGAGAGTCCAAGGTAATTCAGCTTATCTTTGGA
GCTCGAGGTCTTCGTTGGGAACTGAAAGTCAAGATGTTTGCTTGCAAAGGAATTTGTTATGTTTTGG
TAGTAGCGACTCCATGGGGCATAAGTTAAGGATTCGTACTCCAAGTGCCACGACCCGAAGATTGACA
AAGGACTTTAATCCTTTAAAGGTAGTCTGCATTGATTATCCAAGACCAGAGCTAGACAATACAGTTA
ACTATTTGGAGGCGGCGTTATTATCATCATCGTTTCGTACTTCCTCACGCCCAACTAAACCATTGGA
GATTGTTATTGCTGGTGCAGGTTTGGGTGGTTTGTCTACAGCAAAATATCTGGCAGATGCTGGTCAC
AAACCGATATTGCTGGAGGCAAGAGATGTCCTAGGTGGGAAGGTAGCTGCATGGAAAGATGATGATG
GAGATTGGTACGAGACTGGGTTGCACATATTCTTTGGGGCTTACCCAAATATGCAGAACCTGTTTGG
AGAACTAGGGATTGATGATCGGTTGCAGTGGAAGGAACATTCAATGATATTTGCGATGCCTAACAAG
CCAGGGGAGTTCAGCCGCTTTGATTTTCCTGAAGCTCTTCCTGCGCCATTAAATGGAATTTTGGCCA
TACTAAAGAACAACGAAATGCTTACGTGGCCCGAGAAAGTCAAATTTGCTATTGGACTCTTGCCAGC
AATGCTTGGAGGGCAATCTTATGTTGAAGCTCAAGACGGTTTAAGTGTTAAGGACTGGATGAGAAAG
CAAGGTGTGCCTGATAGGGTGACAGATGAGGTGTTCATTGCCATGTCAAAGGCACTTAACTTCATAA
ACCCTGACGAGCTTTCGATGCAGTGCATTTTGATTGCTTTGAACAGATTTCTTCAGGAGAAACATGG
TTCAAAAATGGCCTTTTTAGATGGTAACCCTCCTGAGAGACTTTGCATGCCGATTGTGGAACATATT
GAGTCAAAAGGTGGCCAAGTCAGACTAAACTCACGAATAAAAAAGATCGAGCTGAATGAGGATGGAA
GTGTCAAATGTTTTATACTGAATAATGGCAGTACAATTAAAGGAGATGCTTTTGTGTTTGCCACTCC
AGTGGATATCTTGAAGCTTCTTTTGCCTGAAGACTGGAAAGAGATCCCATATTTCCAAAAGTTGGAG
AAGCTAGTGGGAGTTCCTGTGATAAATGTCCATATATGGTTTGACAGAAACTGAAGAACACATCTG
ATAATCTGCTCTTCAGCAGAAGCCCGTTGCTCAGTGTGTACGCTGACATGTCTGTTACATGTAAGGA
ATATTACAACCCCAATCAGTCTATGTTGGAATTGGTATTTGCACCCGCAGAAGAGTGGATAAATCGT
AGTGACTCAGAAATTATTGATGCTACAATGAAGGAACTAGCGAAGCTTTTCCCTGATGAAATTTCGG
CAGATCAGAGCAAAGCAAAATATTGAAGTATCATGTTGTCAAAACCCCAAGGTCTGTTTATAAAAC
TGTGCCAGGTTGTGAACCCTGTCGGCCCTTGCAAAGATCCCCTATAGAGGGTTTTTATTTAGCTGGT
GACTACACGAAACAGAAGTACTTGGCTTCAATGGAAGGTGCTGTCTTATCAGGAAAGCTTTGTGCAC
AAGCTATTGTACAGGATTACGAGTTACTTCTTGGCCGGAGCCAGAAGATGTTGGCAGAAGCAAGCGT
AGTTAGCATAGTGAACTAA

SEQ ID NO:2

Figure 12
Control     200nt ds RNA     ssDNA oligos (1+2+3+4+5+6) SEQ ID NOs: 16, 17, 20, 21, 24, 25, and 26
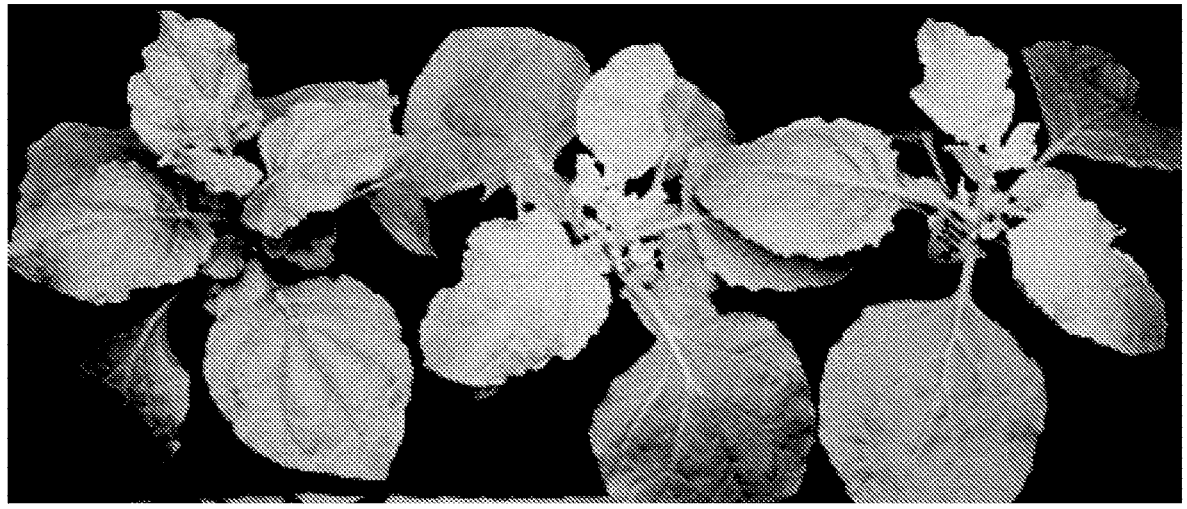
A
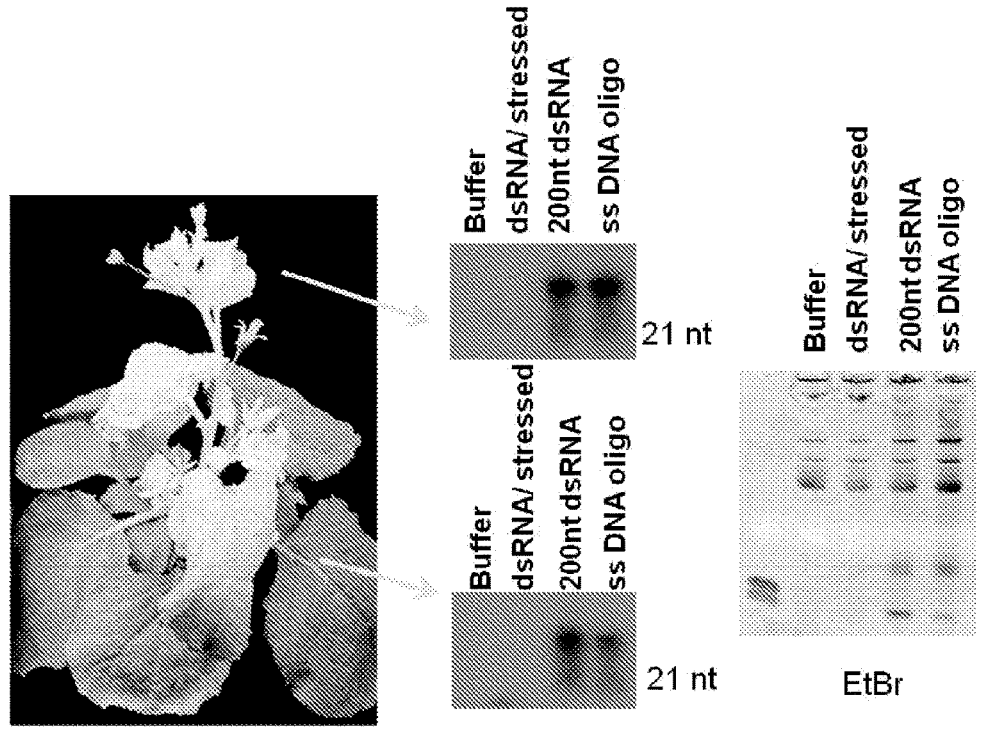
B

Figure 16

```
                        10                  20
Palmer      T-----CAA-------TTTCATCT-------ATTGGA-------AGTGAT   SEQ ID NO:37
              :::         ::  ::::         ::: ::        ::  :
Benthamiana ATGCCCCAAATCGGACTTGTATCTGCTGTTAATTTGAGAGTCCAAGGTAA   SEQ ID NO:38
                10        20        30        40        50

30                  40        50
Palmer      TT---------TTTGG--------GTCATTCTGTGAGAAATTTCAGTG--
             ::         :::::        ::: :::  ::  ::: :    :::
Benthamiana TTCAGCTTATCTTTGGAGCTCGAGGTC-TTCGTTGGGAACTGAAAGTCAA
              60        70        80        90

60
Palmer      --------------------TTAGTAAAGTTT----------------AT
                                :: :: : ::::                  ::
Benthamiana GATGTTTGCTTGCAAAGGAATTTGTTATGTTTTGGTAGTAGCGACTCCAT
              100       110       120       130       140

70        80        90
Palmer      GGAGCA-AAGCAAAGAAATGGGC-----ACTGCC----------------
             ::  ::: :::  :::  :  :      :  ::::
Benthamiana GGGGCATAAGTTAAGGATTCGTACTCCAAGTGCCACGACCCGAAGATTGA
              150       160       170       180       190

100       110       120       130
Palmer      --------------CTTTAAAGGTTGTTTGTATAGATTATCCTAGGCCA
                          :::::::::: :: :: :: ::::::::: :: :::
Benthamiana CAAAGGACTTTAATCCTTTAAAGGTAGTCTGCATTGATTATCCAAGACCA
              200       210       220       230       240

140       150       160       170       180
Palmer      GAGCTTGAAAGTACATCCAATTTCTTGGAAGCCGCCTACTTATCTTCTAC
             :::::  ::  ::::       ::  ::::: ::: ::   :::::  ::  :
Benthamiana GAGCTAGACAATACAGTTAACTATTTGGAGGCGGCGTTATTATCATCATC
              250       260       270       280       290

190       200       210       220       230
Palmer      TTTTCGGAATTCGCCTCGTCCTCAGAAGCCATTAGAAGTTGTAATTGCTG
             :::::  :  :::   :: ::   ::         :::::: ::  :::::::::
Benthamiana GTTTCGTACTTCCTCACGCCCAACTAAACCATTGGAGATTGTTATTGCTG
              300       310       320       330       340

240       250       260       270       280
Palmer      GAGCAGGTTTGGCTGGTCTATCCACGGCAAAGTATTTAGCTGATGCAGGT
             :  ::::::::: :  :::: :::: :: ::  ::::: : ::  ::::: :::
Benthamiana GTGCAGGTTTGGGTGGTTTGTCTACAGCAAAATATCTGGCAGATGCTGGT
                350       360       370       380       390

290       300       310       320       330
Palmer      CACAAACCCATATTGTTGGAAGCACGAGATGTTTAGGAGGAAAGGTTGC   SEQ ID NO:37
             :::::::::  ::::::  ::::  :::  ::::::::   :: ::::: ::
Benthamiana CACAAACCGATATTGCTGGAGGCAAGAGATGTCCTAGGTGGGAAGGTAGC   SEQ ID NO:38
                400       410       420       430       440
```

Figure 16 (continued)

```
                340       350       360       370       380
Palmer      AGCGTGGAAGGATGAGGATGGTGACTGGTATGAGACTGGGCTACATATAT        SEQ ID NO:37
            ::  :::::  :::::  :::::  ::  :::::  :::::::::  :  ::  ::::
Benthamiana TGCATGGAAAGATGATGATGGAGATTGGTACGAGACTGGGTTGCACATAT        SEQ ID NO:38
                450       460       470       480       490

390       400       410       420       430
Palmer      TCTTTGGGGCATATCCAAATGTCCAAAATCTATTTGGAGAACTTGGTATA
            ::::::::::  ::  ::::::  :  ::  ::  ::  :::::::::::  ::  ::
Benthamiana TCTTTGGGGCTTACCCAAATATGCAGAACCTGTTTGGAGAACTAGGGATT
                500       510       520       530       540

440       450       460       470       480
Palmer      AATGACCGACTGCAATGGAAGGAGCACTCTATGATTTTTGCAATGCCCAG
            ::::  ::    ::::  ::::::::::  ::  ::  :::::  :::::  :::::  :
Benthamiana GATGATCGGTTGCAGTGGAAGGAACATTCAATGATATTTGCGATGCCTAA
                550       560       570       580       590

490       500       510       520       530
Palmer      CAAGCCCGGTGAATTCAGTCGCTTTGATTTTCCCGAAATCCTGCCTGCAC
            ::::::  ::  ::  :::::  :::::::::::::  :::    ::  :::::  :
Benthamiana CAAGCCAGGGGAGTTCAGCCGCTTTGATTTTCCTGAAGCTCTTCCTGCGC
                600       610       620       630       640

540       550       560       570       580
Palmer      CATTAAATGGCATATGGGCAATCCTAAGAAATAATGAAATGCTAACCTGG
            ::::::::::  ::  :  :::  ::  ::::    ::  ::  :::::::::  ::  :::
Benthamiana CATTAAATGGAATTTTGGCCATACTAAAGAACAACGAAATGCTTACGTGG
                650       660       670       680       690

590       600       610       620       630
Palmer      CCAGAAAAAATCAAGTTTGCCATTGGCTTGTTGCCTGCTATGGCAGGCGG
            ::  ::  :::  ::::  :::::  :::::    :  :::::  :::  :::    ::  ::
Benthamiana CCCGAGAAAGTCAAATTTGCTATTGGACTCTTGCCAGCAATGCTTGGAGG
                700       710       720       730       740

640       650       660       670       680
Palmer      ACAGTCATATGTTGAAGCACAAGATGGTTTGAGTGTCCAAGAGTGGATGA
            ::  ::  ::::::::::  :::::  :::::    :  ::  ::::::::
Benthamiana GCAATCTTATGTTGAAGCTCAAGACGGTTTAAGTGTTAAGGACTGGATGA
                750       760       770       780       790

690       700       710       720       730
Palmer      GAAAACAAGGAGTACCCGATCGTGTAACTGATGATGTGTTTATTGCCATG
            ::::  :::::  ::  ::  :::  :  ::  ::  :::::  :::::  :::::::::
Benthamiana GAAAGCAAGGTGTGCCTGATAGGGTGACAGATGAGGTGTTCATTGCCATG
                800       810       820       830       840

740       750       760       770       780
Palmer      TCAAAGGCACTGAACTTCATAAATCCCGATGAACTTTCAATGCAGTGCAT        SEQ ID NO:37
            ::::::::::::  :::::::::::  ::  ::  ::  :::::  :::::::::::
Benthamiana TCAAAGGCACTTAACTTCATAAACCCTGACGAGCTTTCGATGCAGTGCAT        SEQ ID NO:38
                850       860       870       880       890
```

Figure 16 (continued)

```
                790       800       810       820       830
Palmer       CTTGATTGCTCTGAACCGATTCCTGCAGGAGAAACATGGTTCTAAGATGG   SEQ ID NO:37
             :::::::::: ::::: :::: :: :::::::::::::::::: :: ::::
Benthamiana  TTTGATTGCTTTGAACAGATTTCTTCAGGAGAAACATGGTTCAAAAATGG   SEQ ID NO:38
                900       910       920       930       940

840       850       860       870       880
Palmer       CCTTCCTAGACGGAAACCCTCCAGAGAGGCTGTGCATGCCTATTGTTAAA
             :::: :::: :: ::::::::: ::::: :: :::::::: ::::: ::
Benthamiana  CCTTTTTAGATGGTAACCCTCCTGAGAGACTTTGCATGCCGATTGTGGAA
                950       960       970       980       990

890       900       910       920       930
Palmer       CACATCGAGTCACTAGGTGGTGAAGTTAAACTTAACTCTCGTATACAAAA
             :: :: :::::: ::::::: :::: : ::: :::::: :: ::: ::::
Benthamiana  CATATTGAGTCAAAAGGTGGCCAAGTCAGACTAAACTCACGAATAAAAAA
                1000      1010      1020      1030      1040

940       950       960       970       980
Palmer       GATTCAGTTGGACCAGAGTGGAAGCGTGAAGAGTTTTTTGCTAAATAACG
             :::  :: :: :  ::   ::::::  ::  ::::: : ::  :::: :
Benthamiana  GATCGAGCTGAATGAGGATGGAAGTGTCAAATGTTTTATACTGAATAATG
                1050      1060      1070      1080      1090

990       1000      1010      1020      1030
Palmer       GGAGGGAAATACGAGGAGATGCCTATGTTTTTGCCACCCCAGTTGACATC
             :  ::    :::  :::::::::::: : :::  :::::: :: :: :::
Benthamiana  GCAGTACAATTAAAGGAGATGCTTTTGTGTTTGCCACTCCAGTGGATATC
                1100      1110      1120      1130      1140

1040      1050      1060      1070      1080
Palmer       TTGAAGCTGTTACTACCTGATACTTGGAAGGAAATCTCATACTTCAAAAA
             :::::::::   :   :::::  :::::  :: :::: ::: ::: ::::
Benthamiana  TTGAAGCTTCTTTTGCCTGAAGACTGGAAAGAGATCCCATATTTCCAAAA
                1150      1160      1170      1180      1190

1090      1100      1110      1120      1130
Palmer       ACTTGAGAAATTAGTGGGCGTTCCTGTGATTAATGTTCACATATGGTTTG
             :  ::::: :::::::::::  ::::::::::: :: :: :::::::::
Benthamiana  GTTGGAGAAGCTAGTGGGAGTTCCTGTGATAAATGTCCATATATGGTTTG
                1200      1210      1220      1230      1240

1140      1150      1160      1170      1180
Palmer       ACAGAAAATTAAAGAATACATATGACCATCTACTCTTCAGCAGGAGTCCT
             :::::::::: : :::: :::: ::: ::::  :::::::::: :: ::
Benthamiana  ACAGAAAACTGAAGAACACATCTGATAATCTGCTCTTCAGCAGAAGCCCG
                1250      1260      1270      1280      1290

1190      1200      1210      1220      1230
Palmer       CTTTTGAGTGTCTATGCTGATATGTCGGAGACATGCAAGGAATATAAGGA   SEQ ID NO:37
             :  : ::::: :: ::::: :::::: : :::::::::::: ::: : :
Benthamiana  TTGCTCAGTGTGTACGCTGACATGTCTGTTACATGTAAGGAATATTACAA   SEQ ID NO:38
                1300      1310      1320      1330      1340
```

Figure 16 (continued)

```
                 1240      1250      1260      1270      1280
Palmer       TCCAAATAGATCCATGCTGGAATTGGTTTTTGCACCCGCGGAGGAATGGA   SEQ ID NO:37
             ::  :::    ::  :::  ::::::::::  ::::::::::::  ::  ::  ::::
Benthamiana  CCCCAATCAGTCTATGTTGGAATTGGTATTTGCACCCGCAGAAGAGTGGA   SEQ ID NO:38
                 1350      1360      1370      1380      1390

1290      1300      1310      1320      1330
Palmer       TTTCACGAAGCGACACTGATATTATAGAGGCAACAATGAAAGAGCTTGCC
             :       ::  ::  :::    :  ::  :::::  ::  ::  ::::::::  ::  ::  ::
Benthamiana  TAAATCGTAGTGACTCAGAAATTATTGATGCTACAATGAAGGAACTAGCG
                 1400      1410      1420      1430      1440

1340      1350      1360      1370      1380
Palmer       AAGCTTTTCCCGGATGAAATCGCTGCCGATGGAAGCAAGGCCAAGATCCT
             ::::::::::  :::::::::   :  ::  :::    :::::  ::  ::  ::  :
Benthamiana  AAGCTTTTCCCTGATGAAATTTCGGCAGATCAGAGCAAAGCAAAAATATT
                 1450      1460      1470      1480      1490

1390      1400      1410      1420      1430
Palmer       CAAATATCATGTCGTCAAAACTCCAAGGTCGGTTTATAAGACTGTACCGG
             ::  :::::::::  :::::::::  :::::::::  :::::::::  :::::  ::  :
Benthamiana  GAAGTATCATGTTGTCAAAACCCCAAGGTCTGTTTATAAAACTGTGCCAG
                 1500      1510      1520      1530      1540

1440      1450      1460      1470      1480
Palmer       ATTGTGAACCTTGTCGGCCGCTGCAAAGATCACCAATAGAGGGTTTCTAT
             ::::::::::  :::::::::  :::::::::::  ::  :::::::::::  :::
Benthamiana  GTTGTGAACCCTGTCGGCCCTTGCAAAGATCCCCTATAGAGGGTTTTTAT
                 1550      1560      1570      1580      1590

1490      1500      1510      1520      1530
Palmer       TTAGCTGGTGATTACACAAAACAAAAATATTTGGCTTCTATGGAAGGTGC
             ::::::::::  :::::  :::::  ::  ::  :::::::::  ::::::::::
Benthamiana  TTAGCTGGTGACTACACGAAACAGAAGTACTTGGCTTCAATGGAAGGTGC
                 1600      1610      1620      1630      1640

1540      1550      1560      1570      1580
Palmer       TGTCTTATCTGGGAAGCTTTGTGCACAGGCTATCGTACAGGATTATGA--
             ::::::::::  ::  :::::::::::  :::::  :::::::::  ::  ::
Benthamiana  TGTCTTATCAGGAAAGCTTTGTGCACAAGCTATTGTACAGGATTACGAGT
                 1650      1660      1670      1680      1690

1590      1600      1610
Palmer       ----TCT--GCTG--------AGTTCTCG--AGCACAAAGAGAA-TTGGC
             :::    ::  :          ::  :  :  :    ::  ::    :::  :  ::  ::
Benthamiana  TACTTCTTGGCCGGAGCCAGAAGATGTTGGCAGAAGCAAGCGTAGTTAGC
                 1700      1710      1720      1730      1740

Palmer       G-----------   SEQ ID NO:37

Benthamiana  ATAGTGAACTAA   SEQ ID NO:38
                 1750      1760
```

Figure 19
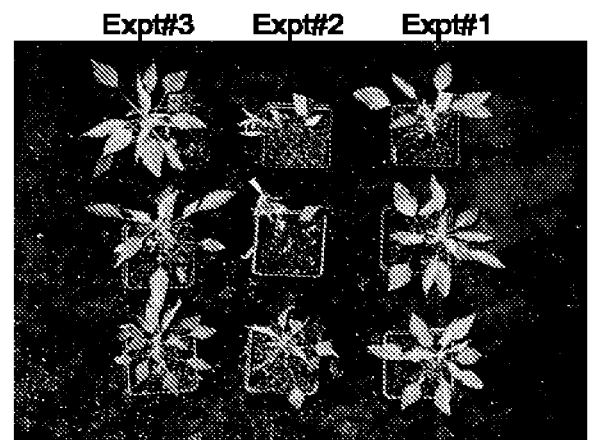
R31 (35 copies EPSPS)
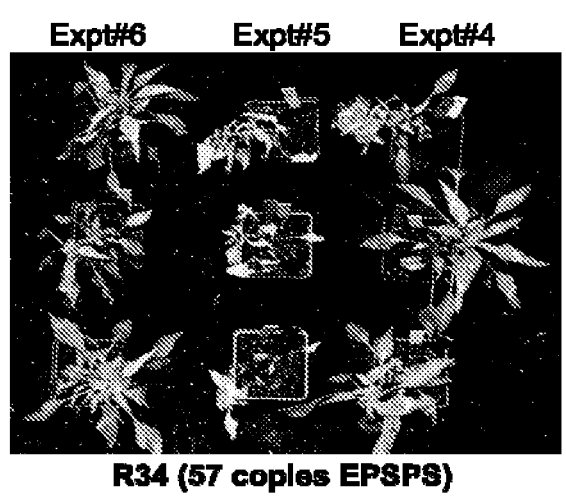
R34 (57 copies EPSPS)
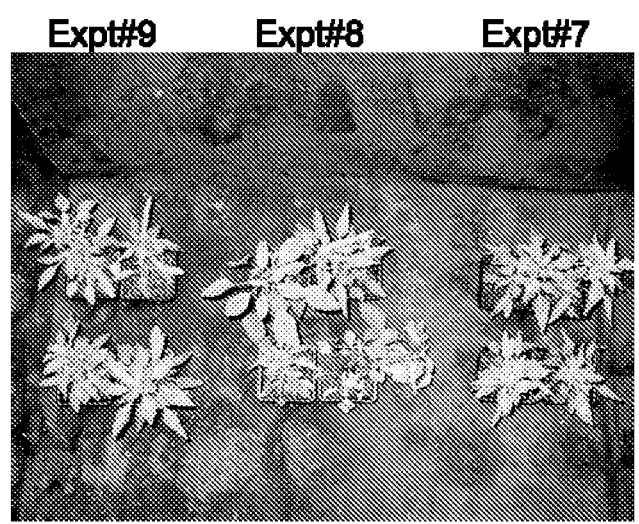
R28 (87 copies EPSPS)

Figure 20

ATGGCTCAAGCTACT**ACCATCAACAATGGTGTCCATACTGGTCAATTGCACCATACTTTACCCAAAA
CCCAGTTACCCAAATCTTCAAAAACTCTTAATTTTGGATCAAACTTGAGAATTTCTCCAAAGTTCAT
GTCTTTAACCAATAAAAGAGTTGGTGGGCAATCATC**AATTGTTCCCAAGATTCAAGCTTCTGTTGCT
GCTGCAGCTGAGAAACCTTCATCTGTCCCAGAAATTGTGTTACAACCCATCAAAGAGATCTCTGGTA
CTGTTCAATTGCCTGGGTCAAAGTCTTTATCCAATCGAATCCTTCTTTTAGCTGCTTTGTCTGAGGG
CACAACAGTGGTCGACAACTTGCTGTATAGTGATGATATTCTTTATATGTTGGACGCTCTCAGAACT
CTTGGTTTAAAAGTGGAGGATGATAGTACAGCCAAAAGGGCAGTCGTA**GAGGGTTGTGGTGGTCTGT
TTCCTGTTGGTAAAGATGGAAAGGAAGAGATTCAACTTTTCCTTGGTAATGCAGGAACAGCGATGCG
CCCATTGACAGCTGCGGTTGCCGTTGC*TGGAGGAAATTCAAGTTATGTGCTT*GATGGAGTACCAAGA
ATGAGGGAGCGCCCCATTGGGGATCTGGTAGCAGGTCTAAAGCAACTTGGTTCAGATGTAGATTGTT
TTCTTGGCACAAATTGCCCTCCTGTTCGGGTCAATGCTAAAGGAGGCCTTCC**AGGGGGCAAGGTCAA
GCTCT*CTGGATCGGTTAGTAGCCAATATTT*AACTGCACTTCTCATGGCTACTCCTTTGGGTCTTGGA
GACGTGGAGATTGAGATAGTTGATAAATTGATTTCTGTACCGTATGTTGAAATGACAATAAAGTTGA
TGGAACGCTTTGGAGTATCCGTAGAACATAGTGATAGTTGGGACAGGTTCTACATTCGAGGTGGTCA
GAAATACAAATCTCCTGGAAAGGCATATGTTGAGGGTGATGCTTCAAGTGCTAGCTACTTCCTAGCC
GGAGCCGCCGTCACTGGTGGGACTGTCACTGTCAAGGGTTGTGGAACAAGCAGTTTACAGGGTGATG
TAAAATTTGCCGAAGTTCTTGAGAAGATGGGTTGCA**AGGTCACCTGGACAGAGAATAGTGTAACTGT
TACTGGACCACCCAGGGATTCATCTGGAAAGAAACATCTGCGTGCTATCGACGTCAACATGAACAAA
ATGCCAGATGTTGCTATGACTCTTGCAGTTGTTGCCTTGTATGCAGATGGGCCCACCGCCATCAGAG
ATGTGGCTAGCTGGAGAGTGAAGGAAACCGAACGGATGATTGCCATTTGCACAGA**ACTGAGAAAGCT
TGGGGCAACAGTTGAGGAAGGATCTGATTACTGTGTGATCACTCCGCCTGAAAAGCTAAACCCCACC
GCCATTGAAACTTATGACGATCACCGAATGGCCATGGCATTCTCTCTTGCTGCCTGTGCAGATGTTC
CCGTCACTATCCTTGATCCGGGATGCACCCGTAAAACCTTCCCGGACTACTTTGATGTTTTAGAAAA
GTTCGCCAAGCATTGA

SEQ ID NO:40

Figure 21
A
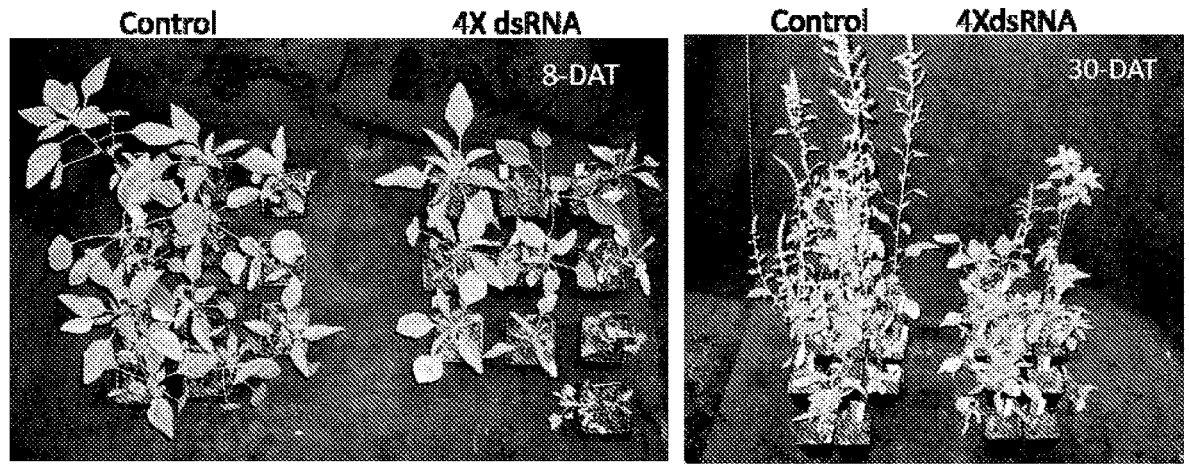
B

Figure 23
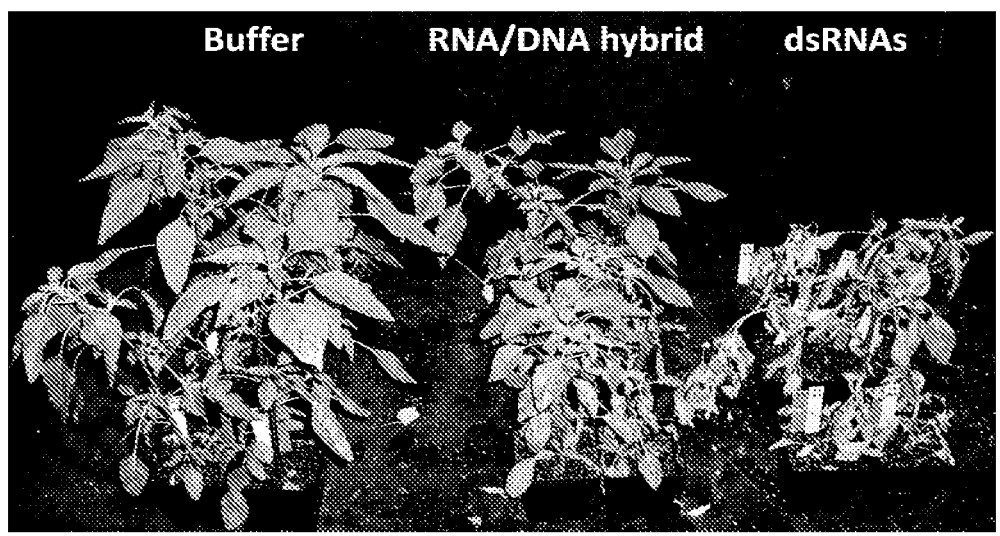
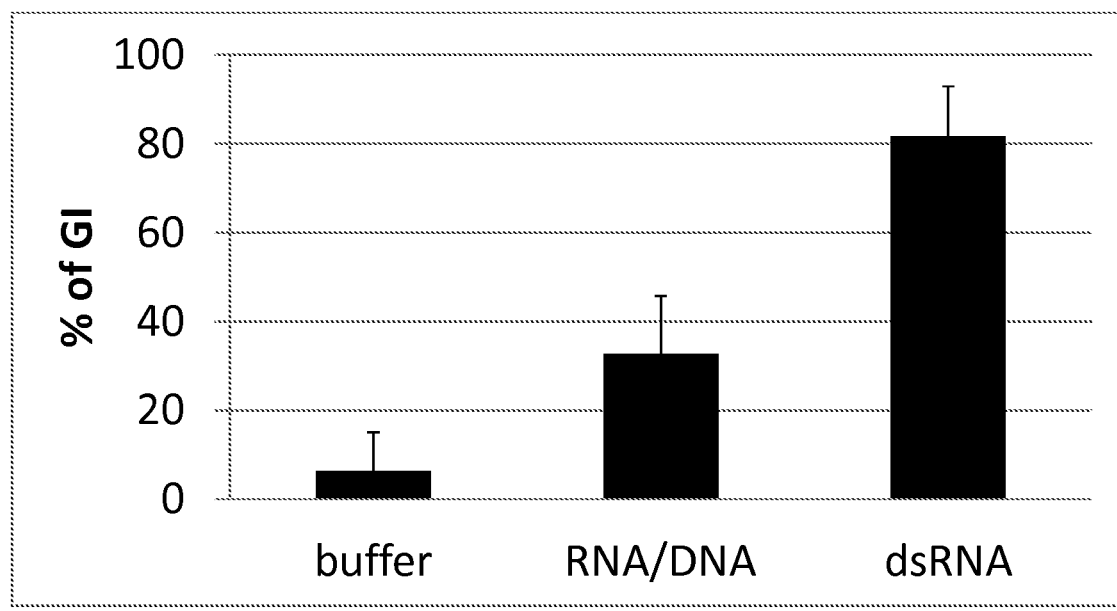

Figure 25
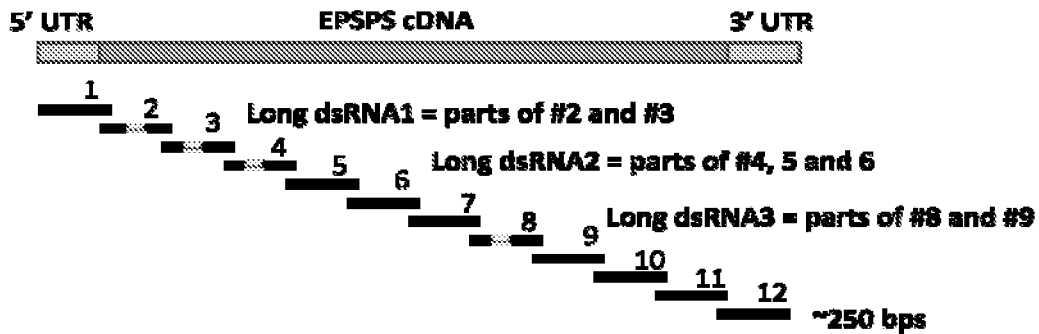
A
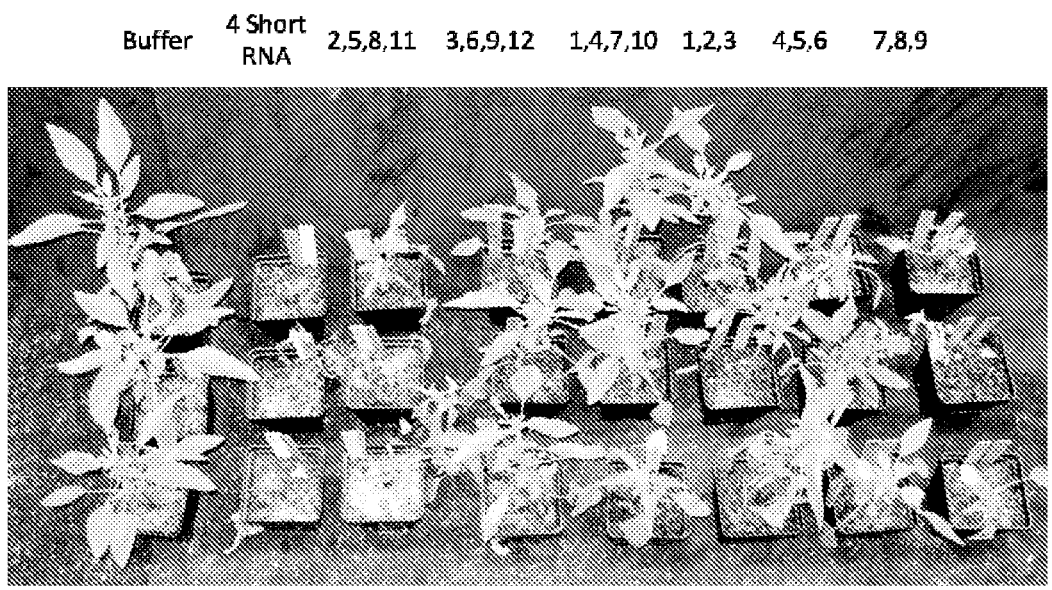
B
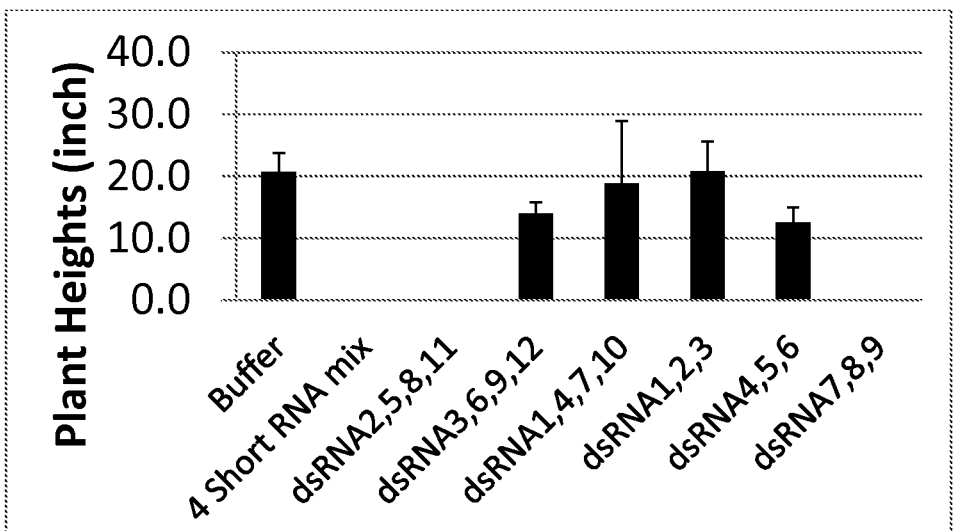
C

Figure 29
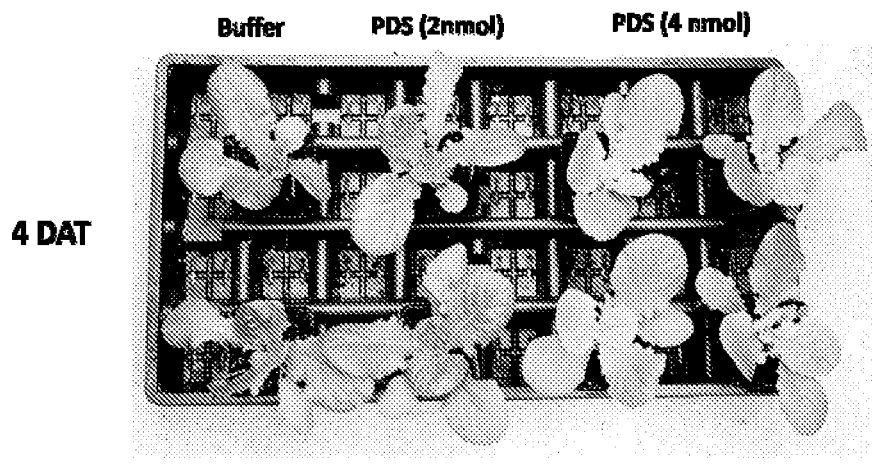
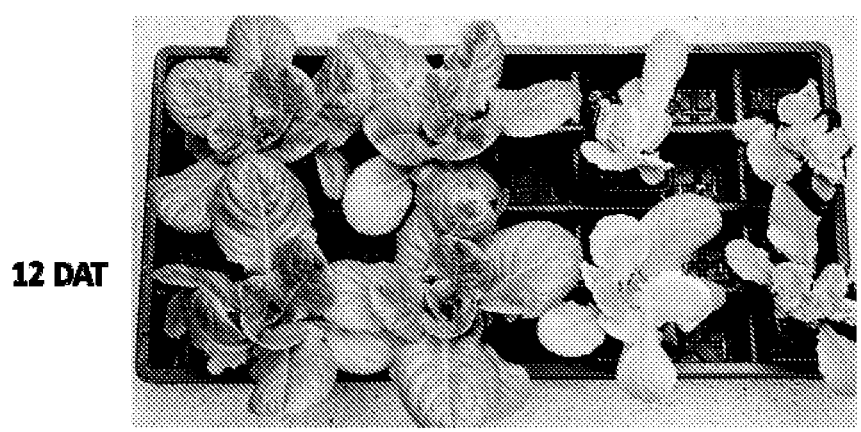
A
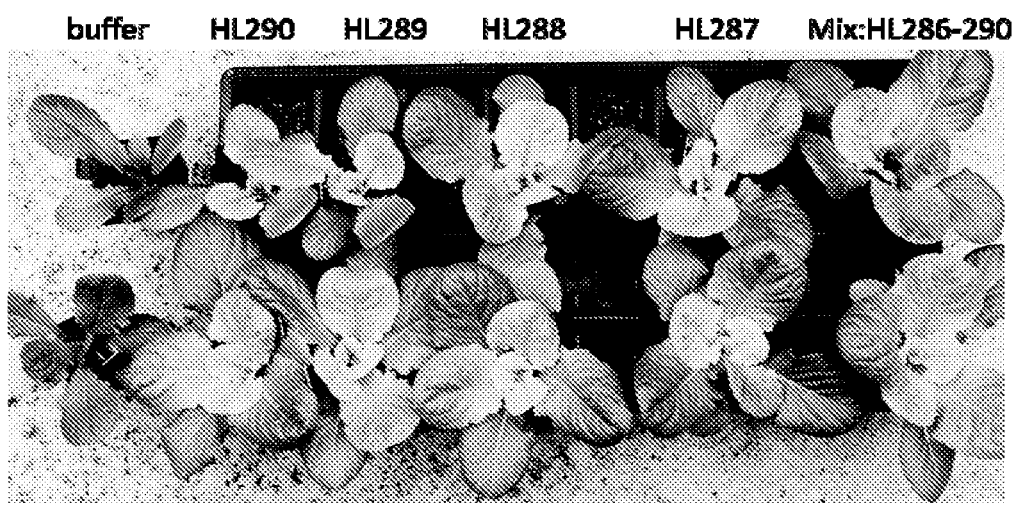
B

Figure 34

```
        810       820       830       840       850       860
PDS-2_  GTATGAACTTTCAGAATATTATACCGGATCAATATATTATGCT--GAAATATT--TTTCG
                ||||  ||||   ||   ||  |||  |   ||||
PDS-1_  GCTGTATCATATCTTCTTCTTTAGAACACTAATAAATTAAACTTCGAGATAATGATTTCT
        330       340       350       360       370       380

870       880       890       900       910
PDS-2_  GAC-----TTTAAATAATTTCTT-TATTTAAATTTATTTTTATACAAAAATAACTAAATT
        |||     |  ||||  ||  | |  |||   ||||     || | ||||||    ||||
PDS-1_  GACAAGAGTATAAACAAGTGCATCTATGAAGATTTGAGGTTGTCCAAAAAAGTGACAATT
        390       400       410       420       430       440

920       930       940       950       960       970
PDS-2_  TCAATTACTTTTAAA----ATTATGATTATTTTTCAATTACCACT-TATACATCCTGC--
        |    |  |  ||||     |||    ||||||  ||  |  |||  ||  |  |  |
PDS-1_  TTGGGTTCCTATAAACTGTATTTACATTATTGTT-ATTTGCAACTATAAAAATTTTAGAT
        450       460       470       480       490

980       990       1000      1010
PDS-2_  TATTTTGAAT---------TTCACCCGAAA-GAAC-TACTACTATACGTGGATC---CTC
        |||||  ||          |||| |  ||| ||| | |||  |  |   |||    |||
PDS-1_  TATTTCCAAGCTCAGTTTCTTCAACTTAAATGAAGGTAGCACTTGAATTTCATCAGCCTC
        500       510       520       530       540       550

1020      1030      1040      1050      1060      1070
PDS-2_  AATGACCCAGTAACCCAAGTGGGAGATGTGTGCAAAGTGGTCAAATCTTAGAAGGAATGA
        ||||||||||||||||| |||||||||  | |||||||||||||  |||||||||||
PDS-1_  TATGACCCAGTAACCCATGTGGGAGATGGGAGCAAAGTGGTCAAACTTTAGAAGGAAT
        560       570       580       590       600       610
```

PDS-1 promoter sequence (SEQ ID NO:319)

and

PDS-2 promoter sequence (SEQ ID NO:320)

Comparison of spermine (SPM), spermidine (SPMD), ammonium sulfate (AMS)

SEQUENCE LISTING

<160> NUMBER OF SEQ ID NOS: 320

<210> SEQ ID NO 1
<211> LENGTH: 1557
<212> TYPE: DNA
<213> ORGANISM: Amaranthus palmeri

<400> SEQUENCE: 1

```
atggctcaag ctactaccat caacaatggt gtccatactg gtcaattgca ccatactta      60 cccaaaaccc agttacccaa atcttcaaaa actcttaatt ttggatcaaa cttgagaatt     120
tctccaaagt tcatgtcttt aaccaataaa agagttggtg ggcaatcatc aattgttccc     180
aagattcaag cttctgttgc tgctgcagct gagaaacctt catctgtccc agaaattgtg     240
ttacaaccca tcaaagagat ctctggtact gttcaattgc ctgggtcaaa gtctttatcc     300
aatcgaatcc ttcttttagc tgctttgtct gagggcacaa cagtggtcga caacttgctg     360
tatagtgatg atattcttta tatgttggac gctctcagaa ctcttggttt aaaagtggag     420
gatgatagta cagccaaaag ggcagtcgta gagggttgtg gtggtctgtt tcctgttggt     480
aaagatggaa aggaagagat tcaactttc cttggtaatg caggaacagc gatgcgccca      540
ttgacagctg cggttgccgt tgctggagga aattcaagtt atgtgcttga tggagtacca     600
agaatgaggg agcgccccat tggggatctg gtagcaggtc taaagcaact tggttcagat     660
gtagattgtt ttcttggcac aaattgccct cctgttcggg tcaatgctaa aggaggcctt     720 ccaggggca aggtcaagct ctctggatcg gttagtagcc aatatttaac tgcacttctc     780
atggctactc ctttgggtct tggagacgtg gagattgaga tagttgataa attgattct     840 gtaccgtatg ttgaaatgac aataaagttg atggaacgct ttgagtatc cgtagaacat     900
```

```
agtgatagtt gggacaggtt ctacattcga ggtggtcaga aatacaaatc tcctggaaag      960
gcatatgttg agggtgatgc ttcaagtgct agctacttcc tagccggagc cgccgtcact     1020
ggtgggactg tcactgtcaa gggttgtgga acaagcagtt tacagggtga tgtaaaattt     1080
gccgaagttc ttgagaagat gggttgcaag gtcacctgga cagagaatag tgtaactgtt     1140
actggaccac ccagggattc atctggaaag aaacatctgc gtgctatcga cgtcaacatg     1200
aacaaaatgc cagatgttgc tatgactctt gcagttgttg ccttgtatgc agatgggccc     1260
accgccatca gagatgtggc tagctggaga gtgaaggaaa ccgaacggat gattgccatt     1320
tgcacagaac tgagaaagct tggggcaaca gttgaggaag gatctgatta ctgtgtgatc     1380
actccgcctg aaaagctaaa ccccaccgcc attgaaactt atgacgatca ccgaatggcc     1440
atggcattct ctcttgctgc ctgtgcagat gttcccgtca ctatccttga tccgggatgc     1500
acccgtaaaa ccttcccgga ctactttgat gttttagaaa agttcgccaa gcattga       1557

<210> SEQ ID NO 2
<211> LENGTH: 1761
<212> TYPE: DNA
<213> ORGANISM: Nicotiana benthamiana

<400> SEQUENCE: 2
atgccccaaa tcggacttgt atctgctgtt aatttgagag tccaaggtaa ttcagcttat       60
ctttggagct cgaggtcttc gttgggaact gaaagtcaag atgtttgctt gcaaaggaat      120
ttgttatgtt ttggtagtag cgactccatg gggcataagt taaggattcg tactccaagt      180
gccacgaccc gaagattgac aaaggacttt aatcctttaa aggtagtctg cattgattat      240
ccaagaccag agctagacaa tacagttaac tatttggagg cggcgttatt atcatcatcg      300
tttcgtactt cctcacgccc aactaaacca ttggagattg ttattgctgg tgcaggtttg      360
ggtggtttgt ctacagcaaa atatctggca gatgctggtc acaaaccgat attgctggag      420
gcaagagatg tcctaggtgg gaaggtagct gcatggaaag atgatgatgg agattggtac      480
gagactgggt tgcacatatt ctttggggct tacccaaata tgcagaacct gtttggagaa      540
ctagggattg atgatcggtt gcagtggaag gaacattcaa tgatatttgc gatgcctaac      600
aagccagggg agttcagccg ctttgatttt cctgaagctc ttcctgcgcc attaaatgga      660
attttggcca tactaaagaa caacgaaatg cttacgtggc ccgagaaagt caaatttgct      720
attggactct tgccagcaat gcttggaggg caatcttatg ttgaagctca agacggttta      780
agtgttaagg actggatgag aaagcaaggt gtgcctgata gggtgacaga tgaggtgttc      840
attgccatgt caaaggcact taacttcata aaccctgacg agctttcgat gcagtgcatt      900
ttgattgctt tgaacagatt tcttcaggag aaacatggtt caaaaatggc cttttttagat     960 ggtaaccctc ctgagagact ttgcatgccg attgtggaac atattgagtc aaaaggtggc    1020
caagtcagac taaactcacg aataaaaaag atcgagctga tgaggatgg aagtgtcaaa     1080 tgttttatac tgaataatgg cagtacaatt aaaggagatg cttttgtgtt tgccactcca     1140
gtggatatct tgaagcttct tttgcctgaa gactggaaag agatcccata tttccaaaag     1200
ttggagaagc tagtgggagt tcctgtgata aatgtccata tatggtttga cagaaaactg     1260
aagaacacat ctgataatct gctcttcagc agaagcccgt tgctcagtgt gtacgctgac     1320
atgtctgtta catgtaagga atattacaac cccaatcagt ctatgttgga attggtatt      1380 gcacccgcag aagagtggat aaatcgtagt gactcagaaa ttattgatgc tacaatgaag     1440
gaactagcga agcttttccc tgatgaaatt tcggcagatc agagcaaagc aaaaatattg     1500
```

| | | |
|---|---|---|
| aagtatcatg ttgtcaaaac cccaaggtct gtttataaaa ctgtgccagg ttgtgaaccc | 1560 | |
| tgtcggccct tgcaaagatc ccctatagag ggttttttatt tagctggtga ctacacgaaa | 1620 | |
| cagaagtact tggcttcaat ggaaggtgct gtcttatcag gaaagctttg tgcacaagct | 1680 | |
| attgtacagg attacgagtt acttcttggc cggagccaga agatgttggc agaagcaagc | 1740 | |
| gtagttagca tagtgaacta a | 1761 | |

<210> SEQ ID NO 3
<211> LENGTH: 559
<212> TYPE: DNA
<213> ORGANISM: artificial sequence
<220> FEATURE:
<223> OTHER INFORMATION: Synthetic Construct

<400> SEQUENCE: 3

| | |
|---|---|
| ggcccatagg cctttttcta aaataggccc atttaagcta ttaacaatct tcaaaagtac | 60 |
| cacatcgctt aggtaaagaa agcagctgag tttatatatg gttagagacg aagtagtgat | 120 |
| tgcgacgagc gacgtctcgc cctcatcgca atccacgcca ttgagcttga ggccattggc | 180 |
| gacggccgag aggcggtcgc ttaagattag catgtccttg acgcggagtt cttccagacc | 240 |
| gttcatcacg gtcgcccctt ccgcgaaggc ggcggcgaca gcgagaatcg atattcgtc | 300 |
| gatcatcgaa ggcgcgcggt cttccggcac cgtgacgcat aaacacggtg ccggaagacc | 360 |
| gcgcgccttc gatgatcgac gaatatccga ttctcgctgt cgccgccgcc ttcgcggaag | 420 |
| gggcgaccgt gatgaacggt ctggaagaac tccgcgtcaa ggaaagcgac cgcctctcgg | 480 |
| ccgtcgccaa tggcctcaag ctcaatggcg tggattgcga tgagggcgag acgtcgctcg | 540 |
| tcgttttttt tggcaaaaa | 559 |

<210> SEQ ID NO 4
<211> LENGTH: 10
<212> TYPE: DNA
<213> ORGANISM: artificial sequence
<220> FEATURE:
<223> OTHER INFORMATION: Synthetic Construct

<400> SEQUENCE: 4

| | |
|---|---|
| tcccacatcg | 10 |

<210> SEQ ID NO 5
<211> LENGTH: 13
<212> TYPE: DNA
<213> ORGANISM: artificial sequence
<220> FEATURE:
<223> OTHER INFORMATION: Synthetic Construct

<400> SEQUENCE: 5

| | |
|---|---|
| aagattagca cgg | 13 |

<210> SEQ ID NO 6
<211> LENGTH: 11
<212> TYPE: DNA
<213> ORGANISM: artificial sequence
<220> FEATURE:
<223> OTHER INFORMATION: Synthetic Construct

<400> SEQUENCE: 6

| | |
|---|---|
| acgcataaaa t | 11 |

<210> SEQ ID NO 7

```
<211> LENGTH: 6
<212> TYPE: DNA
<213> ORGANISM: artificial sequence
<220> FEATURE:
<223> OTHER INFORMATION: Synthetic Construct

<400> SEQUENCE: 7 tttttt                                                                    6

<210> SEQ ID NO 8
<211> LENGTH: 20
<212> TYPE: DNA
<213> ORGANISM: Amaranthus palmeri

<400> SEQUENCE: 8
accctccacg actgcccttt                                                    20

<210> SEQ ID NO 9
<211> LENGTH: 19
<212> TYPE: DNA
<213> ORGANISM: Amaranthus palmeri

<400> SEQUENCE: 9
gtttccttca ctctccagc                                                     19

<210> SEQ ID NO 10
<211> LENGTH: 20
<212> TYPE: DNA
<213> ORGANISM: Amaranthus palmeri

<400> SEQUENCE: 10
gtagcttgag ccattattgt                                                    20

<210> SEQ ID NO 11
<211> LENGTH: 20
<212> TYPE: DNA
<213> ORGANISM: Amaranthus palmeri

<400> SEQUENCE: 11
gttgatggta gtagcttgag                                                    20

<210> SEQ ID NO 12
<211> LENGTH: 20
<212> TYPE: DNA
<213> ORGANISM: Amaranthus palmeri

<400> SEQUENCE: 12
accctccacg actgcccttt                                                    20

<210> SEQ ID NO 13
<211> LENGTH: 19
<212> TYPE: DNA
<213> ORGANISM: Amaranthus palmeri

<400> SEQUENCE: 13
gtttccttca ctctccagc                                                     19

<210> SEQ ID NO 14
<211> LENGTH: 18
<212> TYPE: DNA
<213> ORGANISM: Hordeum vulgare

<400> SEQUENCE: 14
aagcggttga gcactgaa                                                      18
```

<210> SEQ ID NO 15
<211> LENGTH: 20
<212> TYPE: DNA
<213> ORGANISM: Amaranthus palmeri

<400> SEQUENCE: 15
accctccacg actgcccttt                                                   20

<210> SEQ ID NO 16
<211> LENGTH: 40
<212> TYPE: DNA
<213> ORGANISM: artificial sequence
<220> FEATURE:
<223> OTHER INFORMATION: Synthetic Construct

<400> SEQUENCE: 16
taatacgact cactataggg caagagatgt cctaggtggg                              40

<210> SEQ ID NO 17
<211> LENGTH: 44
<212> TYPE: DNA
<213> ORGANISM: artificial sequence
<220> FEATURE:
<223> OTHER INFORMATION: Synthetic Construct

<400> SEQUENCE: 17
taatacgact cactatagga cagatttctt caggagaaac atgg                         44

<210> SEQ ID NO 18
<211> LENGTH: 21
<212> TYPE: DNA
<213> ORGANISM: artificial sequence
<220> FEATURE:
<223> OTHER INFORMATION: Synthetic Construct

<400> SEQUENCE: 18
gcaagagatg tcctaggtgg g                                                 21

<210> SEQ ID NO 19
<211> LENGTH: 25
<212> TYPE: DNA
<213> ORGANISM: artificial sequence
<220> FEATURE:
<223> OTHER INFORMATION: Synthetic Construct

<400> SEQUENCE: 19
acagatttct tcaggagaaa catgg                                             25

<210> SEQ ID NO 20
<211> LENGTH: 41
<212> TYPE: DNA
<213> ORGANISM: artificial sequence
<220> FEATURE:
<223> OTHER INFORMATION: Synthetic Construct

<400> SEQUENCE: 20
taatacgact cactataggc atctccttta attgtactgc c                            41

<210> SEQ ID NO 21
<211> LENGTH: 41
<212> TYPE: DNA
<213> ORGANISM: artificial sequence
<220> FEATURE:
<223> OTHER INFORMATION: Synthetic Construct

<400> SEQUENCE: 21
taatacgact cactataggt ttaattgtac tgccattatt c         41

<210> SEQ ID NO 22
<211> LENGTH: 22
<212> TYPE: DNA
<213> ORGANISM: artificial sequence
<220> FEATURE:
<223> OTHER INFORMATION: Synthetic Construct

<400> SEQUENCE: 22
catctccttt aattgtactg cc                              22

<210> SEQ ID NO 23
<211> LENGTH: 22
<212> TYPE: DNA
<213> ORGANISM: artificial sequence
<220> FEATURE:
<223> OTHER INFORMATION: Synthetic Construct

<400> SEQUENCE: 23
tttaattgta ctgccattat tc                              22

<210> SEQ ID NO 24
<211> LENGTH: 25
<212> TYPE: DNA
<213> ORGANISM: artificial sequence
<220> FEATURE:
<223> OTHER INFORMATION: Synthetic Construct

<400> SEQUENCE: 24
cacttccatc ctcattcagc tcgat                           25

<210> SEQ ID NO 25
<211> LENGTH: 24
<212> TYPE: DNA
<213> ORGANISM: artificial sequence
<220> FEATURE:
<223> OTHER INFORMATION: Synthetic Construct

<400> SEQUENCE: 25
acacctcatc tgtcaccta tcag                             24

<210> SEQ ID NO 26
<211> LENGTH: 24
<212> TYPE: DNA
<213> ORGANISM: artificial sequence
<220> FEATURE:
<223> OTHER INFORMATION: Synthetic Construct

<400> SEQUENCE: 26
cagtctcgta ccaatctcca tcat                            24

<210> SEQ ID NO 27
<211> LENGTH: 41
<212> TYPE: DNA
<213> ORGANISM: artificial sequence
<220> FEATURE:
<223> OTHER INFORMATION: Synthetic Construct

<400> SEQUENCE: 27
taatacgact cactataggg atccatgata tcgtgaacat c         41

<210> SEQ ID NO 28
<211> LENGTH: 38

```
<212> TYPE: DNA
<213> ORGANISM: artificial sequence
<220> FEATURE:
<223> OTHER INFORMATION: Synthetic Construct

<400> SEQUENCE: 28
taatacgact cactataggg gcaaagaaaa atgcgtcg                                38

<210> SEQ ID NO 29
<211> LENGTH: 21
<212> TYPE: DNA
<213> ORGANISM: artificial sequence
<220> FEATURE:
<223> OTHER INFORMATION: Synthetic Construct

<400> SEQUENCE: 29
atccatgata tcgtgaacat c                                                 21

<210> SEQ ID NO 30
<211> LENGTH: 18
<212> TYPE: DNA
<213> ORGANISM: artificial sequence
<220> FEATURE:
<223> OTHER INFORMATION: Synthetic Construct

<400> SEQUENCE: 30
gcaaagaaaa atgcgtcg                                                     18

<210> SEQ ID NO 31
<211> LENGTH: 40
<212> TYPE: DNA
<213> ORGANISM: artificial sequence
<220> FEATURE:
<223> OTHER INFORMATION: Synthetic Construct

<400> SEQUENCE: 31
tgttttatac tgaataatgg cagtacaatt aaaggagatg                             40

<210> SEQ ID NO 32
<211> LENGTH: 15
<212> TYPE: DNA
<213> ORGANISM: artificial sequence
<220> FEATURE:
<223> OTHER INFORMATION: Synthetic Construct

<400> SEQUENCE: 32
catctccttt aattg                                                        15

<210> SEQ ID NO 33
<211> LENGTH: 18
<212> TYPE: DNA
<213> ORGANISM: artificial sequence
<220> FEATURE:
<223> OTHER INFORMATION: Synthetic Construct

<400> SEQUENCE: 33
catctccttt aattgtac                                                     18

<210> SEQ ID NO 34
<211> LENGTH: 21
<212> TYPE: DNA
<213> ORGANISM: artificial sequence
<220> FEATURE:
<223> OTHER INFORMATION: Synthetic Construct

<400> SEQUENCE: 34
```
catctccttt aattgtactg c                                            21

<210> SEQ ID NO 35
<211> LENGTH: 33
<212> TYPE: DNA
<213> ORGANISM: artificial sequence
<220> FEATURE:
<223> OTHER INFORMATION: Synthetic Construct

<400> SEQUENCE: 35
catctccttt aattgtactg ccattattca gta                               33

<210> SEQ ID NO 36
<211> LENGTH: 21
<212> TYPE: DNA
<213> ORGANISM: artificial sequence
<220> FEATURE:
<223> OTHER INFORMATION: Synthetic Construct

<400> SEQUENCE: 36
gcagtacaat taaaggagat g                                            21

<210> SEQ ID NO 37
<211> LENGTH: 1614
<212> TYPE: DNA
<213> ORGANISM: Amaranthus palmeri

<400> SEQUENCE: 37
tcaatttcat ctattggaag tgattttttg ggtcattctg tgagaaattt cagtgttagt    60
aaagtttatg gagcaaagca agaaatggg cactgcccctt taaaggttgt ttgtatagat   120
tatcctaggc cagagcttga agtacatcc aatttcttgg aagccgccta cttatcttct   180
acttttcgga attcgcctcg tcctcagaag ccattagaag ttgtaattgc tggagcaggt   240
ttggctggtc tatccacggc aaagtattta gctgatgcag gtcacaaacc catattgttg   300
gaagcacgag atgttttagg aggaaaggtt gcagcgtgga aggatgagga tggtgactgg   360
tatgagactg ggctacatat attctttggg gcatatccaa atgtccaaaa tctatttgga   420
gaacttggta taaatgaccg actgcaatgg aaggagcact ctatgatttt tgcaatgccc   480
agcaagcccg gtgaattcag tcgctttgat tttcccgaaa tcctgcctgc accattaaat   540
ggcatatggg caatcctaag aaataatgaa atgctaacct ggccagaaaa atcaagttt   600
gccattggct tgttgcctgc tatggcaggc ggacagtcat atgttgaagc acaagatggt   660
ttgagtgtcc aagagtggat gagaaaacaa ggagtacccg atcgtgtaac tgatgatgtg   720
tttattgcca tgtcaaaggc actgaacttc ataaatcccg atgaacttc aatgcagtgc   780
atcttgattg ctctgaaccg attcctgcag gagaaacatg ttctaagat ggccttccta   840
gacggaaacc ctccagagag gctgtgcatg cctattgtta aacacatcga gtcactaggt   900
ggtgaagtta aacttaactc tcgtatacaa aagattcagt tggaccagag tggaagcgtg   960
aagagttttt tgctaaataa cgggagggaa atacgaggag atgcctatgt ttttgccacc  1020
ccagttgaca tcttgaagct gttactacct gatacttgga aggaaatctc atacttcaaa  1080
aaacttgaga aattagtggg cgttcctgtg attaatgttc acatatggtt tgacagaaaa  1140
ttaaagaata catatgacca tctactcttc agcaggagtc ctctttgag tgtctatgct  1200
gatatgtcgg agacatgcaa ggaatataag gatccaaata gatccatgct ggaattggtt  1260
tttgcacccg cggaggaatg gatttcacga agcgacactg atattataga ggcaacaatg  1320
aaagagcttg ccaagctttt cccggatgaa atcgctgccg atggaagcaa ggccaagatc  1380

```
ctcaaatatc atgtcgtcaa aactccaagg tcggtttata agactgtacc ggattgtgaa    1440
ccttgtcggc cgctgcaaag atcaccaata gagggtttct atttagctgg tgattacaca    1500
aaacaaaaat atttggcttc tatggaaggt gctgtcttat ctgggaagct tgtgcacag     1560 gctatcgtac aggattatga tctgctgagt tctcgagcac aaagagaatt ggcg          1614

<210> SEQ ID NO 38
<211> LENGTH: 1761
<212> TYPE: DNA
<213> ORGANISM: Nicotiana benthamiana

<400> SEQUENCE: 38
atgccccaaa tcggacttgt atctgctgtt aatttgagag tccaaggtaa ttcagcttat      60
ctttggagct cgaggtcttc gttgggaact gaaagtcaag atgtttgctt gcaaaggaat    120
ttgttatgtt ttggtagtag cgactccatg gggcataagt taaggattcg tactccaagt    180
gccacgaccc gaagattgac aaaggacttt aatcctttaa aggtagtctg cattgattat    240
ccaagaccag agctagacaa tacagttaac tatttggagg cggcgttatt atcatcatcg    300
tttcgtactt cctcacgccc aactaaacca ttggagattg ttattgctgg tgcaggtttg    360
ggtggtttgt ctacagcaaa atatctggca gatgctggtc acaaaccgat attgctggag    420
gcaagagatg tcctaggtgg gaaggtagct gcatggaaag atgatgatgg agattggtac    480
gagactgggt tgcacatatt ctttggggct tacccaaata tgcagaacct gtttggagaa    540
ctagggattg atgatcggtt gcagtggaag gaacattcaa tgatatttgc gatgcctaac    600
aagccagggg agttcagccg ctttgatttt cctgaagctc ttcctgcgcc attaaatgga    660
attttggcca tactaaagaa caacgaaatg cttacgtggc ccgagaaagt caaatttgct    720
attggactct gccagcaat gcttggaggg caatcttatg ttgaagctca agacggttta    780
agtgttaagg actggatgag aaagcaaggt gtgcctgata gggtgacaga tgaggtgttc    840
attgccatgt caaaggcact taacttcata acccctgacg agctttcgat gcagtgcatt    900
ttgattgctt tgaacagatt tcttcaggag aaacatggtt caaaaatggc cttttttagat    960 ggtaaccctc ctgagagact ttgcatgccg attgtgaaac atattgagtc aaaaggtggc   1020
caagtcagac taaactcacg aataaaaaag atcgagctga atgaggatgg aagtgtcaaa   1080
tgttttatac tgaataatgg cagtacaatt aaaggagatg cttttgtgtt tgccactcca   1140
gtggatatct tgaagcttct tttgcctgaa gactggaaag agatcccata tttccaaaag   1200
ttggagaagc tagtgggagt tcctgtgata aatgtccata tatggtttga cagaaaactg   1260
aagaacacat ctgataatct gctcttcagc agaagcccgt tgctcagtgt gtacgctgac   1320
atgtctgtta catgtaagga atattacaac cccaatcagt ctatgttgga attggtattt   1380
gcacccgcag aagagtggat aaatcgtagt gactcagaaa ttattgatgc tacaatgaag   1440
gaactagcga agcttttccc tgatgaaatt tcggcagatc agagcaaagc aaaaatattg   1500
aagtatcatg ttgtcaaaac cccaaggtct gtttataaaa ctgtgccagg ttgtgaaccc   1560
tgtcggccct tgcaaagatc ccctatagag ggttttttatt tagctggtga ctacacgaaa   1620
cagaagtact tggcttcaat ggaaggtgct gtcttatcag gaaagctttg tgcacaagct   1680
attgtacagg attacgagtt acttcttggc cggagccaga agatgttggc agaagcaagc   1740
gtagttagca tagtgaacta a                                              1761

<210> SEQ ID NO 39
```

```
<211> LENGTH: 22
<212> TYPE: DNA
<213> ORGANISM: Nicotiana benthamiana

<400> SEQUENCE: 39
ggcagtacaa ttaaaggaga tg                                               22

<210> SEQ ID NO 40
<211> LENGTH: 1557
<212> TYPE: DNA
<213> ORGANISM: Amaranthus palmeri

<400> SEQUENCE: 40
atggctcaag ctactaccat caacaatggt gtccatactg gtcaattgca ccatactta        60 cccaaaaccc agttacccaa atcttcaaaa actcttaatt ttggatcaaa cttgagaatt      120
tctccaaagt tcatgtcttt aaccaataaa agagttggtg gcaatcatc aattgttccc       180 aagattcaag cttctgttgc tgctgcagct gagaaacctt catctgtccc agaaattgtg      240
ttacaaccca tcaagagat ctctggtact gttcaattgc ctgggtcaaa gtctttatcc      300
aatcgaatcc ttcttttagc tgctttgtct gagggcacaa cagtggtcga caacttgctg      360
tatagtgatg atattcttta tgttggac gctctcagaa ctcttggttt aaaagtggag       420
gatgatagta cagccaaaag ggcagtcgta gagggttgtg gtggtctgtt tcctgttggt      480
aaagatggaa aggaagagat tcaactttc cttggtaatg caggaacagc gatgcgccca      540
ttgacagctg cggttgccgt tgctggagga aattcaagtt atgtgcttga tggagtacca      600
agaatgaggg agcgccccat tggggatctg gtagcaggtc taaagcaact tggttcagat      660
gtagattgtt ttcttggcac aaattgccct cctgttcggg tcaatgctaa aggaggcctt      720
ccagggggca aggtcaagct ctctggatcg gttagtagcc aatatttaac tgcacttctc      780
atggctactc ctttgggtct tggagacgtg gagattgaga tagttgataa attgatttct      840
gtaccgtatg ttgaaatgac aataaagttg atggaacgct ttggagtatc cgtagaacat      900
agtgatagtt gggacaggtt ctacattcga ggtggtcaga atacaaatc tcctggaaag      960 gcatatgttg agggtgatgc ttcaagtgct agctacttcc tagccggagc cgccgtcact     1020
ggtgggactg tcactgtcaa gggttgtgga acaagcagtt tacagggtga tgtaaaattt     1080
gccgaagttc ttgagaagat gggttgcaag gtcacctgga cagagaatag tgtaactgtt     1140
actggaccac ccagggattc atctggaaag aaacatctgc gtgctatcga cgtcaacatg     1200
aacaaaatgc cagatgttgc tatgactctt gcagttgttg ccttgtatgc agatgggccc     1260
accgccatca gagatgtggc tagctggaga gtgaaggaaa ccgaacggat gattgccatt     1320
tgcacagaac tgagaaagct tggggcaaca gttgaggaag gatctgatta ctgtgtgatc     1380
actccgcctg aaaagctaaa ccccaccgcc attgaaactt atgacgatca ccgaatggcc     1440
atggcattct ctcttgctgc ctgtgcagat gttcccgtca ctatccttga tccgggatgc     1500
acccgtaaaa ccttcccgga ctactttgat gttttagaaa agttcgccaa gcattga       1557

<210> SEQ ID NO 41
<211> LENGTH: 250
<212> TYPE: DNA
<213> ORGANISM: Amaranthus palmeri
<220> FEATURE:
<221> NAME/KEY: misc_feature
<222> LOCATION: (27)..(27)
<223> OTHER INFORMATION: n is a, c, g, or t

<400> SEQUENCE: 41
```

```
cgccagggct gcagacgcgt tacgtantcg gatccagaat tcgtgattaa cgtcacagca    60
tgtcatgtaa aacacgcgaa tcagaccggt ccactcttgt tttaatttga gacaattttg   120
atgttgagtc atcccacacc aaccccaaaa aattcaacaa caaactctta taatgattcc   180
ctctactcta ctagagtcta caccaaccca ctttctcttt gcccaccaaa actttggttt   240
ggtaagaact                                                          250

<210> SEQ ID NO 42
<211> LENGTH: 244
<212> TYPE: DNA
<213> ORGANISM: Amaranthus palmeri

<400> SEQUENCE: 42
caccaaccca ctttctcttt gcccaccaaa actttggttt ggtaagaact aagccctctt    60
ctttcccttc tctctcttaa aagcctaaaa tccacctaac ttttcagcc aacaaacaac    120 gccaaattca gaggaagaat aatgatggct caagctacta ccatcaacaa tggtgtccat   180
actggtcaat tgcaccatac tttacccaaa acccagttac ccaaatcttc aaaaactctt   240
aatt                                                                244

<210> SEQ ID NO 43
<211> LENGTH: 250
<212> TYPE: DNA
<213> ORGANISM: Amaranthus palmeri

<400> SEQUENCE: 43
ccatacttta cccaaaaccc agttacccaa atcttcaaaa actcttaatt ttggatcaaa    60
cttgagaatt tctccaaagt tcatgtcttt aaccaataaa agagttggtg ggcaatcatc   120
aattgttccc aagattcaag cttctgttgc tgctgcagct gagaaacctt catctgtccc   180
agaaattgtg ttacaaccca tcaaagagat ctctggtact gttcaattgc ctgggtcaaa   240
gtctttatcc                                                          250

<210> SEQ ID NO 44
<211> LENGTH: 250
<212> TYPE: DNA
<213> ORGANISM: Amaranthus palmeri

<400> SEQUENCE: 44
tcaaagagat ctctggtact gttcaattgc ctgggtcaaa gtctttatcc aatcgaatcc    60
ttcttttagc tgctttgtct gagggcacaa cagtggtcga caacttgctg tatagtgatg   120
atattcttta tatgttggac gctctcagaa ctcttggttt aaaagtggag gatgatagta   180
cagccaaaag ggcagtcgta gagggttgtg gtggtctgtt cctgttggt aaagatggaa    240 aggaagagat                                                          250

<210> SEQ ID NO 45
<211> LENGTH: 250
<212> TYPE: DNA
<213> ORGANISM: Amaranthus palmeri

<400> SEQUENCE: 45
gagggttgtg gtggtctgtt cctgttggt aaagatggaa aggaagagat tcaactttc     60 cttggtaatg caggaacagc gatgcgccca ttgacagctg cggttgccgt tgctggagga   120
aattcaagtt atgtgcttga tggagtacca agaatgaggg agcgcccat tggggatctg   180
```

<210> SEQ ID NO 46
<211> LENGTH: 250
<212> TYPE: DNA
<213> ORGANISM: Amaranthus palmeri

<400> SEQUENCE: 46

| tggttcagat gtagattgtt ttcttggcac aaattgccct cctgttcggg tcaatgctaa | 60 |
| aggaggcctt ccaggggggca aggtcaagct ctctggatcg gttagtagcc aatatttaac | 120 |
| tgcacttctc atggctactc ctttgggtct tggagacgtg gagattgaga tagttgataa | 180 |
| attgatttct gtaccgtatg ttgaaatgac aataaagttg atggaacgct ttggagtatc | 240 |
| cgtagaacat | 250 |

<210> SEQ ID NO 47
<211> LENGTH: 250
<212> TYPE: DNA
<213> ORGANISM: Amaranthus palmeri

<400> SEQUENCE: 47

| ttgaaatgac aataaagttg atggaacgct ttggagtatc cgtagaacat agtgatagtt | 60 |
| gggacaggtt ctacattcga ggtggtcaga atacaaatc tcctggaaag gcatatgttg | 120 |
| agggtgatgc ttcaagtgct agctacttcc tagccggagc cgccgtcact ggtgggactg | 180 |
| tcactgtcaa gggttgtgga acaagcagtt tacagggtga tgtaaaattt gccgaagttc | 240 |
| ttgagaagat | 250 |

<210> SEQ ID NO 48
<211> LENGTH: 250
<212> TYPE: DNA
<213> ORGANISM: Amaranthus palmeri

<400> SEQUENCE: 48

| acaagcagtt tacagggtga tgtaaaattt gccgaagttc ttgagaagat gggttgcaag | 60 |
| gtcacctgga cagagaatag tgtaactgtt actggaccac ccagggattc atctggaaag | 120 |
| aaacatctgc gtgctatcga cgtcaacatg aacaaaatgc cagatgttgc tatgactctt | 180 |
| gcagttgttg ccttgtatgc agatgggccc accgccatca gagatgtggc tagctggaga | 240 |
| gtgaaggaaa | 250 |

<210> SEQ ID NO 49
<211> LENGTH: 250
<212> TYPE: DNA
<213> ORGANISM: Amaranthus palmeri

<400> SEQUENCE: 49

| agatgggccc accgccatca gagatgtggc tagctggaga gtgaaggaaa ccgaacggat | 60 |
| gattgccatt tgcacagaac tgagaaagct tggggcaaca gttgaggaag atctgattaa | 120 |
| ctgtgtgatc actccgcctg aaaagctaaa ccccaccgcc attgaaactt atgacgatca | 180 |
| ccgaatggcc atggcattct ctcttgctgc ctgtgcagat gttcccgtca ctatccttga | 240 |
| tccgggatgc | 250 |

<210> SEQ ID NO 50
<211> LENGTH: 257

```
<212> TYPE: DNA
<213> ORGANISM: Amaranthus palmeri

<400> SEQUENCE: 50
ctcttgctgc ctgtgcagat gttcccgtca ctatccttga tccgggatgc acccgtaaaa      60
ccttcccgga ctactttgat gttttagaaa agttcgccaa gcattgatga gtagctatat     120
acgagatcct taaattgtac gccgaaggtt ttgatttgag tctaatagta gataaaaggc     180
tataaataaa ctggctttct gcttgagtaa ttatgaaatt ctttgtatta tgtttgtgag     240
atttgaagta gcttata                                                     257

<210> SEQ ID NO 51
<211> LENGTH: 273
<212> TYPE: DNA
<213> ORGANISM: Amaranthus palmeri

<400> SEQUENCE: 51
taattatgaa attctttgta ttatgtttgt gagatttgaa gtagcttata aattacaatg      60
tactaaagtc tagaaataag ttatgtatct tttaaatcaa tgagaaatgc atacttgaaa     120
ggcttgacct tgtatttgtg acctaaagag tactaacttt ggagtttcca actcatttgt     180
ttatctcatt tttttttaat ttttgattta aattgtttat ttttatgagt aatcatgtat     240
ctttcttatt ctaaccaaat gtaatactcc ttc                                   273

<210> SEQ ID NO 52
<211> LENGTH: 301
<212> TYPE: DNA
<213> ORGANISM: Amaranthus palmeri

<400> SEQUENCE: 52
tatgagtaat catgtatctt tcttattcta accaaatgta atactccttc caactctctt      60
taaacgtcca cactctgggc acagagtgta atagtgtggt ggttggagtc ttttaagtga     120
ttataataat tgtaaatgtg gtagttagaa tattttaagt aatgtaggtg gggtattatg     180
gtcttgttga acataggata tttaggtaaa aaatctatgc aaaaaaagga aagtaagcaa     240
ataaagcgaa ttgacctgaa agaaaagtg gacatgtata gtgagttgga ggaagtattt     300
t                                                                      301

<210> SEQ ID NO 53
<211> LENGTH: 1710
<212> TYPE: DNA
<213> ORGANISM: Lactuca sativa

<400> SEQUENCE: 53
atgtctctgt ttggaaatgt ttctgccatt aactcaagtg gaaagtgtat agtaatgaat      60
ctttcaagca cacaaatcac ttcaagagat tgtttcaaga ttacctcagg gcaaaaagat     120
gttttgtcat ttggatgctg tgatgctatg ggtaacagat tgcaattccc aagtgctcgt     180
tcttttacac caagatcaaa gaagaatgtc tcccctctaa aggtagtttg tgttgattat     240
ccaagaccag atcttgataa cacatctaat ttccttggaag ctgctcactt gtcttcaacc     300
ttcagaactt ccccacgccc atctaagcca ttgaagatta taattgctgg tgcaggtttta    360 gctggtttat caactgctaa gtatttagct gatgcaggtc acaagccaat tttactagaa    420
gcaagagatg ttcttggtgg aaaggtggca gcttggaaag atgatgatgg agattggtat    480
gagacaggtt tacacatatt ctttggagct tacccaaatg tacaaaattt atttggagag    540
```

-continued

| | |
|---|---|
| ctaggaatta atgatagatt acagtggaag gagcattcta tgatatttgc aatgccaaat | 600 |
| aagcctggag aatttagtag gtttgacttc ccagatgttt tacctgcacc attgaatgga | 660 |
| attttttgcta tattgaggaa caatgaaatg ctgacgtggc ctgagaaagt gaagtttgca | 720 |
| attgggctgt tgcctgcaat gttaggtgga caggcttatg ttgaggccca agatgggctt | 780 |
| agtgttcagg actggatgag aaagcaaggt atacctgatc gagttactac tgaagtgttt | 840 |
| attgcaatgt caaaagcatt aaactttata aatccagatg aactttcaat gcaatgtatt | 900 |
| ctcattgctc taaaccgttt tcttcaggaa agcatggtt ccaagatggc attttttagat | 960 |
| gggagcccac cagaaaagact ttgcaagcca attgttgacc acatcgagtc actcggtggc | 1020 |
| caagtcagag tcaactcacg aatacaaaaa attgagttaa acaaagacgg aactgtccgg | 1080 |
| aactttctat tgagtgatgg gaatgttcta gaagctgatg cttatgtttt cgctacccct | 1140 |
| gttgacattc tcaagcttct tttacccgaa gaatggaaac caattccata tttcaaaaaa | 1200 |
| ttagagaagt tagtcggtgt tcctgttata acgttcata tatggttga cagaaagctg | 1260 |
| aaaaacacat atgatcactt acttttcagt aggtcacctc tgctgagtgt gtatgctgac | 1320 |
| atgtcagtga catgtaagga atattatgat ccgaataagt caatgttgga gttggttctt | 1380 |
| gctccagctg aggaatggat ttcaagaagt gacactgata ttattgatgc aacaatgagt | 1440 |
| gaactttcaa ggcttttttcc tgatgaaatt gcagctgatc aaagtaaagc aaaaatcttg | 1500 |
| aaatataaag ttgttaaaac accaaggtct gtttataaaa ctgttccaga ttgtgaacca | 1560 |
| tgtcgacccc tacaaagatc tccaattcaa ggatttttatt tatctggtga ttatactaaa | 1620 |
| caaaagtatt tggcttcaat gggggggtgct gtttttatctg gaaaaatttg tgcacaagct | 1680 |
| attttacaag attatgagat gcttgctaca | 1710 |

<210> SEQ ID NO 54
<211> LENGTH: 42
<212> TYPE: DNA
<213> ORGANISM: artificial sequence
<220> FEATURE:
<223> OTHER INFORMATION: Synthetic Construct

<400> SEQUENCE: 54

| | |
|---|---|
| taatacgact cactataggg tttggagctt acccaaatgt ac | 42 |

<210> SEQ ID NO 55
<211> LENGTH: 45
<212> TYPE: DNA
<213> ORGANISM: artificial sequence
<220> FEATURE:
<223> OTHER INFORMATION: Synthetic Construct

<400> SEQUENCE: 55

| | |
|---|---|
| taatacgact cactataggg aggccacgtc agcatttcat tgttc | 45 |

<210> SEQ ID NO 56
<211> LENGTH: 23
<212> TYPE: DNA
<213> ORGANISM: artificial sequence
<220> FEATURE:
<223> OTHER INFORMATION: Synthetic Construct

<400> SEQUENCE: 56

| | |
|---|---|
| ccattcaatg gtgcaggtaa aac | 23 |

<210> SEQ ID NO 57
<211> LENGTH: 21

```
<212> TYPE: DNA
<213> ORGANISM: artificial sequence
<220> FEATURE:
<223> OTHER INFORMATION: Synthetic Construct

<400> SEQUENCE: 57
catagaatgc tccttccact g                                            21

<210> SEQ ID NO 58
<211> LENGTH: 33
<212> TYPE: DNA
<213> ORGANISM: artificial sequence
<220> FEATURE:
<223> OTHER INFORMATION: Synthetic Construct

<400> SEQUENCE: 58
caaataaatt ttgtacattt gggtaagctc caa                               33

<210> SEQ ID NO 59
<211> LENGTH: 2349
<212> TYPE: DNA
<213> ORGANISM: Solanum lycopersicum

<400> SEQUENCE: 59
gggtttatct cgcaagtgtg gctatggtgg gacgtgtcaa attttggatt gtagccaaac    60
atgagatttg atttaaaggg aattggccaa atcaccgaaa gcaggcatct tcatcataaa   120
ttagtttgtt tatttataca gaattatacg cttttactag ttatagcatt cggtatcttt   180
ttctgggtaa ctgccaaacc accacaaatt tcaagtttcc atttaactct tcaacttcaa   240
cccaaccaaa tttatttgct taattgtgca gaaccactcc ctatatcttc taggtgcttt   300
cattcgttcc gagtaaaatg cctcaaattg gacttgtttc tgctgttaac ttgagagtcc   360
aaggtagttc agcttatctt tggagctcga ggtcgtcttc tttgggaact gaaagtcgag   420
atggttgctt gcaaaggaat tcgttatgtt ttgctggtag cgaatcaatg ggtcataagt   480
taaagattcg tactccccat gccacgacca gaagattggt taaggacttg gggcctttaa   540
aggtcgtatg cattgattat ccaagaccag agctggacaa tacagttaac tatttggagg   600
ctgcattttt atcatcaacg ttccgtgctt ctccgcgccc aactaaacca ttggagattg   660
ttattgctgg tgcaggtttg ggtggtttgt ctacagcaaa atatttggca gatgctggtc   720
acaaaccgat actgctggag gcaagggatg ttctaggtgg aaaggtagct gcatggaaag   780
atgatgatgg agattggtac gagactggtt tgcatatatt ctttggggct tacccaaata   840
ttcagaacct gtttggagaa ttagggatta acgatcgatt gcaatggaag gaacattcaa   900
tgatatttgc aatgccaagc aagccaggag aattcagccg ctttgatttc tccgaagctt   960
tacccgctcc tttaaatgga attttagcca tcttaaagaa taacgaaatg cttacatggc  1020
cagagaaagt caaatttgca attggactct tgccagcaat gcttggaggg caatcttatg  1080
ttgaagctca agatgggata agtgttaagg actggatgag aaagcaaggt gtgccggaca  1140
gggtgacaga tgaggtgttc attgctatgt caaaggcact caactttata aaccctgacg  1200
aactttcaat gcagtgcatt ttgatcgcat tgaacaggtt tcttcaggag aaacatggtt  1260
caaaaatggc ctttttagat ggtaatcctc ctgagagact ttgcatgccg attgttgaac  1320
acattgagtc aaaaggtggc caagtcagac tgaactcacg aataaaaaag attgagctga  1380
atgaggatgg aagtgtcaag agtttttatac tgagtgacgg tagtgcaatc gagggagatg  1440
cttttgtgtt tgccgctcca gtggatattt tcaagcttct attgcctgaa gactggaaag  1500
```

-continued

| | |
|---|---|
| agattccata tttccaaaag ttggagaagt tagtcggagt acctgtgata aatgtacata | 1560 |
| tatggtttga cagaaaactg aagaacacat atgatcattt gctcttcagc agaagctcac | 1620 |
| tgctcagtgt gtatgctgac atgtctgtta catgtaagga atattacaac cccaatcagt | 1680 |
| ctatgttgga attggttttt gcacctgcag aagagtggat atctcgcagc gactcagaaa | 1740 |
| ttattgatgc aacgatgaag gaactagcaa cgcttttttcc tgatgaaatt tcagcagatc | 1800 |
| aaagcaaagc aaaatattg aagtaccatg ttgtcaaaac tccgaggtct gtttataaaa | 1860 |
| ctgtgccagg ttgtgaaccc tgtcggcctt tacaaagatc cccaatagag gggttttatt | 1920 |
| tagccggtga ctacacgaaa cagaaatact tggcttcaat ggaaggcgct gtcttatcag | 1980 |
| gaaagctttg tgctcaagct attgtacagg attatgagtt acttgttgga cgtagccaaa | 2040 |
| agaagttgtc ggaagcaagc gtagtttagc tttgtggtta ttatttagct tctgtacact | 2100 |
| aaatttatga tgcaagaagc gttgtacaca acatatagaa gaagagtgcg aggtgaagca | 2160 |
| agtaggagaa atgttaggaa agctcctata caaaaggatg gcatgttgaa gattagcatc | 2220 |
| tttttaatcc caagttttaaa tataaagcat atttttatgta ccactttctt tatctggggt | 2280 |
| ttgtaatccc tttatatctt tatgcaatct ttacgttagt taaaaaaaa aaaaaaaaa | 2340 |
| aaaactcga | 2349 |

<210> SEQ ID NO 60
<211> LENGTH: 200
<212> TYPE: DNA
<213> ORGANISM: artificial sequence
<220> FEATURE:
<223> OTHER INFORMATION: Synthetic Construct

<400> SEQUENCE: 60

| | |
|---|---|
| tcgcagcgac tcagaaatta ttgatgcaac gatgaaggaa ctagcaacgc ttttttcctga | 60 |
| tgaaatttca gcagatcaaa gcaaagcaaa atattgaag taccatgttg tcaaaactcc | 120 |
| gaggtctgtt tataaaactg tgccaggttg tgaaccctgt cggcctttac aaagatcccc | 180 |
| aatagagggg ttttatttag | 200 |

<210> SEQ ID NO 61
<211> LENGTH: 43
<212> TYPE: DNA
<213> ORGANISM: artificial sequence
<220> FEATURE:
<223> OTHER INFORMATION: Synthetic Construct

<400> SEQUENCE: 61

| | |
|---|---|
| taatacgact cactataggg tcgcagcgac tcagaaatta ttg | 43 |

<210> SEQ ID NO 62
<211> LENGTH: 45
<212> TYPE: DNA
<213> ORGANISM: artificial sequence
<220> FEATURE:
<223> OTHER INFORMATION: Synthetic Construct

<400> SEQUENCE: 62

| | |
|---|---|
| taatacgact cactataggg gtaaaggccg acagggttca caacc | 45 |

<210> SEQ ID NO 63
<211> LENGTH: 21
<212> TYPE: RNA
<213> ORGANISM: artificial sequence
<220> FEATURE:
<223> OTHER INFORMATION: Synthetic Construct -continued

<400> SEQUENCE: 63
cuaccaucaa caaugguguc c                                            21

<210> SEQ ID NO 64
<211> LENGTH: 21
<212> TYPE: RNA
<213> ORGANISM: artificial sequence
<220> FEATURE:
<223> OTHER INFORMATION: Synthetic Construct

<400> SEQUENCE: 64
ggacaccauu guugauggua g                                            21

<210> SEQ ID NO 65
<211> LENGTH: 21
<212> TYPE: RNA
<213> ORGANISM: artificial sequence
<220> FEATURE:
<223> OTHER INFORMATION: Synthetic Construct

<400> SEQUENCE: 65
gucgacaacu ugcuguauag u                                            21

<210> SEQ ID NO 66
<211> LENGTH: 21
<212> TYPE: RNA
<213> ORGANISM: artificial sequence
<220> FEATURE:
<223> OTHER INFORMATION: Synthetic Construct

<400> SEQUENCE: 66
acuauacagc aaguugucga c                                            21

<210> SEQ ID NO 67
<211> LENGTH: 21
<212> TYPE: RNA
<213> ORGANISM: artificial sequence
<220> FEATURE:
<223> OTHER INFORMATION: Synthetic Construct

<400> SEQUENCE: 67
ggucaccugg acagagaaua g                                            21

<210> SEQ ID NO 68
<211> LENGTH: 21
<212> TYPE: RNA
<213> ORGANISM: artificial sequence
<220> FEATURE:
<223> OTHER INFORMATION: Synthetic Construct

<400> SEQUENCE: 68
cuauucucug uccaggugac c                                            21

<210> SEQ ID NO 69
<211> LENGTH: 21
<212> TYPE: RNA
<213> ORGANISM: artificial sequence
<220> FEATURE:
<223> OTHER INFORMATION: Synthetic Construct

<400> SEQUENCE: 69
aaugccagau guugcuauga c                                            21

<210> SEQ ID NO 70

```
<211> LENGTH: 21
<212> TYPE: RNA
<213> ORGANISM: artificial sequence
<220> FEATURE:
<223> OTHER INFORMATION: Synthetic Construct

<400> SEQUENCE: 70
gucauagcaa caucuggcau u                                              21

<210> SEQ ID NO 71
<211> LENGTH: 2827
<212> TYPE: DNA
<213> ORGANISM: Amaranthus palmeri

<400> SEQUENCE: 71
atggcaacaa tggcttccct agtgagtttg ggaagctctg gagcaacttg ctcagggcaa      60
ttggaggttt cctttcatt ggttaagaaa attacattgc ctagaagaaa ttgtagttgc     120
aattttaggc aattaggagg ggggaggaga tggcgttacg tttcggtgtg tagactttct     180
gtcactactg attatgtttc tgagcaagga atgctgtttt ctcttgaaaa tgcatatagt     240
gagagtaaag aagagggtct catcttgaag ccttctccta agccggtttt gaaatccggg     300
tctgatggaa atcggaaatt ggggagagt tcggtggcgt tttcgagtaa tgggaaattg      360
gataatgtag aggagaggaa gaaggttatt gattcattgg atgaggtatt agaaaaggcc     420
gagagattag aaacggcgaa cttacaagca gataatagaa aggatagcac aaatgtaaat     480
aaaccgtctc cgagtgtaag tagttcaacc aatggtaaac ctgtaaataa tttgaacaaa     540
gggaagccta agctgcgaa gagcgtttgg agaaagggaa atccagtttc tactgtgcaa      600
aaagtagtgc aagaatctcc gaagattgaa aaggttgaga gagtggaagc tcgaacgacc     660
agccaatcgt ctgaaacgat aagacccccca gtgccactac agaggcctga gattaagttg     720
caggcaaagc cttctactgc tcctccaccc atgcctaaga agccggtttt gaaggatgtg     780
gggatgtcct ccagagctga tgggaaggac cagtctgtga atctaaaga gaggaagcct      840 attctagtgg acaaatttgc caccaagaag gcatcagttg atccgtcgat tgctcaagca     900
gtaattgccc caccaaaacc tgctaaattt ccttctggaa agtttaaaga tgattatcgg     960
aagaagggtc ttgcagctgg tgggccgaag aggcgtatgg tcaatgatga tgatattgaa    1020
atgcatgaag acacttcaga gctcggtctt tctattcctg gtgctgctac ggctcggaaa    1080
ggcaggaaat ggagtaaggc aagtcgcaag gctgccagac gccaagcagc tagagatgcc    1140
gctcctgtta aagtggaaat cttagaggtt gaagaaaagg gcatgtcgac cgaagaatta    1200
gcatacaact tggctattag cgaaggtgaa attcttgggt acctgtattc taagggata     1260 aaaccagatg tgtgcaaac tcttgacaag gcaatggtaa agatgatatg tgaaagatat    1320
gacgtggagg ttttggacgc actttctgaa caaatggaag aaatggctcg aagaaggaa     1380 atttcgacg aagatgacct tgacaagctt gaagataggc ctcctgtgct tactataatg    1440
ggtcatgtag atcatggcaa gacgaccctt ctggattata cggaagag caaggttgct    1500 gcttctgaag ctggtgggat tacacaaggt attggtgctt ataaagtgga agtaccggtt    1560
gatggcaagt gctgccttg tgtctttctt gacactcccg gacacgaggc gttcggggca    1620
atgagggctc gtggagcaag agtgacagat attgctatta gttgtagc tgctgacgat      1680 gggatccgtc ctcaaacaaa tgaagccata gcacatgcaa aagcagctgg tgtacctatt    1740
gtggttgcaa ttaataagat tgacaaggat ggggctaatc cggaccgtgt gatgcaagag    1800 cttttcatcaa ttggtctaat gccagaggat tggggtggtg atacccccaat ggtcaagata    1860
```

```
agtgctctaa aaggtgaaaa tgtggacgag ttactcgaga cagccatgct tgtcgccgag    1920
ttgcaagagt taaaggctaa tcctcagagg aacgctaagg gcactgtaat tgaggctggt    1980
cttcataaat caaaaggacc cattgccact tttattgtgc agaatggtac cctcaaacaa    2040
ggggatactg tagtttgtgg ggaagcattt gggaaggttc gtgccctatt tgatcacgga    2100
gggaatcgcg ttgatgaagc tggtccatct attcccgtgc aggttattgg attgaataat    2160
gttccttttg ccggtgatga gttcgaggta gtgagttccc ttgatatagc tcgtgaaaag    2220
gcagaggtcc gtgcagagtc tttacgaaat gagcgtatag ctgctaaggc cggagacgga    2280
aaggttacgc tgtcatcctt ggcatcggct gtttcttcag ggaagatggc tggtttggat    2340
ttgcaccagt taaatatcat tttgaaggtt gatgttcagg gatcaatcga ggcattgagg    2400
caagctctag aagttcttcc tcaagataac gtcactttga agtttctctt acaagcgacc    2460
ggagatgtta ctacaagtga tgttgatctt gcagttgcta gtaaagctat tatcttgggg    2520
ttcaatgtga aggcaccagg ttctgtcgaa aaattagcag ataacaaagg tgttgaaatt    2580
cggctttata aagtcattta tgatctaatt gacgacatgc ggagtgcaat ggaaggaatg    2640
ctagatcccg ttgaggaaca agttgcaatt ggttcagccg aagtgcgggc tacattcagt    2700
agtggtagtg gccgtgtcgc tggatgcatg gtgaccgagg gaaagattac caaaggctgt    2760
gggattcgag tgatacggaa gggaaaaact gtccacgttg gagttcttga ttcgttgcgt    2820
cgagtaa                                                             2827

<210> SEQ ID NO 72
<211> LENGTH: 200
<212> TYPE: DNA
<213> ORGANISM: artificial sequence
<220> FEATURE:
<223> OTHER INFORMATION: Synthetic Construct

<400> SEQUENCE: 72
tttcgagtaa tgggaaattg gataatgtag aggagaggaa gaaggttatt gattcattgg     60
atgaggtatt agaaaaggcc gagagattag aaacggcgaa cttacaagca gataatagaa    120
aggatagcac aaatgtaaat aaaccgtctc cgagtgtaag tagttcaacc aatggtaaac    180
ctgtaaataa tttgaacaaa                                                200

<210> SEQ ID NO 73
<211> LENGTH: 160
<212> TYPE: RNA
<213> ORGANISM: artificial sequence
<220> FEATURE:
<223> OTHER INFORMATION: Synthetic Construct

<400> SEQUENCE: 73
uucgaguaau gggaaauugg auaauguaga ggagaggaag aagguuauug auucauugga     60
ugagguauua gaaaaggccg agagauuaga aacggcgaac uuacaagcag auaauagaaa    120
ggauagcaca aauguaaaua aaccgucucc gaguguaagu                          160

<210> SEQ ID NO 74
<211> LENGTH: 160
<212> TYPE: RNA
<213> ORGANISM: artificial sequence
<220> FEATURE:
<223> OTHER INFORMATION: Synthetic Construct

<400> SEQUENCE: 74
```

```
acuuacacuc ggagacgguu uauuuacauu ugugcuaucc uuucuauuau cugcuuguaa    60
guucgccguu ucuaaucucu cggccuuuuc uaauaccuca uccaaugaau caauaaccuu   120
cuuccucucc ucuacauuau ccaauuuccc auuacucgaa                         160

<210> SEQ ID NO 75
<211> LENGTH: 22
<212> TYPE: DNA
<213> ORGANISM: artificial sequence
<220> FEATURE:
<223> OTHER INFORMATION: Synthetic Construct

<400> SEQUENCE: 75
atttctccaa acgctcttcg ca                                            22

<210> SEQ ID NO 76
<211> LENGTH: 22
<212> TYPE: DNA
<213> ORGANISM: artificial sequence
<220> FEATURE:
<223> OTHER INFORMATION: Synthetic Construct

<400> SEQUENCE: 76
atccaatttc ccattactcg aa                                            22

<210> SEQ ID NO 77
<211> LENGTH: 22
<212> TYPE: DNA
<213> ORGANISM: artificial sequence
<220> FEATURE:
<223> OTHER INFORMATION: Synthetic Construct

<400> SEQUENCE: 77
gtttctaatc tctcggcctt tt                                            22

<210> SEQ ID NO 78
<211> LENGTH: 21
<212> TYPE: DNA
<213> ORGANISM: artificial sequence
<220> FEATURE:
<223> OTHER INFORMATION: Synthetic Construct

<400> SEQUENCE: 78
ttgaactact tacactcgga g                                             21

<210> SEQ ID NO 79
<211> LENGTH: 21
<212> TYPE: DNA
<213> ORGANISM: artificial sequence
<220> FEATURE:
<223> OTHER INFORMATION: Synthetic Construct

<400> SEQUENCE: 79
taaccttctt cctctcctct a                                             21

<210> SEQ ID NO 80
<211> LENGTH: 21
<212> TYPE: DNA
<213> ORGANISM: artificial sequence
<220> FEATURE:
<223> OTHER INFORMATION: Synthetic Construct

<400> SEQUENCE: 80
gtccttccca tcagctctgg a                                             21
```

```
<210> SEQ ID NO 81
<211> LENGTH: 20
<212> TYPE: DNA
<213> ORGANISM: artificial sequence
<220> FEATURE:
<223> OTHER INFORMATION: Synthetic Construct

<400> SEQUENCE: 81
cgtagcagca ccaggaatag                                             20

<210> SEQ ID NO 82
<211> LENGTH: 21
<212> TYPE: DNA
<213> ORGANISM: artificial sequence
<220> FEATURE:
<223> OTHER INFORMATION: Synthetic Construct

<400> SEQUENCE: 82
cagcagctac aactataata g                                           21

<210> SEQ ID NO 83
<211> LENGTH: 25
<212> TYPE: RNA
<213> ORGANISM: artificial sequence
<220> FEATURE:
<223> OTHER INFORMATION: Synthetic Construct

<400> SEQUENCE: 83
cuaccaucaa caauggguguc cauac                                      25

<210> SEQ ID NO 84
<211> LENGTH: 27
<212> TYPE: RNA
<213> ORGANISM: artificial sequence
<220> FEATURE:
<223> OTHER INFORMATION: Synthetic Construct

<400> SEQUENCE: 84
guauggacac cauuguugau gguagua                                     27

<210> SEQ ID NO 85
<211> LENGTH: 23
<212> TYPE: RNA
<213> ORGANISM: artificial sequence
<220> FEATURE:
<223> OTHER INFORMATION: Synthetic Construct

<400> SEQUENCE: 85 aguuggugggg caaucaucaa uug                                        23

<210> SEQ ID NO 86
<211> LENGTH: 27
<212> TYPE: RNA
<213> ORGANISM: artificial sequence
<220> FEATURE:
<223> OTHER INFORMATION: Synthetic Construct

<400> SEQUENCE: 86
aacaauugau gauugcccac caacucu                                     27

<210> SEQ ID NO 87
<211> LENGTH: 24
<212> TYPE: RNA
<213> ORGANISM: artificial sequence
<220> FEATURE:
<223> OTHER INFORMATION: Synthetic Construct
```

```
<400> SEQUENCE: 87
ggucgacaac uugcuguaua guga                                          24

<210> SEQ ID NO 88
<211> LENGTH: 27
<212> TYPE: RNA
<213> ORGANISM: artificial sequence
<220> FEATURE:
<223> OTHER INFORMATION: Synthetic Construct

<400> SEQUENCE: 88
aucacuauac agcaaguugu cgaccuc                                       27

<210> SEQ ID NO 89
<211> LENGTH: 24
<212> TYPE: RNA
<213> ORGANISM: artificial sequence
<220> FEATURE:
<223> OTHER INFORMATION: Synthetic Construct

<400> SEQUENCE: 89
ugcaagguca ccuggacaga gaaa                                          24

<210> SEQ ID NO 90
<211> LENGTH: 27
<212> TYPE: RNA
<213> ORGANISM: artificial sequence
<220> FEATURE:
<223> OTHER INFORMATION: Synthetic Construct

<400> SEQUENCE: 90
uauucucugu ccaggugacc uugcaac                                       27

<210> SEQ ID NO 91
<211> LENGTH: 21
<212> TYPE: RNA
<213> ORGANISM: artificial sequence
<220> FEATURE:
<223> OTHER INFORMATION: Synthetic Construct

<400> SEQUENCE: 91
aacaugaaca aaaugccaga u                                             21

<210> SEQ ID NO 92
<211> LENGTH: 21
<212> TYPE: RNA
<213> ORGANISM: artificial sequence
<220> FEATURE:
<223> OTHER INFORMATION: Synthetic Construct

<400> SEQUENCE: 92
aucuggcauu uuguucaugu u                                             21

<210> SEQ ID NO 93
<211> LENGTH: 27
<212> TYPE: RNA
<213> ORGANISM: artificial sequence
<220> FEATURE:
<223> OTHER INFORMATION: Synthetic Construct

<400> SEQUENCE: 93
guauggacac cauuguugau gguagua                                       27

<210> SEQ ID NO 94
<211> LENGTH: 27
```

```
<212> TYPE: RNA
<213> ORGANISM: artificial sequence
<220> FEATURE:
<223> OTHER INFORMATION: Synthetic Construct

<400> SEQUENCE: 94
uacuaccauc aacaauggug uccauac                                              27

<210> SEQ ID NO 95
<211> LENGTH: 27
<212> TYPE: RNA
<213> ORGANISM: artificial sequence
<220> FEATURE:
<223> OTHER INFORMATION: Synthetic Construct

<400> SEQUENCE: 95
aauaauugau gauugcccac caacucu                                              27

<210> SEQ ID NO 96
<211> LENGTH: 27
<212> TYPE: RNA
<213> ORGANISM: artificial sequence
<220> FEATURE:
<223> OTHER INFORMATION: Synthetic Construct

<400> SEQUENCE: 96
agaguuggug ggcaaucauc aauuauu                                              27

<210> SEQ ID NO 97
<211> LENGTH: 27
<212> TYPE: RNA
<213> ORGANISM: artificial sequence
<220> FEATURE:
<223> OTHER INFORMATION: Synthetic Construct

<400> SEQUENCE: 97
aucacuauac agcaaguugu cgaccac                                              27

<210> SEQ ID NO 98
<211> LENGTH: 27
<212> TYPE: RNA
<213> ORGANISM: artificial sequence
<220> FEATURE:
<223> OTHER INFORMATION: Synthetic Construct

<400> SEQUENCE: 98
guggucgaca acuugcugua uagugau                                              27

<210> SEQ ID NO 99
<211> LENGTH: 27
<212> TYPE: RNA
<213> ORGANISM: artificial sequence
<220> FEATURE:
<223> OTHER INFORMATION: Synthetic Construct

<400> SEQUENCE: 99
uauucucugu ccaggugacc uugcaac                                              27

<210> SEQ ID NO 100
<211> LENGTH: 27
<212> TYPE: RNA
<213> ORGANISM: artificial sequence
<220> FEATURE:
<223> OTHER INFORMATION: Synthetic Construct

<400> SEQUENCE: 100
``` guugcaagguu caccuggaca gagaaua				27

<210> SEQ ID NO 101
<211> LENGTH: 29
<212> TYPE: RNA
<213> ORGANISM: artificial sequence
<220> FEATURE:
<223> OTHER INFORMATION: Synthetic Construct

<400> SEQUENCE: 101
gguauggaca ccauuguuga ugguaguac				29

<210> SEQ ID NO 102
<211> LENGTH: 29
<212> TYPE: RNA
<213> ORGANISM: artificial sequence
<220> FEATURE:
<223> OTHER INFORMATION: Synthetic Construct

<400> SEQUENCE: 102
gcuaccauca acaauggugu ccauaccac				29

<210> SEQ ID NO 103
<211> LENGTH: 29
<212> TYPE: RNA
<213> ORGANISM: artificial sequence
<220> FEATURE:
<223> OTHER INFORMATION: Synthetic Construct

<400> SEQUENCE: 103
gaagaauuga ugauugccca ccaacucac				29

<210> SEQ ID NO 104
<211> LENGTH: 29
<212> TYPE: RNA
<213> ORGANISM: artificial sequence
<220> FEATURE:
<223> OTHER INFORMATION: Synthetic Construct

<400> SEQUENCE: 104
gaguuggugg gcaaucauca auuauucac				29

<210> SEQ ID NO 105
<211> LENGTH: 27
<212> TYPE: RNA
<213> ORGANISM: artificial sequence
<220> FEATURE:
<223> OTHER INFORMATION: Synthetic Construct

<400> SEQUENCE: 105
gaucacuaua cagcaaguug ucgacac				27

<210> SEQ ID NO 106
<211> LENGTH: 27
<212> TYPE: RNA
<213> ORGANISM: artificial sequence
<220> FEATURE:
<223> OTHER INFORMATION: Synthetic Construct

<400> SEQUENCE: 106
gucgacaacu ugcuguauag ugaucac				27

<210> SEQ ID NO 107
<211> LENGTH: 29
<212> TYPE: RNA
<213> ORGANISM: artificial sequence

```
<220> FEATURE:
<223> OTHER INFORMATION: Synthetic Construct

<400> SEQUENCE: 107
guauucucug uccaggugac cuugcacac                                          29

<210> SEQ ID NO 108
<211> LENGTH: 29
<212> TYPE: RNA
<213> ORGANISM: artificial sequence
<220> FEATURE:
<223> OTHER INFORMATION: Synthetic Construct

<400> SEQUENCE: 108
gugcaagguc accuggacag agaauacac                                          29

<210> SEQ ID NO 109
<211> LENGTH: 58
<212> TYPE: RNA
<213> ORGANISM: artificial sequence
<220> FEATURE:
<223> OTHER INFORMATION: Synthetic Construct

<400> SEQUENCE: 109
guauggacac cauuguugau gguaguagaa auacuaccau caacaauggu guccauac          58

<210> SEQ ID NO 110
<211> LENGTH: 58
<212> TYPE: RNA
<213> ORGANISM: artificial sequence
<220> FEATURE:
<223> OTHER INFORMATION: Synthetic Construct

<400> SEQUENCE: 110
aauaauugau gauugcccac caacucugaa aagaguuggu gggcaaucau caauuauu          58

<210> SEQ ID NO 111
<211> LENGTH: 58
<212> TYPE: RNA
<213> ORGANISM: artificial sequence
<220> FEATURE:
<223> OTHER INFORMATION: Synthetic Construct

<400> SEQUENCE: 111
aucacuauac agcaaguugu cgaccacgaa aguggucgac aacuugcugu auagugau          58

<210> SEQ ID NO 112
<211> LENGTH: 58
<212> TYPE: RNA
<213> ORGANISM: artificial sequence
<220> FEATURE:
<223> OTHER INFORMATION: Synthetic Construct

<400> SEQUENCE: 112
uauucucugu ccaggugacc uugcaacgaa aguugcaagg ucaccuggac agagaaua          58

<210> SEQ ID NO 113
<211> LENGTH: 168
<212> TYPE: RNA
<213> ORGANISM: artificial sequence
<220> FEATURE:
<223> OTHER INFORMATION: Synthetic Construct

<400> SEQUENCE: 113
gaucacaaau uugccgguuu augaucaaau acggaacaua agacagauac acuugaacac        60
```

```
caugauucgc auuggggug ugguuacucg ucguucugga guauuccuc agugaugca    120 ggugaaguau gacugcaaua aauguggggc uauccugggu cccuuuuu              168
```

<210> SEQ ID NO 114
<211> LENGTH: 168
<212> TYPE: RNA
<213> ORGANISM: artificial sequence
<220> FEATURE:
<223> OTHER INFORMATION: Synthetic Construct

<400> SEQUENCE: 114

```
aaaaagggac ccaggauagc cccacauuua uugcagucau acuucaccug caucaacuga    60
gggaauacuc cagaacgacg aguaaccaca ccccaaugc gaaucauggu guucaagugu    120
aucugucuua uguuccguau uugaucauaa accggcaaau uugugauc                168
```

<210> SEQ ID NO 115
<211> LENGTH: 25
<212> TYPE: RNA
<213> ORGANISM: artificial sequence
<220> FEATURE:
<223> OTHER INFORMATION: Synthetic Construct

<400> SEQUENCE: 115

```
uuuucuaaua ccucauccaa ugaau                                         25
```

<210> SEQ ID NO 116
<211> LENGTH: 25
<212> TYPE: RNA
<213> ORGANISM: artificial sequence
<220> FEATURE:
<223> OTHER INFORMATION: Synthetic Construct

<400> SEQUENCE: 116

```
auucauugga ugagguauua gaaaa                                         25
```

<210> SEQ ID NO 117
<211> LENGTH: 25
<212> TYPE: RNA
<213> ORGANISM: artificial sequence
<220> FEATURE:
<223> OTHER INFORMATION: Synthetic Construct

<400> SEQUENCE: 117

```
uaucugcuug uaaguucgcc guuuc                                         25
```

<210> SEQ ID NO 118
<211> LENGTH: 25
<212> TYPE: RNA
<213> ORGANISM: artificial sequence
<220> FEATURE:
<223> OTHER INFORMATION: Synthetic Construct

<400> SEQUENCE: 118

```
gaaacggcga acuuacaagc agaua                                         25
```

<210> SEQ ID NO 119
<211> LENGTH: 25
<212> TYPE: RNA
<213> ORGANISM: artificial sequence
<220> FEATURE:
<223> OTHER INFORMATION: Synthetic Construct

<400> SEQUENCE: 119

```
ggagacgguu uauuuacauu ugugc                                         25
```

<210> SEQ ID NO 120
<211> LENGTH: 25
<212> TYPE: RNA
<213> ORGANISM: artificial sequence
<220> FEATURE:
<223> OTHER INFORMATION: Synthetic Construct

<400> SEQUENCE: 120
gcacaaaugu aaauaaaccg ucucc                                              25

<210> SEQ ID NO 121
<211> LENGTH: 25
<212> TYPE: RNA
<213> ORGANISM: artificial sequence
<220> FEATURE:
<223> OTHER INFORMATION: Synthetic Construct

<400> SEQUENCE: 121
uauuuacagg uuuaccauug guuga                                              25

<210> SEQ ID NO 122
<211> LENGTH: 25
<212> TYPE: RNA
<213> ORGANISM: artificial sequence
<220> FEATURE:
<223> OTHER INFORMATION: Synthetic Construct

<400> SEQUENCE: 122
ucaaccaaug guaaaccugu aaaua                                              25

<210> SEQ ID NO 123
<211> LENGTH: 185
<212> TYPE: RNA
<213> ORGANISM: artificial sequence
<220> FEATURE:
<223> OTHER INFORMATION: Synthetic Construct

<400> SEQUENCE: 123
gacggaaacc cuccagagag gcugugcaug ccuauuguua aacacaucga gucacuaggu        60
ggugaaguua aacuuaacuc ucguauacaa aagauucagu uggaccagag uggaagcgug       120
aagaguuuuu ugcuaaauaa cgggagggaa auacgaggag augccuaugu uuuugccacc       180
ccagu                                                                  185

<210> SEQ ID NO 124
<211> LENGTH: 185
<212> TYPE: RNA
<213> ORGANISM: artificial sequence
<220> FEATURE:
<223> OTHER INFORMATION: Synthetic Construct

<400> SEQUENCE: 124
acuggggugg caaaaacaua ggcaucuccu cguauuuccc uccguuauu uagcaaaaaa         60 cucuucacgc uuccacucug guccaacuga aucuuugua uacgagaguu aaguuuaacu       120
ucaccaccua gugacucgau guguuuaaca auaggcaugc acagccucuc uggagggu uu      180 ccguc                                                                  185

<210> SEQ ID NO 125
<211> LENGTH: 22
<212> TYPE: DNA
<213> ORGANISM: artificial sequence
<220> FEATURE:

<223> OTHER INFORMATION: Synthetic Construct

<400> SEQUENCE: 125
gtgatattac ctccaacacg at                                        22

<210> SEQ ID NO 126
<211> LENGTH: 21
<212> TYPE: DNA
<213> ORGANISM: artificial sequence
<220> FEATURE:
<223> OTHER INFORMATION: Synthetic Construct

<400> SEQUENCE: 126
atagtaagca caggatcgga g                                         21

<210> SEQ ID NO 127
<211> LENGTH: 21
<212> TYPE: DNA
<213> ORGANISM: artificial sequence
<220> FEATURE:
<223> OTHER INFORMATION: Synthetic Construct

<400> SEQUENCE: 127
ctttcaatcc actgtcaacc g                                         21

<210> SEQ ID NO 128
<211> LENGTH: 22
<212> TYPE: DNA
<213> ORGANISM: artificial sequence
<220> FEATURE:
<223> OTHER INFORMATION: Synthetic Construct

<400> SEQUENCE: 128
atcaagcgtt cgaagacctc at                                        22

<210> SEQ ID NO 129
<211> LENGTH: 21
<212> TYPE: DNA
<213> ORGANISM: artificial sequence
<220> FEATURE:
<223> OTHER INFORMATION: Synthetic Construct

<400> SEQUENCE: 129
cagcaatggc ggtaggtaac a                                         21

<210> SEQ ID NO 130
<211> LENGTH: 21
<212> TYPE: DNA
<213> ORGANISM: artificial sequence
<220> FEATURE:
<223> OTHER INFORMATION: Synthetic Construct

<400> SEQUENCE: 130
gcaattgccc gaatccttttt a                                        21

<210> SEQ ID NO 131
<211> LENGTH: 21
<212> TYPE: DNA
<213> ORGANISM: artificial sequence
<220> FEATURE:
<223> OTHER INFORMATION: Synthetic Construct

<400> SEQUENCE: 131
tagctcaata tcaaggtcct a                                         21

```
<210> SEQ ID NO 132
<211> LENGTH: 21
<212> TYPE: DNA
<213> ORGANISM: artificial sequence
<220> FEATURE:
<223> OTHER INFORMATION: Synthetic Construct

<400> SEQUENCE: 132
tcataagcac cctctataca c                                              21

<210> SEQ ID NO 133
<211> LENGTH: 20
<212> TYPE: DNA
<213> ORGANISM: artificial sequence
<220> FEATURE:
<223> OTHER INFORMATION: Synthetic Construct

<400> SEQUENCE: 133
ttcttaacct cgtcgagatg                                                20

<210> SEQ ID NO 134
<211> LENGTH: 21
<212> TYPE: DNA
<213> ORGANISM: artificial sequence
<220> FEATURE:
<223> OTHER INFORMATION: Synthetic Construct

<400> SEQUENCE: 134
atacccgagt atccttgcaa a                                              21

<210> SEQ ID NO 135
<211> LENGTH: 21
<212> TYPE: DNA
<213> ORGANISM: artificial sequence
<220> FEATURE:
<223> OTHER INFORMATION: Synthetic Construct

<400> SEQUENCE: 135
tagggcccac ggccttggag t                                              21

<210> SEQ ID NO 136
<211> LENGTH: 21
<212> TYPE: DNA
<213> ORGANISM: artificial sequence
<220> FEATURE:
<223> OTHER INFORMATION: Synthetic Construct

<400> SEQUENCE: 136
agcggatata acctcagcta g                                              21

<210> SEQ ID NO 137
<211> LENGTH: 21
<212> TYPE: DNA
<213> ORGANISM: artificial sequence
<220> FEATURE:
<223> OTHER INFORMATION: Synthetic Construct

<400> SEQUENCE: 137
cttcgtggcc caacgaatga c                                              21

<210> SEQ ID NO 138
<211> LENGTH: 21
<212> TYPE: DNA
<213> ORGANISM: artificial sequence
<220> FEATURE:
<223> OTHER INFORMATION: Synthetic Construct
```

```
<400> SEQUENCE: 138
caagctcggg tccctgcttg c                                              21

<210> SEQ ID NO 139
<211> LENGTH: 21
<212> TYPE: DNA
<213> ORGANISM: artificial sequence
<220> FEATURE:
<223> OTHER INFORMATION: Synthetic Construct

<400> SEQUENCE: 139
ggaaggtaga tgacatgagt t                                              21

<210> SEQ ID NO 140
<211> LENGTH: 21
<212> TYPE: DNA
<213> ORGANISM: artificial sequence
<220> FEATURE:
<223> OTHER INFORMATION: Synthetic Construct

<400> SEQUENCE: 140
gatggcatag ttaccactgt c                                              21

<210> SEQ ID NO 141
<211> LENGTH: 21
<212> TYPE: DNA
<213> ORGANISM: artificial sequence
<220> FEATURE:
<223> OTHER INFORMATION: Synthetic Construct

<400> SEQUENCE: 141
tccgtagctt acataccgaa g                                              21

<210> SEQ ID NO 142
<211> LENGTH: 21
<212> TYPE: DNA
<213> ORGANISM: artificial sequence
<220> FEATURE:
<223> OTHER INFORMATION: Synthetic Construct

<400> SEQUENCE: 142
tccaagtgaa taggagaaac a                                              21

<210> SEQ ID NO 143
<211> LENGTH: 21
<212> TYPE: DNA
<213> ORGANISM: artificial sequence
<220> FEATURE:
<223> OTHER INFORMATION: Synthetic Construct

<400> SEQUENCE: 143
agcagcttct gcgtcttcta c                                              21

<210> SEQ ID NO 144
<211> LENGTH: 21
<212> TYPE: DNA
<213> ORGANISM: artificial sequence
<220> FEATURE:
<223> OTHER INFORMATION: Synthetic Construct

<400> SEQUENCE: 144
acagcacgca cgccaagacc g                                              21

<210> SEQ ID NO 145
<211> LENGTH: 21
```

-continued

```
<212> TYPE: DNA
<213> ORGANISM: artificial sequence
<220> FEATURE:
<223> OTHER INFORMATION: Synthetic Construct

<400> SEQUENCE: 145
cgatgtaagg aatttggtaa a                                              21

<210> SEQ ID NO 146
<211> LENGTH: 21
<212> TYPE: DNA
<213> ORGANISM: artificial sequence
<220> FEATURE:
<223> OTHER INFORMATION: Synthetic Construct

<400> SEQUENCE: 146 cgagggatt gcagcagaag a                                               21

<210> SEQ ID NO 147
<211> LENGTH: 21
<212> TYPE: DNA
<213> ORGANISM: artificial sequence
<220> FEATURE:
<223> OTHER INFORMATION: Synthetic Construct

<400> SEQUENCE: 147
gtaggagaat acggtgaagt a                                              21

<210> SEQ ID NO 148
<211> LENGTH: 21
<212> TYPE: DNA
<213> ORGANISM: artificial sequence
<220> FEATURE:
<223> OTHER INFORMATION: Synthetic Construct

<400> SEQUENCE: 148
gaccccaaga aaatcgtctg c                                              21

<210> SEQ ID NO 149
<211> LENGTH: 19
<212> TYPE: DNA
<213> ORGANISM: artificial sequence
<220> FEATURE:
<223> OTHER INFORMATION: Synthetic Construct

<400> SEQUENCE: 149
gtcttacaag ggttctcaa                                                 19

<210> SEQ ID NO 150
<211> LENGTH: 21
<212> TYPE: DNA
<213> ORGANISM: artificial sequence
<220> FEATURE:
<223> OTHER INFORMATION: Synthetic Construct

<400> SEQUENCE: 150
atctatgttc acctccctgt g                                              21

<210> SEQ ID NO 151
<211> LENGTH: 21
<212> TYPE: DNA
<213> ORGANISM: artificial sequence
<220> FEATURE:
<223> OTHER INFORMATION: Synthetic Construct

<400> SEQUENCE: 151
```
ataaaccatt agctttcccg g                                              21

<210> SEQ ID NO 152
<211> LENGTH: 21
<212> TYPE: DNA
<213> ORGANISM: artificial sequence
<220> FEATURE:
<223> OTHER INFORMATION: Synthetic Construct

<400> SEQUENCE: 152
tttattggaa caagcggagt t                                              21

<210> SEQ ID NO 153
<211> LENGTH: 21
<212> TYPE: DNA
<213> ORGANISM: artificial sequence
<220> FEATURE:
<223> OTHER INFORMATION: Synthetic Construct

<400> SEQUENCE: 153
tatagcacca cttcccgata g                                              21

<210> SEQ ID NO 154
<211> LENGTH: 21
<212> TYPE: DNA
<213> ORGANISM: artificial sequence
<220> FEATURE:
<223> OTHER INFORMATION: Synthetic Construct

<400> SEQUENCE: 154
gcaccacgag gatcacaaga a                                              21

<210> SEQ ID NO 155
<211> LENGTH: 21
<212> TYPE: DNA
<213> ORGANISM: artificial sequence
<220> FEATURE:
<223> OTHER INFORMATION: Synthetic Construct

<400> SEQUENCE: 155
ccacccgaga aacctctcca a                                              21

<210> SEQ ID NO 156
<211> LENGTH: 21
<212> TYPE: DNA
<213> ORGANISM: artificial sequence
<220> FEATURE:
<223> OTHER INFORMATION: Synthetic Construct

<400> SEQUENCE: 156
cagtcttgac gagtgattcc t                                              21

<210> SEQ ID NO 157
<211> LENGTH: 22
<212> TYPE: DNA
<213> ORGANISM: artificial sequence
<220> FEATURE:
<223> OTHER INFORMATION: Synthetic Construct

<400> SEQUENCE: 157
gttcttcagg gctaaatcgg ga                                             22

<210> SEQ ID NO 158
<211> LENGTH: 22
<212> TYPE: DNA
<213> ORGANISM: artificial sequence
<220> FEATURE:
<223> OTHER INFORMATION: Synthetic Construct

<400> SEQUENCE: 158
gttcaagagc ttcaacgaga ac                                              22

<210> SEQ ID NO 159
<211> LENGTH: 22
<212> TYPE: DNA
<213> ORGANISM: artificial sequence
<220> FEATURE:
<223> OTHER INFORMATION: Synthetic Construct

<400> SEQUENCE: 159
atacaaactc caacgcgtcc ag                                              22

<210> SEQ ID NO 160
<211> LENGTH: 22
<212> TYPE: DNA
<213> ORGANISM: artificial sequence
<220> FEATURE:
<223> OTHER INFORMATION: Synthetic Construct

<400> SEQUENCE: 160
ctcttggaaa gcatcagtac ca                                              22

<210> SEQ ID NO 161
<211> LENGTH: 22
<212> TYPE: DNA
<213> ORGANISM: artificial sequence
<220> FEATURE:
<223> OTHER INFORMATION: Synthetic Construct

<400> SEQUENCE: 161
ctagaaagat acccacccaa tt                                              22

<210> SEQ ID NO 162
<211> LENGTH: 22
<212> TYPE: DNA
<213> ORGANISM: artificial sequence
<220> FEATURE:
<223> OTHER INFORMATION: Synthetic Construct

<400> SEQUENCE: 162
actagaattc aaacacccac cc                                              22

<210> SEQ ID NO 163
<211> LENGTH: 22
<212> TYPE: DNA
<213> ORGANISM: artificial sequence
<220> FEATURE:
<223> OTHER INFORMATION: Synthetic Construct

<400> SEQUENCE: 163
tttctgctca ttcaactcct cc                                              22

<210> SEQ ID NO 164
<211> LENGTH: 22
<212> TYPE: DNA
<213> ORGANISM: artificial sequence
<220> FEATURE:
<223> OTHER INFORMATION: Synthetic Construct

<400> SEQUENCE: 164
tatgtatgtg cccggttagc tt                                              22

```
<210> SEQ ID NO 165
<211> LENGTH: 21
<212> TYPE: DNA
<213> ORGANISM: artificial sequence
<220> FEATURE:
<223> OTHER INFORMATION: Synthetic Construct

<400> SEQUENCE: 165
tcatatccaa gccagatcct c                                              21

<210> SEQ ID NO 166
<211> LENGTH: 21
<212> TYPE: DNA
<213> ORGANISM: artificial sequence
<220> FEATURE:
<223> OTHER INFORMATION: Synthetic Construct

<400> SEQUENCE: 166
tgcatcacac atcaccaaga t                                              21

<210> SEQ ID NO 167
<211> LENGTH: 21
<212> TYPE: DNA
<213> ORGANISM: artificial sequence
<220> FEATURE:
<223> OTHER INFORMATION: Synthetic Construct

<400> SEQUENCE: 167
gtactcctgt tcaatgccat a                                              21

<210> SEQ ID NO 168
<211> LENGTH: 21
<212> TYPE: DNA
<213> ORGANISM: artificial sequence
<220> FEATURE:
<223> OTHER INFORMATION: Synthetic Construct

<400> SEQUENCE: 168
attgatacca gcatagagac a                                              21

<210> SEQ ID NO 169
<211> LENGTH: 21
<212> TYPE: DNA
<213> ORGANISM: artificial sequence
<220> FEATURE:
<223> OTHER INFORMATION: Synthetic Construct

<400> SEQUENCE: 169
agcaattctc tctagaatgt a                                              21

<210> SEQ ID NO 170
<211> LENGTH: 21
<212> TYPE: DNA
<213> ORGANISM: artificial sequence
<220> FEATURE:
<223> OTHER INFORMATION: Synthetic Construct

<400> SEQUENCE: 170
catcattcct catcgactta g                                              21

<210> SEQ ID NO 171
<211> LENGTH: 21
<212> TYPE: DNA
<213> ORGANISM: artificial sequence
<220> FEATURE:
<223> OTHER INFORMATION: Synthetic Construct
```

<400> SEQUENCE: 171
ctctcgttgc cctctccata a                                          21

<210> SEQ ID NO 172
<211> LENGTH: 21
<212> TYPE: DNA
<213> ORGANISM: artificial sequence
<220> FEATURE:
<223> OTHER INFORMATION: Synthetic Construct

<400> SEQUENCE: 172
caacgcccca ggagaaagtt c                                          21

<210> SEQ ID NO 173
<211> LENGTH: 195
<212> TYPE: RNA
<213> ORGANISM: artificial sequence
<220> FEATURE:
<223> OTHER INFORMATION: Synthetic Construct

<400> SEQUENCE: 173
cugaagcugg ugaaggugaa gauggacgaa ugaaaucugc gauuggaauu gggacccuuc   60
uucaggaugg cuugggagau acgaucaggg ugucucuaac agaaccacca gaagaggaga  120
uagacccuug cagaagguug gcaaaucuug gaacaaaagc agcugaaauu cagcaaggag  180
uggcaccauu ugaag                                                 195

<210> SEQ ID NO 174
<211> LENGTH: 195
<212> TYPE: RNA
<213> ORGANISM: artificial sequence
<220> FEATURE:
<223> OTHER INFORMATION: Synthetic Construct

<400> SEQUENCE: 174
cuucaaaugg ugccacuccu ugcugaauuu cagcugcuuu uguuccaaga uuugccaacc   60
uucugcaagg gucuaucucc ucuucggug guucuguuag agacacccug aucguaucuc  120
ccaagccauc cugaagaagg gucccaauuc caaucgcaga uuucauucgu ccaucuucac  180
cuucaccagc uucag                                                 195

<210> SEQ ID NO 175
<211> LENGTH: 183
<212> TYPE: RNA
<213> ORGANISM: artificial sequence
<220> FEATURE:
<223> OTHER INFORMATION: Synthetic Construct

<400> SEQUENCE: 175
ucccaucaaa guucccuaca aaauaugugc aguuccuau cuuccuugcc gccauucaua    60
caaacuaugu ugauuguaca aggggcuug gugauuugu ucuuucuaag aguguugaca   120
augagauugu acuguggag ccaauuauga aggagcaauc uccggagag gguucaguug   180 aca                                                               183

<210> SEQ ID NO 176
<211> LENGTH: 183
<212> TYPE: RNA
<213> ORGANISM: artificial sequence
<220> FEATURE:
<223> OTHER INFORMATION: Synthetic Construct

<400> SEQUENCE: 176 ugcaacuga  acccucucca  ggagauugcu  ccuucauaau  uggcucccac  aguacaaucu    60
cauugucaac  acucuuagaa  agaacaaaau  caccaagcca  ccuuguacaa  ucaacauagu   120
uuguaugaau  ggcggcaagg  aagauaggaa  acugcacaua  uuuuguaggg  aacuuugaug   180
gga                                                                      183

<210> SEQ ID NO 177
<211> LENGTH: 143
<212> TYPE: RNA
<213> ORGANISM: artificial sequence
<220> FEATURE:
<223> OTHER INFORMATION: Synthetic Construct

<400> SEQUENCE: 177
uugugcuuaa  aacaucgacc  agacagacaa  uauuucuucc  uguuguugga  cuaguugauc    60
cugauacgcu  gaaaccuggu  gauuuaguug  gugucaacaa  agauaguuau  cuuauccugg   120
acacucugcc  gucggaauau  gau                                              143

<210> SEQ ID NO 178
<211> LENGTH: 143
<212> TYPE: RNA
<213> ORGANISM: artificial sequence
<220> FEATURE:
<223> OTHER INFORMATION: Synthetic Construct

<400> SEQUENCE: 178
aucauauucc  gacggcagag  uguccaggau  aagauaacua  ucuuuguuga  caccaacuaa    60
aucaccaggu  uucagcguau  caggaucaac  uaguccaaca  acaggaagaa  auauugucug   120
ucuggucgau  guuuuaagca  caa                                              143

<210> SEQ ID NO 179
<211> LENGTH: 159
<212> TYPE: RNA
<213> ORGANISM: artificial sequence
<220> FEATURE:
<223> OTHER INFORMATION: Synthetic Construct

<400> SEQUENCE: 179
cgcugcaguu  ggugaaguag  aucccggcaa  ggggauuuca  cuccgguuuc  cacgucuggu    60
ucguauccga  gaggauaaau  cuccagagga  cgccacauca  ucugagcagg  uggcggauau   120
guacagaucu  caagcaaaca  auccacaccg  caaaaagag                            159

<210> SEQ ID NO 180
<211> LENGTH: 159
<212> TYPE: RNA
<213> ORGANISM: artificial sequence
<220> FEATURE:
<223> OTHER INFORMATION: Synthetic Construct

<400> SEQUENCE: 180
cucuuuuugc  ggguggauu  guuugcuuga  gaucuguaca  uauccgccac  cugcucagau     60
gauguggcgu  ccucuggaga  uuuauccucu  cggauacgaa  ccagacgugg  aaaccggagu   120 gaaaucccu  ugccgggauc  uacuucacca  acugcagcg                             159

<210> SEQ ID NO 181
<211> LENGTH: 159
<212> TYPE: RNA
<213> ORGANISM: artificial sequence

```
<220> FEATURE:
<223> OTHER INFORMATION: Synthetic Construct

<400> SEQUENCE: 181
uaaagauggc ggaaaaaucg acuaugauaa auugauugac aaauucggcu gucagcgacu    60
ugauuuaucg cucauucaga gaauugagcg caucacugcu cguccugcuc auguauuucu   120
ucgccgcaac guuucuucg cucaccguga uuugaauga                           159

<210> SEQ ID NO 182
<211> LENGTH: 159
<212> TYPE: RNA
<213> ORGANISM: artificial sequence
<220> FEATURE:
<223> OTHER INFORMATION: Synthetic Construct

<400> SEQUENCE: 182
ucauucaaau cacggugagc gaagaaaacg uugcggcgaa gaaauacaug agcaggacga    60
gcagugaugc gcucaauucu cugaaugagc gauaaaucaa gucgcugaca gccgaauuug   120
ucaaucaauu uaucauaguc gauuuuccg ccaucuuua                           159

<210> SEQ ID NO 183
<211> LENGTH: 150
<212> TYPE: RNA
<213> ORGANISM: artificial sequence
<220> FEATURE:
<223> OTHER INFORMATION: Synthetic Construct

<400> SEQUENCE: 183
ugaagcugau gcugaaggaa aggauauuga ugcuagugaa guaguucgcc caagggugcc    60
auuagaagcu ugccuagcua gcuacucagc uccggaggag gugauggacu ucuacagcac   120
ugcauugaag gcaaaggcaa cugcuacaaa                                    150

<210> SEQ ID NO 184
<211> LENGTH: 150
<212> TYPE: RNA
<213> ORGANISM: artificial sequence
<220> FEATURE:
<223> OTHER INFORMATION: Synthetic Construct

<400> SEQUENCE: 184
uuuguagcag uugccuuugc cuucaaugca gugcuguaga aguccaucac cuccuccgga    60
gcugaguagc uagcuaggca agcuucuaau ggcacccuug ggcgaacuac uucacuagca   120
ucaauauccu uuccuucagc aucagcuuca                                    150

<210> SEQ ID NO 185
<211> LENGTH: 155
<212> TYPE: RNA
<213> ORGANISM: artificial sequence
<220> FEATURE:
<223> OTHER INFORMATION: Synthetic Construct

<400> SEQUENCE: 185
acaccugccc uaacaucucg ggguuuucuc gaagaagauu uuguuaaagu ggccgaguau    60
uuugaugcug cuguuaagcu ggcucuaaaa aucaaggcug acacaaaagg aacaaaguug   120
aaggacuucg uugccaccuu gcagucuggu guuuu                              155

<210> SEQ ID NO 186
<211> LENGTH: 155
<212> TYPE: RNA
```

```
<213> ORGANISM: artificial sequence
<220> FEATURE:
<223> OTHER INFORMATION: Synthetic Construct

<400> SEQUENCE: 186
aaaacaccag acugcaaggu ggcaacgaag uccuucaacu uuguuccuuu ugugucagcc      60
uugauuuuua gagccagcuu aacagcagca ucaaaauacu cggccacuuu aacaaaaucu    120
ucuucgagaa aaccccgaga uguuagggca ggugu                                155

<210> SEQ ID NO 187
<211> LENGTH: 159
<212> TYPE: RNA
<213> ORGANISM: artificial sequence
<220> FEATURE:
<223> OTHER INFORMATION: Synthetic Construct

<400> SEQUENCE: 187
ugaacuacga agcaggcaaa uucuccaaaa guaaaggcau uggaguuuuu gggaaugacg      60
ccaagaauuc uaauauaccu guagaagugu ggagauacua ucugcuaaca aacaggccug    120
agguaucaga cacauuguuc acuugggcgg aucuucaag                           159

<210> SEQ ID NO 188
<211> LENGTH: 159
<212> TYPE: RNA
<213> ORGANISM: artificial sequence
<220> FEATURE:
<223> OTHER INFORMATION: Synthetic Construct

<400> SEQUENCE: 188
cuugaagauc cgcccaagug aacaaugugu cugauaccuc aggccuguuu guuagcagau      60
aguaucucca cacucuaca gguauauuag aauucuuggc gucauuccca aaaacuccaa     120
ugccuuuacu uuuggagaau ugccugcuu cguaguuca                            159

<210> SEQ ID NO 189
<211> LENGTH: 24
<212> TYPE: DNA
<213> ORGANISM: artificial sequence
<220> FEATURE:
<223> OTHER INFORMATION: Synthetic Construct

<400> SEQUENCE: 189
tcccatctcc cacatgggtt actg                                            24

<210> SEQ ID NO 190
<211> LENGTH: 24
<212> TYPE: DNA
<213> ORGANISM: artificial sequence
<220> FEATURE:
<223> OTHER INFORMATION: Synthetic Construct

<400> SEQUENCE: 190
cagtaaccca tgtgggagat ggga                                            24

<210> SEQ ID NO 191
<211> LENGTH: 22
<212> TYPE: DNA
<213> ORGANISM: artificial sequence
<220> FEATURE:
<223> OTHER INFORMATION: Synthetic Construct

<400> SEQUENCE: 191
ggctgatgaa attcaagtgc ta                                              22
```

<210> SEQ ID NO 192
<211> LENGTH: 21
<212> TYPE: DNA
<213> ORGANISM: artificial sequence
<220> FEATURE:
<223> OTHER INFORMATION: Synthetic Construct

<400> SEQUENCE: 192
aaactgagct tggaaataat c                                              21

<210> SEQ ID NO 193
<211> LENGTH: 22
<212> TYPE: DNA
<213> ORGANISM: artificial sequence
<220> FEATURE:
<223> OTHER INFORMATION: Synthetic Construct

<400> SEQUENCE: 193
gaacccaaaa ttgtcacttt tt                                             22

<210> SEQ ID NO 194
<211> LENGTH: 24
<212> TYPE: DNA
<213> ORGANISM: artificial sequence
<220> FEATURE:
<223> OTHER INFORMATION: Synthetic Construct

<400> SEQUENCE: 194
atgcacttgt ttatactctt gtca                                           24

<210> SEQ ID NO 195
<211> LENGTH: 21
<212> TYPE: DNA
<213> ORGANISM: artificial sequence
<220> FEATURE:
<223> OTHER INFORMATION: Synthetic Construct

<400> SEQUENCE: 195
atttattagt gttctaaaga a                                              21

<210> SEQ ID NO 196
<211> LENGTH: 24
<212> TYPE: DNA
<213> ORGANISM: artificial sequence
<220> FEATURE:
<223> OTHER INFORMATION: Synthetic Construct

<400> SEQUENCE: 196
tgtagtagct tataagatta gctt                                           24

<210> SEQ ID NO 197
<211> LENGTH: 22
<212> TYPE: DNA
<213> ORGANISM: artificial sequence
<220> FEATURE:
<223> OTHER INFORMATION: Synthetic Construct

<400> SEQUENCE: 197
gttgtccctt ttatgggtct tt                                             22

<210> SEQ ID NO 198
<211> LENGTH: 21
<212> TYPE: DNA
<213> ORGANISM: artificial sequence
<220> FEATURE:

<223> OTHER INFORMATION: Synthetic Construct

<400> SEQUENCE: 198
cccgtgcaat ttctgggaag c						21

<210> SEQ ID NO 199
<211> LENGTH: 24
<212> TYPE: DNA
<213> ORGANISM: artificial sequence
<220> FEATURE:
<223> OTHER INFORMATION: Synthetic Construct

<400> SEQUENCE: 199
attagttttt tatacacgaa agat					24

<210> SEQ ID NO 200
<211> LENGTH: 24
<212> TYPE: DNA
<213> ORGANISM: artificial sequence
<220> FEATURE:
<223> OTHER INFORMATION: Synthetic Construct

<400> SEQUENCE: 200
atctttcgtg tataaaaaac taat					24

<210> SEQ ID NO 201
<211> LENGTH: 22
<212> TYPE: DNA
<213> ORGANISM: artificial sequence
<220> FEATURE:
<223> OTHER INFORMATION: Synthetic Construct

<400> SEQUENCE: 201
ttggtggttt ggccacttcc gt					22

<210> SEQ ID NO 202
<211> LENGTH: 21
<212> TYPE: DNA
<213> ORGANISM: artificial sequence
<220> FEATURE:
<223> OTHER INFORMATION: Synthetic Construct

<400> SEQUENCE: 202
tttgtttgct atttagctgg a						21

<210> SEQ ID NO 203
<211> LENGTH: 24
<212> TYPE: DNA
<213> ORGANISM: artificial sequence
<220> FEATURE:
<223> OTHER INFORMATION: Synthetic Construct

<400> SEQUENCE: 203
caatttgcag caactcgcac tgga					24

<210> SEQ ID NO 204
<211> LENGTH: 22
<212> TYPE: DNA
<213> ORGANISM: artificial sequence
<220> FEATURE:
<223> OTHER INFORMATION: Synthetic Construct

<400> SEQUENCE: 204
tcccaccatt ggctattccg ac					22

```
<210> SEQ ID NO 205
<211> LENGTH: 21
<212> TYPE: DNA
<213> ORGANISM: artificial sequence
<220> FEATURE:
<223> OTHER INFORMATION: Synthetic Construct

<400> SEQUENCE: 205
ctgtctctct ttttaatttc t                                              21

<210> SEQ ID NO 206
<211> LENGTH: 24
<212> TYPE: DNA
<213> ORGANISM: artificial sequence
<220> FEATURE:
<223> OTHER INFORMATION: Synthetic Construct

<400> SEQUENCE: 206
ccactttgca cacatctccc actt                                           24

<210> SEQ ID NO 207
<211> LENGTH: 22
<212> TYPE: DNA
<213> ORGANISM: artificial sequence
<220> FEATURE:
<223> OTHER INFORMATION: Synthetic Construct

<400> SEQUENCE: 207
gaggatccac gtatagtagt ag                                             22

<210> SEQ ID NO 208
<211> LENGTH: 21
<212> TYPE: DNA
<213> ORGANISM: artificial sequence
<220> FEATURE:
<223> OTHER INFORMATION: Synthetic Construct

<400> SEQUENCE: 208
tttaaataaa gaaattattt a                                              21

<210> SEQ ID NO 209
<211> LENGTH: 40
<212> TYPE: DNA
<213> ORGANISM: artificial sequence
<220> FEATURE:
<223> OTHER INFORMATION: Synthetic Construct

<400> SEQUENCE: 209
taatacgact cactataggg cttgagttta taacgaagct                          40

<210> SEQ ID NO 210
<211> LENGTH: 39
<212> TYPE: DNA
<213> ORGANISM: artificial sequence
<220> FEATURE:
<223> OTHER INFORMATION: Synthetic Construct

<400> SEQUENCE: 210
taatacgact cactataggg cttctaattt tcaaggacg                           39

<210> SEQ ID NO 211
<211> LENGTH: 24
<212> TYPE: DNA
<213> ORGANISM: artificial sequence
<220> FEATURE:
<223> OTHER INFORMATION: Synthetic Construct
```

<400> SEQUENCE: 211
agcttctaat tttcaaggac gata                                    24

<210> SEQ ID NO 212
<211> LENGTH: 25
<212> TYPE: DNA
<213> ORGANISM: artificial sequence
<220> FEATURE:
<223> OTHER INFORMATION: Synthetic Construct

<400> SEQUENCE: 212
gtcatgtgac tccactttga ttttg                                   25

<210> SEQ ID NO 213
<211> LENGTH: 25
<212> TYPE: DNA
<213> ORGANISM: artificial sequence
<220> FEATURE:
<223> OTHER INFORMATION: Synthetic Construct

<400> SEQUENCE: 213
ctcaattccg ataaatttaa gaaat                                   25

<210> SEQ ID NO 214
<211> LENGTH: 26
<212> TYPE: DNA
<213> ORGANISM: artificial sequence
<220> FEATURE:
<223> OTHER INFORMATION: Synthetic Construct

<400> SEQUENCE: 214
cgaagctatt ggaccgacct aatttc                                  26

<210> SEQ ID NO 215
<211> LENGTH: 26
<212> TYPE: DNA
<213> ORGANISM: artificial sequence
<220> FEATURE:
<223> OTHER INFORMATION: Synthetic Construct

<400> SEQUENCE: 215
ggaattgagg gcttcccaga aattgc                                  26

<210> SEQ ID NO 216
<211> LENGTH: 25
<212> TYPE: DNA
<213> ORGANISM: artificial sequence
<220> FEATURE:
<223> OTHER INFORMATION: Synthetic Construct

<400> SEQUENCE: 216 atgactttt gattggtgaa actaa                                    25

<210> SEQ ID NO 217
<211> LENGTH: 45
<212> TYPE: DNA
<213> ORGANISM: artificial sequence
<220> FEATURE:
<223> OTHER INFORMATION: Synthetic Construct

<400> SEQUENCE: 217
taatacgact cactataggt ggaactccaa cacacaaaaa atttc              45

<210> SEQ ID NO 218
<211> LENGTH: 41

```
<212> TYPE: DNA
<213> ORGANISM: artificial sequence
<220> FEATURE:
<223> OTHER INFORMATION: Synthetic Construct

<400> SEQUENCE: 218
taatacgact cactataggt tgaaaaataa tcataatttt a                    41

<210> SEQ ID NO 219
<211> LENGTH: 22
<212> TYPE: DNA
<213> ORGANISM: artificial sequence
<220> FEATURE:
<223> OTHER INFORMATION: Synthetic Construct

<400> SEQUENCE: 219
gcataatata ttgatccggt at                                        22

<210> SEQ ID NO 220
<211> LENGTH: 24
<212> TYPE: DNA
<213> ORGANISM: artificial sequence
<220> FEATURE:
<223> OTHER INFORMATION: Synthetic Construct

<400> SEQUENCE: 220
ctgaaagttc atacataggt actc                                      24

<210> SEQ ID NO 221
<211> LENGTH: 22
<212> TYPE: DNA
<213> ORGANISM: artificial sequence
<220> FEATURE:
<223> OTHER INFORMATION: Synthetic Construct

<400> SEQUENCE: 221
ggtactccaa ttttcagtat at                                        22

<210> SEQ ID NO 222
<211> LENGTH: 24
<212> TYPE: DNA
<213> ORGANISM: artificial sequence
<220> FEATURE:
<223> OTHER INFORMATION: Synthetic Construct

<400> SEQUENCE: 222
ctgaaaattg gagtacctat gtat                                      24

<210> SEQ ID NO 223
<211> LENGTH: 27
<212> TYPE: DNA
<213> ORGANISM: artificial sequence
<220> FEATURE:
<223> OTHER INFORMATION: Synthetic Construct

<400> SEQUENCE: 223
atgtatgaac tttcagaata ttatacc                                   27

<210> SEQ ID NO 224
<211> LENGTH: 22
<212> TYPE: DNA
<213> ORGANISM: artificial sequence
<220> FEATURE:
<223> OTHER INFORMATION: Synthetic Construct

<400> SEQUENCE: 224
```

```
taccggatca atatattatg ct                                             22

<210> SEQ ID NO 225
<211> LENGTH: 647
<212> TYPE: DNA
<213> ORGANISM: Amaranthus palmeri

<400> SEQUENCE: 225
ttcaaaatga atttaaaatt atataaaaat caatatggac acaagaccgg atatcaatcc     60
gacccgaaat agttgacttg aaatcaacct gatgacccga atgaacacct ctagttatca    120
ctaacaaggg tcagattgcg tacatcaaac ccctcaaatc ctgcttaggt gggagcttgt    180
caatggctta ggggtaacgg aatgtgtgt gctatgtaca ttgtgcatct attcttatgc     240
ttatttatgt tgagttagtt ttttttttgg atcaaatata aagagcttaa cttttgtatt    300
ttcttgatgt ggtgtagtgg tgatgaagat caggctgaga gaatctaaat tggccaaaat    360
tctgagagaa caagaagtga gttcagccct tcgtgctgct ggtgttggtg tgattagttg    420
catcatacag agagatgaag gcgaactcc gatgaggcat tcattctatt ggtcagcaga     480
aaaacaatat tatagtgagg agcctttact acgtcatttg gaaccccctc tatctatgta    540
tctcgagctg gtactagtct ctgaaccgat tgcctttctt ctgctttgtt attttgtgtg    600
atatttcgac ttaagtctaa tttacatcgt tttgtacatt tgttatc                  647

<210> SEQ ID NO 226
<211> LENGTH: 738
<212> TYPE: DNA
<213> ORGANISM: Amaranthus palmeri

<400> SEQUENCE: 226
ttttgctttt ttactattat ttccttcttt tcaaggattt gagttgttta ttgctgactg     60
cttcctatgt attacccata tgtctctgta taggcattac gggagctgta cctacatcta    120
actcctatac aacgtgtgaa tattgcccgg catcctaatc gccccacttt tcttgaccac    180
gtattcagca tcacagaaaa ggtttctgat ttattataat ttttgtcatt tgtattcact    240
cttcaataaa gtacatccat tatcaatctt tacggaggtt gttcacacaa cttcttgttt    300
cattttgcat aattagtttg tggaactaca tggagatcgt gctggttatg atgaccctgc    360
tatagttact ggccttggta cgatagatgg taggcgttat atgttcattg gtcatcaaaa    420
gggaagaaat acgaaggaaa atattgcacg gaatttcggg atgcctactc ctcatgggta    480
aatgctttac tataatgttt tactttaatt taattaccta tgttatttag gatgaaaatg    540
aatactttc ttattactat tacttaggtt cctaatgcac aaaaaccgta attattaatg     600
taccctaatg gaattaacac atggtaatta agctctccgc tttgtgtaat taatccaatt    660
ttttagagag tcaaatagtt caggttaaac tagagctttt catacccaaa taataaaacc    720
aagggtaaat ttccaaaa                                                  738

<210> SEQ ID NO 227
<211> LENGTH: 880
<212> TYPE: DNA
<213> ORGANISM: Amaranthus palmeri

<400> SEQUENCE: 227
atgtgatcaa ttaaagaaaa agtctaatta tatgagcccg tctcacagtg acggagctat     60
catagagccc atgggtcac gtgcccttcg gggttttag aaaaaattca agtatactt       120
ttctattaat aagagtaaaa atgtaaaatt aatattaaac tcttttgata ataaatactc    180
```

| | |
|---|---|
| tctcacttta gtaattttgt cttatttatt tattttatct catgtgttta ataaggtcag | 240 |
| ttgacttatt ttgttccatt ttcttttatg gtatgccgta tttaaaattt tagcaagtaa | 300 |
| agataaaata gttgttaatc ttacaaataa aactctatcg aaatttcatc cattagttaa | 360 |
| tgtccccaaa aagtccgaac tacaaatcga ccactgtcat cacatggtga gatagtctca | 420 |
| tataaaacga gttcagttat taaaggaaaa taggaaacac gaaacagtta atttaggcgg | 480 |
| ggcctatgta ttatccaaat gtgatactcc agtccacatt actcagtcct tccaattgaa | 540 |
| cagttggctt aatctaccaa gcgcgtggcc ataaatgcct ctaacacttt tcaatctctc | 600 |
| agataactct cacaccactt atcatcacaa ttcacaatta ctctaattct ttttattcct | 660 |
| ttccatgtcg ctaattttct actgattcag gttttattct cagcttttat caatttatt | 720 |
| tcatgctttt tatgtcaatt tcttgtttcg cattttgtct tccacttgct gtctgtttta | 780 |
| ttaatcaatt ttgtatgatt gttggaataa ttgtatgtat ttttcatgat tttcctctta | 840 |
| tggaggttca taatgtattg ctagatttgt ttactttcac | 880 |

<210> SEQ ID NO 228
<211> LENGTH: 453
<212> TYPE: DNA
<213> ORGANISM: Amaranthus palmeri

<400> SEQUENCE: 228

| | |
|---|---|
| aatttgagcg ggaaaatttt aatatcatta aatagtcttt gctttagtat atagaatagt | 60 |
| taaaattaat agtcaaactt attgtaatag catgcactaa tctataataa tcttatcctg | 120 |
| aaagctataa taaaattata aaaaaatata tgtgaaaaac taatttgagc gggaaaattt | 180 |
| taaccaaggg ctaacacgta tcattaaata gtctttactt tagtatatag aatgataatt | 240 |
| aacgatcata aaacaaaatt gtcactttca gtagcaaact tacaaaatga gcagagtacc | 300 |
| tcatatcata aaattgcttc tttctcattt gttgtgttgc tctcatttta ggagttcatc | 360 |
| gtttatatcg tcgtcttacc actcaatcac ttttagattt attagtagca cttcctcaat | 420 |
| ctacagcagc aatttctaca gttcaacaac ctc | 453 |

<210> SEQ ID NO 229
<211> LENGTH: 3953
<212> TYPE: DNA
<213> ORGANISM: Amaranthus palmeri

<400> SEQUENCE: 229

| | |
|---|---|
| ggaaaattta cctagaataa tccaatttat tcgtgatttt tctacaaatt ccaacttcaa | 60 |
| ggggtatttg cctaaagtaa ttaaacttgg atacccgat gacctgctat agtagataat | 120 |
| ttaccagaaa attaaaaatg aaaattaatt taaaattaga gaaaaatttt gaaatttcat | 180 |
| ataaaaaatt ttaaataata aaaaaatat aaatttttt gaacatttta ttttaatcta | 240 |
| tcttttttga aaaaataaaa cttagttata gcaagtgatc tggtcaccgg gtttactcta | 300 |
| ggaaaatatc cctcaaagtt gagattattc atggttaata aataggtgag attattatag | 360 |
| aaaaattacg aataaattgg attattgttg gtaattttt tttcaaaact atccctagga | 420 |
| aggaccttat tagtgattct ccctctactt tggaggagta tattgtggac ttcccatctt | 480 |
| ccttaattgt attgtaactt ttaactattg attcttaaa aaaagaact tataaaattg | 540 |
| tagggttaat aaaatctaag attttatcta atttcacttt gattattccg attttgtatt | 600 |
| cacattattt taaatgacat tcgtcaaata aaaaaaaata gttcattgc attccaattt | 660 |

-continued

```
tgttgactag ggggattaaa gaaagaatag tatcaataat cgtaatgtag caagtagtac    720
aaaagaagta tatttcaata tgtcaaactt tgatctcgtt gtaacttgta atttgtacga    780
tgcggtgtga atgacatact tcaccttttt cattatttta tactggtagt gacatgggat    840
tattattgcg atatttgcag taatgaaaat tttttggtt gttgctttta caaacaaaaa    900
ttctaccgaa ttttttatta atttaattca acacgttggt gttacccatg atttataggt    960
ctgggtccgc cactgctagc taacattaaa caatttaaca aactcaatac accaacctaa   1020
aaataaaatt tttttggcca taattttag aattttagtt tttaaacatt atatttggga   1080
attttttttc cttttatata tataaaataa aaaaaaatcc aaaaaagggg acacacatta   1140
atacacactt gaaagcatcg atgatatcga agaaaaacca gatggggtgc ccaattatct   1200
tcgtctcctt cgatattatc gaattcatta acaacattat atcaaaaacc aaccaaatta   1260
ccaactttcg aaaccaatat tcgccgtatt tttctctatt caacaatccc tacaatggcg   1320
gcattgccag cttcttcttc tcctgcaatt tcggaatcac ccacttgcaa ttttcttcct   1380
attcaaaaaa tcactaccac tcgctttcta aggtttcatt cggttttact cccaagccta   1440
aatttggcct tttctccaag gtttattttc tatctctttt ttaattggtt aatcaattgg   1500
attgttgaat ttttcagggt ttaacggtat aatatttgtg ggttttttcg agtacattct   1560
gggtttgtag tattggattt ggcattgctt ttaattttg agattgggtt ttttgggttt   1620
tatttggttc ttgtgattca aggttattga tttgctgcat taaactgtat ttatggaatg   1680
atgtcaatta actgttacat tacattgctt tatggttttc atcatgctga ttagtgatta   1740
ctgtgtttga atctcttgct tctctatgta ctatttaatc tgatacaaca agtacaacct   1800
agaaaacagg ttaaagggaa atctataagc ttagtaaatt aacacttgaa agaagctaat   1860 gacgagaga ggggtctttt tggagaaggc agttttcata ttattgctca gttctctagt   1920
gcagctttac ttcacttaga cactcttaag tagaggtcat aggtgttcag aatagatcca   1980
aagacccgat atttaccgga cttgtaaac aacttaaccc gacttcaaaa tgaatttaca   2040
atcatataaa agcaatatgg acttaaaccg attttgaacc gaccttgacc ggttgatccg   2100
aatgaatgcc tctactctta agcatgtcaa ctgtaatatg aaatagaatt ataatataaa   2160
ctaagttcat gttttcttca actacaaatg aaatttatg acccaaataa tgtgtgaata   2220 ccccagcaa taggttgaat ggcatttagt tcagttgatt ttagcagacc acatctgccc   2280
tcatattcca ttgttcagtt tagttgttag tagctgtaca taatagacta attaagttgt   2340
cattttgatc catgttatgg ttgtctggga taaacggatt ggaattgtat aataaaagtt   2400
tgggttagtt tattttgctc taggaggggt tatgtcatat gtgcactctg ttggcaaccc   2460
gacaatgcaa aacattttca tacttggtac gttgttgcgt gttttgtgcc cttcgtattt   2520
tgtaactgtt gatgaatgtg taaaaatata ctacatgatc atatgctagt aggtcttctt   2580
cacctagtaa agaaattttt ctaacacgag aagttcaaaa catattccca ttaccattat   2640
ccaacatcag tacccgagtc caagtaacat agggtgtccc tttatgatag tataagaatt   2700
ggtgcatgaa aaacgcgtga ttgtagcgag gatagtaggc gggagaggta caggatttga   2760
aaattttgaa ttgctaaaac gctatcagga tcttgttttt cttactttga tgttgctttt   2820
ttgaaatttg atccaaattg ttaaattatt gagactaatt cctgttgatc ctgtcgtgaa   2880
ctttgtagaa tctttcaggc cgcattctca cagtgaaggc tcaattaaac aaggtgagtc   2940 ttttttttgtc ttaactctta tgcagttcat tatctcttct actgatgaga aaaccactat   3000
ttggcctaat tctaatttcc ttctaggttg ctttggatgg ttcaaatcat gctccatcac   3060
```

```
cttcgcacga aaaatctggg ctaccagccc aagaaaagaa gaacgatgag ccgtctagtg    3120
aatcttctcc tgcagcatca gtgtctgaag aacgagtctc cgaattcttg agccaagttg    3180
ccggtcttgt caagtatgta acattcttta ttttcattct tccacacact cgcaatttgg    3240
ataacgagat gtctttagag acgtctgggg aacaagggga aaatgagtct agaggttgct    3300
agagagaacg agataaatac taatatatat gaatatttca taatccacat taaaaaaata    3360
caattgaatt tgcattatgg tgaactacca agaatcgaa tatttttta tactccatgt    3420 tttgtggtct agacttgtgg attctagaga cattgtagag ttgcaattaa acaactgga    3480 ctgtgagata ttgatccgca agcaggaagc tattcctcaa ccacaaattc ctaatcctac    3540
acatgtcgtt gcaatgcaac caccaccacc tgctgtagcg tctgccccag ctcccgtctc    3600
ttcaccagcc actcctcgtc ctgcgttacc tgccccagcg cctgctgcca cgtcagctaa    3660
gccatcactt ccacctctca agagccctat gtcaggcaca ttctaccgta gtccagctcc    3720
tggcgagccg cctttcgtga aggtaagtgt atacccctttt tttagtgttg tatttctgtg    3780
ttatatcaat ttttgcattt tgtgaagctg aaaataaatc tttcattttc cataggttgg    3840
agataaagtt aagaaaggac aagtcatatg cattatcgag gctatgaagt tgatgaatga    3900
aatcgaggta cgtatgttat tgctttaaac ttcatgcctt aggccgtgaa gtt           3953

<210> SEQ ID NO 230
<211> LENGTH: 595
<212> TYPE: DNA
<213> ORGANISM: Amaranthus palmeri

<400> SEQUENCE: 230
acaaaaagca caaattcaat aatatactct ttaagtttgt ttatcttcta attagttcgg      60
ttaaaacggt tccccacttt cttctccgac tctcacaatt atcttcccct attcattttt     120
cttccaccct ctctaatggc ggctgtttcc ttcaatatca atggtggaaa gattggaact     180
ttatgttcaa gacacgaatt cgtttgtggg tttgtaagaa aatttcattt tagaactcat     240
acttctatat ttgaaaaaca tatgccaaaa acttcaaggt ttaaagcaat ggaagtttct     300
gcaaatgcaa cagtaaatat agttcctgtt tcagctcatt ctaggtaatt ttatttctcg     360
aaaatttccg atttacaatt aaattaatct tgttttgtag gtaatgaatt gcagaagaaa     420
tagatggatt cttatttgtt tattggtatt tgtttataaa ttttttgttta tattagttttc    480 tgaattgtga ttattctgat tgtatgtcaa ggtttaggtt gttattaata aatgtaaatt     540
ggattgattg aagttgcaat aaggtgatgg cgtgatgctg attgttgtaa atttt          595

<210> SEQ ID NO 231
<211> LENGTH: 667
<212> TYPE: DNA
<213> ORGANISM: Amaranthus palmeri

<400> SEQUENCE: 231
caacaatgag aatttagaat ccatatcaat cttgatattc aagggtattt aagtaattaa      60
agaacaacca ttgttaagcg cctccactat cttcttcctt ctcattctcc attctcgctt     120
agctttcctc tcgcactaat tacctccatt tgcaaccttt caagctttca acaatggcgt     180
ccacttcttc aaacccacca ttttcctctt ttactaaacc taacaaaatc cctaatctgc     240
aatcatccat ttacgctatc cctttgtcca attctcttaa acccacttct tcttcttcaa     300
tcctccgccg ccccccttcaa atctcatcat cttcttctca atcacctaaa cctaaacctc     360
```

```
cttccgctac tataactcaa tcaccttcat ctctcaccga tgataaaccc tcttcttttg      420
tttcccgatt tagccctgaa gaacccagaa aaggttgcga tgttctcgtt gaagctcttg      480
aacgtgaagg tgttaccgat gttttttgctt accctggtgg agcatccatg gaaatccatc    540
aagctcttac tcgttctaat atcattagaa atgttcttcc tcgacatgaa caaggtgggg     600
ttttcgctgc tgaaggctac gctcgtgcta ctggacgcgt tggagtttgt attgccactt    660
ctggtcc                                                              667

<210> SEQ ID NO 232
<211> LENGTH: 2415
<212> TYPE: DNA
<213> ORGANISM: Amaranthus palmeri

<400> SEQUENCE: 232
atttggataa cttttccctt tgattcgaat cggattattt ttaatacagt attatgaact       60
gatttaatga agtggagga agtttcaatt tttaaagttg taggtgtaat gttttctcat       120
tttggatatg aaagtggagg aagtttcaat ttcgaatcat gtttgccagt tgattcaatg     180
aatgctcttg gaaatgacca agagttcaag gcttcttgtt ataaaacatt tcaattttga     240
tctaagaatg aactatttag aacttaaagt aattaaatta ttagttataa cttataaaaa     300
aattcaattt taaccttaaa tttataaatt atgaccttaa aaagatcaag tattgaacgc    360
atatttagaa aaattataat tcggcttatc agtctcatat tgagacggtc tcgtccaaga    420
caagttgtat catttatata atcaaatata attatgagtg tattcatgta ggtttcaact    480
ttaaagccta ggtgaaagat atgttgtagc atctttgtga aagtcagcct ataacttggt    540
tctaaaattt tgaagcataa ccatatagtc cctcgaattc attcaagttg tccaatttac    600
ttttttatac ttgccgagac aacatttaaa cccttaatat ttctaattaa tcttaattaa   660
aaattatgaa aatttgatat taataatctt tgtattgaaa cgaatttaac aagatctcac    720
atgactatgt tttaacttat agattaaaaa aaaatacaaa ttaagagtga taagtgaata   780
gtgccccaaa acaaatggga caacttagat gaattggagg taatattagg tagcaagtga    840
tcactttaac atcaaaattg atcacttata ggttcaaatt gaaacttta ctttaattga      900 tatgtttaaa tactacttta aattgaaatt gatattttta aggtcaaaat tgaaaccttt     960
aagattataa ttgaaaattg gcagaagaaa acaaagaga aagaatataa gacacgcaaa    1020
ttgtaccgat ctactcttat ttcaatttga gacggtctcg cccaagacta gatgttcggt    1080
catcctacac caaccccaaa aaattcaaca acaaagtctt ataatgattc cctctaatct    1140
actacagtct acaccaaccc actttctctt tgcccaccaa aactttggtt tggtaagaac    1200
taagccctct tctttccctt ctctctctct taaaagcctg aaaaatccac ctaactttt    1260 tttaagccaa caaacaacgc caaattcaga gaaagaataa tggctcaagc tactaccatc   1320
aacaatggtg tccaaactgg tcaattgcac catactttac ccaaatccca gttacccaaa   1380
tcttcaaaaa ctcttaattt tggatcaaac ttgagaattt ctccaaagtt catgtctttta  1440 accaataaaa aagagttggt gggcaatcat tcaattgttc ccaagattca agcttctgtt    1500
gctgctgcag ctgagaaacc ttcatctgtc ccagaaattt gttacaacc catcaaagag    1560 atctctggta ctgttcaatt gcctgggtca agtctttat ccaatcgaat ccttctttta    1620
gctgctttgt ctgaggtatt tatttctcaa ctgcgaaaac aatctctatt tgatattgga    1680
atttatatta catactccat cttgttgtaa ttgcattagt agatacttat gttttgacct    1740
ttgttcattt gtttgttgaa ttggtagtgt tgagaatttg aatgtaatta tttgttttc    1800
```

```
catgtgaatt taatctgatt aaatccactt cttatttatg ttaagttgca atgatgtttg   1860
ccaaatggtt atcattgaag gataagtttg cctacttttg accctcccaa cttcgcggtg   1920
gtagagccat tttatgttat tgggggaaat tagaaagatt tatttgtttt gcctttcgaa   1980
atagtagcgt tcgtgattct gatttgggtg tctttataga tatgatatat gggttattca   2040
tgtaatgtgt aggtttatgc attatgttgg atgcatgtct ggtgttattg ctgtaaatgg   2100
atgaatgttt ttatttggag acatttttc attcattttt tcccttttta attggaactg    2160
gaagagggaa agttattggg agtaattaaa aggttgtgag ttcgatacac tgcatcaaag   2220
acgaagaact tgacatagat gttgaaggct aatccttatc actgcttgaa ttcaatatgt   2280
atctgaaaat tttacccctc tatatgcatc tgtttttgct aataaagtgt ttttggacta   2340
tcatgttttg tgatgcttaa gagggtgata ttactgagat aaatggaaat atcaaaataa   2400
catctattgt gaagt                                                    2415

<210> SEQ ID NO 233
<211> LENGTH: 3049
<212> TYPE: DNA
<213> ORGANISM: Amaranthus palmeri

<400> SEQUENCE: 233
caagcttcaa ttatcgtttt caaaataagt atttcaaagt ctataaagat attgtataag     60
ttttagttca aatttaataa gttttttttt tttttttttt tttttttttg aaaatccaaa    120
ttgaataagt taatarttaa attatgacat ataattatga catataattt gaccatgata    180
ttttacaatc taacttaatt ttgaacttat tatttctaat attcaattat cgttctaaaa    240
ataagtattt aaattgtata gatatattgt ataacattta gttcaaattt aattattgat    300
agttttattg actatttatt tggkgtttga aattcatcca tagaatgata gaataacacc    360 atttttata taacttcgtt ctaaaatttt gaagcataac catatactcc ctccaattca    420
tccaagttgt ccaatttact ttttcatact tgccgaggca acatttaaac ccttaatatt    480
tctaattaat gttaattaaa aattatgaaa atttgatatt aataatcctt gtattgaaac    540
aaatctaaca agatcccaca tgactatgtt ttaacttata gattaagaat aaaatacaaa    600
ttaagagtaa taagtgaata gtgtcccaaa acaaatagga caacttggat gaattggagg    660
tagtattagg tagcaagtga tcactttaac atcaaaattg atcagttaca ggttcaaatt    720 gaaacttttta ctttaattga tatgttaaa tactactttta aattgaaatt gatattctta    780
aggtcaaaat tgaaaacttt aagattataa ttgaaaaatg cccagaagat gaaaaaacag    840
agagaaagca tgtaagacac gcaaattgaa ccagtctact cttgtttcaa tttgagacgg    900
tctcgcccaa gaccagatgt tcagtcatcc tacaccaacc caaaaaaatt caacaacaaa    960
ctcttataat gattccctct aatctactag agtctacacc aacccacttt ctctttgccc   1020
accaaaactt tggtttggtg agaactaagc cctcttcttt cccttctctc tcttaaaagc   1080
ctaaaaccca ccaacttttt cagccaagaa acaacgcgaa attcagagga agaataatgg   1140
ctcaagctac taccatcaac aatggtgtcc atactggtca attgcaccat actttaccca   1200
aaacccagtt acccaaatct tcaaaaactc ttaattttgg atcaaacttg agaatttctc   1260
caaagttcat gtctttaacc aataaaagag ttggtgggca atcatcaatt gttcccaaga   1320
ttcaagcttc tgttgctgct gcagctgaga accttcatc tgtcccagaa attgtgttac    1380
aacccatcaa agagatctct ggtactgttc aattgcctgg gtcaaagtct ttatccaatc   1440
```

-continued

| | |
|---|---|
| gaatccttct tttagctgct tgtctgagg gcacaacagt ggtcgacaac ttgctgtata | 1500 |
| gtgatgatat tctttatatg ttggacgctc tcagaactct tggttaaaa gtggaggatg | 1560 |
| atagtacagc caaaagggca gtcgtagagg gttgtggtgg tctgtttcct gttggtaaag | 1620 |
| atggaaagga agagattcaa cttttccttg gtaatgcagg aacagcgatg cgcccattga | 1680 |
| cagctgcggt tgccgttgct ggaggaaatt caagttatgt gcttgatgga gtaccaagaa | 1740 |
| tgagggagcg ccccattggg gatctggtag caggtctaaa gcaacttggt tcagatgtag | 1800 |
| attgttttct tggcacaaat tgccctcctg ttcgggtcaa tgctaaagga ggccttccag | 1860 |
| ggggcaaggt caagctctct ggatcggtta gtagccaata tttaactgca cttctcatgg | 1920 |
| ctactccttt gggtcttgga gacgtggaga ttgagatagt tgataaattg atttctgtac | 1980 |
| cgtatgttga aatgacaata aagttgatgg aacgctttgg agtatccgta gaacatagtg | 2040 |
| atagttggga caggttctac attcgaggtg gtcagaaata caaatctcct ggaaaggcat | 2100 |
| atgttgaggg tgatgcttca agtgctagct acttcctagc cggagccgcc gtcactggtg | 2160 |
| ggactgtcac tgtcaagggt tgtggaacaa gcagtttaca ggtataatgt taacccttac | 2220 |
| ccttcacatt gttctgctaa attctagagg acccttcaa ttctgggtgg gataagcacg | 2280 |
| gcaatttgac cgcaaaaaaa ttgcaaaatt attctgctga tagaacatct cgagatgaga | 2340 |
| tcatattgag ttttggcgtc aacataaacc taatcaaata atgaaaaata caaacatcat | 2400 |
| atggtttctt ttgtctttat gactagacac tctctattat tccttgattg ggatcttatt | 2460 |
| tgaaattgct gtgtagccta cacctcatgt tcagattttg ttcgtatacc agactttttct | 2520 |
| tgattgggat cttatttgtc ccctggattt tgcataggt gatgtaaaat ttgccgaagt | 2580 |
| tcttgagaag atgggttgca aggtcacctg gacagagaat agtgtaactg ttactggacc | 2640 |
| acccaggat tcatctggaa agaaacatct gcgtgctatc gacgtcaaca tgaacaaaat | 2700 |
| gccagatgtt gctatgactc ttgcagttgt tgccttgtat gcagatgggc ccaccgccat | 2760 |
| cagagatgtg gctagctgga gagtgaagga aaccgaacgg atgattgcca tttgcacaga | 2820 |
| actgagaaag cttggggcaa cagttgagga aggatctgat tactgtgtga tcactccgcc | 2880 |
| tgaaaagcta aaccccaccg ccattgaaac ttatgacgat caccgaatgg ccatggcatt | 2940 |
| ctctcttgct gcctgtgcag atgttcccgt cactatcctt gatccgggat gcacccgtaa | 3000 |
| aaccttcccg gactactttg atgttttaga aaagttcgcc aagcattga | 3049 |

<210> SEQ ID NO 234
<211> LENGTH: 1113
<212> TYPE: DNA
<213> ORGANISM: Amaranthus palmeri

<400> SEQUENCE: 234

| | |
|---|---|
| tcttaatttg tattttatta ttaatctata agttaaaaca tagtcaagtg agatcttgtt | 60 |
| tgattcgtct ctatgcaagg attttcatat caacttttca taattttga ttatacacaa | 120 |
| ttacaaatat taacgaacga ataagtgcat taaaaagagt gcaaaagca aatgggacac | 180 |
| ttgtgttgaa taggagggag tatacattaa gatgaatcta acgagatctc acatggatat | 240 |
| aatttgtctt ctatatatgt ctaaaaaatc ttgatcaaat ttctctttcc aaaatagaat | 300 |
| attctaaatg gaagaacat taagaaacgg agggagtact tataagttaa gatagttggg | 360 |
| ggtatttagg taaaaaaatc tatgccaaaa gtagaaagtg gacaattaga gtgactttac | 420 |
| taaataagga agtggacat ttaaaatgaa tcggagggag catattaact ttattttcaa | 480 |
| agtgtgaaac ataatcatat ttaggtaaaa aaattatcaa tttaacgtca aaattgatca | 540 |

```
caaataggtt aaaattgaaa ttttttatgt taattgatct attgttcact ttaaattgaa      600
attgatatcc tttaaggtta aaattaatac ctctaaaatt aaaattatta aaggcccaga      660
aaataaaaaa aaaagaagac aggctattag taaaattatt aagtatgtaa ggttgataca      720
cgcgcgaatt gagccggccc acttttagtt tcaatttgaa acagtctcaa tcaagaccaa      780
ttatttatta ttttattatt ttattgtttt aagctcaatg ggttggactt gataaattat      840
attttgagga gacgggctat tagtaaaatt aatagttgga atcttttttg atatactata      900
aaaagaggta tctggtggag ccttaaatct gcgcaattga agtcctcaat acacatctcg      960
ctcttcttat tctctttcat ctatttcctc ctttgatcaa actacgccat gtctctctta     1020
aatgatctcg ttaaccttaa tctctctgaa actaccgata agattatcgc tgaatacata     1080
tggtaataca acaatccttc ctcttttca ttt                                   1113

<210> SEQ ID NO 235
<211> LENGTH: 882
<212> TYPE: DNA
<213> ORGANISM: Amaranthus palmeri
<220> FEATURE:
<221> NAME/KEY: misc_feature
<222> LOCATION: (451)..(459)
<223> OTHER INFORMATION: n is a, c, g, or t

<400> SEQUENCE: 235
aaaaaaccgt cttatttgta gaaaataaaa aactaaaaag tagtatcaac ttttagacta       60
gtcataagtg agtggcatca aacttgttct ataaaaaggg aagagttcct caacttgaga      120 ttcatattt ttgtgatttc taaatagaag aacatactca tcttccactt ctcttattca      180 tcaaattta tttgttcccc aaaaaaacat gtctcttctt acagatctca tcaatcttaa      240
tctttctgac tccactgaga agatcattgc tgaatacata tggtcagttt tcatcccttt      300 ttttttacctt taatcccact ttttgttttt acccaccatt ttttcatct attttctctt     360 aaagatttta acttttact ttttgtgta tataacattc attttttcaa ttgggtaggt       420
tagaaaattt ctataaataa ataaataaat nnnnnnnnnt acctaatcc cacttttgt       480 ttctacccac cattttttc atcaatttt cttaaagatt ttaactttt ttaacttttt       540 cttggttttt gtgtatatac caatcattta ttttcactag tgtaggttaa aaaatatcta      600
aaaataaata aaatagaata aaaatgtaat cactagatta acccatgaat tatttcccctt    660 gttttactc aaacttttta cccttgttaa aaaataatg atataaataa attttgagg        720 gtttgttaaa cccatatgta atctatatcg aaaaaattag atagcgggtt ttgttgtgga     780
caaactaaat aacaaattta ggaataaact tttgagggtt tattgaaaaa ataacccata     840
tttaatctat atcgaaaaaa tgatagcgag ctttgtatag at                        882

<210> SEQ ID NO 236
<211> LENGTH: 1083
<212> TYPE: DNA
<213> ORGANISM: Amaranthus palmeri

<400> SEQUENCE: 236
cgtcgaagta gaagacgcgg aagctgcttt taacatcagc gtttcgcatg gggctattcc       60
ctgtgtttct cctattcaat tggaaaacgg tgtcgttta tctgaggttc atttatatgg      120
ggatgttgtg cttcggtatg taagctacgg aaatgaatgt ggggatgtgt tttttcttcc     180
tgggtttgag gaaatgccgg aggaatcatc gtttagagga cttgattttg gcattcgaag     240
```

```
gttggatcat gctgtaggga atgtccctga gttggctcct gcaattgctt atttgaagaa      300
gtttactggg tttcatgagt ttgctgagtt tacagctgaa gatgttggga cgagtgaaag      360
tggattgaat tcagccgtat tggcaaacaa tgatgaaatg gtgttgtttc cgatgaatga      420
acctgtgtat gggacaaaaa ggaagagcca aattcaaact tatttggagc ataatgaagg      480
ggctggtgta cagcatttgg cttttgatgag tgaagacata ttttggactt aagggagat      540 gaggaagaga agtgttcttg gtgggtttga gtttatgccg tcgccgcctc cgacttatta      600
ccggaatttg aggaacagag ctgctgatgt attgagtgag gagcagatga aggagtgtga      660
agagttgggg attttggtgg ataaagatga tcagggcact ttgcttcaaa tcttcaccaa      720
acctattgga gacaggtaaa ttttaatctt gctttcaatt gcttttgctt gatggattga      780
ctagcaaatt tgatcgcatt tgttgctta tgacttga tgatacttcc tctgtttcga         840
aatactcgct acattcgcta cattttgttt tgtgcactat tcatcgttca gcttatttt      900 acatattgcg actaatgtgt aactaaaaat atagtcaagt gggatcttgt ttgaatcgtc      960
taatggcata ctttcatcat attaaatttt tataatttt agattagtgt agtttaagat     1020
attaatgctc aaaattgtgc attggattgc gtaaaaagt gaaatgtagc aagtattatg     1080
aaa                                                                  1083

<210> SEQ ID NO 237
<211> LENGTH: 788
<212> TYPE: DNA
<213> ORGANISM: Amaranthus palmeri

<400> SEQUENCE: 237
aaaaccaaag gaaataagtt ataggtagga aaaattgtta ttgaagttaa tgtagtaaac       60
tagtaactta aactgtgata ccccggattt agcttaaaaa gagattgata gactactcat     120
atcaacaagg tgcatcttct tttctaggga gcccatttgc taagaactct acagttaagc     180
gtgcttggtg gggagcaatc ttaggatggg tgacctcctg ggaagttttc ctgggtgcgc     240
acgggtgagg ccaaagtgcg ttaaaaagac ttgtgttggt ctgtggggct tgtctacagt     300
ctccatgagt agtcaccggc ggtacgagag gccggggtgt tacataaaca gactcaaagg     360
cgctaagcca agtagccaat agcaacatgt gtggcctgcg gacagtcaca aaaacacaca     420
atttcttatt tttactctct tttatctctt ttaggcttta gccatcaaca ataaaacaac     480
atgataaagc aattcattta ctgctaaatt ccaacaattt ggtccctttt tcctgttctt     540 tcagttttcac atacctctt atcaatctat atccaaaact atttcatttt ccaaactctt    600
ttaaacccaa aaatcaaaac ttttgattga agaacaaact ttgggggttt tggaaaatga     660
gtcattttgg atatgcttgt gctactcaat ccacatcaag atatgttctt ttaggaaatt     720
caaataaccc cacttcaatt tcatctattg gaagtgattt tttgggtcat tctgtgagaa     780
atttcagt                                                             788

<210> SEQ ID NO 238
<211> LENGTH: 2631
<212> TYPE: DNA
<213> ORGANISM: Amaranthus palmeri

<400> SEQUENCE: 238
tggtacctac cctgtttaca ttttcaattt cccccttttt tctctactac tcctactta       60 ttgattctta tccatgtgtg ttctatggga attgacatta attgttcagg tgtgtatgct     120
ggtgatcctt ctaagttgag tatgaaagct gcatttggaa aggtctggac cttagagcaa     180
```

```
aagggtggta gtatcattgc cggtacactc aaaactattc aggaaaggaa gaataatcct    240
ccaccgcctc gagacccgtc cgtaatcacc attactcatt gctttccttc accttgtatc    300
ttaccttaat atacatgtat ttaattgata atgtcacatt gcctcatttg cagccgcctt    360
cctaaaccta agggccagac tgttggatcc tttaggaaag ggctcattat gttacctacc    420
gccattgctg ctaggtatct tttgactctc aaatcttaaa tatttctcat cttctccttc    480
tgctaatact agtatgttta ccatcttttt attttttag gcttggcagt aaagtcaaac     540
tatcgtggac actttctaat attgataagt cgctcaatgg tgaatacaat ctcacttatc    600
aaacacccga tggaccggtt tctgttagga ccaaagcggt tgtcatgact gtcccttcat    660
acattgcaag tagcctgctt cgtccgctct cagtgagtat cattcttttcc ttcatttctt    720 ttcgtttatt gttgtccaat gtcttgttaa acaccagttt ggccttgtgc tcgtgaatta    780
tggctacaat gttaactgat tcaggcactg tgggagatgc ctaagtttct aaaacctctg    840
cgcataatgt ttgtttggat gttaggaatt gcattgaaaa attgcttttg tgatgttgat    900
gttaatacca attacaagtg tgttcttcaa cttctgcaat accttgttcg agtgagcttg    960
agggggttta gattagtgtc caatgtgaaa ctagcaaatg aactccaagc gctgggatag    1020
gtccttggga tggagcccct gatacccaag acagtattca aaccctctaa gtagagtgag    1080
agatcaagga aagaaactgg gtggttcctc aaatcgtaaa aaatgaatac agtgtcatga    1140
ttgctaatct tatcacaaat cgtaaaaaat gaattatggt cgattttgga ctattttgg    1200 gtcattttga gtgaatctcg aacttaaaaa gcgagtcttc tagcagttct tgttacagcg    1260
gggcatacat aggtaggaat ttggttttt actatttgag cctttgact gttgtggccg     1320 gtaatatgga atagtctagc acttctgcgt gtgtacaact agtatttatt gtaattatgt    1380
gatcgcactt aactctcaga taaaaccctta agcactaaca ttttgttttg gttgaaggaa    1440
tcaggaggaa agaaaattga gggatttgtt ggtatataga ttccttttgtt tggataacaa    1500 aattggagtg gagagatttg gaaggaagaa ttttataggg attagttccc attacactta    1560
tgttgattac aaaatttctc caaaagtgga agattttga gtgaaaatgt ttttttatttc    1620 tcttcctctc cctttctttc cctcttaaac aaacaaggaa agttaatctt atcattccgt    1680
accttcccct tctgttcttt tttttctctc caaaattctt atcctaacgt agtgttattg    1740
tcactgtctt atgaacgaga attcttttct tcctaatact gcttgtgttg cacagtcaat    1800
gatttagcta gatcatcttt ggttagctac tcaaatatt tacataaaat acttgtagaa     1860
ataaatacca ataggtcttg tcaagaagta gtttcaatgc tataagtttt aaccaatcct    1920
caaaatttac accatggaga tatctgcgga taagaactag taactgtagc agctgtaact    1980
gttgcaatca gttttatggt ttgccttgca aatcaaactt tggatgttgt ttgccttaca    2040
atttgttact attacgtgaa gtttagtgtt cgcccttcac attgtacttt ggttttttgtt    2100 ttccttgcaa tttgctcttt gaagtataaa gtgctgagtg ctgagtgctg agtgctgacc    2160
tttcctgctc aggatgttgc tgcagattct cttctcaat tttactatcc accagtcgca     2220
gcagtgtccc tttcttatcc caaagaagca attagaccag aatgcttgat cgatggagaa    2280
ctaaaaggat tcgggcaatt gcatcctcgc agccagggtg tggaaacctt gggtatatgc    2340
tcccattcaa ctatatctca atttttatga gtattttctt ttctctgaat tattcaattt    2400
ggtgacgtta aattttgatt gtactcgaca ggaacaattt atagttcatc tcttttccct    2460
ggtcgagcac cacctggtag gaccttgatc ttgagctaca ttggaggtgc tacaaatgtt    2520
```

-continued

```
ggcatattac aaaaggcaag tcatttatac aattatatct gttgtatcct caaataagtg    2580
ggtatcaatc ctgacgacat gcttgcttgt atcgatgcag agtgaagatg a             2631
```

<210> SEQ ID NO 239
<211> LENGTH: 23
<212> TYPE: DNA
<213> ORGANISM: Euphorbia heterophylla

<400> SEQUENCE: 239

```
agtttacagg gagatgtaaa gtt                                              23
```

<210> SEQ ID NO 240
<211> LENGTH: 23
<212> TYPE: DNA
<213> ORGANISM: Euphorbia heterophylla

<400> SEQUENCE: 240

```
agtttgcagg gagatgtgaa att                                              23
```

<210> SEQ ID NO 241
<211> LENGTH: 23
<212> TYPE: DNA
<213> ORGANISM: Ambrosia trifida

<400> SEQUENCE: 241

```
agtttacagg gggatgtaaa gtt                                              23
```

<210> SEQ ID NO 242
<211> LENGTH: 23
<212> TYPE: DNA
<213> ORGANISM: Abutilon theophrasti

<400> SEQUENCE: 242

```
agtttgcagg gtgatgtaaa att                                              23
```

<210> SEQ ID NO 243
<211> LENGTH: 23
<212> TYPE: DNA
<213> ORGANISM: Xanthium strumarium

<400> SEQUENCE: 243

```
agtttgcagg gtgatgtgaa att                                              23
```

<210> SEQ ID NO 244
<211> LENGTH: 23
<212> TYPE: DNA
<213> ORGANISM: Ipomoea hederacea

<400> SEQUENCE: 244

```
agtttacagg gggatgttaa gtt                                              23
```

<210> SEQ ID NO 245
<211> LENGTH: 23
<212> TYPE: DNA
<213> ORGANISM: Chenopodium album

<400> SEQUENCE: 245

```
agtttacagg gtgatgtaaa att                                              23
```

<210> SEQ ID NO 246
<211> LENGTH: 23
<212> TYPE: DNA
<213> ORGANISM: Digitaria sanguinalis

<400> SEQUENCE: 246
agtttgcagg gtgatgtgaa att                                              23

<210> SEQ ID NO 247
<211> LENGTH: 23
<212> TYPE: DNA
<213> ORGANISM: Senna obtusifolia

<400> SEQUENCE: 247
agtttacagg gagatgtaaa att                                              23

<210> SEQ ID NO 248
<211> LENGTH: 23
<212> TYPE: DNA
<213> ORGANISM: Amaranthus rudis/tuberculatus

<400> SEQUENCE: 248
agtttacagg gtgatgtaaa att                                              23

<210> SEQ ID NO 249
<211> LENGTH: 23
<212> TYPE: DNA
<213> ORGANISM: Amaranthus palmeri

<400> SEQUENCE: 249
agtttacagg gtgatgtaaa att                                              23

<210> SEQ ID NO 250
<211> LENGTH: 23
<212> TYPE: DNA
<213> ORGANISM: Amaranthus palmeri

<400> SEQUENCE: 250
agtttacagg gtgatgtaaa att                                              23

<210> SEQ ID NO 251
<211> LENGTH: 54
<212> TYPE: DNA
<213> ORGANISM: Euphorbia heterophylla

<400> SEQUENCE: 251
tcgatgtgaa catgaacaaa atgccagatg tcgctatgac attggctgtg gttg           54

<210> SEQ ID NO 252
<211> LENGTH: 55
<212> TYPE: DNA
<213> ORGANISM: Euphorbia heterophylla

<400> SEQUENCE: 252
tcgatgtgaa tatgaacaaa atgccagatg ttgctatgac attagctgtg gttgc          55

<210> SEQ ID NO 253
<211> LENGTH: 55
<212> TYPE: DNA
<213> ORGANISM: Ambrosia trifida

<400> SEQUENCE: 253
tcgatgttaa catgaacaaa atgccagatg ttgccatgac gcttgcagtc gttgc          55

<210> SEQ ID NO 254
<211> LENGTH: 55
<212> TYPE: DNA

```
<213> ORGANISM: Abutilon theophrasti

<400> SEQUENCE: 254
ttgatgtcaa catgaacaaa atgccagatg ttgccatgac tctcgctgtt gttgc       55

<210> SEQ ID NO 255
<211> LENGTH: 55
<212> TYPE: DNA
<213> ORGANISM: Xanthium strumarium

<400> SEQUENCE: 255
ttgatgtcaa catgaacaaa atgcctgatg tcgcaatgac tcttgctgtg gttgc       55

<210> SEQ ID NO 256
<211> LENGTH: 55
<212> TYPE: DNA
<213> ORGANISM: Ipomoea hederacea

<400> SEQUENCE: 256
ttgatgtcaa catgaacaaa atgccagatg ttgccatgac tcttgctgta gttgc       55

<210> SEQ ID NO 257
<211> LENGTH: 55
<212> TYPE: DNA
<213> ORGANISM: Chenopodium album

<400> SEQUENCE: 257
ttgatgtcaa catgaacaaa atgccagatg tcgcaatgac tcttgctgtt gttgc       55

<210> SEQ ID NO 258
<211> LENGTH: 55
<212> TYPE: DNA
<213> ORGANISM: Digitaria sanguinalis

<400> SEQUENCE: 258
ttgacgtcaa catgaacaaa atgcctgatg tcgcaatgac tcttgctgtg gttgc       55

<210> SEQ ID NO 259
<211> LENGTH: 55
<212> TYPE: DNA
<213> ORGANISM: Senna obtusifolia

<400> SEQUENCE: 259
ttgatgtcaa catgaacaag atgccagatg ttgccatgac gcttgctgta gttgc       55

<210> SEQ ID NO 260
<211> LENGTH: 55
<212> TYPE: DNA
<213> ORGANISM: Amaranthus rudis/tuberculatus

<400> SEQUENCE: 260
tcgacgtcaa catgaataaa atgccagatg ttgctatgac tcttgcagtt gttgc       55

<210> SEQ ID NO 261
<211> LENGTH: 55
<212> TYPE: DNA
<213> ORGANISM: Amaranthus palmeri

<400> SEQUENCE: 261
tcgacgtcaa catgaacaaa atgccagatg ttgctatgac tcttgcagtt gttgc       55

<210> SEQ ID NO 262
<211> LENGTH: 55
```

<212> TYPE: DNA
<213> ORGANISM: Amaranthus palmeri

<400> SEQUENCE: 262
tcgacgtcaa catgaacaaa atgccagatg ttgctatgac tcttgcagtt gttgc       55

<210> SEQ ID NO 263
<211> LENGTH: 55
<212> TYPE: DNA
<213> ORGANISM: artificial sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 263
tngangtcaa catgaacaaa atgccagatg tngcnatgac ncttgcngtn gttgc       55

<210> SEQ ID NO 264
<211> LENGTH: 21
<212> TYPE: RNA
<213> ORGANISM: artificial sequence
<220> FEATURE:
<223> OTHER INFORMATION: Synthetic Construct

<400> SEQUENCE: 264
aacaugaaca aaaugccaga u                                            21

<210> SEQ ID NO 265
<211> LENGTH: 21
<212> TYPE: RNA
<213> ORGANISM: artificial sequence
<220> FEATURE:
<223> OTHER INFORMATION: Synthetic Construct

<400> SEQUENCE: 265
aucuggcauu uuguucaugu u                                            21

<210> SEQ ID NO 266
<211> LENGTH: 22
<212> TYPE: RNA
<213> ORGANISM: artificial sequence
<220> FEATURE:
<223> OTHER INFORMATION: Synthetic Construct

```
<400> SEQUENCE: 266
aacaugaaca aaaugccaga ug                                            22

<210> SEQ ID NO 267
<211> LENGTH: 22
<212> TYPE: RNA
<213> ORGANISM: artificial sequence
<220> FEATURE:
<223> OTHER INFORMATION: Synthetic Construct

<400> SEQUENCE: 267
caucuggcau uuuguucaug uu                                            22

<210> SEQ ID NO 268
<211> LENGTH: 24
<212> TYPE: RNA
<213> ORGANISM: artificial sequence
<220> FEATURE:
<223> OTHER INFORMATION: Synthetic Construct

<400> SEQUENCE: 268
caacaugaac aaaaugccag augu                                          24

<210> SEQ ID NO 269
<211> LENGTH: 24
<212> TYPE: RNA
<213> ORGANISM: artificial sequence
<220> FEATURE:
<223> OTHER INFORMATION: Synthetic Construct

<400> SEQUENCE: 269
acaucuggca uuuuguucau guug                                          24

<210> SEQ ID NO 270
<211> LENGTH: 35
<212> TYPE: RNA
<213> ORGANISM: artificial sequence
<220> FEATURE:
<223> OTHER INFORMATION: Synthetic Construct

<400> SEQUENCE: 270
ucgacgucaa caugaacaaa augccagaug uugcu                              35

<210> SEQ ID NO 271
<211> LENGTH: 35
<212> TYPE: RNA
<213> ORGANISM: artificial sequence
<220> FEATURE:
<223> OTHER INFORMATION: Synthetic Construct

<400> SEQUENCE: 271
agcaacaucu ggcauuuugu ucauguugac gucga                              35

<210> SEQ ID NO 272
<211> LENGTH: 45
<212> TYPE: RNA
<213> ORGANISM: artificial sequence
<220> FEATURE:
<223> OTHER INFORMATION: Synthetic Construct

<400> SEQUENCE: 272
ucgacgucaa caugaacaaa augccagaug uugcuaugac ucuug                   45

<210> SEQ ID NO 273
<211> LENGTH: 45
```

```
<212> TYPE: RNA
<213> ORGANISM: artificial sequence
<220> FEATURE:
<223> OTHER INFORMATION: Synthetic Construct

<400> SEQUENCE: 273
caagagucau agcaacaucu ggcauuuugu ucauguugac gucga                45

<210> SEQ ID NO 274
<211> LENGTH: 55
<212> TYPE: RNA
<213> ORGANISM: artificial sequence
<220> FEATURE:
<223> OTHER INFORMATION: Synthetic Construct

<400> SEQUENCE: 274
ucgacgucaa caugaacaaa augccagaug uugcuaugac ucuugcaguu guugc       55

<210> SEQ ID NO 275
<211> LENGTH: 55
<212> TYPE: RNA
<213> ORGANISM: artificial sequence
<220> FEATURE:
<223> OTHER INFORMATION: Synthetic Construct

<400> SEQUENCE: 275
gcaacaacug caagagucau agcaacaucu ggcauuuugu ucauguugac gucga       55

<210> SEQ ID NO 276
<211> LENGTH: 45
<212> TYPE: DNA
<213> ORGANISM: artificial sequence
<220> FEATURE:
<223> OTHER INFORMATION: Synthetic Construct

<400> SEQUENCE: 276
taatacgact cactataggg ctttattgaa tttagctatg taatc                45

<210> SEQ ID NO 277
<211> LENGTH: 41
<212> TYPE: DNA
<213> ORGANISM: artificial sequence
<220> FEATURE:
<223> OTHER INFORMATION: Synthetic Construct

<400> SEQUENCE: 277
taatacgact cactataggg tttatcaacc aaatgtgcag c                    41

<210> SEQ ID NO 278
<211> LENGTH: 49
<212> TYPE: DNA
<213> ORGANISM: artificial sequence
<220> FEATURE:
<223> OTHER INFORMATION: Synthetic Construct

<400> SEQUENCE: 278
taatacgact cactataggg ttgtctgtac ataattgtga gatttgtgg            49

<210> SEQ ID NO 279
<211> LENGTH: 21
<212> TYPE: DNA
<213> ORGANISM: artificial sequence
<220> FEATURE:
<223> OTHER INFORMATION: Synthetic Construct

<400> SEQUENCE: 279
```
ctgtgatcat catatgtatc a                                              21

<210> SEQ ID NO 280
<211> LENGTH: 21
<212> TYPE: DNA
<213> ORGANISM: artificial sequence
<220> FEATURE:
<223> OTHER INFORMATION: Synthetic Construct

<400> SEQUENCE: 280
ccttaactct ccagctagca a                                              21

<210> SEQ ID NO 281
<211> LENGTH: 21
<212> TYPE: DNA
<213> ORGANISM: artificial sequence
<220> FEATURE:
<223> OTHER INFORMATION: Synthetic Construct

<400> SEQUENCE: 281
cagcccgcaa atgtttcatt c                                              21

<210> SEQ ID NO 282
<211> LENGTH: 21
<212> TYPE: DNA
<213> ORGANISM: artificial sequence
<220> FEATURE:
<223> OTHER INFORMATION: Synthetic Construct

<400> SEQUENCE: 282
gccgtcaatg gccgcattgc t                                              21

<210> SEQ ID NO 283
<211> LENGTH: 21
<212> TYPE: DNA
<213> ORGANISM: artificial sequence
<220> FEATURE:
<223> OTHER INFORMATION: Synthetic Construct

<400> SEQUENCE: 283
tccttccctc agaaagggca g                                              21

<210> SEQ ID NO 284
<211> LENGTH: 21
<212> TYPE: DNA
<213> ORGANISM: artificial sequence
<220> FEATURE:
<223> OTHER INFORMATION: Synthetic Construct

<400> SEQUENCE: 284
ttgcctcatg ctgctaatct g                                              21

<210> SEQ ID NO 285
<211> LENGTH: 789
<212> TYPE: DNA
<213> ORGANISM: Nicotiana benthamiana

<400> SEQUENCE: 285
cttatatgtg cttaagccta acgtgcaccc ggcccttaa ccccagcagt tttcaatcta      60
cctaccgtct ctaccatttt cttctagttg gtgaaaattt ctaactttga gaaaacaagc    120
caaagttttt gtttctaaga acgcaaaatg agtgaaattt tttgcagcaa tggcacagat    180
tagcagcatg aggcaaggga tacagacccc taatcttaat tcctattttc ctaaaaccca    240
aaaggttcct cttttttcgc attctatctt ctttggatca agaaaataa cccaaaattc     300

```
agcaaaatct tgtgggtgt gtaagaaaga ttcagttttg agggtggcaa agtcacctt      360 taggatttgt gcatcagtgg ccactgcaca gaagcccaac gagattgtgc tgcaacccat      420
caaagatata tcaggcactg ttaaattgcc tggttctaaa tccctttcca accgtattct      480
ccttcttgct gcccttctg agggaaggac tgttgttgac aatttactga gtagtgatga      540
cattcattac atgcttggtg cgttgaaaac acttggactt catgtagaag atgacaatga      600
aaaccaacga gcaattgtgg aaggttgtgg tgggcagttt cctgtcggcg agaagtctga      660
ggaagaaatc caactattcc ttggaaatgc aggaacagca atgcggccat tgacggcagc      720
agttactgta gctggaggac attcaagata tgtacttgat ggagttccta ggatgagaga      780
gagaccgat                                                              789
```

```
<210> SEQ ID NO 286
<211> LENGTH: 799
<212> TYPE: DNA
<213> ORGANISM: Nicotiana benthamiana

<400> SEQUENCE: 286
cactgacgtt ggattagagg taggctcctt atatgtgctt aagcctaacg tgcagccggc       60 ccccaaccc agcagttttc aatctaccta ccgtctctac cattttctta tagtagttga      120
aaatttctaa ctttgagaaa acaagccaaa gttttgtttc taagaacaca aagggagtga      180
aattttttgc agcaatggca cagattagca gcatgaggca agggatacag accccctaatc      240 ttaattccta ttttcctaaa acccaaaagg ttcctctttt ttcgcattct atcttcattg      300
gatcaaagaa aataacccaa aattcagcaa atctttgtg ggtgtgtaag aaagattcag      360
ttttgagggt ggcaaagtca ccttttagga tttgtgcatc agtggccact gcacagaagc      420
ctaacgagat tgtgctgcaa cctatcaaag atatatcagg cactgttaaa ttacctggtt      480
ctaaatccct ttccaatcgt attctccttc ttgctgccct ttctgaggga aggactgttg      540
ttgacaattt actgagtagt gatgacattc attacatgct tggtgcattg aaaacacttg      600
gacttcatgt agaagatgac aatgaaaacc aacgagcaat cgtagaaggt tgtggtgggc      660
agtttcctgt cggcaagaag tctgaggaag aaatccaact attccttgga aatgcaggaa      720
cagcaatgcg gccattgacg gcagcagtta ctgtagctgg tggacattct agatatgtac      780
ttgatggagt tcctaggat                                                   799
```

```
<210> SEQ ID NO 287
<211> LENGTH: 845
<212> TYPE: DNA
<213> ORGANISM: Nicotiana benthamiana

<400> SEQUENCE: 287
aaattcttgg ttcgaggagg tcagaagtac aagtctcctg gaaaagcata tgttgaagga       60
gatgcctcaa gtgctagcta cttttttggcg ggtgcagctg tcacaggtgg aactgtcact      120
gttgaaggtt gtggaacaag cagtttacag ggggatgtta agtttgctga ggtcctcgaa      180
aagatggggg cagaagttac atggacagag aacagtgtca cggttaaagg acctccaagg      240
aactcttctg gaatgaaaca tttgcgggct gttgacgtta acatgaacaa atgccagat      300 gttgccatga ctcttgctgt agttgcactt tttgctgata gtcctactgc cataagagat      360
gttgctagct ggagagttaa ggaaactgag cggatgattg ccatatgcac agaacttagg      420
aagttgggtg caacagttgt agaagggcca gactactgca taatcactcc acctgaaaag      480
```

```
ttaaaagtag cggaaattga tacatatgat gatcacagaa tggccatggc tttctctctt    540
gcggcttgtg ctgatgttcc agtcaccatt aaggaccccg gttgtactcg caaaaccttc    600
cccaactact ttgacgttct ccagcagtat tccaagcatt aaaccacttt ccattaagaa    660
ttttgaaaaa gagagacttt gacaacaatg gtgtcatacc ggaagagaaa agctttgatc    720
caagctttca actccttttc atttgtcatg tgatgatcat tgtatttgtt gaagttgagc    780
tgcttttctt ttgtccagaa gacatgtatg gatactatta ctatatagtt aaggtgaact    840
cagca                                                                845
```

```
<210> SEQ ID NO 288
<211> LENGTH: 21
<212> TYPE: DNA
<213> ORGANISM: artificial sequence
<220> FEATURE:
<223> OTHER INFORMATION: Synthetic Construct

<400> SEQUENCE: 288
ccacatggtc cagtatctgc c                                               21

<210> SEQ ID NO 289
<211> LENGTH: 21
<212> TYPE: DNA
<213> ORGANISM: artificial sequence
<220> FEATURE:
<223> OTHER INFORMATION: Synthetic Construct

<400> SEQUENCE: 289
caagcaagga acccatccat t                                               21

<210> SEQ ID NO 290
<211> LENGTH: 21
<212> TYPE: DNA
<213> ORGANISM: artificial sequence
<220> FEATURE:
<223> OTHER INFORMATION: Synthetic Construct

<400> SEQUENCE: 290
ggccacacct gcatgcattg c                                               21

<210> SEQ ID NO 291
<211> LENGTH: 21
<212> TYPE: DNA
<213> ORGANISM: artificial sequence
<220> FEATURE:
<223> OTHER INFORMATION: Synthetic Construct

<400> SEQUENCE: 291
gtgttcacgg tagacaaatc c                                               21

<210> SEQ ID NO 292
<211> LENGTH: 21
<212> TYPE: DNA
<213> ORGANISM: artificial sequence
<220> FEATURE:
<223> OTHER INFORMATION: Synthetic Construct

<400> SEQUENCE: 292
tgcactgcac ttgacgcacg t                                               21

<210> SEQ ID NO 293
<211> LENGTH: 21
<212> TYPE: DNA
<213> ORGANISM: artificial sequence
```

<220> FEATURE:
<223> OTHER INFORMATION: Synthetic Construct

<400> SEQUENCE: 293
aactgatgca ttgcacttga c    21

<210> SEQ ID NO 294
<211> LENGTH: 21
<212> TYPE: DNA
<213> ORGANISM: artificial sequence
<220> FEATURE:
<223> OTHER INFORMATION: Synthetic Construct

<400> SEQUENCE: 294
caaatcagga aggtatgaga g    21

<210> SEQ ID NO 295
<211> LENGTH: 21
<212> TYPE: DNA
<213> ORGANISM: artificial sequence
<220> FEATURE:
<223> OTHER INFORMATION: Synthetic Construct

<400> SEQUENCE: 295
tgtcaaggtt ttgtttcctg g    21

<210> SEQ ID NO 296
<211> LENGTH: 543
<212> TYPE: DNA
<213> ORGANISM: Nicotiana benthamiana

<400> SEQUENCE: 296
gcaatggctt cctcagttct ttcctcagca gcagttgcca cccgcagcaa tgttgctcaa    60
gctaacatgg ttgcaccttt cacaggtctt aagtctgctg cctcattccc tgtttcaaga   120
aagcaaaacc ttgacatcac ttccattgcc agcaacggcg gaagagtgca atgcatgcag   180
gtgtggccac caattaacat gaagaagtat gagactctct cataccttcc cgatttgagc   240
caggagcaat gctctccga  aattgagtac cttttgaaga atggatgggt tccttgcttg   300
gaattcgaga ctgagaaagg atttgtctac cgtgaacacc acaagtcacc aggatactat   360
gatggcagat actggaccat gtggaagcta cctatgttcg gatgcactga tgccacccaa   420
gtgttggctg aggtgggaga ggcgaagaag gaatacccac aggcctgggt ccgtatcatt   480
ggatttgaca acgtgcgtca agtgcagtgc atcagtttca ttgcctccaa gcctgacggc   540
tac                                                                 543

<210> SEQ ID NO 297
<211> LENGTH: 543
<212> TYPE: DNA
<213> ORGANISM: Nicotiana benthamiana

<400> SEQUENCE: 297
acaatggctt cctcagttct ttcctcagca gcagttgcca cccgcagcaa tgttgctcaa    60
gctaacatgg ttgcaccttt cactggtctt aagtcagctg ccttttccc  tgtttcaagg   120
aagcaaaacc ttgacatcac ttccattgcc agcaacggcg gaagagtgca atgcatgcag   180
gtgtggccac caattaacaa gaagaagtac gagactctct cataccttcc tgatctgagc   240
gtggagcaat gcttagcga  aattgagtac ctcttgaaaa atggatgggt tccttgcttg   300
gaattcgaga ctgagcgcgg atttgtctac cgtgaacacc acaagtcacc gggatactat   360

```
gacggcagat actggaccat gtggaagttg cctatgttcg gatgcactga tgccacccaa    420
gtgttggccg aggtggaaga ggcgaagaag gcatacccac aggcctggat ccgtattatt    480
ggattcgaca acgtgcgtca agtgcagtgc atcagtttca ttgcctacaa gccagaaggc    540
tac                                                                  543
```

<210> SEQ ID NO 298
<211> LENGTH: 486
<212> TYPE: DNA
<213> ORGANISM: Nicotiana benthamiana

<400> SEQUENCE: 298

```
caagccaaca tggttgcacc cttcactggc ctcaagtccg cctcctcctt ccctgttacc     60
aggaaacaaa accttgacat tacctccatt gctagcaatg gtggaagagt tcaatgcatg    120
caggtgtggc caccaattaa catgaagaag tacgagacac tctcatacct tcctgatttg    180
agccaggagc aattgcttag tgaagttgag taccttttga aaaatggatg ggttccttgc    240
ttggaattcg agactgagcg tggattcgtc taccgtgaac accacaactc accaggatac    300
tacgatggca gatactggac catgtggaag ttgcccatgt tcgggtgcac tgatgccact    360
caggtgttgg ctgaggtcga ggaggcaaag aaggcttacc cacaagcctg ggttagaatc    420
attggattcg acaacgtccg tcaagtgcaa tgcatcagtt ttatcgcctc caagccagaa    480
ggctac                                                               486
```

<210> SEQ ID NO 299
<211> LENGTH: 537
<212> TYPE: DNA
<213> ORGANISM: Nicotiana benthamiana

<400> SEQUENCE: 299

```
ggctcagtta tgtcctcagc tgccgctgtt tccaccggcg ccaatgctgt tcaagccagc     60
atggtcgcac ccttcactgg cctcaaggcc gcctcctcct tcccggtttc caggaaacaa    120
aaccttgaca ttacttccat tgctagaaat ggtggaagag tccaatgcat gcaggtgtgg    180
ccgccaatta caagaagaa gtacgagaca ctctcatacc ttcctgattt gagcgtggag    240
caattgctta gcgaaattga gtacctttg aaaaatggat gggttccttg cttggaattc    300
gagactgagc atggattcgt ctaccgtgaa caccaccact caccaggata ctacgatggc    360
agatactgga cgatgtggaa gttgcccatg ttcgggtgca ccgatgccac tcaggtcttg    420
gctgaggtag aggaggccaa gaaggcttac cacaagcct gggtcagaat cattggattc    480
gacaacgtcc gtcaagtgca atgcatcagt ttcatcgcct acaagcccga aggctat      537
```

<210> SEQ ID NO 300
<211> LENGTH: 21
<212> TYPE: DNA
<213> ORGANISM: artificial sequence
<220> FEATURE:
<223> OTHER INFORMATION: Synthetic Construct

<400> SEQUENCE: 300

```
ggaggcaaaa tacgagcctc a                                               21
```

<210> SEQ ID NO 301
<211> LENGTH: 21
<212> TYPE: DNA
<213> ORGANISM: artificial sequence
<220> FEATURE:
<223> OTHER INFORMATION: Synthetic Construct

<400> SEQUENCE: 301
cactaatctt aataccaaac t                                              21

<210> SEQ ID NO 302
<211> LENGTH: 25
<212> TYPE: DNA
<213> ORGANISM: artificial sequence
<220> FEATURE:
<223> OTHER INFORMATION: Synthetic Construct

<400> SEQUENCE: 302
tatgggtcat tagcataggc attat                                          25

<210> SEQ ID NO 303
<211> LENGTH: 21
<212> TYPE: DNA
<213> ORGANISM: artificial sequence
<220> FEATURE:
<223> OTHER INFORMATION: Synthetic Construct

<400> SEQUENCE: 303
tctcaagaat atcacgctcc c                                              21

<210> SEQ ID NO 304
<211> LENGTH: 24
<212> TYPE: DNA
<213> ORGANISM: artificial sequence
<220> FEATURE:
<223> OTHER INFORMATION: Synthetic Construct

<400> SEQUENCE: 304
cccttgggga cgctggcagg tcac                                           24

<210> SEQ ID NO 305
<211> LENGTH: 40
<212> TYPE: DNA
<213> ORGANISM: artificial sequence
<220> FEATURE:
<223> OTHER INFORMATION: Synthetic Construct

<400> SEQUENCE: 305
taatacgact cactataggg ggagagagct agatcttttg                          40

<210> SEQ ID NO 306
<211> LENGTH: 41
<212> TYPE: DNA
<213> ORGANISM: artificial sequence
<220> FEATURE:
<223> OTHER INFORMATION: Synthetic Construct

<400> SEQUENCE: 306
taatacgact cactataggc acagtatttc ttcctccaac c                        41

<210> SEQ ID NO 307
<211> LENGTH: 21
<212> TYPE: DNA
<213> ORGANISM: artificial sequence
<220> FEATURE:
<223> OTHER INFORMATION: Synthetic Construct

<400> SEQUENCE: 307
ttgctcatct taaatacatg t                                              21

<210> SEQ ID NO 308

```
<211> LENGTH: 24
<212> TYPE: DNA
<213> ORGANISM: artificial sequence
<220> FEATURE:
<223> OTHER INFORMATION: Synthetic Construct

<400> SEQUENCE: 308
tcatcttaaa tacatgtttt gtca                                          24

<210> SEQ ID NO 309
<211> LENGTH: 22
<212> TYPE: DNA
<213> ORGANISM: artificial sequence
<220> FEATURE:
<223> OTHER INFORMATION: Synthetic Construct

<400> SEQUENCE: 309
ttatcttcag ggatacatta gc                                            22

<210> SEQ ID NO 310
<211> LENGTH: 24
<212> TYPE: DNA
<213> ORGANISM: artificial sequence
<220> FEATURE:
<223> OTHER INFORMATION: Synthetic Construct

<400> SEQUENCE: 310
aatactgctt gctcatctta aata                                          24

<210> SEQ ID NO 311
<211> LENGTH: 21
<212> TYPE: DNA
<213> ORGANISM: artificial sequence
<220> FEATURE:
<223> OTHER INFORMATION: Synthetic Construct

<400> SEQUENCE: 311
gacaattcca agttcagttt c                                             21

<210> SEQ ID NO 312
<211> LENGTH: 24
<212> TYPE: DNA
<213> ORGANISM: artificial sequence
<220> FEATURE:
<223> OTHER INFORMATION: Synthetic Construct

<400> SEQUENCE: 312
ccgttttaga tcaccataaa gaga                                          24

<210> SEQ ID NO 313
<211> LENGTH: 21
<212> TYPE: DNA
<213> ORGANISM: artificial sequence
<220> FEATURE:
<223> OTHER INFORMATION: Synthetic Construct

<400> SEQUENCE: 313
ttgtctggta atatcacaat c                                             21

<210> SEQ ID NO 314
<211> LENGTH: 2937
<212> TYPE: DNA
<213> ORGANISM: Nicotiana benthamiana

<400> SEQUENCE: 314
atggtgagga agaggagaac tgagttacct ggttctggtg agagctctgg gtctcaagaa   60
```

-continued

```
actggcggac agggtcgtgg ccagcatcca cagcagctgc accaagctac ctcccagact    120
ccatatcaaa ctgcaatgac tactcagcca ataccttatg caagaccaac tgaaacatcc    180
tccgaagctg gttcctcatc tcagccacct gagcaggcag ctctacaagt gacacaacag    240
ttccagcaac ttgctttgca acaagaagcg gctacaacgc aagcagttcc acctgcatca    300
agcaaattac taaggtttcc cctgcgtcca gggaagggga gcaatggtat gagatgcata    360
gtcaaagcca atcacttctt cgcagagctg cctgacaaag acttgcacca gtatgatgtc    420
acaatttctc cagaggtgtc atcacgtggc gtcaaccgtg ctgtcatggc caactggtg     480 aagctgtacc aagaatctca tcttgggaag agacttccag catatgatgg aaggaaaagt    540
ctatacactg cagggcccct tccatttgtt caaaaagact tcaaaataac tcttattgat    600
gatgaggatg ggcctggtgg tgctagaagg gaaagggaat ttaaagttgt gatcaaattg    660
gctgcccgtg ctgatcttca tcacttggga atgttttag aagggaaaca ggctgatgca     720
cctcaagagg cgcttcaagt tctggatatt gttctgcgtg agttgccaac atctaggttt    780
tgtcctgtgg gtcgttcttt ctattcccgt gatttagggc gaaagcaacc attgggtgaa    840
ggtttagaaa gttggcgtgg gttctatcaa agcattcgcc ccacacaaat gggcttatca    900
ctgaacatcg atatgtcttc cactgcattc attgagccac tgccagtcat tgattttgtg    960
acacagcttc tgaaccgaga gtgtgccatct agaccactgt ctgatgctgg ccgtgtaaag   1020
ataaaaaaag ctctgagagg tgtgaaggtg gaggttactc atcgtggaaa tatgcggagg   1080
aagtaccgca tttcgggttt aacatctcaa gcaacaagag agttgacctt ccctgttgat   1140
gaaaatggta cagtgaaatc tgtaattgag tattttcgag aaacatatgg gtttgtaatt   1200
cagcatactc agtggccttg tctacaagtt ggaaatcagc agagacctaa ttacttgcca   1260
atggaagtct gcaagattgt ggagggacaa aggtactcaa agcgcttgaa tgagagacag   1320
attactgcac ttctgaaagt gacctgccag cgtccccaag ggagggagcg tgatattctt   1380
gagaccgtac atcataatgc ctatgctaat gacccatatg ccaaggagtt tggtattaag   1440
attagtgaca agttggcaca agttgaggct cgtattttgc ctccacctcg gcttaaatat   1500
catgataacg gtcgagaaaa ggactgcctg ccacaagttg gccaatggaa tatgatgaat   1560
aagaaaatgg taaatggagg gacggtgaac aattggatct gcataaactt ctctcgcaat   1620
gtgcaagata gtgttgctca tgggttttgc tctgagcttg cacaaatgtg ccagatatct   1680
ggcatgaatt tcaatccaaa tcctgttctg ccaccttcga gtgcacgccc tgatcaggtc   1740
gaaagagtat tgaaaactcg atttcatgat gctatgacta agttgcagct gcatgggaga   1800
gagcttgatt tgctagttgt catcttgcca gacaataatg gatctctttta tggtgatctg   1860 aagcgcattt gtgagactga actaggagtc gtctcacagt gctgtttgac aaaacatgta   1920
tttaagatga gcaaacagta tctagccaat gtagcgctga aaatcaatgt gaaggtggga   1980
gggagaaaca ctgtgcttgt tgatgcaata tcgaggcgaa ttcctcttgt cagcgaccgg   2040
cctaccatca tttttggtgc agatgtcacc caccctcacc ctggggagga ctctagccca   2100
tccattgccg cggtggttgc ttctcaagat tggcctgaga ttacaaagta tgctggtcta   2160
gtttctgctc aagcccatag gcaagagctt attcaggatc tgtacacgac taggcaagat   2220
cctgttaagg ggacagttgc tggtggaatg attaaggact tacttatatc cttccgaaga   2280
gctactggac aaaagcccca gagaataatt ttctataggg atggtgttag tgaaggacaa   2340
ttttatcaag tgcttctgtt cgaacttgat gcgatccgca agcatgtgc gtctttggag    2400
```

-continued

| | |
|---|---|
| ccaaattatc agcccccagt cacatttgtt gtggttcaga aacgacatca cacaaggctt | 2460 |
| tttgccaata accaccgtga cagaaatgca gttgacagga gcgggaacat tatacctggt | 2520 |
| actgttgtag attcaaagat atgccaccccg acagagtttg atttctatct ttgtagccat | 2580 |
| gccggcatac agggtacgag ccgtccagct cactaccatg ttctatggga cgagaacaaa | 2640 |
| ttcacagccg atgcgctgca gtcttttgacc aacaacctct gctatacata tgcaaggtgc | 2700 |
| acgcgttccg tctccatcgt tcccctgca tattatgcac atttggcagc tttccgtgct | 2760 |
| cgatttttata tggagccgga gacatctgac ggtggttcag taacaagtgg ggctgctggt | 2820 |
| ggcagagggg gtggtgcagg agctgctgga aggaacaccc gagccccaag tgctggtgct | 2880 |
| gctgttagac ctcttcctgc gctcaaggat aatgtgaaga gggttatgtt ctactgc | 2937 |

<210> SEQ ID NO 315
<211> LENGTH: 3274
<212> TYPE: DNA
<213> ORGANISM: Nicotiana benthamiana

<400> SEQUENCE: 315

| | |
|---|---|
| cacctatcac tctctttctc tctctacaaa catatcgtgc cgtttctctc tcggcctctc | 60 |
| ttcgtgtttt agggcaccgt ggtggttggt atccaggcgg cggttttgag ttattaccat | 120 |
| ggtgcggaag aagaggactg atgttcctgg tggtgctgag agttttgagt cccatgaaac | 180 |
| tggaggggca cgaggtggtg cccaacgccc atcacagcag cagcaacatc agcatcagca | 240 |
| aggcggagga agaggctggg cacctcagca tggaggacat ggtggccgtg gtggtggggg | 300 |
| agctccacgt ggtggaatgg cccctcaaca atcctatggt ggacctcctg aatactacca | 360 |
| acagggcagg ggaactcaac agtatcaacg aggtggagga caaccccagc gccgtggtgg | 420 |
| catgggggc cgtggggcac ggccaccagt acccgagctg caccaagcaa cccagactcc | 480 |
| acatcagcct gtaccatatg aagaccatcc agaaacatac tcagaggctg gttcctcgtc | 540 |
| tcagccacct gaaccaacga cacagcaagt gactcagcaa ttccagcaac ttgttgtgca | 600 |
| gccagaagca gctgcaaccc aagcaataca accagcatcg agcaagtcga tgaggtttcc | 660 |
| actccggcca ggaaagggta gtactggtat tagatgcata gttaaggcca atcacttctt | 720 |
| tgccgagtta cctgacaaag atctgcacca gtatgatgtt tcaattactc ctgaggtcgc | 780 |
| ctctcggggt gtcaaccggg ccgtcatgga gcagctggtg aagctttata gagaatccca | 840 |
| tcttgggaag aggcttccag cctatgacgg aagaaaaagt ctatacacag cagggcccct | 900 |
| ccctttttgtt caaaaggatt ttaaaatcac tctaattgat gatgatgatg acctggtgg | 960 |
| tgctaggagg gaaagagagt ttaaagttgt gatcaagctg gcggctcgtg ctgatcttca | 1020 |
| tcacttgggg atgttcttac aagggagaca ggctgatgca ccgcaagaag cacttcaggt | 1080 |
| gctggatatt gtgctacgtg agttgccaac atctaggtat tgtcctgtgg gccgctcttt | 1140 |
| ctattcccct catttaggac gaagacaacc actgggtgaa ggtttagaga gctggcgtgg | 1200 |
| cttctatcaa agtattcgtc ctacacagat gggattatcc ctgaatattg atatgtcttc | 1260 |
| cacggctttc attgagccac tgccgattat tgacttcgtg agccagcttc tgaatcggga | 1320 |
| tatctcttct agaccactgt ctgatgctga ccgcgttaag ataaagaagg cactgagagg | 1380 |
| tgtaaaggtg ggggtcactc atcgtggaaa tatgcggagg aagtatcgca tttctggctt | 1440 |
| gacgtctcaa gcaacaagag agttgacttt tcctgtcgat gaaggggta cgatgaaagc | 1500 |
| tgttgtggaa tattttcggg aaaacctatgg ttttgtcatt cggcataccc agtggccttg | 1560 |
| tcttcaagtt ggaaatacgc agaggccaaa ttacttgcca atggaagtat gtaagattgt | 1620 |

| | | | | |
|---|---|---|---|---|
| agagggacag | agatactcaa | agcgcttgaa | tgagaggcag | ataacagcac ttctaaaagt | 1680 |
| gacctgccaa | cgtcctcaag | agagagaacg | tgatattctt | cagactgttc atcacaatgc | 1740 |
| ttatgctgat | gacccatatg | cgaaggagtt | tggtattaag | atcagtgagg agcttgctca | 1800 |
| agttgaggct | cgcgttttgc | ctgcaccttg | gcttaaatac | catgatacag gtcgagagaa | 1860 |
| agactgtctg | ccacaagtgg | gccagtggaa | tatgatgaat | aagaaaatgg ttaatggagg | 1920 |
| aacagtgaac | aactggatct | gtgtaaactt | ttctcgcaat | gtgcaagaca cagttgcacg | 1980 |
| tggattttgt | tccgagcttg | cacaaatgtg | catgatatcc | ggaatgaact tcaatcccaa | 2040 |
| tcctgttcta | ccaccagtga | gtgctcgccc | tgatcaagtt | gagagagtct tgaaaactcg | 2100 |
| atttcacgat | gctatgacaa | agttgcagcc | aaatgggaga | gagctagatc ttttgattgt | 2160 |
| gatattacca | gacaataacg | gctctcttta | tggtgatcta | aaacggattt gtgaaactga | 2220 |
| acttggaatt | gtctcacaat | gctgcttgac | aaaacatgta | tttaagatga gcaagcagta | 2280 |
| tttagctaat | gtatccctga | agataaatgt | gaaggttgga | ggaagaaata ctgtgctggt | 2340 |
| tgatgcgctc | tctagacgaa | ttccccttgt | cagcgaccgc | ccaactatca tttttggtgc | 2400 |
| agatgtcacc | catccccacc | ctggggagga | ttctagcccg | tcaattgctg cggtggttgc | 2460 |
| ttctcaagat | tggcctgaaa | ttacaaagta | tgctggtttg | gtttctgctc aagcgcatag | 2520 |
| gcaagagctt | atacaagatc | tgtacaagac | ttggcaagat | ccagttagag gacctgtgac | 2580 |
| tggtggcatg | ataaaggaat | tacttatttc | cttccgtcga | gcaactggac agaagccgca | 2640 |
| gagaattata | ttctcagagg | atggtgttag | tgaaggacaa | ttttaccaag ttcttctttt | 2700 |
| tgaacttgat | gcaatccgca | aggcatgtgc | atctttagaa | cccaactatc agccccggt | 2760 |
| tacgtttgtt | gtggtccaga | aacggcatca | tactaggttg | tttgccaata accaccacga | 2820 |
| cagaaatgca | gttgatcgga | gtgggaacat | tttgcctggt | accgttgtag attcaaagat | 2880 |
| atgccaccct | actgaatttg | atttctatct | ctgtagccat | gccggcatac agggtactag | 2940 |
| ccgcccagct | cattatcatg | ttctgtggga | tgagaacaat | tttactgctg acgccctgca | 3000 |
| gtctttgact | aacaatcttt | gctatacata | tgctaggtgt | actcgttctg tctccattgt | 3060 |
| tccaccagca | tattatgcac | atttggcagc | tttccgtgct | cggttttaca tggagccaga | 3120 |
| gacatctgat | aatggatcag | tcacaagcgc | agctgcttca | aacagaggag gtttaggagc | 3180 |
| tatgggaagg | agcacgcgag | caccaggtgc | tggtgctgct | gtaaggcccc ttcctgctct | 3240 |
| caaggagaat | gttaagaggg | ttatgtttta | ttgt | | 3274 |

<210> SEQ ID NO 316
<211> LENGTH: 3907
<212> TYPE: DNA
<213> ORGANISM: Zea mays

<400> SEQUENCE: 316

| | | | | |
|---|---|---|---|---|
| acctacttcc | ccctcgcccc | tctcatggtc | tctctcgcgc | ccagatctgc tactagacgg | 60 |
| caccgctgca | gcgcgtcgtg | tcgcgggggt | tggtggcagg | cagcgagagc ttgccgttcc | 120 |
| tctctctcag | ttgtcaggtc | ctaggctcac | ctcaccggct | cccagcccgc ttctatttct | 180 |
| tcctccccga | ccccgtgcag | gtggcagtcc | agtccacgcc | accaaccgcg aggcgaacca | 240 |
| aaccaaccca | ctctccccaa | ccccgcgcgc | ccaggccgcc | cgccctacca accatcggcg | 300 |
| tcggcaatgg | cggccatggc | gaccaaggcc | gccgcgggca | ccgtgtcgct ggacctcgcc | 360 |
| gcgccgccgg | cggcggcagc | ggcggcggcg | gtgcaggcgg | gtgccgagga gatcgtgctg | 420 |

```
cagcccatca aggagatctc cggcaccgtc aagctgccgg ggtccaagtc gctttccaac    480
cggatcctcc tgctcgccgc cctgtccgag gtgagcgatt ttggtgcttg ctgcgctgcc    540
ctgtctcact gctacctaaa tgttttgcct gtcgaatacc atggattctc ggtgtaatcc    600
atctcacgat cagatgcacc gcatgtcgca tgcctagctc tctctaattt gtctagtagt    660
ttgtatacgg attaatattg ataaatcggt accgcaaaag ctaggtgtaa ataaacacta    720
gaaaattgga tgttccccta tcggcctgta ctcggctact cgttcttgtg atggcatgct    780
gtctcttctt ggtgtttggt gaacaacctt atgaaatttg ggcgcaaaga actcgccctc    840
aagggttgat cttatgccat cgtcatgata acagtggag cacggacgat cctttacgtt     900 gttttttaaca aactttgtca gaaaactagc atcattaact tcttaatgac gatttcacaa    960
caaaaaaagg taacctcgct actaacataa caaaatactt gttgcttatt aattatatgt    1020 ttttttaatct ttgatcaggg gacaacagtg gttgataacc tgttgaacag tgaggatgtc   1080
cactacatgc tcggggcctt gaggactctt ggtctctctg tcgaagcgga caaagctgcc   1140
aaaagagctg tagttgttgg ctgtggtgga agttcccag ttgaggattc taaagaggaa     1200
gtgcagctct tcttggggaa tgctggaact gcaatgcggc cattgacagc agctgttact   1260
gctgctggtg gaaatgcaac gtatgttcc tctctttctc tctacaatac ttgctggagt     1320
tagtatgaaa cccatgggta tgtctagtgg cttatggtgt attggttttt gaacttcagt   1380
tacgtgcttg atggagtacc aagaatgagg gagagaccca ttggcgactt ggttgtcgga   1440
ttgaagcagc ttggtgcaga tgttgattgt tccttggca ctgactgccc acctgttcgt     1500
gtcaatggaa tcgagggct acctggtggc aaggttagct actaagggcc acatgttaca     1560
ttcttctgta aatggtacaa ctattgtcga gcttttgcat ttgtaaggaa agcattgatt   1620
gatctgaatt tgatgctaca ccacaaaata tcctacaaat ggtcatccct aactagcaaa   1680
caatgaagta atacttggca tgtgtttatc aaattaattt ccatcttctg gggcattgcc   1740
tgttttctag tctaatagca tttgttttta gcattaatta gctcttacaa ttgttatgtt   1800
ctacaggtca agctgtctgg ctccatcagc agtcagtact tgagtgcctt gctgatggct   1860
gctcctttgg ctcttgggga tgtggagatt gaaatcattg ataaattaat ctccattccc   1920
tacgtcgaaa tgacattgag attgatggag cgttttggtg tgaaagcaga gcattctgat   1980
agctgggaca gattctacat taagggaggt caaaaataca agtaagctct gtaatgtatt   2040
tcactacttt gatgccaatg tttcagtttt cagttttcca aacagtcgca tcaatatttg   2100
aatagatgca ctgtagaaaa aaaatcattg cagggaaaaa ctagtactga gtattttgac   2160
tgtaaattat tttaccagtc ggaatatagt cagtctattg gagtcaagag cgtgaaccga   2220
aatagccagt taattatccc attatacaga ggacaaccat gtatactatt gaaacttggt   2280
ttataagaga atctaggtag ctggactcgt agctgcttgg catggatacc ttcttatctt   2340
taggaaaaga cacttgattt ttttttttctg tggccctcta tgatgtgtga acctgcttct   2400
ctattgcttt agaaggatat atctatgtcg ttatgcaaca tgcttccctt agccatttgt   2460
actgaaatca gtttcataag ttcgttagtg gttccctaaa cgaaaccttg ttttttctttg   2520 caatcaacag gtcccctaaa aatgcctatg ttgaaggtga tgcctcaagc gcaagctatt   2580
tcttggctgg tgctgcaatt actggaggga ctgtgactgt ggaaggttgt ggcaccacca   2640
gtttgcaggt aaagatttct tggctggtgc tacaataact gcttttgtct ttttggtttc   2700
agcattgttc tcagagtcac taaataacat tatcatctgc aaatgtcaaa tagacatact   2760
taggtgaatt catgtaaccg tttccttaca aatttgctga aacctcaggg tgatgtgaag   2820
```

| | | |
|---|---|---|
| tttgctgagg tactggagat gatgggagcg aaggttacat ggaccgagac tagcgtaact | 2880 |
| gttactggcc caccgcggga gccatttggg aggaaacacc tcaaggcgat tgatgtcaac | 2940 |
| atgaacaaga tgcctgatgt cgccatgact cttgctgtgg ttgccctctt tgccgatggc | 3000 |
| ccgacagcca tcagagacgg taaaacattc tcagccctac aaccatgcct cttctacatc | 3060 |
| actacttgac aagactaaaa actattggct cgttggcagt ggcttcctgg agagtaaagg | 3120 |
| agaccgagag gatggttgcg atccggacgg agctaaccaa ggtaaggcta catacttcac | 3180 |
| atgtctcacg tcgtctttcc atagctcgct gcctcttagc ggcttgcctg cggtcgctcc | 3240 |
| atcctcggtt gctgtctgtg ttttccacag ctgggagcat ctgttgagga agggccggac | 3300 |
| tactgcatca tcacgccgcc ggagaagctg aacgtgacgg cgatcgacac gtacgacgac | 3360 |
| cacaggatgg ccatggcctt ctcccttgcc gcctgtgccg aggtcccgt gaccatccgg | 3420 |
| gaccctgggt gcacccggaa gaccttcccc gactacttcg atgtgctgag cactttcgtc | 3480 |
| aagaattaat aaagcgtgcg atactaccac gcagcttgat tgaagtgata ggcttgtgct | 3540 |
| gaggaaatac atttctttg ttctgttttt tctctttcac gggattaagt tttgagtctg | 3600 |
| taacgttagt tgtttgtagc aagtttctat ttcggatctt aagtttgtgc actgtaagcc | 3660 |
| aaatttcatt tcaagagtgg ttcgttggaa taataagaat aataaattac gtttcagtgg | 3720 |
| ctgtcaagcc tgctgctacg ttttaggaga tggcattaga cattcatcat caacaacaat | 3780 |
| aaaaccttt agcctcaaac aataatagtg aagttatttt ttagtcctaa acaagttgca | 3840 |
| ttaggatata gttaaaacac aaaagaagct aaagttaggg tttagacatg tggatattgt | 3900 |
| tttccat | 3907 |

<210> SEQ ID NO 317
<211> LENGTH: 2149
<212> TYPE: DNA
<213> ORGANISM: Zea mays

<400> SEQUENCE: 317

| | | |
|---|---|---|
| acctacttcc ccctcgcccc tctcatggtc tctctcgcgc ccagatctgc tactagacgg | 60 |
| caccgctgca gcgcgtcgtg tcgcgggggt tggtggcagg cagcgagagc ttgccgttcc | 120 |
| tctctctcag ttgtcaggtc ctaggctcac ctcaccggct cccagcccgc ttctatttct | 180 |
| tcctccccga ccccgtgcag gtggcagtcc agtccacgcc accaaccgcg aggcgaacca | 240 |
| aaccaaccca ctctccccaa ccccgcgcgc ccaggccgcc cgccctacca accatcggcg | 300 |
| tcggcaatgg cggccatggc gaccaaggcc gccgcgggca ccgtgtcgct ggacctcgcc | 360 |
| gcgccgccgg cggcggcagc ggcggcggcg gtgcaggcgg gtgccgagga gatcgtgctg | 420 |
| cagcccatca aggagatctc cggcaccgtc aagctgccgg ggtccaagtc gctttccaac | 480 |
| cggatcctcc tgctcgccgc cctgtccgag gggacaacag tggttgataa cctgttgaac | 540 |
| agtgaggatg tccactacat gctcgggggcc ttgaggactc ttggtctctc tgtcgaagcg | 600 |
| gacaaagctg ccaaaagagc tgtagttgtt ggctgtggtg gaaagttccc agttgaggat | 660 |
| tctaaagagg aagtgcagct cttcttgggg aatgctggaa ctgcaatgcg gccattgaca | 720 |
| gcagctgtta ctgctgctgg tggaaatgca acttacgtgc ttgatggagt accaagaatg | 780 |
| agggagagac ccattggcga cttggttgtc ggattgaagc agcttggtgc agatgttgat | 840 |
| tgtttccttg gcactgactg cccacctgtt cgtgtcaatg gaatcggagg gctacctggt | 900 |
| ggcaaggtca agctgtctgg ctccatcagc agtcagtact tgagtgcctt gctgatggct | 960 |

```
gctcctttgg ctcttgggga tgtggagatt gaaatcattg ataaattaat ctccattccc    1020
tacgtcgaaa tgacattgag attgatggag cgttttggtg tgaaagcaga gcattctgat    1080
agctgggaca gattctacat taagggaggt caaaaataca agtcccctaa aaatgcctat    1140
gttgaaggtg atgcctcaag cgcaagctat ttcttggctg gtgctgcaat tactggaggg    1200
actgtgactg tggaaggttg tggcaccacc agtttgcagg gtgatgtgaa gtttgctgag    1260
gtactggaga tgatgggagc gaaggttaca tggaccgaga ctagcgtaac tgttactggc    1320
ccaccgcggg agccatttgg gaggaaacac ctcaaggcga ttgatgtcaa catgaacaag    1380
atgcctgatg tcgccatgac tcttgctgtg gttgccctct tgccgatggc ccgacagcc    1440 atcagagacg tggcttcctg gagagtaaag gagaccgaga ggatggttgc gatccggacg    1500
gagctaacca gctgggagc atctgttgag gaagggccgg actactgcat catcacgccg    1560
ccggagaagc tgaacgtgac ggcgatcgac acgtacgacg accacaggat ggccatggcc    1620
ttctcccttg ccgcctgtgc cgaggtcccc gtgaccatcc gggaccctgg gtgcacccgg    1680
aagaccttcc ccgactactt cgatgtgctg agcactttcg tcaagaatta ataaagcgtg    1740
cgatactacc acgcagcttg attgaagtga taggcttgtg ctgaggaaat acatttcttt    1800
tgttctgttt tttctctttc acgggattaa gttttgagtc tgtaacgtta gttgtttgta    1860
gcaagtttct atttcggatc ttaagtttgt gcactgtaag ccaaatttca tttcaagagt    1920
ggttcgttgg aataataaga ataataaatt acgtttcagt ggctgtcaag cctgctgcta    1980
cgttttagga gatggcatta gacattcatc atcaacaaca ataaaacctt ttagcctcaa    2040
acaataatag tgaagttatt ttttagtcct aaacaagttg cattaggata tagttaaaac    2100
acaaaagaag ctaaagttag ggtttagaca tgtggatatt gttttccat                2149

<210> SEQ ID NO 318
<211> LENGTH: 240
<212> TYPE: DNA
<213> ORGANISM: Zea mays

<400> SEQUENCE: 318
tacttgagtg ccttgctgat ggctgctcct ttggctcttg gggatgtgga gattgaaatc      60
attgataaat taatctccat tccgtacgtc gaaatgacat tgagattgat ggagcgtttt    120
ggtgtgaaag cagagcattc tgatagctgg gacagattct acattaaggg aggtcaaaaa    180
tacaagtccc ctaaaaatgc ctatgttgaa ggtgatgcct caagcgcaag ctatttcttg    240

<210> SEQ ID NO 319
<211> LENGTH: 297
<212> TYPE: DNA
<213> ORGANISM: Nicotiana benthamiana

<400> SEQUENCE: 319
gctgtatcat atcttcttct ttagaacact aataaattaa acttcgagat aatgatttct      60
gacaagagta taaacaagtg catctatgaa gatttgaggt tgtccaaaaa agtgacaatt    120
ttgggttcct ataaactgta tttacattat tgttatttgc aactataaaa attttagatt    180
atttccaagc tcagtttctt caacttaaat gaaggtagca cttgaatttc atcagcctct    240
atgacccagt aacccatgtg ggagatggga gcaaagtggt caaactttag aaggaat      297

<210> SEQ ID NO 320
<211> LENGTH: 269
<212> TYPE: DNA
<213> ORGANISM: Nicotiana benthamiana
```

```
<400> SEQUENCE: 320
gtatgaactt tcagaatatt ataccggatc aatatattat gctgaaatat ttttcggact        60
ttaaataatt tctttattta aatttatttt tatacaaaaa taactaaatt tcaattactt       120
ttaaaattat gattattttt caattaccac ttatacatcc tgctattttg aatttcaccc       180
gaaagaacta ctactatacg tggatcctca atgacccagt aacccaagtg ggagatgtgt       240
gcaaagtggt caaatcttag aaggaatga                                         269
```

POLYNUCLEOTIDE MOLECULES FOR GENE REGULATION IN PLANTS

CROSS-REFERENCE TO RELATED APPLICATIONS AND INCORPORATION OF SEQUENCE LISTING

This application is a Divisional of U.S. patent application Ser. No. 13/042,856 filed 8 Mar. 2011, issued as U.S. Pat. No. 9,121,022, which claims the benefit of priority of U.S. Provisional Patent Applications 61/311,762 filed 8 Mar. 2010, 61/349,807 filed 28 May 2010, and 61/381,556 filed 10 Sep. 2010, which are incorporated by reference in their entirety herein. The sequence listing that is contained in the file named "38-21_56855 D.txt", which is 133 kilobytes (measured in operating system MS-Windows) and was created on 7 Mar. 2011 and was filed in U.S. patent application Ser. No. 13/042,856 on 8 Mar. 2011 is incorporated herein by reference.

FIELD OF THE INVENTION

Disclosed herein are polynucleotide molecules for regulating genes in plants and methods of making and using such molecules.

BACKGROUND

The failure of herbicides to control resistant weeds is a problem especially when such weeds are growing in field of herbicide resistant crops that may have lower herbicide resistance than the weed. Herbicide-resistant weeds are identified with a variety of modes of action. Resistance resulting from selection for multiple copies of genes producing herbicide targetted proteins in pigweed is reported by Gaines et al. (2010) *Proc. Natl. Acad. Sci. USA*, 107(3): 1029-1034. Resistance resulting from mutations in genes producing herbicide targetted proteins in goosegrass, prickly lettuce, and ryegrass are reported by Baerson et al. (2002) *Plant Physiol.*, 129(3):1265-1275; Preston et al. (2006) *Pesticide Biochem. Physiol.*, 84(3):227-235; and Wakelin et al. (2006) *Weed Res. (Oxford)*, 46(5):432-440. Vacuolar sequestration of glyphosate is an observed mechanism in glyphosate resistant horseweed; see Ge et al. (2010) *Pest Management Sci.*, 66:576-576. Resistance resulting from expression of enzymes that metabolize herbicides to an inactive chemical form in hairy crabgrass is reported by Hidayat et al. (1997) *Pesticide Biochem. Physiol.*, 57(2): 137-146. Reddy et al. (2008) *J. Agric. Food Chem.*, 56(6): 2125-2130 reported the accumulation of aminomethylphosphonic acid in plant species treated with glyphosate.

SUMMARY OF THE INVENTION

This invention provides polynucleotide molecules and methods for regulating genes in plants, e. g., by providing RNA for systemic regulation of genes. Various aspects of the invention provide polynucleotide molecules and methods for regulating endogenous genes and transgenes in a plant cell and polynucleotide molecules. The polynucleotides, compositions, and methods disclosed herein are useful for regulating endogenous genes of a plant pest or pathogen. In an aspect of the invention, the polynucleotide molecules are provided in compositions that can permeate or be absorbed into living plant tissue to initiate systemic gene silencing of endogenous genes or transgenes, or of their transcribed RNA. In some aspects of the invention polynucleotide molecules ultimately provide to a plant, or allow the production in cells in a plant, RNA that is capable of hybridizing under physiological conditions in a plant cell to RNA transcribed from a target endogenous gene or target transgene in the plant cell, thereby effecting regulation of the target gene, e. g., silencing or suppression of the target gene. In other aspects of the invention polynucleotide molecules disclosed herein are useful also for ultimately providing to a plant, or allowing the production in cells of a plant, RNA that is capable of hybridizing under physiological conditions to RNA transcribed from a target gene in a cell of an invertebrate pest or of a viral pathogen of the plant, thereby effecting regulation of the target gene, e. g., silencing or suppression of the target gene. In some aspects, the silencing or suppression of the target gene leads to the upregulation of another gene that is itself affected or regulated by the target gene's expression.

The compositions and methods of this invention are believed to operate through one or more of the several natural cellular pathways involved in RNA-mediated gene suppression as generally described in reviews by Brodersen and Voinnet (2006), *Trends Genetics,* 22:268-280; Tomari and Zamore (2005) *Genes & Dev.,* 19:517-529; Vaucheret (2006) *Genes Dev.,* 20:759-771; Meins et al. (2005) *Annu. Rev. Cell Dev. Biol.,* 21:297-318; and Jones-Rhoades et al. (2006) *Annu. Rev. Plant Biol.,* 57:19-53. RNA-mediated gene suppression generally involves a double-stranded RNA (dsRNA) intermediate that is formed intramolecularly within a single RNA molecule or intermolecularly between two RNA molecules. This longer dsRNA intermediate is processed by a ribonuclease of the RNase III family (Dicer or Dicer-like ribonuclease) to one or more shorter double-stranded RNAs, one strand of which is incorporated into the RNA-induced silencing complex ("RISC"). For example, the siRNA pathway involves the cleavage of a longer double-stranded RNA intermediate to small interfering RNAs ("siRNAs"). The size of siRNAs is believed to range from about 19 to about 25 base pairs, but the most common classes of siRNAs in plants include those containing 21 base pairs or 24 base pairs. See, Hamilton et al. (2002) *EMBO J.,* 21:4671-4679. As used herein, "oligonucleotide" means a polynucleotide molecule having a length of 18-25 nucleotides, similar to the size of processed small RNA molecules in gene silencing mechanisms. Various embodiments of this invention include compositions including oligonucleotides or polynucleotides or a mixture of both.

Aspects of the invention include compositions and methods for: providing single-stranded RNA molecules in a plant cell for systemic regulation of genes; herbicidal treatment with compositions including surfactant and a plant lethal agent which provides single-stranded RNA for suppression of an endogenous gene in a plant cell; topical coating onto a plant surface including a surfactant (e. g., an organosilicone surfactant) and an oligonucleotide or polynucleotide molecule for suppression of an endogenous gene in a plant cell; topically applied compositions for inducing systemic silencing of a target gene in a plant including (a) an agent for conditioning of a plant to permeation by polynucleotides and (b) polynucleotide molecules; and, herbicidal treatment with compositions including (a) an agent for conditioning of a plant to permeation by polynucleotide molecules, (b) polynucleotide molecules. Optionally these compositions can include a non-nucleotide herbicide.

In other aspects the invention provides methods for: controlling herbicide-resistant volunteer plants; investigating reverse genetics by modulating an endogenous gene in a plant by applying onto tissue of a growing plant a composition for providing single-stranded RNA molecules in a plant cell for systemic regulation of genes; inducing systemic silencing of a target gene including topical application of polynucleotides to a plant; inducing systemic silencing of a target gene in a plant by (a) conditioning of a plant to permeation by polynucleotides and (b) topically applying polynucleotides to the plant; investigating reverse genetics by modulating an endogenous gene in a plant by topically applying onto a living plant a topically applied composition including polynucleotide molecules and an agent for conditioning of a plant to permeation by such polynucleotide molecules.

In other aspects the invention provides a plant with exogenous DNA or RNA for suppressing an endogenous gene, where the exogenous DNA is not integrated into a chromosome of the plant, the exogenous RNA is not transcribed from DNA integrated into a chromosome of the plant, and the endogenous gene is suppressed by topical application of a polynucleotide to the plant. These and other aspects of the invention are described in greater detail in the following sections.

BRIEF DESCRIPTION OF THE DRAWINGS

FIG. 1 presents SEQ ID NO:1, a nucleotide sequence encoding Palmer amaranth EPSPS.

FIG. 2 presents SEQ ID NO:3 which is a nucleotide sequence of a synthesized Pol III gene.

FIG. 3 illustrates the morbidity of Palmer amaranth plants treated with a dsRNA. FIG. 3A depicts the plants 7 days after the glyphosate treatment. FIG. 3B depicts surfactant-treated plants that were treated with the long dsRNA solution followed by glyphosate treatment after 72 hours. FIG. 3C depicts surfactant-treated plants that were treated with the short dsRNA solution followed by glyphosate treatment after 72 hours.

FIG. 5 presents SEQ ID NO:2 which is a nucleotide sequence of a *Nicotiana benthamiana* phytoene desaturase.

FIG. 10 depicts the nucleotide sequence of a *Nicotiana benthamiana* phytoene desaturase (SEQ ID NO:2).

FIG. 12A illustrates apical leaf bleaching in *Nicotiana benthamiana* plants topically treated with buffer ("Control"), a 200-mer dsRNA polynucleotide with an RNA sequence corresponding to the segment consisting of nucleotides 914-1113 of SEQ ID NO:2 ("200 nt dsRNA"), and a combination of single-stranded DNA oligonucleotides and polynucleotides (SEQ ID NOs:16, 17, 20, 21, 24, 25, and 26) ("ssDNA oligos") as described in Example 10. FIG. 12B illustrates results of northern blot analysis of RNA isolated from *Nicotiana benthamiana* plants treated with buffer (control), the 200-mer dsRNA polynucleotide, and the ssDNA oligonucleotides. Also shown is RNA isolated from plants that had been stressed by being kept at 4 degrees Celsius and in the dark overnight prior to treatment with the 200-mer dsRNA polynucleotides.

FIG. 16 illustrates an alignment of the Palmer amaranth and *Nicotiana benthamiana* PDS DNA sequences showing about 71% identity (1252/1762) as described in Example 11.

FIG. 19 illustrates results of assays on different glyphosate-resistant Palmer amaranth lines (3 plants per replicate) treated with the conditions listed in Table 6, as described in Example 13. Photographs were taken at 7 days after glyphosate treatment (experiments 1-6) or at 9 days after glyphosate treatment (experiments 7-9).

FIG. 20 illustrates location of two small RNAs identified as abundant in EPSPS dsRNA-treated Palmer amaranth plants and which are shown as italicized underlined nucleotides at positions 564-588 and 743-767 of the full-length EPSPS (SEQ ID NO:40), as described in Example 14. The EPSPS sequence also shows the location of the four oligonucleotide-size "short" EPSPS dsRNA molecules (underlined, non-italicized text) and the three "long" double-stranded RNA polynucleotides (bolded text as described in Example 1.

FIG. 21A illustrates results of treating Palmer amaranth plants with surfactant followed by dsRNA at one of three application amounts, followed by herbicide, as described in Example 17. FIG. 21B illustrates results of assay 1 carried out on glyphosate-resistant Palmer amaranth grown from field-collected seeds as described in Example 17; plants are shown at 8 days and 30 days after treatment with herbicide.

FIG. 23 illustrates results of treating glyphosate-resistant Palmer amaranth plants with either EPSPS dsRNAs or EPSPS DNA/RNA hybrids, as described in Example 19.

FIG. 25A illustrates twelve dsRNA polynucleotides corresponding to DNA segments of approximately 250 bp each covering in a tiling manner the full coding sequence and part of the 5' and 3' untranslated regions of the Palmer EPSPS gene, as described in Example 21; the four oligonucleotide-size "short" EPSPS dsRNA molecules as described in Example 1 and FIG. 1 are located in the tiling segments 2, 3, 4, and 8 respectively, and are shown as light grey bars within those segments. FIG. 25B and FIG. 25C illustrates results of treating glyphosate-resistant Palmer amaranth plants with dsRNAs designed from these tiling segments or the four "short" dsRNA molecules or buffer.

FIG. 29A illustrates systemic silencing in lettuce plants evidenced by bleaching observed at 4 or 12 days after topical treatment with polynucleotides, as described in Example 24. FIG. 29B depicts the systemic silencing evidenced by bleaching observed at 4 after topical treatment with the four individual anti-sense ssDNAs ("HL287", SEQ ID NO:43; "HL288", SEQ ID NO:44; "HL289", SEQ ID NO:45; and "HL290", SEQ ID NO:46) or with a mixture of all four.

FIG. 30 also illustrates the stunting of the tomato plants treated with PDS polynucleotides (lower panel).

FIG. 34 illustrates an alignment of the *Nicotiana benthamiana* PDS locus 1 promoter (SEQ ID NO:319) and PDS locus 2 promoter (SEQ ID NO:320), as described in Example 30.

DETAILED DESCRIPTION OF THE INVENTION

Figure 4:
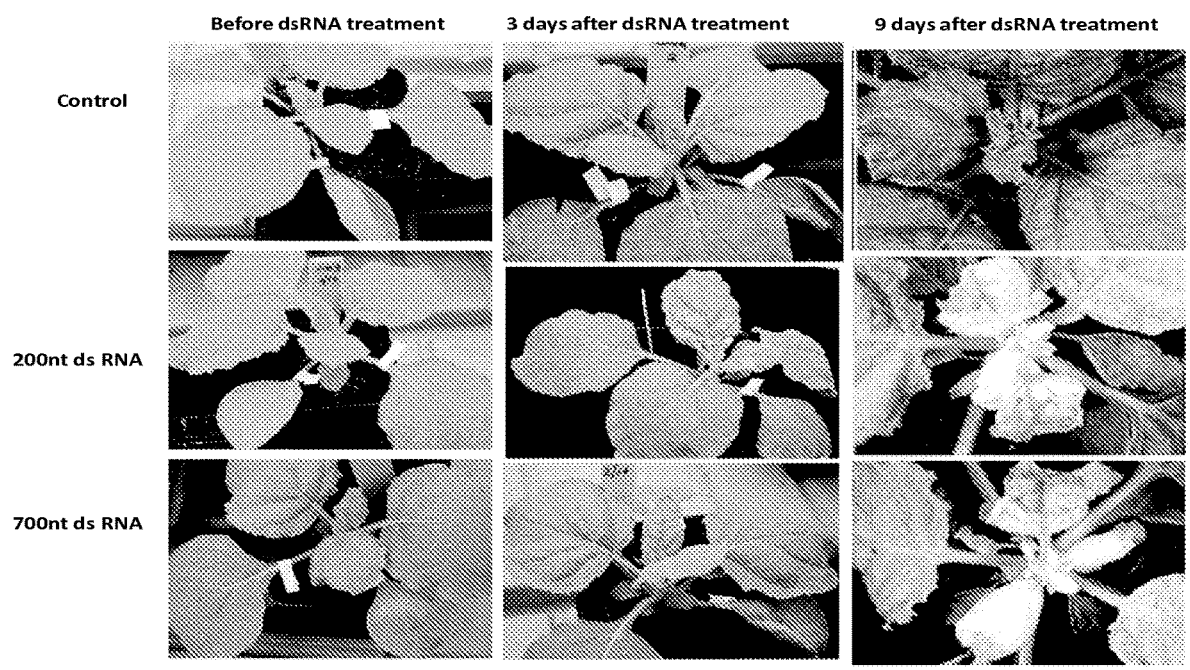
FIG. 4 illustrates the bleaching in *Nicotiana benthamiana* plants treated with a dsRNA composition.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art. Where a term is provided in the singular, the inventors also contemplate aspects of the invention described by the plural of that term. By "non-transcribable" polynucleotides is meant that the polynucleotides do not comprise a complete polymerase II transcription unit. As used here "solution" refers to homogeneous mixtures and non-homogeneous mixtures such as suspensions, colloids, micelles, and emulsions.

Polynucleotides

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Embodiments of this invention include compositions including oligonucleotides having a length of 18-25 nucleotides (e. g., 18-mers, 19-mers, 20-mers, 21-mers, 22-mers, 23-mers, 24-mers, or 25-mers), or medium-length polynucleotides having a length of 26 or more nucleotides (e. g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

Polynucleotide compositions used in the various embodiments of this invention include compositions including oligonucleotides or polynucleotides or a mixture of both, including RNA or DNA or RNA/DNA hybrids or chemically modified oligonucleotides or polynucleotides or a mixture thereof. In some embodiments, the polynucleotide may be a combination of ribonucleotides and deoxyribonucleotides, e. g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In some embodiments, the polynucleotide includes non-canonical nucleotides such as inosine, thiouridine, or pseudouridine. In some embodiments, the polynucleotide includes chemically modified nucleotides. Examples of chemically modified oligonucleotides or polynucleotides are well known in the art; see, e. g., Verma and Eckstein (1998) *Annu. Rev. Biochem.*, 67:99-134. For example, the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labelled with a fluorescent moiety (e. g., fluorescein or rhodamine) or other label (e. g., biotin).

The polynucleotides can be single- or double-stranded RNA or single- or double-stranded DNA or double-stranded DNA/RNA hybrids or modified analogues thereof, and can be of oligonucleotide lengths or longer. In more specific embodiments of the invention the polynucleotides that provide single-stranded RNA in the plant cell are selected from the group consisting of (a) a single-stranded RNA molecule, (b) a single-stranded RNA molecule that self-hybridizes to form a double-stranded RNA molecule, (c) a double-stranded RNA molecule, (d) a single-stranded DNA molecule, (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule, (h) a double-stranded DNA molecule including a modified Pol III gene that is transcribed to an RNA molecule, (i) a double-stranded, hybridized RNA/DNA molecule, or combinations thereof. In some embodiments these polynucleotides include chemically modified nucleotides or non-canonical nucleotides. In embodiments of the method the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In one embodiment the polynucleotides include single-stranded DNA or single-stranded RNA that self-hybridizes to form a hairpin structure having an at least partially double-stranded structure including at least one segment that will hybridize under physiological conditions in the cell to RNA transcribed from the gene targetted for suppression. Not intending to be bound by any mechanism, it is believed that such polynucleotides are or will produce single-stranded RNA with at least one segment that will hybridize under physiological conditions in a cell to RNA transcribed from the gene targetted for suppression. In certain other embodiments the polynucleotides further includes a promoter, generally a promoter functional in a plant, e. g., a pol II promoter, a pol III promoter, a pol IV promoter, or a pol V promoter.

In some embodiments, the polynucleotide compositions are formulated with counter-ions or other molecules that are known to associate with nucleic acid molecules, e. g., tetraalkyl ammonium ions, trialkyl ammonium ions, sulfonium ions, lithium ions, and polyamines such as spermine, spermidine, or putrescine. In some embodiments, the polynucleotide compositions are formulated with a non-polynucleotide herbicide (e. g., the chemical herbicides disclosed herein in the section headed "Herbicide-Tolerance Proteins") or with a transferring agent or permeability-enhancing agent (see the section headed "Permeability-Enhancing Agents and Treatments").

The polynucleotides are designed to induce systemic regulation or suppression of an endogenous gene in a plant and are designed to have a sequence essentially identical or essentially complementary to the sequence (which can be coding sequence or non-coding sequence) of an endogenous gene of a plant or to the sequence of RNA transcribed from an endogenous gene of a plant. By "essentially identical" or "essentially complementary" is meant that the polynucleotides (or at least one strand of a double-stranded polynucleotide) are designed to hybridize under physiological conditions in cells of the plant to the endogenous gene or to RNA transcribed from the endogenous gene to effect regulation or suppression of the endogenous gene.

Embodiments of single-stranded polynucleotides functional in this invention have sequence complementarity that need not be 100% but is at least sufficient to permit hybridization to RNA transcribed from the target gene to form a duplex under physiological conditions in a plant cell to permit cleavage by a gene silencing mechanism. Thus, in embodiments the segment is designed to be essentially identical to, or essentially complementary to, a sequence of 18 or more contiguous nucleotides in either the target gene or messenger RNA transcribed from the target gene. By "essentially identical" is meant having 100% sequence identity or at least about 83, 84, 85, 86, 87, 88, 89, 90, 91, 92, 93, 94, 95, 96, 97, 98, or 99% sequence identity when compared to the sequence of 18 or more contiguous nucleotides in either the target gene or RNA transcribed from the target gene; by "essentially complementary" is meant having 100% sequence complementarity or at least about 83, 84, 85, 86, 87, 88, 89, 90, 91, 92, 93, 94, 95, 96, 97, 98, or 99% sequence complementarity when compared to the sequence of 18 or more contiguous nucleotides in either the target gene or RNA transcribed from the target gene. In some embodiments of this invention polynucleotide molecules are designed to have 100% sequence identity with or complementarity to one allele of a given target gene (e. g., coding or non-coding sequence of a gene for an herbicide-tolerance protein, an herbicide-deactivating protein, a stress-response gene, or an essential gene); in other embodiments the polynucleotide molecules are designed to have 100% sequence identity with or complementarity to multiple alleles of a given target gene.

In one aspect of the invention the polynucleotides are modified RNA polymerase III genes, e. g., genes that transcribe 7SL signal recognition particle RNA or U6 spliceosomal RNA (Pol III genes) or polynucleotides containing a functional Pol III promoter sequence. In one embodiment, the polynucleotides are modified Pol III genes containing sense and anti-sense DNA corresponding to RNA of the targetted gene identified for regulation replacing the DNA sequence originally transcribed by the Pol III gene.

The polynucleotides useful in this invention typically effect regulation or modulation (e. g., suppression) of gene expression during a period during the life of the treated plant of at least 1 week or longer and typically in systemic fashion. For instance, within days of treating a plant leaf with a polynucleotide composition of this invention, primary and transitive siRNAs can be detected in other leaves lateral to and above the treated leaf and in apical tissue.

Methods of making polynucleotides are well known in the art. Commercial preparation of oligonucleotides often provides 2 deoxyribonucleotides on the 3' end of the sense strand. Long polynucleotide molecules can be synthesized from commercially available kits, e. g., kits from Ambion have DNA ligated on the 5' end that encodes a bacterial T7 polymerase promoter that makes RNA strands that can be assembled into a dsRNA. Alternatively, dsRNA molecules can be produced from expression cassettes in bacterial cells that have regulated or deficient RNase III enzyme activity. Long polynucleotide molecules can also be assembled from multiple RNA or DNA fragments. In some embodiments design parameters such as Reynolds score and Tuschl rules are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

The polynucleotide compositions of this invention are useful in compositions, such as solutions of polynucleotide molecules, at low concentrations, alone or in combination with other components (e. g., surfactants, salts, and non-polynucleotide herbicides) either in the same solution or in separately applied solutions. While there is no upper limit on the concentrations and dosages of polynucleotide molecules that can useful in the methods of this invention, lower effective concentrations and dosages will generally be sought for efficiency. The concentrations can be adjusted in consideration of the volume of spray applied to plant leaves. In one embodiment, a useful treatment for herbaceous plants using 25-mer oligonucleotide molecules is about 1 nanomole of oligonucleotide molecules per plant, e. g., from about 0.05 to 1 nanomole per plant. Other embodiments for herbaceous plants include useful ranges of about 0.05 to about 100 nanomoles, or about 0.1 to about 20 nanomoles, or about 1 nanomole to about 10 nanomoles of polynucleotides per plant. Very large plants, trees, or vines may require correspondingly larger amounts of polynucleotides. When using long dsRNA molecules that can be processed into multiple oligonucleotides, lower concentrations can be used. In the examples to below to illustrate embodiments of the invention the factor 1× when applied to oligonucleotide molecules is arbitrarily used to denote a treatment of 0.8 nanomoles of polynucleotide molecule per plant; 10×, 8 nanomoles of polynucleotide molecule per plant; and 100×, 80 nanomoles of polynucleotide molecule per plant, For example, in example 23 plants were treated with an aqueous solution comprising a 100× treatment of EPSPS dsRNA (264 micrograms or 80 nanomoles) per plant.

Single-Stranded RNA Molecules

This invention provides polynucleotide molecules for providing single-stranded RNA for systemic regulation of genes in a plant cell. More specifically, the invention also provides compositions and methods for inducing systemic regulation (e. g., systemic suppression or silencing) of a target gene in a plant by topical application to the plant of a polynucleotide molecule with a segment in a nucleotide sequence essentially identical to, or essentially complementary to, a sequence of 18 or more contiguous nucleotides in either the target gene or RNA transcribed from the target gene, whereby the composition permeates the interior of the plant and induces systemic regulation of the target gene by the action of single-stranded RNA that hybridizes to the transcribed RNA, e. g., messenger RNA. The polynucleotide molecule can be one or more polynucleotide molecules with a single such segment, multiples of such a segment, multiple different such segments, or combination thereof.

Transferring Agents, Permeability-Enhancing Agents and Treatments

The compositions and methods of this invention can comprise transferring agents or permeability-enhancing agents and treatments to condition the surface of plant tissue, e. g., leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transferring agent enables a pathway for polynucleotides through cuticle wax barriers, stomata and/or cell wall or membrane barriers and into plant cells. Suitable agents to facilitate transfer of the composition into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning includes (a) surfactants, (b) an organic solvents or an aqueous solutions or aqueous mixtures of organic solvents, (c) oxidizing agents, (e) acids, (f) bases, (g) oils, (h) enzymes, or combinations thereof. Embodiments of the method can optionally include an incubation step, a neutralization step (e. g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e. g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e. g., plant-sourced oils, crop oils (such as those listed in the 9th Compendium of Herbicide Adjuvants, publicly available on line at www.herbicide.adjuvants.com) can be used, e. g., paraffinic oils, polyol fatty acid esters, or oils with short-chain molecules modified with amides or polyamines such as polyethyleneimine or N-pyrrolidine.

Such agents for conditioning of a plant to permeation by polynucleotides are applied to the plant by any convenient method, e.g., spraying or coating with a powder, emulsion, suspension, or solution; similarly, the polynucleotide molecules are applied to the plant by any convenient method, e. g., spraying or wiping a solution, emulsion, or suspension.

Examples of useful surfactants include sodium or lithium salts of fatty acids (such as tallow or tallowamines or phospholipids) and organosilicone surfactants. Other useful surfactants include organosilicone surfactants including nonionic organosilicone surfactants, e. g., trisiloxane ethoxylate surfactants or a silicone polyether copolymer such as a copolymer of polyalkylene oxide modified heptamethyl trisiloxane and allyloxypolypropylene glycol methylether (commercially available as SILWET® L-77 surfactant having CAS Number 27306-78-1 and EPA Number: CAL.REG.NO. 5905-50073-AA, currently available from Momentive Performance Materials, Albany, New York). When SILWET L-77 surfactant is used as a pre-spray treatment of plant leaves or other surfaces, concentrations in the range of about 0.015 to about 2 percent by weight (wt %) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt %) are efficacious in preparing a leaf or other plant surface for transfer of polynucleotide molecules into plant cells from a topical application on the surface.

Useful physical agents can include (a) abrasives such as carborundum, corundum, sand, calcite, pumice, garnet, and the like, (b) nanoparticles such as carbon nanotubes or (c) a physical force. Carbon nanotubes are disclosed by Kam et al. (2004) *J. Am. Chem. Soc.*, 126 (22):6850-6851, Liu et al. (2009) *Nano Lett.*, 9(3):1007-1010, and Khodakovskaya et al. (2009) *ACS Nano*, 3(10):3221-3227. Physical force agents can include heating, chilling, the application of positive pressure, or ultrasound treatment. Embodiments of the method can optionally include an incubation step, a neutralization step (e. g., to neutralize an acid, base, or oxidizing agent, or to inactivate an enzyme), a rinsing step, or combinations thereof. The methods of the invention can further include the application of other agents which will have enhanced effect due to the silencing of certain genes. For example, when a polynucleotide is designed to regulate genes that provide herbicide resistance, the subsequent application of the herbicide can have a dramatic effect on herbicide efficacy.

Agents for laboratory conditioning of a plant to permeation by polynucleotides include, e. g., application of a chemical agent, enzymatic treatment, heating or chilling, treatment with positive or negative pressure, or ultrasound treatment. Agents for conditioning plants in a field include chemical agents such as surfactants and salts.

Target Genes and Essential Genes

Compositions and methods of the invention are useful for modulating the expression of an endogenous or transgenic target gene in a plant cell. In various embodiments, a target gene includes coding (protein-coding or translatable) sequence, non-coding (non-translatable) sequence, or both coding and non-coding sequence. Compositions of the invention can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species. Examples of target genes include endogenous plant genes and transgenes expressed in plant cells. Other examples of target genes include endogenous genes of plant viral pathogens or endogenous genes of invertebrate plant pests.

Target genes can include genes encoding herbicide-tolerance proteins, non-coding sequences including regulatory RNAs, and essential genes, which are genes necessary for sustaining cellular life or to support reproduction of an organism. Embodiments of essential genes include genes involved in DNA or RNA replication, gene transcription, RNA-mediated gene regulation, protein synthesis, energy production, and cell division. One example of a compendium of essential genes is described in Zhang et al. (2004) *Nucleic Acids Res.*, 32:D271-D272, and is available at tubic.tju.edu.cn/deg/; version DEG 5.4 lists 777 essential genes for *Arabidopsis thaliana*. Examples of essential genes include translation initiation factor (TIF) and ribulose-1,5-bisphosphate carboxylase oxygenase (RuBisCO). Target genes can include genes encoding transcription factors and genes encoding enzymes involved in the biosynthesis or catabolism of molecules in plants such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin.

Compositions and Methods

Single-stranded RNA molecules of this invention can be provided directly to the plant cell as RNA or provided indirectly, e. g., where a polynucleotide molecule in the treatment composition causes in cells of a plant the production of the single-stranded RNA that is capable of hybridizing to the target gene's transcript. In many embodiments compositions of polynucleotide molecules further include one or more permeability enhancing agents to facilitate transfer of the polynucleotide molecules into a plant cell, such as agents for conditioning of a plant to permeation by polynucleotides. In aspects of the invention methods include one or more applications of the polynucleotide composition and one or more applications of a permeability-enhancing agent for conditioning of a plant to permeation by polynucleotides. When the agent for conditioning to permeation is an organosilicone surfactant, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

An aspect of the invention provides a method for inducing systemic silencing of a target gene in a plant including (a) conditioning of a plant to permeation by polynucleotides and (b) topical application of polynucleotide molecules to the plant, where the polynucleotide molecules include at least one segment of 18 or more contiguous nucleotides cloned from or otherwise identified from the target gene in either anti-sense or sense orientation, whereby the polynucleotide molecules permeate the interior of the plant and induce systemic silencing of the target gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (i. e., protein-encoding), (b) non-coding, or (c) both coding and non-coding parts of the target gene. Non-coding parts include DNA (or the RNA encoded by the DNA) encoding RNA regulatory sequences (e. g., promoters, introns, 5' or 3' untranslated regions, and microRNAs, trans-acting siRNAs, natural anti-sense siRNAs, and other small RNAs with regulatory function) or encoding RNAs having structural or enzymatic function (e. g., ribozymes, ribosomal RNAs, t-RNAs, aptamers, and riboswitches).

In various embodiments of the method for inducing systemic silencing of a target gene in a plant the target gene is (a) an endogenous gene of the plant, (b) an endogenous gene of a viral pathogen of the plant, (c) an endogenous gene of an invertebrate pest of the plant, (d) an endogenous gene of a symbiont of an invertebrate pest of the plant, or (e) an man-made gene inserted into a transgenic plant. In embodiments where the target gene is endogenous to a plant, the target gene (a) is an endogenous gene of the plant that is essential for maintaining the growth or life of the plant, (b) encodes a protein that provides herbicide resistance to the plant, or (c) transcribes to an RNA regulatory molecule. In embodiments of the method for inducing systemic silencing of a target gene in a plant, the conditioning includes application of a chemical agent, abrasion, wounding, enzymatic treatment, heating or chilling, treatment with positive or negative pressure, ultrasound treatment, or combinations thereof. In some embodiments, the conditioning includes application of a surfactant, such as organosilicone surfactants, e. g., a silicone polyether copolymer such as a copolymer of polyalkylene oxide modified heptamethyl trisiloxane and allyloxypolypropylene glycol methylether (commercially available as SILWET® L-77 surfactant). In embodiments of the method, the conditioning includes application of (a) a surfactant, (b) an organic solvent or an aqueous solution or aqueous mixture of an organic solvent, (c) a polypropylene glycol or an aqueous solution or aqueous mixture of polypropylene glycol, (d) nanoparticles, (e) an oxidizing agent, (f) an acid or a base, or (g) an oil, or of a combination thereof. Embodiments of the method can optionally include an incubation step, a neutralization step (e. g., to neutralize an acid, base, or oxidizing agent, or to inactivate an enzyme), a rinsing step, or combinations thereof.

The invention provides topical compositions for inducing systemic silencing of a target gene in a plant including (a) an agent for conditioning of a plant to permeation by polynucleotides and (b) polynucleotide molecules with at least one segment of 18 or more contiguous nucleotides essentially identical or complementary to the sequence of nucleotides of the target gene in either anti-sense or sense orientation. Such compositions can be used for the various methods disclosed herein including methods for investigating reverse genetics by modulating an endogenous gene in a plant, and as herbicidal compositions for the disclosed methods of weed control and volunteer plant control. Another aspect of the invention provides a plant including exogenous DNA or RNA for suppressing an endogenous gene, wherein the exogenous DNA is not integrated into a chromosome of the plant and the exogenous RNA is not transcribed from DNA integrated into a chromosome of the plant, and wherein the endogenous gene is suppressed by topical application of a polynucleotide to the plant. Alternatively, the exogenous DNA or RNA can be designed for suppressing an endogenous plant gene involved in responding to a pest or pathogen to provide control of plant pests or diseases. Such plant can be grown from seed or produced by a cutting, cloning, or grafting process (i. e., a plant not grown from a seed). Such plant is a row crop plant, a fruit, a vegetable, a tree, or an ornamental plant. For example, in embodiments of the inventions disclosed herein the plant is a row crop plant (e. g., corn, soybean, cotton, canola, sugar beet, alfalfa, sugarcane, rice, and wheat), or is a vegetable (e. g., tomato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra), or is an culinary plant (e. g., basil, parsley, coffee, or tea), or is a fruit (e. g., apple, pear, cherry, peach, plum, apricot, banana, plantain, table grape, wine grape, citrus, avocado, mango, or berry), or is a tree grown for ornamental or commercial use (e. g., a fruit or nut tree, or is an ornamental plant (e. g., an ornamental flowering plant or shrub or turf grass). Embodiments of a plant produced by a cutting, cloning, or grafting process (i. e., a plant not grown from a seed) include fruit trees and plants including citrus, apples, avocados, tomatoes, eggplant, cucumber, melons, watermelons, and grapes as well as various ornamental plants.

Methods for Investigating Reverse Genetics

In yet another aspect, the invention provides a method for investigating reverse genetics by regulating or modulating an endogenous target gene in a plant; such method includes applying onto tissue of a growing plant a composition for providing (directly or indirectly) single-stranded RNA of this invention for systemic regulation of genes in a plant cell. In embodiments of such a method, messenger RNA encoding a protein or regulatory RNA gene is targetted by a polynucleotide of the invention, effecting modulation of the gene during a period of at least 1 week during the life of the plant, e. g., to identify traits that can be imparted by topical application of polynucleotides. The method can further include additional steps, e. g., exposing the plant to an array of compounds to identify herbicide interactions or exposing the plant to abiotic stress (e. g., water deficit stress, nutrient deficit stress, heat stress, cold stress, salinity stress) or to biotic treatments (e. g., challenge with an insect or nematode pest or with a viral, fungal, or bacterial pathogen or exposure to a chemical compound or biological treatment) to identify responses by the plant to the stress or treatment. In another aspect of the invention libraries of plants with a variety of transiently silenced genes are screened against libraries of compounds (e. g., herbicides, phytohormones, endogenous or exogenous defense elicitors such as salicylic acid or harpins, deficiencies of molecules providing a plant nutrient such as nitrogen, phosphorous, potassium, sulfur, calcium, magnesium, iron, and zinc) to identify interactions with such compounds. Examples of plants useful in such screens include *Amaranthus palmeri* and *Nicotiana benthamiana*.

Methods for Transgene Silencing

In still yet another aspect of the invention, this method can be used to silence a transgene being expressed in a plant, thus providing a negative control that is an event-independent measurement of a transgene's contribution to plant performance or effect on a trait. Imparting a negative control effect may require multiple successive treatments with the polynucleotide molecules of this invention during the life cycle of a plant.

Specific Applications

In a related aspect the compositions and methods of the invention are also useful for transiently silencing one or more genes in a growing plant cell or whole plant to effect a desired phenotype in response to culture conditions, environmental or abiotic or biotic stress, or change in market demand during the growing season or in the post-harvest environment. For example, compositions and methods of the invention are useful for transiently suppressing a biosynthetic or catabolic gene in order to produce a plant or plant product with a desired phenotype, such as a desired nutritional composition of a crop plant product, e. g., suppressing a FAD2 gene to effect a desired fatty acid profile in soybean or canola or other oilseed or suppressing a lignin biosynthetic genes such as COMT and CCOMT to provide more easily digestible forage plants. Similarly, compositions and methods of the invention are useful for transiently suppressing an RNA regulatory molecule such as a microRNA (miRNA) or an endogenous miRNA decoy such as an endogenous miRNA, miRNA precursor, or miRNA decoy as disclosed in US Patent Application Publication 2009/0070898 which is incorporated herein by reference. Embodiments of the invention are useful for suppressing an endogenous plant gene involved in responding to a pest or pathogen, thus providing control of plant pests or diseases. The polynucleotides, compositions, and delivery methods disclosed herein are further useful in suppressing an endogenous target gene of an invertebrate pest of a plant, e. g., lepidopteran or coleopteran pests which can ingest RNA from the plant, thus providing control of plant pests or pest-induced diseases, e. g., by use of a topical spray for crop plants, vegetables, or fruit trees with DNA or RNA molecules targeting an invertebrate essential gene or a gene of a symbiont of the invertebrate pest. The polynucleotides, compositions, and delivery methods disclosed herein are further useful in providing control of a viral pathogen, e. g., by use of a topical anti-viral spray for crop plants, vegetables, or fruit trees with DNA or RNA molecules targeting a viral gene.

Herbicidal Compositions and Methods

An aspect of the invention provides a liquid herbicidal composition comprising polynucleotide molecules as a plant lethal agent which provides at least one species of single-stranded RNA which can hybridize under physiological conditions in a plant cell to RNA transcribed from endogenous gene(s) in the plant cell. In some embodiments, the target gene encodes a protein that provides tolerance to an herbicide or encodes a gene essential for maintaining the growth or life of the plant. The liquid herbicidal composition can further include permeability-enhancing agents, non-nucleotide herbicides, or combinations thereof and can be used in a multi-step treatment with the non-nucleotide herbicide and/or the permeability-enhancing agents applied separately. An embodiment of the liquid herbicidal composition is a liquid including an organosilicone surfactant as permeability-enhancing agent and oligonucleotides or polynucleotides as plant lethal agent which provide to cells of the plant single-stranded RNA capable of hybridizing under physiological conditions in the plant cells to RNA transcribed from a target gene in the plant cell to effect silencing of the target gene. In one embodiment a liquid herbicidal composition effective against glyphosate-resistant plants includes an organosilicone surfactant such as SILWET® L-77 surfactant and polynucleotide molecules for providing single-stranded RNA capable of hybridizing under physiological conditions in the plant cells to the RNA transcript of an endogenous or transgenic EPSPS gene encoding an EPSPS protein that provides tolerance to glyphosate When the polynucleotide molecule is designed to hybridize under physiological conditions in a plant cell to mRNA encoding an endogenous, protein or non-protein coding RNA that essential for maintaining plant growth or life and to effect gene silencing and reduction of the essential protein, the polynucleotide molecule can function as a plant lethal agent, i.e., a nucleotide herbicide. These herbicidal compositions including polynucleotide molecules can be adapted for topical coating onto leaves of a growing plant or for application onto roots or cut stems, e. g., of hydroponically grown or pot-grown plants.

An aspect of the invention provides a composition adapted for topical coating onto leaves or other surfaces of a living plant including a permeability-enhancing agent, e.g., a surfactant such as an organosilicone surfactant, and oligonucleotides or polynucleotides that provide (directly or indirectly) single-stranded RNA that can hybridize under physiological conditions in a plant cell to RNA transcribed from an endogenous plant gene in the cell. In one embodiment the endogenous plant gene is an endogenous plant gene encoding a protein that provides herbicide tolerance to herbicides such as glyphosate, dicamba, or sulfonylurea. Examples of such proteins that provide herbicide tolerance are disclosed below in the section "Herbicide-Tolerance Proteins".

Another aspect of the invention provides a method for controlling herbicide-resistant volunteer plants growing in a field of herbicide-resistant crop plants including applying onto the leaves or other surface of the volunteer plants a composition that provides to, or allows the production in, cells of the volunteer plants a single-stranded RNA molecule that is capable of hybridizing under physiological conditions in cells of the volunteer plants to RNA that is transcribed from an endogenous gene in the cells, wherein the endogenous gene (i) is an essential gene for maintaining the growth or life of the volunteer plant, (ii) encodes a protein that provides herbicide resistance to the volunteer plant, or (iii) transcribes to an RNA regulatory agent (e. g., promoters, also miRNA precursors, miRNAs, trans-acting siRNAs, and other non-coding RNAs having a regulatory function such as aptamers and riboswitches). The composition that provides to, or allows the production in, cells of the volunteer plants a single-stranded RNA molecule that is capable of hybridizing under physiological conditions in cells of the volunteer plants to RNA that is transcribed from an endogenous gene in the cells includes at least one polynucleotide molecule selected from the group consisting of (a) a single-stranded RNA molecule, (b) a single-stranded RNA molecule that self-hybridizes to form a double-stranded RNA molecule, (c) a double-stranded RNA molecule, (d) a single-stranded DNA molecule, (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule, (h) a double-stranded DNA molecule including a modified Pol III gene that is transcribed to an RNA molecule, and (i) a double-stranded, hybridized RNA/DNA molecule; In embodiments for silencing or suppression of an endogenous gene of a volunteer plant that encodes a protein that provides herbicide resistance to the volunteer plant, the method can include applying onto the volunteer plant a quantity of the herbicide for which the protein provides resistance. Compositions and methods of the invention are useful in controlling herbicide-tolerant (resistant) weeds or volunteer herbicide-tolerant (resistant) transgenic plants that may be growing in crop fields, e. g., a field of herbicide-resistant crop plants such as corn, soybean, cotton, canola, sugar beet, alfalfa, sugarcane, rice, wheat, as well as fruit and vegetable crops. In some such embodiments the weed or the volunteer plant is pigweed (e. g., Palmer amaranth) and other amaranth species, mare's tail (horseweed), waterhemp, giant ragweed, common ragweed, johnsongrass, goosegrass, ryegrass, hairy crabgrass, prickly lettuce, velvetleaf, alfalfa, corn, soybean, canola, cotton, sugar beet, sugarcane, rice, or wheat. In some such embodiments the endogenous gene encodes a protein that provides herbicide tolerance; examples of such proteins are disclosed herein in the section "Herbicide-Tolerance Proteins". In other such embodiments single-stranded RNA selectively suppresses a gene in a specific plant species but not in others, to permit selective control of that plant species. In still other such embodiments a non-selective, single-stranded RNA molecule suppresses a common gene in multiple plant species, permitting broader control across a group or taxon of plants. In more specific embodiments the method further includes applying onto the weed or volunteer plant a quantity of non-nucleotide herbicide (e. g., glyphosate, dicamba, glufosinate or sulfonylurea) for which the protein targetted by an RNA molecule provides resistance allowing dual modes of action through reducing production of the target protein by action of the RNA molecule and inhibiting the function of protein that is produced by action of the non-nucleotide herbicide; the herbicide can be applied in a separate (earlier or later) step from, or together with, the nucleotide composition. Applying a polynucleotide composition concurrently with, or followed by, application of a conventional non-nucleotide herbicide in some cases provides weed or volunteer plant control with synergistic effect (i. e., where the combined effect is greater than the sum of effects of the treatments made separately).

Herbicide-Tolerance Proteins

Natural (non-transgenic) and transgenic plants exhibiting herbicide tolerance (resistance) often have a gene that encodes a protein that is responsible for the herbicide tolerance, e. g., a transgene that provides the tolerance, a mutated endogenous gene that provides the tolerance or multiple copies of an endogenous gene that is normally targetted by an herbicide. A strategy for control of such plants is to apply an agent that suppresses, or at least reduces the expression of, the gene encoding the protein that imparts herbicide tolerance. Examples of a protein that provides tolerance to an herbicide include e. g., a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase, a dihydropteroate synthase, a phytoene desaturase, a protoporphyrin IX oxygenase, a hydroxyphenylpyruvate dioxygenase, a para-aminobenzoate synthase, a glutamine synthase, a cellulose synthase, a beta-tubulin, and a serine hydroxymethyltransferase.

Examples of nucleic acids encoding proteins conferring tolerance to herbicides include 5-enolpyruvylshikimate-3-phosphate synthases (EPSPS; see, e. g., U.S. Pat. Nos. 5,627,061, 5,633,435 RE39247, 6,040,497, and 5,094,945, and PCT International Application Publications WO04074443 and WO04009761), glyphosate oxidoreductase (GOX; U.S. Pat. No. 5,463,175), glyphosate decarboxylase (PCT International Application Publication WO05003362, U.S. Pat. No. 7,405,347, and U. S. Patent Application Publication 2004/0177399), glyphosate-N-acetyl transferase (GAT; U.S. Pat. No. 7,714,188) conferring tolerance to glyphosate; dicamba monooxygenase conferring tolerance to auxin-like herbicides such as dicamba (U.S. Pat. No. 7,105,724); phosphinothricin acetyltransferase (pat or bar) conferring tolerance to phosphinothricin or glufosinate (U.S. Pat. No. 5,646,024); 2,2-dichloropropionic acid dehalogenase conferring tolerance to 2,2-dichloropropionic acid (Dalapon) (PCT International Application Publication WO9927116); acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. No. 6,225,105); haloarylnitrilase (Bxn) for conferring tolerance to bromoxynil (U.S. Pat. No. 4,810,648); modified acetyl-coenzyme A carboxylase for conferring tolerance to cyclohexanedione (sethoxydim) and aryloxyphenoxypropionate (haloxyfop) (U.S. Pat. No. 6,414,222); dihydropteroate synthase (sul I) for conferring tolerance to sulfonamide herbicides (U.S. Pat. No. 5,719,046); 32 kDa photosystem II polypeptide (psbA) for conferring tolerance to triazine herbicides (Hirschberg et al., 1983, Science, 222:1346-1349); anthranilate synthase for conferring tolerance to 5-methyltryptophan (U.S. Pat. No. 4,581,847); dihydrodipicolinic acid synthase (dap A) for conferring to tolerance to aminoethyl cysteine (PCT International Application Publication WO8911789); phytoene desaturase (crtI) for conferring tolerance to pyridazinone herbicides such as norflurazon (Japan Patent JP06343473); hydroxyphenylpyruvate dioxygenase, a 4-hydroxyphenylacetic acid oxidase and a 4-hydroxyphenylacetic 1-hydrolase (U.S. Pat. No. 7,304,209) for conferring tolerance to cyclopropylisoxazole herbicides such as isoxaflutole (U.S. Pat. No. 6,268, 549); modified protoporphyrinogen oxidase I (protox) for conferring tolerance to protoporphyrinogen oxidase inhibitors (U.S. Pat. No. 5,939,602); aryloxyalkanoate dioxygenase (AAD-1) for conferring tolerance to an herbicide containing an aryloxyalkanoate moiety (WO05107437); a serine hydroxymethyltransferase (US Patent Application Publication 2008/0155716), a glufosinate-tolerant glutamine synthase (US Patent Application Publication 2009/0018016). Examples of such herbicides include phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac). The nucleotide sequences of the nucleic acids encoding herbicide-tolerance proteins and the sequences of the herbicide-tolerance proteins, as disclosed in the U. S. patent and patent application publications cited in this paragraph are incorporated herein by reference.

Aspects of this invention provide polynucleotides and methods that directly or indirectly provide to a plant cell RNAs that hybridize to RNA encoding such herbicide-tolerance proteins at a level to be lethal to the plant or at least at a level to reduce herbicide tolerance. Due to the sequence degeneracy of the DNA encoding herbicide-tolerance proteins it is possible to design a polynucleotide for use in this invention that is specifically effective in a particular plant. Due to conservation of domains of DNA among a multitude of plants it is possible to design a polynucleotide for use in this invention that is effective across a variety of plants.

In an embodiment the polynucleotide is admixed with the corresponding herbicide to potentiate the activity of the herbicide by providing improved herbicidal activity. In an embodiment the polynucleotide is utilized separately from the herbicide but in combination with an application of the herbicide as a pre- or post-treatment. In embodiments the organosilicone surfactant is advantageously combined with the herbicide and the polynucleotide or is combined with one or the other when the compositions are applied in a sequential manner. Plants in a greenhouse setting can be treated using a track sprayer or laboratory sprayer with a 11001XR spray nozzle to deliver the sample solution at a determined rate (e. g., 140 L/ha) at 0.25 MPa pressure. In the field the treatment solution can be applied with a $CO_2$ pressurized backpack sprayer calibrated to deliver the appropriate rate of the composition with a 11015 flat fan spray nozzle with a customized single nozzle assembly (to minimize waste) at a spray pressure of 0.25 MPa; the single nozzle sprayer provides an effective spray swath of 60 cm above the canopy of 3 to 12 inch tall growing plants.

Example 1

This example illustrates the utility of the polynucleotide molecules of this invention in controlling herbicide resistant weeds. Genotypes of glyphosate-resistant Palmer amaranth were identified as having multiple copies, e. g., from 4 to more than 100 copies, of the gene encoding 5-enolpyruvyl-shikimate-3-phosphate synthase (EPSPS) which is targetted by the glyphosate compounds in herbicide treatments.

With reference to SEQ ID NO:1 as shown in FIG. 1, four oligonucleotide-size "short" dsRNA molecules were designed with an anti-sense strand that is capable of hybridizing to the mRNA transcribed from the Palmer amaranth EPSPS gene at positions 14-38 (short dsRNA-1), positions 153-177 (short dsRNA-2), 345-369 (short dsRNA-3), and 1105-1129 (short dsRNA-4), as indicated by underlined nucleotides in FIG. 1. The four designed short dsRNAs were purchased from Integrated DNA Technologies (IDT); the dsRNAs had a two nucleotide overhang at the 3' end of the anti-sense strand, and had two deoxynucleotides as the terminal nucleotides at the 3' end of the sense strand.

With reference to SEQ ID NO:1 and FIG. 1, three "long" double-stranded RNA polynucleotides were designed with one strand that is capable of hybridizing to the mRNA transcribed from the Palmer amaranth EPSPS gene at positions 16-170 (long dsRNA-1), 451-722 (long dsRNA-2), and 1109-1328 (long dsRNA-3) as indicted by the bolded nucleotides in FIG. 1. The three designed long dsRNAs were made using an Ambion MEGAscript® RNAi Kit, Cat. No. 1626.

Vegetative clones of glyphosate-resistant Palmer amaranth with 16 copies of the endogenous gene encoding EPSPS (Gaines, et al. (2010) *Proceedings of the National Academy of Sciences* 107(3): 1029-1034) were grown in 3.5 inch square pots with SunGro® Redi-earth seedling mix containing 3.5 kg/cubic meter Osmocote® 14-14-14 fertilizer in a greenhouse with 14-hour photoperiod and a daytime temperature of 30 degrees centigrade and night temperature of 20 degrees centigrade; the plants were watered with deionized water as necessary.

A pretreatment surfactant solution for leaf dip was prepared by diluting SILWET L-77 brand organosilicone surfactant with distilled water to 0.1% (v/v). A pretreatment 5% (w/v) carborundum solution was prepared by mixing 2 g carborundum (400 grit) in 40 ml distilled water. A treatment buffer solution was prepared with 10 mM sodium phosphate and 0.01% (v/v) SILWET L-77 organosilicone surfactant in DEPC water (Omega Bio-Tek) and adjusted to pH 6.8. A short dsRNA solution was prepared with equimolar amounts of each of the four short dsRNAs (identified above) in treatment buffer solution at a concentration of 0.005 nanomoles of each short dsRNA per microliter. A long dsRNA solution was prepared with equimolar amounts of each of the three long dsRNAs in treatment buffer at a concentration of 0.0006 nanomoles of each of long dsRNA per microliter. A mixed (short/long) dsRNA solution was prepared with 0.005 nanomoles of each of the four short dsRNAs and 0.0006 nanomoles of each of the three long dsRNAs per microliter.

Vegetative clones of glyphosate-resistant Palmer amaranth with 16 copies of the endogenous gene encoding EPSPS were pre-treated with carborundum solution or surfactant solution to condition the leaves to transfer or permeation of dsRNA. For carborundum solution pre-treatment leaf abrasion was effected by gently rubbing 0.5 ml of the carborundum solution on the upper surface of a leaf, rinsing with water and blotting dry. For surfactant solution pre-treatment four, fully-expanded, mature source leaves were dipped in the surfactant solution and allowed to dry. After leaf pre-treatment by carborundum solution or surfactant solution, the conditioned leaves were treated with either buffer solution (as a control) or 40 microliters of a dsRNA solution (applying 10 microliters of dsRNA solution on each of 4 leaves per plant). Treatment with the short dsRNA solution applied about 0.8 nanomoles of short dsRNA molecules (0.2 nanomoles of each short dsRNA) to each treated plant. Treatment with the long dsRNA solution applied about 0.072 nanomoles of long dsRNA molecules (0.024 nanomoles of each long dsRNA) to each treated plant. Treatment with the mixed (short/long) dsRNA solution applied about 0.8 nanomoles of the short dsRNA molecules and about 0.072 nanomoles of the long dsRNA molecules to each treated plant. Except for controls, all plants were sprayed with a glyphosate herbicide solution (1682 g acid equivalent per hectare of Roundup® WeatherMAX® brand herbicide) immediately, 48, or 72 hours after dsRNA treatment and evaluated at least after 7 days post-glyphosate treatment.

Results

Six surfactant-treated, control plants (no dsRNA molecule treatment) survived glyphosate treatment. See FIG. 3A for a picture of the plants 7 days after the glyphosate treatment.

Two of four carborundum abrasive-treated, control plants (no dsRNA molecule treatment) were killed by glyphosate treatment.

Six surfactant-treated plants that were treated with glyphosate immediately after application of the mixed (short/long) dsRNA solution survived but were stunted.

Six surfactant-treated plants that were treated only with the mixed (short/long) dsRNA solution and no glyphosate survived. Five of six surfactant-treated plants that were treated with the mixed (short/long) dsRNA solutions followed by glyphosate treatment were killed.

Five of six surfactant-treated plants that were treated with glyphosate 48 hours after application of the mixed (short/long) dsRNA solution were killed.

Three of four carborundum-treated plants that were treated with glyphosate 48 hours after application of the mixed (short/long) dsRNA solution were killed.

Five of six surfactant-treated plants, that were treated with the long dsRNA solution, followed by glyphosate treatment after 72 hours, were killed; see FIG. 3B. Six of six surfactant-treated plants, that were treated with the short dsRNA solution, followed by glyphosate treatment after 72 hours, were killed; see FIG. 3C.

Example 2

This example illustrates the utility of the polynucleotide molecules of this invention for improving the control of glyphosate herbicide-sensitive weeds. The mixed (short/long) dsRNA solutions prepared in Example 1 were applied to glyphosate-sensitive velvetleaf plants (a total of 40 microliters applied to two leaves) that had been pre-treated with the surfactant solution used in Example 1. Control plants were treated with buffer only following pre-treatment with the surfactant solution. 48 hours after dsRNA treatment the plants were treated with glyphosate herbicide solution (53 g acid equivalent per hectare of Roundup® WeatherMAX® brand glyphosate herbicide). A two-fold increase in glyphosate activity as estimated by observing plant growth (measured as plant height) was observed in the plants treated with the polynucleotide composition and herbicide as compared to control plants treated with buffer and herbicide. The plants treated with the polynucleotide composition and herbicide survived with severe stunting; the control plants treated with buffer and herbicide survived and fully recovered. Similar results were obtained with other glyphosate herbicide-sensitive weeds, i. e., glyphosate herbicide-sensitive waterhemp, redroot pigweed, giant ragweed, prickly lettuce, tobacco, and dandelion.

Example 3

This example illustrates the utility of the polynucleotide molecules of this invention for controlling weeds in transgenic glyphosate-resistant crops. Transgenic alfalfa, canola, corn, cotton, rice, soybean, sugarcane, sugar beet, and wheat plants having recombinant DNA for expressing a bacterial EPSPS (see U.S. Pat. RE39,247 for a description of glyphosate-resistant "class II" EPSPS genes) are treated with (a) the surfactant solution used in Example 1, (b) the mixed (short/long) dsRNA solution prepared in Example 1, and (c) glyphosate herbicide solution (1682 g acid equivalence per hectare Roundup® WeatherMAX®) 48 hours after dsRNA treatment. After 30 days all transgenic glyphosate-resistant crop plants survive and exhibit no stunting.

Example 4

This example illustrates the utility of the polynucleotide molecules of the invention as herbicidal agents. Two dsRNA polynucleotide molecules were designed to target overlapping segments of mRNA encoding phytoene desaturase in tobacco (*Nicotiana benthamiana*). With reference to SEQ ID NO:2 and FIG. 5, a dsRNA targeting a 192 nt length (shown in bold in FIG. 5) and a 685 nt length (shown in underline in FIG. 5) of the mRNA were made using an Ambion® MEGAscript® kit. Separate dsRNA solutions were prepared. Tobacco plant leaves were pretreated with surfactant solution prepared as in Example 1 and then treated with either one of the dsRNA solutions applying about 0.6 micromoles of dsRNA per plant. On day 9 after dsRNA treatment phytoene desaturase silencing was apparent from visible leaf bleaching on apical leaves; see FIG. 4. At 15 days after treatment with dsRNA one half of the treated plants appeared to be dead and the other half of the plants had most of the above ground tissues bleached. Northern blot analysis indicates the presence of siRNAs corresponding to the dsRNAs used in treatment.

Example 5

This example further illustrates the utility of polynucleotide molecules of the invention as herbicidal agents. dsRNA oligonucleotide molecules are designed to target RNA encoding EPSPS for each of the following plants: ragweed (*Ambrosia artemisiifolia*), giant ragweed (*Ambrosia trifida*), Johnsongrass (*Sorghum halepense*), hairy fleabane (*Conzya bonariensis*), sourgrass (*Digitaria insularis*), liverseedgrass (*Urochloa panicoides*), euphorbia (*Euphorbia heterophylla*), junglerice (*Echinochloa colona*), lambsquarters (*Chenopodium album*), green foxtail (*Setaria viridis*), foxtail millet (*Setaria italic*), barnyard grass (*Echinochloa crus-galli*), crabgrass (*Digitaria sanguinalis*), cocklebur (*Xanthium strumarium*), blackgrass (*Alopecurus myosuroides*), wild oat (*Avena fatua*), sicklepod (*Senna obtusifolia*), morning glories (*Ipomoea* sp.), field bindweed (*Convolvulus arvensis*), shattercane (*Sorghum bicolor*), dayflower (*Commelina*), Spiderwort (*Tradescantia* sp.), ryegrass (*Lolium* sp.), goosegrass (*Eleusine indica*), horseweed (*Conzya canadensis*), buckhorn plantain (*Plantago lanceolata*), pigweed (*Amaranthus palmeri*), rough-fruit amaranth (*Amaranthus tuberculatus*), tumble pigweed (*Amaranthus albus*), smooth pigweed (*Amaranthus hybridus*), redroot pigweed (*Amaranthus retroflexus*), waterhemp (*Amaranthus rudis/tuberculatus*), slender amaranth (*Amaranthus viridis*), Thunberg's amaranth (*Amaranthus thumbergii*), spiny amaranth (*Amaranthus spinosis*), (*Amaranthus rubra*), (*Amaranthus lividus*), Mediterranean amaranth (*Amaranthus graecizans*), rough amaranth (*Amaranthus chlorostachys*), Powell amaranth (*Amaranthus powellii*), Mat amaranth (*Amaranthus blitoides*), Kochia (*Kochia scoparia*), Yellow starthistle (*Centaurea solstitialis*), and Velvetleaf (*Abutilon theophrasti*). Plant leaves are pretreated with surfactant solution prepared as in Example 1 and treated with dsRNA solutions at a treatment of about 1 nanomole per plant. After 15 days treated plants are dead, dying, or stunted.

Example 6

This example further illustrates the utility of polynucleotide molecules of the invention as herbicidal agents. dsRNA oligonucleotide molecules are designed to target RNA encoding acetolactate synthase and phytoene desaturase for each of the plants listed in Example 5. Plant leaves are pretreated with surfactant solution prepared as in Example 1 and treated with dsRNA solutions at a treatment of about 1 nanomole per plant. After 15 days treated plants are dead, dying, or stunted.

Example 7

This example further illustrates the utility of the polynucleotide molecules of the invention as herbicidal agents. The method of Example 4 is repeated to provide short dsRNA oligonucleotides that are designed to target RNA encoding each of the following proteins in Palmer amaranth: a 5-enolpyruvylshikimate-3-phosphate synthase (EPSPS), an acetyl-coenzyme A carboxylase, a dihydropteroate synthase, a protoporphyrin IX oxygenase, a hydroxyphenylpyruvate dioxygenase, a glutamine synthase, D1 protein, a translation initiation factor (TIF), a ribulose-1,5-bisphosphate carboxylase oxygenase (RuBisCO), and a DNA-dependent ATPase (ddATPase). Leaves of separate glyphosate-resistant Palmer amaranth plants are treated with the surfactant solution prepared as in Example 1 and separately each of the dsRNA oligonucleotide molecules in the manner of Example 1 at a treatment of 1 nanomole of dsRNA per plant. After 30 days the treated plants are dead, dying, or stunted.

Example 8

This example illustrates the utility of employing a synthetic Pol III gene in compositions and methods of this invention. With reference to SEQ ID NO:3 and FIG. 2, a synthetic Pol III gene is created using elements from an *Arabidopsis thaliana* U6 snRNA gene to provide a dsDNA molecule with two copies of RGCCCR elements (bold and underlined), an upstream sequence element (USE) having the sequence "TCCCACATCG" (SEQ ID NO:4, bold and underlined), a TATA box (bold and underlined), a "G" nucleotide (bold and underlined), anti-sense DNA (italics) corresponding to a bacterial DNA encoding an EPSPS protein (see U.S. Pat. RE39,247) that imparts resistance to glyphosate herbicide when expressed in transgenic corn plants, an "AAGATTAGCACGG" element (SEQ ID NO:5, bold and underlined) embedded in the anti-sense DNA, an "ACGCATAAAAT" element (SEQ ID NO:6, bold and underlined) followed by sense DNA (lower case) and a "TTTTTT" terminator element (SEQ ID NO:7, bold and underlined). A solution of 0.1 wt % SILWET L-77 brand organosilicone surfactant and a solution of multiple copies of the dsDNA molecule are sprayed onto leaves of volunteer glyphosate-resistant corn plants growing in a field of glyphosate-resistant soybean plants, followed 7 days later by treatment with Roundup WeatherMAX® brand glyphosate herbicide. 15 days later the corn plants are dead and the soybean plants are thriving; control glyphosate-resistant corn plants treated only with surfactant and glyphosate herbicide are thriving.

Example 9

This example illustrates an aspect of the invention. In this example, polynucleotide molecules were applied to and permeated into plant tissue thereby inducing systemic regulation, i. e., silencing, of a target gene (an endogenous EPSPS). More specifically, a composition including single-stranded DNA (ssDNA) oligonucleotides suppressed the expression of an endogenous EPSPS in glyphosate-tolerant Palmer amaranth (*Amaranthus palmeri*).

The anti-sense ssDNA oligonucleotides were designed using IDT SciTools software (available at idtdna.com/Scitools/Applications/Anti-sense/Anti-sense.aspx). The oligonucleotides included four ssDNA oligonucleotides anti-sense to *Amaranthus palmeri* EPSPS (SEQ ID NOs:8, 9, 10, and 11), two chemically modified (phosphorothioate modified) ssDNA oligonucleotides anti-sense to *Amaranthus palmeri* EPSPS (SEQ ID NOs:12 and 13), a control ssDNA oligonucleotide anti-sense to a control gene, barley (*Hordeum vulgare*) seed protein, GenBank ID X97636 (SEQ ID NO:14), and a chemically modified (5'-labelled with Alexa Fluor 488 from Invitrogen) ssDNA oligonucleotide anti-sense to *Amaranthus palmeri* EPSPS (SEQ ID NO:15), as indicated in Table 1.

TABLE 1

Anti-sense ssDNA oligonucleotides

| Name | SEQ ID NO: | Sequence (5' to 3') | Note |
|---|---|---|---|
| Anti-sense_PO1 | 8 | ACCCTCCACGACTGCCCTTT | |
| Anti-sense_PO2 | 9 | GTTTCCTTCACTCTCCAGC | |
| Anti-sense_PO3 | 10 | GTAGCTTGAGCCATTATTGT | |
| Anti-sense_PO4 | 11 | GTTGATGGTAGTAGCTTGAG | |
| Anti-sense_PS1 | 12 | ACCCTCCACGACTGCCCTTT | phosphorothioate modification of the three 5'-terminal and three 3'-terminal nucleotides |

TABLE 1-continued

Anti-sense ssDNA oligonucleotides

| Name | SEQ ID NO: | Sequence (5' to 3') | Note |
|---|---|---|---|
| Anti-sense_PS2 | 13 | GTTTCCTTCACTCTCCAGC | phosphorothioate modification of the three 5'-terminal and three 3'-terminal nucleotides |
| Anti-sense_ck | 14 | AAGCGGTTGAGCACTGAA | Control sequence, barley seed protein, GenBank ID X97636 |
| Anti-sense_PO1_488 | 15 | ACCCTCCACGACTGCCCTTT | 5'-labelled with Alexa Fluor 488 |

Figure 6:
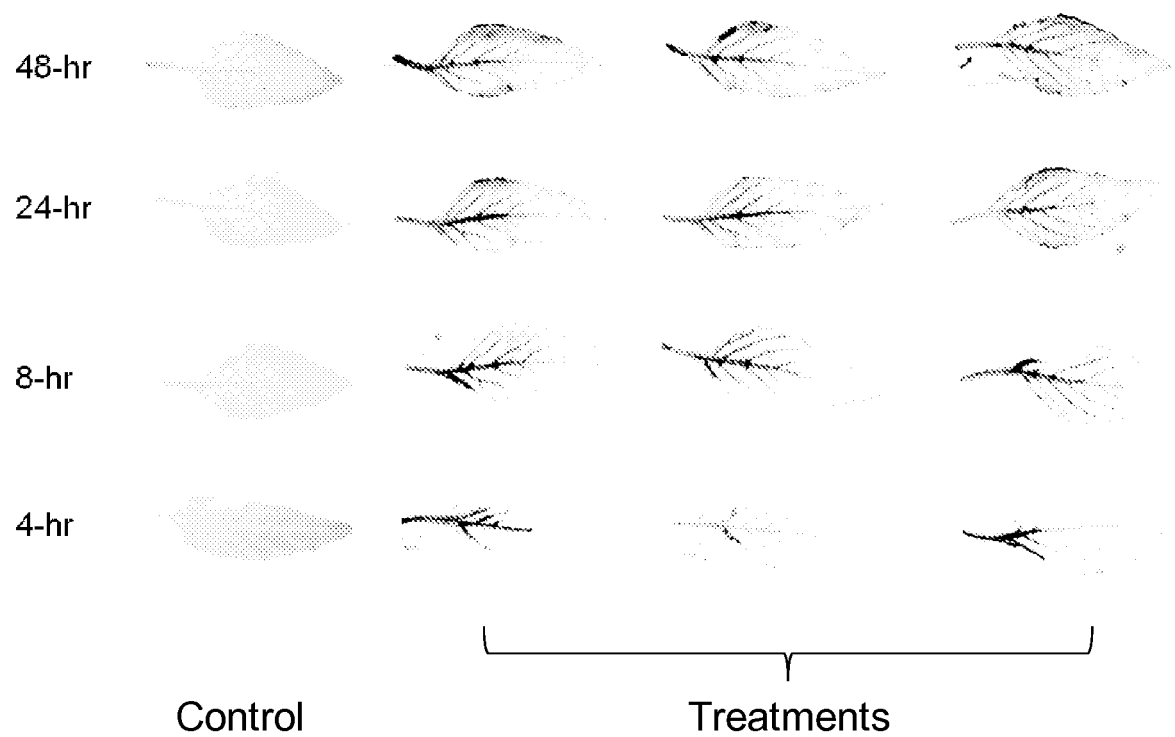
FIG. 6 illustrates 5'-Alexa Fluor 488-labelled anti-sense ssDNA oligonucleotides (SEQ ID NO:15) permeating glyphosate-resistant Palmer amaranth leaves as described in Example 9.

Oligonucleotide uptake was demonstrated with the fluorescently labelled ssDNA oligonucleotides (SEQ ID NO:15) confirming that ssDNA oligonucleotides permeated the leaf tissue. Petioles of detached leaves of glyphosate-resistant Palmer amaranth were placed in 200 mM sucrose solution with fluorescently labelled ssDNA oligonucleotides (SEQ ID NO:15). Leaf images were taken by Bio-Rad PharosFX imager equipped with a 488 nm laser from 4 h up to 48 h after uptake through petiole. Leaves incubated with 200 mM sucrose alone served as control. A slightly time-dependent vascular uptake of the fluorescently labelled ssDNA oligonucleotides was observed (see FIG. 6). Fluorescently labelled ssDNA oligonucleotides were released from vascular tissue into cells as early as 8 h after treatment and were observed to accumulate at the leaf edge at 24 h and 48 h, suggesting a transpiration effect.

EPSPS suppression was demonstrated with detached leaves of glyphosate-resistant Palmer amaranth using the petiole uptake technique. Petioles of detached leaves of glyphosate-resistant Palmer amaranth were placed in 200 mM sucrose solution with oligonucleotides according to the treatments listed in Table 2. Control leaves were permeated with the anti-sense control (SEQ ID NO:14), and additionally treated with or without 50 micrograms/mL glyphosate. EPSPS mRNA, EPSPS protein, and shikimate levels were measured after 48 h incubation. To assess the effects of anti-sense ssDNA oligonucleotides on EPSPS mRNA, total leaf RNA was isolated and quantitative real-time RT-PCR was performed to compare EPSPS mRNA levels. To assess the effects of anti-sense ssDNA oligonucleotides on EPSPS protein, total leaf soluble protein was isolated, separated by SDS-PAGE, and EPSPS protein levels measured by Western blot using antibodies against maize EPSPS_TIPA. Effects of anti-sense ssDNA oligonucleotides on shikimate accumulation as an indication of suppression of EPSPS were assessed in two experiments: in experiment 1, the oligonucleotide-treated leaves were incubated with 50 microgram/mL glyphosate for an additional 48 h either by petiole uptake (control leaves were permeated with the anti-sense control (SEQ ID NO:14), and additionally treated with or without 50 micrograms/mL glyphosate); in experiment 2, leaf disc assays were performed on the oligonucleotide-treated leaves, and shikimate levels measured by HPLC (controls in this case were leaves that had not been treated with oligonucleotides but incubated with 50 microgram/mL glyphosate).

TABLE 2

List of treatments using anti-sense ssDNA oligonucleotides

| Treatment | Anti-sense ssDNAs | Final concentration |
|---|---|---|
| #1 | Anti-sense_PO1 (SEQ ID NO: 8) | 5 microM |
| #2 | Anti-sense_PO2 (SEQ ID NO: 9) | 5 microM |
| #3 | Anti-sense_PS1 (SEQ ID NO: 12) | 5 microM |
| #4 | Anti-sense_PS2 (SEQ ID NO: 13) | 5 microM |
| #5 | Anti-sense_PS1, PS2 (SEQ ID NOs: 12, 13) | 10 microM each (20 microM total) |
| #6 | Anti-sense_PO1, PO2, PO3, PO4 (SEQ ID NOs: 8, 9, 10, 11) | 5 microM each (20 microM total) |
| Control | Anti-sense_ck (SEQ ID NO: 14) | 5 microM or 20 microM |

Figure 7:
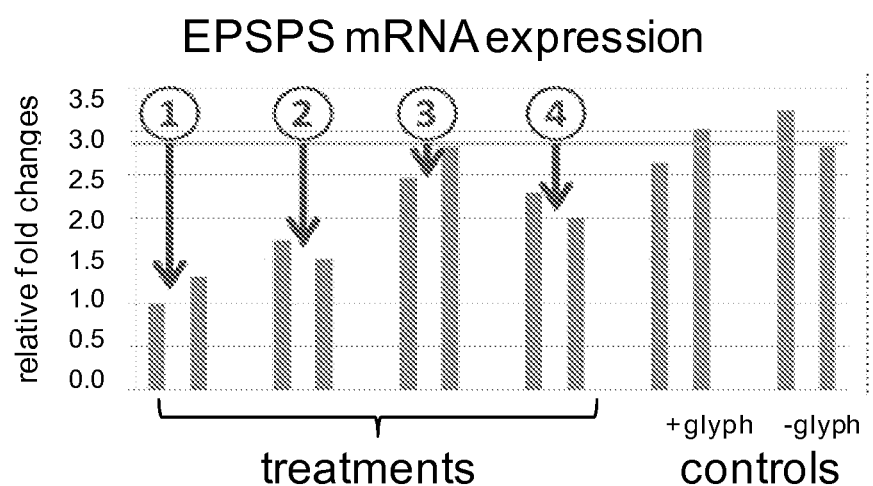
FIG. 7 depicts results of EPSPS mRNA measured in glyphosate-resistant Palmer amaranth leaves treated with anti-sense ssDNA oligonucleotides for EPSPS as described in Example 9. Bars represent replicate experiments for each of treatments #1-#4 (indicated by the numbers enclosed in circles and referring to Table 2) and for controls (leaves permeated with anti-sense ssDNA oligonucleotides for a barley seed protein, SEQ ID NO:14, treated with or without glyphosate).
Figure 8:
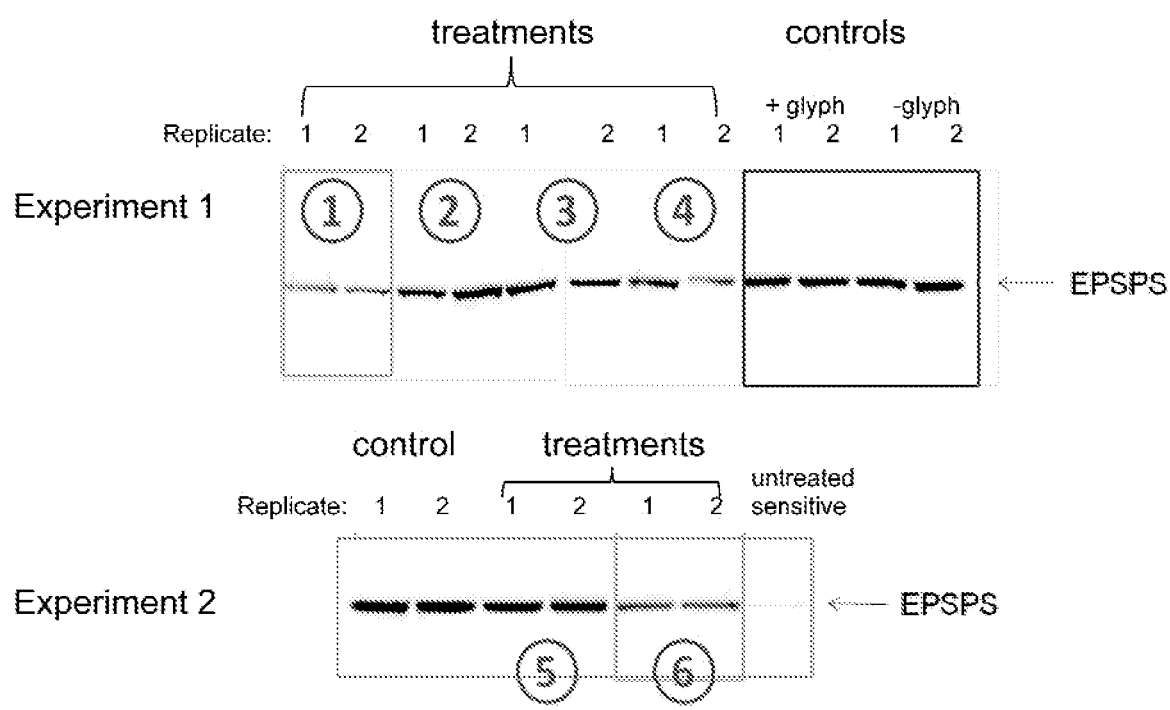
FIG. 8 depicts results of EPSPS protein measured in glyphosate-resistant Palmer amaranth leaves topically treated with anti-sense ssDNA oligonucleotides for EPSPS as described in Example 9; treatments are indicated by the numbers enclosed in circles and refer to Table 2.
Figure 9:
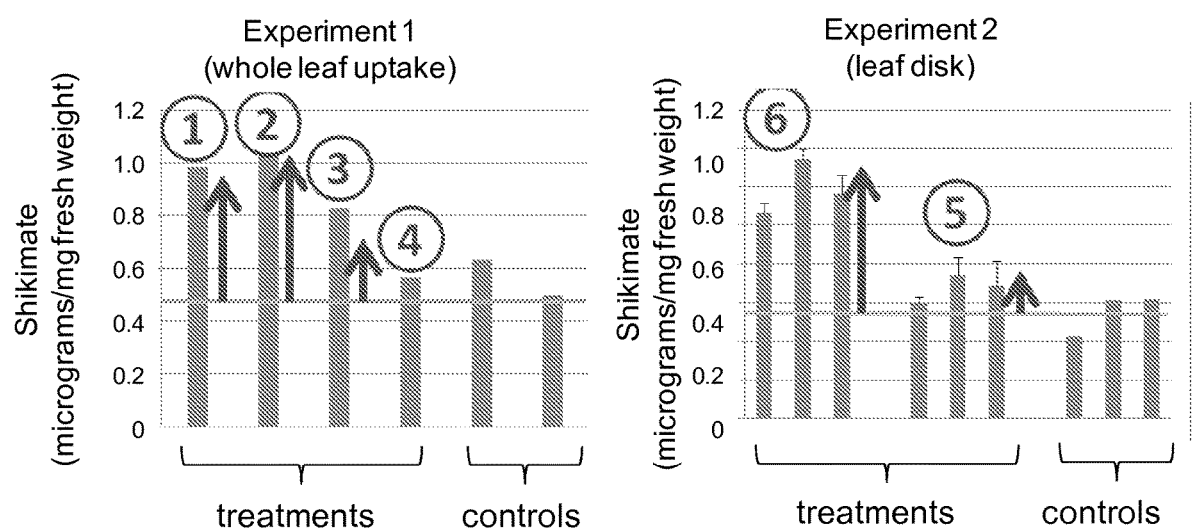
FIG. 9 depicts results of shikimate accumulation measured in glyphosate-resistant Palmer amaranth leaves treated with anti-sense ssDNA oligonucleotides for EPSPS in two experiments as described in Example 9; treatments are indicated by the numbers enclosed in circles and refer to Table 2.

Results for EPSPS mRNA expression, EPSPS protein levels, and shikimate levels are shown in FIGS. 7, 8, and 9, respectively. These results demonstrate that treatment with the anti-sense ssDNA oligonucleotides systematically regulated or suppressed the target gene by decreasing levels of the target gene transcript (EPSPS mRNA) or of the protein (EPSPS) encoded by the target gene in the plant tissue. In this particular experiment, treatments #1 and #6 appeared to be more efficacious in suppressing levels of EPSPS mRNA and protein and in increasing glyphosate efficacy as evidenced by the increased accumulation of shikimate. These results also indicate that glyphosate efficacy is improved by suppressing EPSPS mRNA and protein in glyphosate-resistant Palmer amaranth.

Example 10

This example illustrates an aspect of the invention. In this example, growing plants were treated with a topically applied composition for inducing systemic silencing of a target gene in a plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, tobacco (*Nicotiana benthamiana*) plants were treated with (a) a topically applied surfactant solution for conditioning of the plant to permeation by polynucleotides and (b) a composition including topically applied DNA oligonucleotides or polynucleotides having at least one strand including at least one segment of 18 or more contiguous nucleotides of the target gene in either anti-sense or sense orientation, whereby systemic regulation or suppression of the target gene (a phytoene desaturase, "PDS") was achieved.

Figure 11:
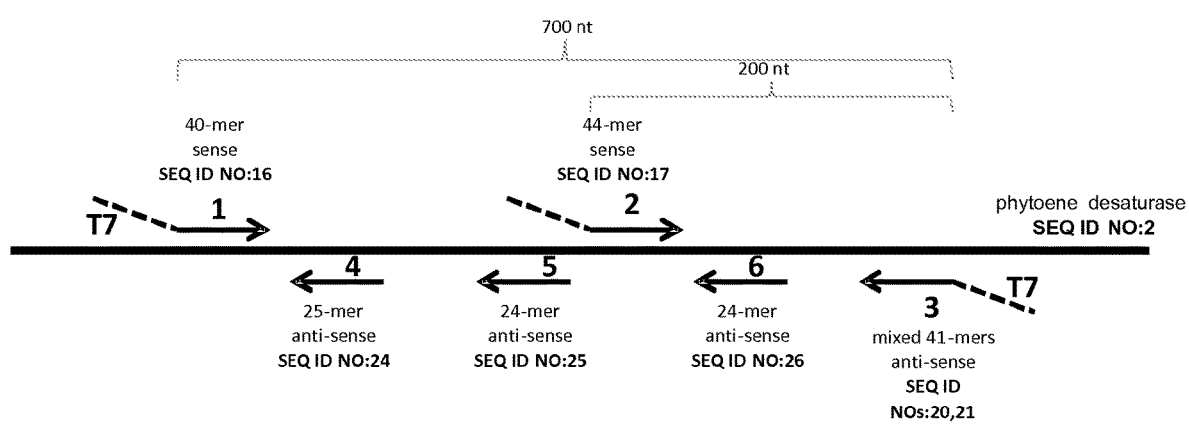
FIG. 11 schematically depicts the location of the sequences of assayed oligonucleotides and polynucleotides (see Table 3) in relation to the phytoene synthase sequence (SEQ ID NO:16) as described in Example 10.

The target gene used was a *Nicotiana benthamiana* phytoene desaturase (SEQ ID NO:2), shown in FIG. 10; the segment consisting of nucleotides 421-1120 of SEQ ID NO:2 (underlined text in FIG. 10) was used to design a 700-mer dsRNA polynucleotide ("PDS 700-mer") and the segment consisting of nucleotides 914-1113 of SEQ ID NO:2 (bolded underlined text in FIG. 10) was used to design a 200-mer dsRNA polynucleotide ("PDS 200-mer"). Sequences of other polynucleotides or oligonucleotides used in the treatments are listed in Table 3. FIG. 11 schematically depicts the location of the sequences of these oligonucleotides and polynucleotides in relation to the phytoene synthase (SEQ ID NO:2) sequence. Non-plant sequences obtained from corn rootworm ("CRW"), SEQ ID NOs:27, 28, 29, and 30 were used as non-homologous controls. Some of the polynucleotides included a T7 promoter sequence (indicated by lower-case text in Table 3) that is a promoter recognized by a bacteriophage T7 RNA polymerase.

TABLE 3

| Description | sense/anti-sense | sequence | Number of nucleotides | SEQ ID NO: |
|---|---|---|---|---|
| oligo 1 with T7 promoter | S | taatacgactcactataggGCAAGAGATGTCCTAGGTGGG | 40 | 16 |
| oligo 2 with T7 promoter | S | taatacgactcactataggACAGATTTCTTCAGGAGAAACATGG | 44 | 17 |
| oligo 1 w/o T7 promoter | S | GCAAGAGATGTCCTAGGTGGG | 21 | 18 |
| oligo 2 w/o T7 promoter | S | ACAGATTTCTTCAGGAGAAACATGG | 25 | 19 |
| oligo 3 mix with T7 promoter | AS | taatacgactcactataggCATCTCCTTTAATTGTACTGCC (SEQ ID NO: 20) and taatacgactcactataggTTTAATTGTACTGCCATTATTC (SEQ ID NO: 21) | 41 (SEQ ID NO: 20), 41 (SEQ ID NO: 21) | 20, 21 |
| oligo 3 mix w/o T7 promoter | AS | CATCTCCTTTAATTGTACTGCC (SEQ ID NO: 22) and TTTAATTGTACTGCCATTATTC (SEQ ID NO: 23) | 22 (SEQ ID NO: 22), 22 (SEQ ID NO: 23) | 22, 23 |
| oligo 4 w/o T7 promoter | AS | CACTTCCATCCTCATTCAGCTCGAT | 25 | 24 |
| oligo 5 w/o T7 promoter | AS | ACACCTCATCTGTCACCCTATCAG | 24 | 25 |
| oligo 6 w/o T7 promoter | AS | CAGTCTCGTACCAATCTCCATCAT | 24 | 26 |
| CRW oligo mixture with T7 promoter | S and AS | taatacgactcactatagggATCCATGATATCGTGAACATC (SEQ ID NO: 27) and taatacgactcactatagggGCAAAGAAAAATGCGTCG (SEQ ID NO: 28) | 41 (SEQ ID NO: 27), 38 (SEQ ID NO: 28) | 27, 28 |
| CRW oligo mixture w/o T7 promoter | S and AS | ATCCATGATATCGTGAACATC (SEQ ID NO: 29) and GCAAAGAAAAATGCGTCG (SEQ ID NO: 29) | 21 (SEQ ID NO: 29), 18 (SEQ ID NO: 30) | 29, 30 |

The following procedure was used for all assays described in this example. Four-week old *Nicotiana benthamiana* plants were used in all assays. Plants were treated with 0.1% SILWET L-77 solution freshly made with ddH2O. Two fully expanded leaves per plant (one cotyledon, one true leaf) were dipped into the SILWET L-77 solution for a few seconds, and allowed to dry for 15-30 minutes before application of the polynucleotide composition. Final concentration for each oligonucleotide or polynucleotide was 25 microM (in 0.01% SILWET L-77, 5 mM sodium phosphate buffer, pH 6.8) unless otherwise stated. 20 microliters of the solution was applied to the top surface of each of the two pre-treated leaves to provide a total of 40 microliters (1 nmol oligonucleotide or polynucleotide) for each plant. Leaf bleaching was observed 3 days post treatment.

FIG. 12A illustrates results of an assay where a 200-mer dsRNA polynucleotide with an RNA sequence corresponding to the "PDS 200-mer" segment (nucleotides 914-1113 of SEQ ID NO:2) and a combination of single-stranded DNA oligonucleotides and polynucleotides (SEQ ID NOs:16, 17, 20, 21, 24, 25, and 26) were separately applied to tobacco plants. The 200-mer dsRNA polynucleotide was applied at a concentration of 0.6 microM. Bleaching of apical leaves was observed after topical treatment with the polynucleotides and oligonucleotides, indicating systemic regulation or suppression of the target phytoene desaturase gene.

FIG. 12B illustrates results of northern blot analysis of RNA isolated from *Nicotiana benthamiana* plants treated with buffer (control), the 200-mer dsRNA polynucleotide, and the ssDNA oligonucleotides. Also shown is RNA isolated from plants that had been stressed by being kept at 4 degrees Celsius and in the dark overnight prior to treatment with the 200-mer dsRNA polynucleotides.

Figure 13:
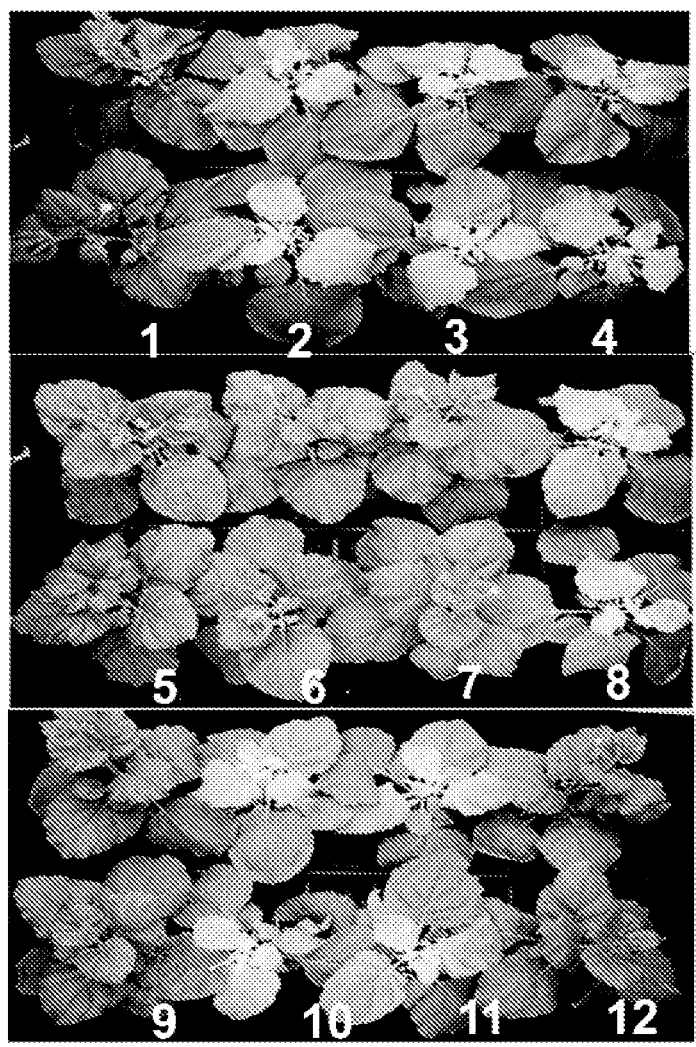
FIG. 13 illustrates apical leaf bleaching in *Nicotiana benthamiana* plants topically treated in duplicate with various combinations of polynucleotides or oligonucleotides (numbers refer to the treatments listed in Table 4) as described in Example 10. The control (Treatment 13 in Table 4) plants are not shown.

FIG. 13 illustrates phenotypes observed at day 12 after treatment in another assay of the effect from twelve combinations of polynucleotides or oligonucleotides (see Table 4). Table 4 also lists observations of visible bleaching of the plants at day 5 after treatment and the results of chlorophyll measurements taken at days 7 and 12 after treatment. Chlorophyll measurements are an indication of suppression of the target gene phytoene desaturase, and measurements were taken at 6 spots on the apical area, focussing on visibly bleached leaves or (in plants without visible bleaching) on leaves in equivalent locations on the plants; lower chlorophyll measurement values indicate suppression of phytoene desaturase. These results show that the combinations of oligonucleotides and polynucleotides in treatments 2, 3, 4, 8, and 11 were effective in systematically regulating (suppressing) the target gene in the treated plants; treatment 1 also effected systematic regulation (suppression) of the target gene to a lesser extent. The 200-mer dsRNA polynucleotide was also effective in systematically regulating (suppressing) the target gene in the treated plants. Oligonucleotides from a non-homologous (corn rootworm) gene (treatments 5 and 6) did not suppress the target phytoene desaturase gene. These results demonstrate that both sense and anti-sense single-stranded DNA oligonucleotides and polynucleotides were effective in systematically regulating (suppressing) the target gene in the treated plants. In this particular example, sense oligonucleotides with the T7 promoter (treatment 1) effected a weak systematic suppression of the phytoene desaturase gene, whereas sense oligonucleotides without the T7 promoter (treatment 7) did not suppress the phytoene desaturase gene. In this particular example, anti-sense oligonucleotides with the T7 promoter (treatment 2) as well as anti-sense oligonucleotides without the T7 promoter (treatment 8) both provided strong bleaching, indicating strong systemic regulation of the target phytoene desaturase gene.

TABLE 4

| Treatment | Description | SEQ ID NO: | Comment | Bleaching (day 5) | Chlorophyll (day 7) | Chlorophyll (day 12) |
|---|---|---|---|---|---|---|
| 1 | Oligos 1 and 2 | 16, 17 | Sense oligos with T7 promoter | weak | 18.6 | 17.5 |
| 2 | Oligo 3 | 20, 21 | Anti-sense oligos with T7 promoter | strong | 12.7 | 1.6 |
| 3 | Oligos 1, 2, and 3 | 16, 17, 20, 21 | Sense and anti-sense oligos with T7 promoter | strong | 11.5 | 2.6 |
| 4 | Oligos 1, 2, 3, 4, 5 and 6 | 16, 17, 20, 21, 24, 25, 26 | Sense and anti-sense oligos with T7 promoter, plus anti-sense oligos without T7 promoter | strong | 15.1 | 2.5 |
| 5 | CRW oligo mixture with T7 promoter | 27, 28 | Sense and anti-sense oligos with T7 promoter | not yet | 30.8 | 37.3 |
| 6 | CRW oligo mixture without T7 promoter | 29, 30 | Sense and anti-sense oligos without T7 promoter | not yet | 34.2 | 38.2 |
| 7 | Oligos 1 and 2 without T7 promoter | 18, 19 | Sense oligos without T7 promoter | not yet | 32.0 | 41.1 |
| 8 | Oligo 3 without T7 promoter | 22, 23 | Anti-sense oligos without T7 promoter | strong | 11.3 | 3.2 |
| 9 | Oligos 1, 2, and 3 w/o T7 promoter and oligos 4, 5, & 6 | 18, 19, 22, 23, 24, 25, 26 | Sense and anti-sense oligos without T7 promoter | not yet | 30.2 | 34.4 |
| 10 | 200-mer dsRNA polynucleotide | RNA sequence corresponding to the "PDS 200-mer" segment consisting of nucleotides 914-1113 of SEQ ID NO: 2 | Sense and anti-sense dsRNA polynucleotide | strong | 11.3 | 4.0 |
| 11 | 1/10$^{th}$ of Experiment 4 oligonucleotide mixture | 16, 17, 20, 21, 24, 25, 26 | Sense and anti-sense oligos with T7 promoter, plus | strong | 11.4 | 4.5 |

TABLE 4-continued

| Treatment | Description | SEQ ID NO: | Comment | Bleaching (day 5) | Chlorophyll (day 7) | Chlorophyll (day 12) |
|---|---|---|---|---|---|---|
| 12 | 1/100$^{th}$ of Experiment 4 oligonucleotide mixture | 16, 17, 20, 21, 24, 25, 26 | anti-sense oligos without T7 promoter Sense and anti-sense oligos with T7 promoter, plus anti-sense oligos without T7 promoter | not yet | 31.0 | 38.0 |
| 13 | Control | (none) | Buffer only | not yet | 31.2 | 38.4 |

Figure 14:
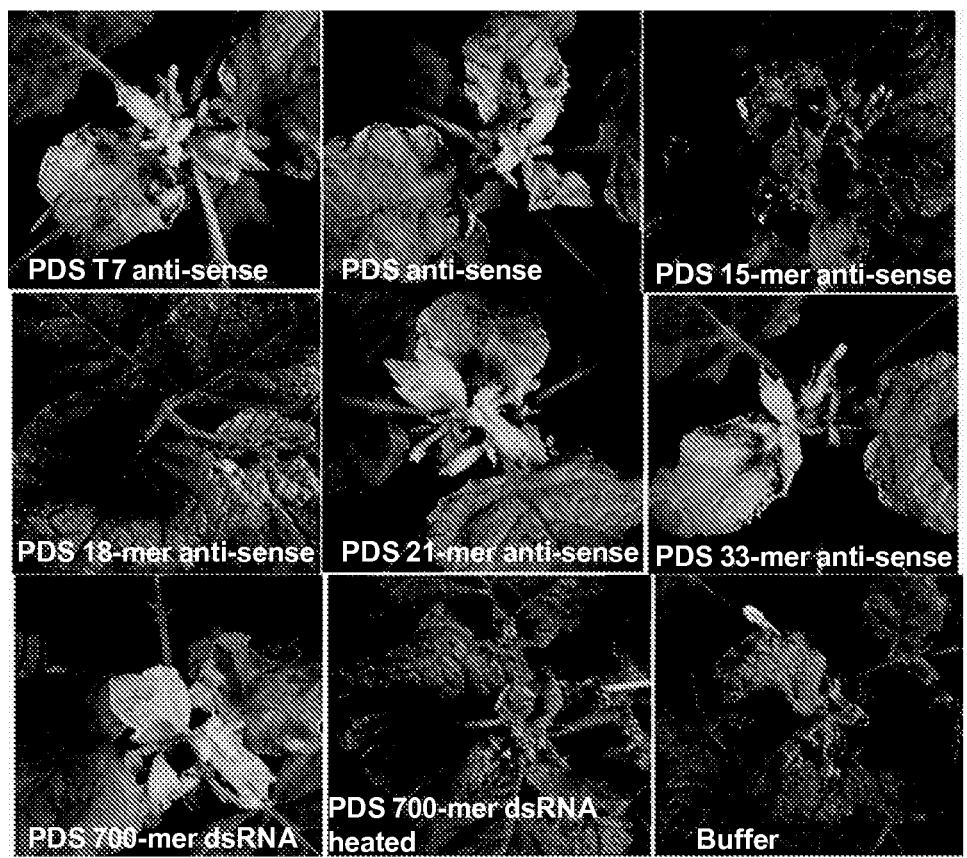
FIG. 14 illustrates apical leaf bleaching in *Nicotiana benthamiana* plants topically treated with the polynucleotides listed in Table 5 as described in Example 10.

Table 5 shows six polynucleotides: a 40-mer segment ("PDS 40-mer sense ssDNA", SEQ ID NO:31) consisting of the 5'-most 40 nucleotides of the "PDS 700-mer" (nucleotides 1081-1120 of SEQ ID NO:2), and four anti-sense single-stranded DNA polynucleotides and one sense single-stranded DNA polynucleotide synthesized based on the "PDS 40-mer sense ssDNA" sequence (SEQ ID NO:31). FIG. 14 illustrates results of topical treatment of tobacco plants with the polynucleotides and oligonucleotides. Strong bleaching of apical leaves indicating systemic regulation or suppression of the target gene phytoene desaturase was observed after topical treatment with the PDS 21-mer anti-sense ssDNA and PDS 33-mer anti-sense ssDNA, as well as after topical treatment with the PCR-amplified and column-purified 700-mer dsRNA polynucleotide ("PDS 700-mer dsRNA"), previously assayed PDS anti-sense 22-mer oligonucleotides with a T7 promoter (SEQ ID NOs:20 and 21) ("PDS T7 anti-sense"), or previously assayed PDS anti-sense 22-mer oligonucleotides without a T7 promoter (SEQ ID NOs:22 and 23) ("PDS anti-sense"). Little or no visible bleaching of apical leaves was observed after topical treatment with the buffer only ("Buffer"), or after topical treatment with heat-denatured (5 minutes at 95 degrees Celsius, then stored on ice) 700-mer dsRNA polynucleotide ("PDS 700-mer dsRNA heated"), the PDS 15-mer anti-sense ssDNA, or the PDS 18-mer anti-sense ssDNA.

TABLE 5

| Description | Sequence | SEQ ID NO: |
|---|---|---|
| PDS 40-mer sense ssDNA | TGTTTTATACTGAATAATGGCAGTACAATTAAAGGAGATG | 31 |
| PDS 15-mer anti-sense ssDNA | CATCTCCTTTAATTG | 32 |
| PDS 18-mer anti-sense ssDNA | CATCTCCTTTAATTGTAC | 33 |
| PDS 21-mer anti-sense ssDNA | CATCTCCTTTAATTGTACTGC | 34 |
| PDS 33-mer anti-sense ssDNA | CATCTCCTTTAATTGTACTGCCATTATTCAGTA | 35 |
| PDS 21-mer sense ssDNA | GCAGTACAATTAAAGGAGATG | 36 |

Figure 15:
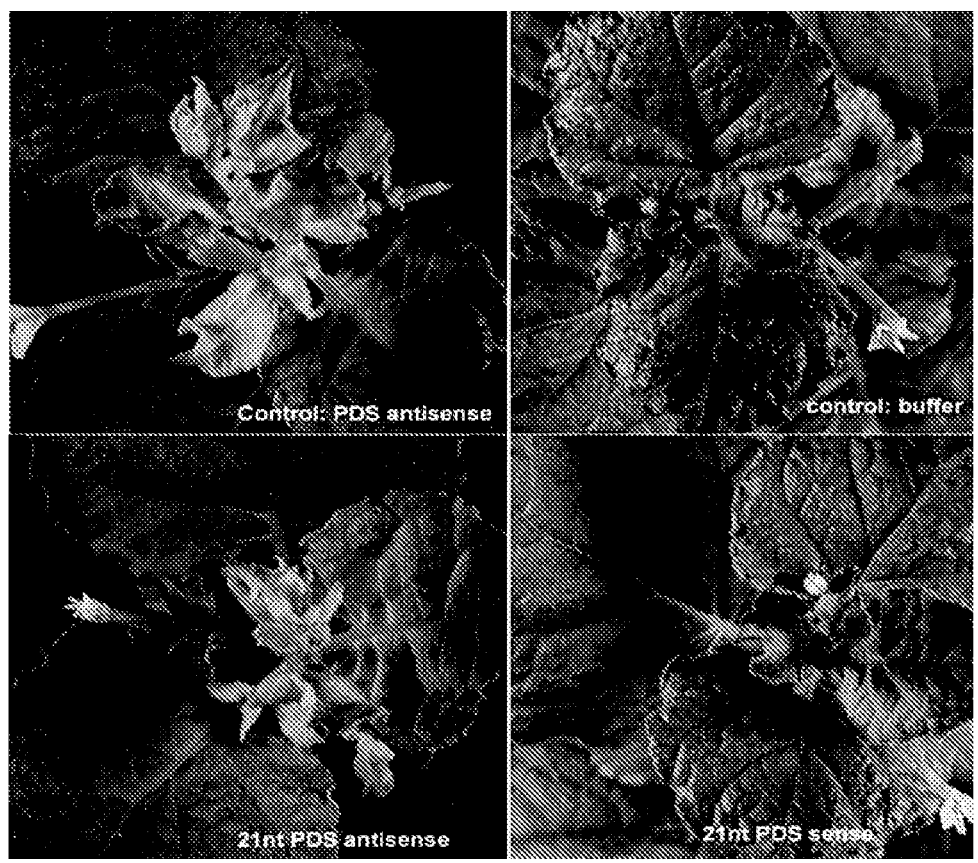
FIG. 15 illustrates apical leaf bleaching observed in *Nicotiana benthamiana* plants after topical treatment with the PDS 21-mer anti-sense ssDNA (SEQ ID NO:34, "21nt PDS anti-sense") or with previously assayed PDS anti-sense 22-mer oligonucleotides without a T7 promoter (SEQ ID NOs:22 and 23) ("PDS anti-sense"). Little or no visible bleaching of apical leaves was observed after topical treatment with the buffer only or after topical treatment with PDS 21-mer sense ssDNA (SEQ ID NO:36, "21nt PDS sense") as described in Example 10.

Results of another assay are shown in FIG. 15, strong bleaching of apical leaves indicating systemic regulation or suppression of the target gene phytoene desaturase was observed after topical treatment with the PDS 21-mer anti-sense ssDNA (SEQ ID NO:34, "21nt PDS anti-sense") or with previously assayed PDS anti-sense 22-mer oligonucleotides without a T7 promoter (SEQ ID NOs:22 and 23) ("PDS anti-sense"). Little or no visible bleaching of apical leaves was observed after topical treatment with the buffer only ("control: buffer"), or after topical treatment with PDS 21-mer sense ssDNA (SEQ ID NO:36, "21nt PDS sense").

Example 11

This example illustrates treatment of growing plants with a topically applied composition for inducing systemic silencing of a target gene in a plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, this example demonstrates the target specificity (sequence specificity) of the polynucleotides.

Palmer amaranth phytoene desaturase (PDS) has the sequence (SEQ ID NO: 37)
TCAATTTCATCTATTGGAAGTGATTTTTTGGGTCATTCTGTGAGAAATTTCAGTGTTAGTAAAGTTTATG

GAGCAAAGCAAAGAAATGGGCACTGCCCTTTAAAGGTTGTTTGTATAGATTATCCTAGGCCAGAGCTT

GAAAGTACATCCAATTTCTTGGAAGCCGCCTACTTATCTTCTACTTTTCGGAATTCGCCTCGTCCTCAG

AAGCCATTAGAAGTTGTAATTGCTGGAGCAGGTTTGGCTGGTCTATCCACGGCAAAGTATTTAGCTGA

TGCAGGTCACAAACCCATATTGTTGGAAGCACGAGATGTTT<u>AGGAGGAAAGGTTGCAGCGTGGAAG</u>

<u>GATGAGGATGGTGACTGGTATGAGACTGGGCTACATATATTCTTTGGGGCATATCCAAATGTCCAAAA</u>

<u>TCTATTTGGAGAACTTGGTATAAATGACCGACTGCAATGGAAGGAGCACTCTATGATTTTTGCAATGC</u>

<u>CCAGCAAGCCCGGTGAATTCAGTCGCTTTGATTTTCCCGAAATCCTGCCTGCACCATTAAATGGCATAT</u>

<u>GGGCAATCCTAAGAAATAATGAAATGCTAACCTGGCCAGAAAAAATCAAGTTTGCCATTGGCTTGTTG</u>

<u>CCTGCTATGGCAGGCGGACAGTCATATGTTGAAGCACAAGATGGTTTGAGTGTCCAAGAGTGGATGAG</u>

<u>AAAACAAGGAGTACCCGATCGTGTAACTGATGATGTGTTTATTGCCATGTCAAAGGCACTGAACTTCA</u>

<u>TAAATCCCGATGAACTTTCAATGCAGTGCATCTTGATTGCTCTGA</u>A*CCGATTCCTGCAGGAGAAACATGG*

*TTCTAAGATGGCCTTCCTAGACGGAAACCCTCCAGAGAGGCTGTGCATGCCTATTGTTAAACACATCGAGTCA*

*CTAGGTGGTGAAGTTAAACTTAACTCTCGTATACAAAAGATTCAGTTGGACCAGAGTGGAAGCGTGAAGAGTT*

*TTTTGCTAAATAACGGGAGGGAAATAC*GAGGAGATGCCTATGTTTTTGCCACCCCAGTTGACATCTTGAA

GCTGTTACTACCTGATACTTGGAAGGAAATCTCATACTTCAAAAAACTTGAGAAATTAGTGGGCGTTC

CTGTGATTAATGTTCACATATGGTTTGACAGAAAATTAAAGAATACATATGACCATCTACTCTTCAGCA

GGAGTCCTCTTTTGAGTGTCTATGCTGATATGTCGGAGACATGCAAGGAATATAAGGATCCAAATAGA

TCCATGCTGGAATTGGTTTTTGCACCCGCGGAGGAATGGATTTCACGAAGCGACACTGATATTATAGA

GGCAACAATGAAAGAGCTTGCCAAGCTTTTCCCGGATGAAATCGCTGCCGATGGAAGCAAGGCCAAG

ATCCTCAAATATCATGTCGTCAAAACTCCAAGGTCGGTTTATAAGACTGTACCGGATTGTGAACCTTGT

CGGCCGCTGCAAAGATCACCAATAGAGGGTTTCTATTTAGCTGGTGATTACACAAAACAAAAATATTT

GGCTTCTATGGAAGGTGCTGTCTTATCTGGGAAGCTTTGTGCACAGGCTATCGTACAGGATTATGATCT

GCTGAGTTCTCGAGCACAAAGAGAATTGGCG.

A 678 base pair dsRNA polynucleotide with an anti-sense strand capable of hybridizing to the RNA encoded by the nucleotides at positions 317-994 (shown as underlined text) in SEQ ID NO:37 and a 198 base pair dsRNA polynucleotide with an anti-sense strand capable of hybridizing to the RNA encoded by the nucleotides at positions 797-994 (shown as italicized and underlined text) in SEQ ID NO:37 were synthesized.

Nicotiana benthamiana phytoene desaturase has the sequence (SEQ ID NO: 38)
ATGCCCCAAATCGGACTTGTATCTGCTGTTAATTTGAGAGTCCAAGGTAATTCAGCTTATCTTTGGAGC

TCGAGGTCTTCGTTGGGAACTGAAAGTCAAGATGTTTGCTTGCAAAGGAATTTGTTATGTTTTGGTAGT

AGCGACTCCATGGGGCATAAGTTAAGGATTCGTACTCCAAGTGCCACGACCCGAAGATTGACAAAGG

ACTTTAATCCTTTAAAGGTAGTCTGCATTGATTATCCAAGACCAGAGCTAGACAATACAGTTAACTATT

TGGAGGCGGCGTTATTATCATCATCGTTTCGTACTTCCTCACGCCCAACTAAACCATTGGAGATTGTTA

TTGCTGGTGCAGGTTTGGGTGGTTTGTCTACAGCAAAATATCTGGCAGATGCTGGTCACAAACCGATA

TTGCTGGAG<u>GCAAGAGATGTCCTAGGTGGGAAGGTAGCTGCATGGAAAGATGATGATGGAGATTGGT</u>

-continued

```
ACGAGACTGGGTTGCACATATTCTTTGGGGCTTACCCAAATATGCAGAACCTGTTTGGAGAACTAGGG

ATTGATGATCGGTTGCAGTGGAAGGAACATTCAATGATATTTGCGATGCCTAACAAGCCAGGGGAGTT

CAGCCGCTTTGATTTTCCTGAAGCTCTTCCTGCGCCATTAAATGGAATTTTGGCCATACTAAAGAACAA

CGAAATGCTTACGTGGCCCGAGAAAGTCAAATTTGCTATTGGACTCTTGCCAGCAATGCTTGGAGGGC

AATCTTATGTTGAAGCTCAAGACGGTTTAAGTGTTAAGGACTGGATGAGAAAGCAAGGTGTGCCTGAT

AGGGTGACAGATGAGGTGTTCATTGCCATGTCAAAGGCACTTAACTTCATAAACCCTGACGAGCTTTC

GATGCAGTGCATTTTGATTGCTTTGAACAGATTTCTTCAGGAGAAACATGGTTCAAAAATGGCCTTTTTAGAT

GGTAACCCTCCTGAGAGACTTTGCATGCCGATTGTGGAACATATTGAGTCAAAAGGTGGCCAAGTCAGACTAA

ACTCACGAATAAAAAAGATCGAGCTGAATGAGGATGGAAGTGTCAAATGTTTTATACTGAATAATGGCAGTACA

ATTAAAGGAGATGCTTTTGTGTTTGCCACTCCAGTGGATATCTTGAAGCTTCTTTTGCCTGAAGACTGG

AAAGAGATCCCATATTTCCAAAAGTTGGAGAAGCTAGTGGGAGTTCCTGTGATAAATGTCCATATATG

GTTTGACAGAAAACTGAAGAACACATCTGATAATCTGCTCTTCAGCAGAAGCCCGTTGCTCAGTGTGT

ACGCTGACATGTCTGTTACATGTAAGGAATATTACAACCCCAATCAGTCTATGTTGGAATTGGTATTTG

CACCCGCAGAAGAGTGGATAAATCGTAGTGACTCAGAAATTATTGATGCTACAATGAAGGAACTAGC

GAAGCTTTTCCCTGATGAAATTTCGGCAGATCAGAGCAAAGCAAAAATATTGAAGTATCATGTTGTCA

AAACCCCAAGGTCTGTTTATAAAACTGTGCCAGGTTGTGAACCCTGTCGGCCCTTGCAAAGATCCCCT

ATAGAGGGTTTTTATTTAGCTGGTGACTACACGAAACAGAAGTACTTGGCTTCAATGGAAGGTGCTGT

CTTATCAGGAAAGCTTTGTGCACAAGCTATTGTACAGGATTACGAGTTACTTCTTGGCCGGAGCCAGA

AGATGTTGGCAGAAGCAAGCGTAGTTAGCATAGTGAACTAA.
```

A 685 base pair dsRNA polynucleotide with an anti-sense strand capable of hybridizing to the RNA encoded by the nucleotides at positions 421-1105 (shown as underlined text) in SEQ ID NO:38 and a 192 base pair dsRNA polynucleotide with an anti-sense strand capable of hybridizing to the RNA encoded by the nucleotides at positions 914-1105 (shown as italicized and underlined text) in SEQ ID NO:38 were synthesized.

An alignment of the Palmer amaranth and *Nicotiana benthamiana* PDS DNA sequences was performed using a global pairwise alignment (stretcher) and is illustrated in FIG. 16; with this method the two sequences showed about 71% identity (1252/1762).

Palmer amaranth plants having 16 copies of EPSPS and 5-8 inches high were treated with 0.1% SILWET L-77 solution freshly made with ddH2O. Four fully expanded leaves per plant were dipped into the SILWET L-77 solution for a few seconds, and allowed to dry for 30 minutes to 1 hour before application of the polynucleotide composition. Individual polynucleotide solutions were made for each of the 678 bp Palmer PDS dsRNA, 198 bp Palmer PDS dsRNA, the 685 bp *Nicotiana benthamiana* PDS dsRNA, and the 192 bp *Nicotiana benthamiana* PDS dsRNA (0.6 micromolar polynucleotide in 0.01% SILWET L-77, 5 mM sodium phosphate buffer, pH 6.8). 10 microliters of polynucleotide solution (or buffer as a control) was applied to the top surface of each of the four pre-treated leaves per plant to provide a total of 40 microliters for each plant. Plants were kept in a growth chamber, and leaf bleaching was observed 3 days post treatment. Plants topically treated with either 678 bp Palmer PDS dsRNA or 198 bp Palmer PDS dsRNA, showed bleaching of leaves (indicating silencing of the endogenous phytoene desaturase) but Palmer amaranth plants topically treated with either 685 bp *Nicotiana benthamiana* PDS dsRNA or 192 bp *Nicotiana benthamiana* PDS dsRNA did not show bleaching of leaves. This sequence specificity demonstrates that the polynucleotide compositions and methods of the invention are useful in selective control of a given species or taxon having a specific target gene sequence, e. g., in controlling herbicide-resistant volunteer plants growing in a field of crop plants resistant to the same herbicide.

Figure 17:
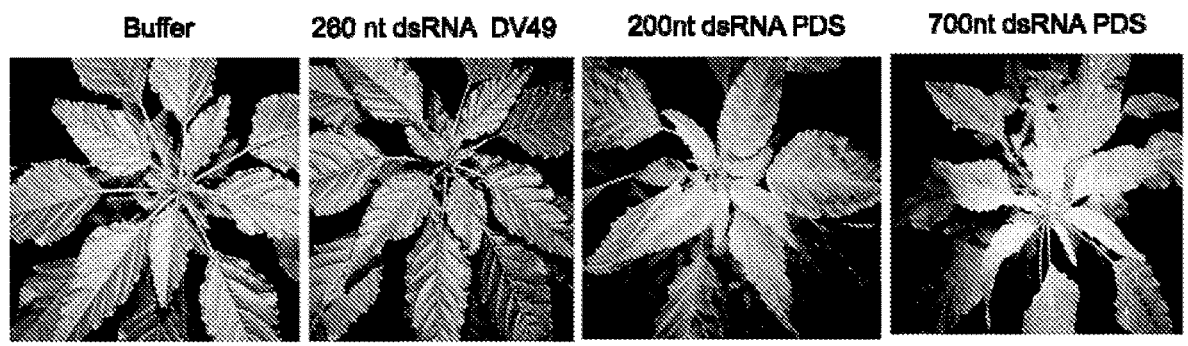
FIG. 17 illustrates apical leaf bleaching observed in Palmer amaranth plants topically treated with 678 bp or 198 bp Palmer PDS dsRNA but not in Palmer amaranth plants topically treated with a 260 base pair dsRNA of corn root worm gene as described in Example 11.

In a separate assay, Palmer amaranth plants topically treated with 678 bp Palmer PDS dsRNA (labelled "700 nt dsRNA PDS") or 198 bp Palmer PDS dsRNA (labelled "200 nt dsRNA PDS") showed bleaching of leaves (indicating silencing of the endogenous phytoene desaturase) but Palmer amaranth plants topically treated with a 260 base pair dsRNA of an invertebrate gene (labelled "260 nt dsRNA DV49", from corn root worm *Diabrotica* virgifera) did not result in a bleaching phenotype, indicating no silencing of the endogenous phytoene desaturase (FIG. 17). This sequence specificity demonstrates that the polynucleotide compositions and methods of the invention are useful in selective control of a given species or taxon.

Example 12

This example describes use of a topically applied composition including at least one polynucleotide strand including at least one segment of 18 or more contiguous nucleotides of a target gene in either anti-sense or sense orientation to induce systemic silencing of a target gene in a plant. More specifically this example demonstrates using a single treatment with a phytoene desaturase (PDS) oligonucleotide to induce systemic silencing in different plant organs including leaves, stems, and flowers.

Figure 18:
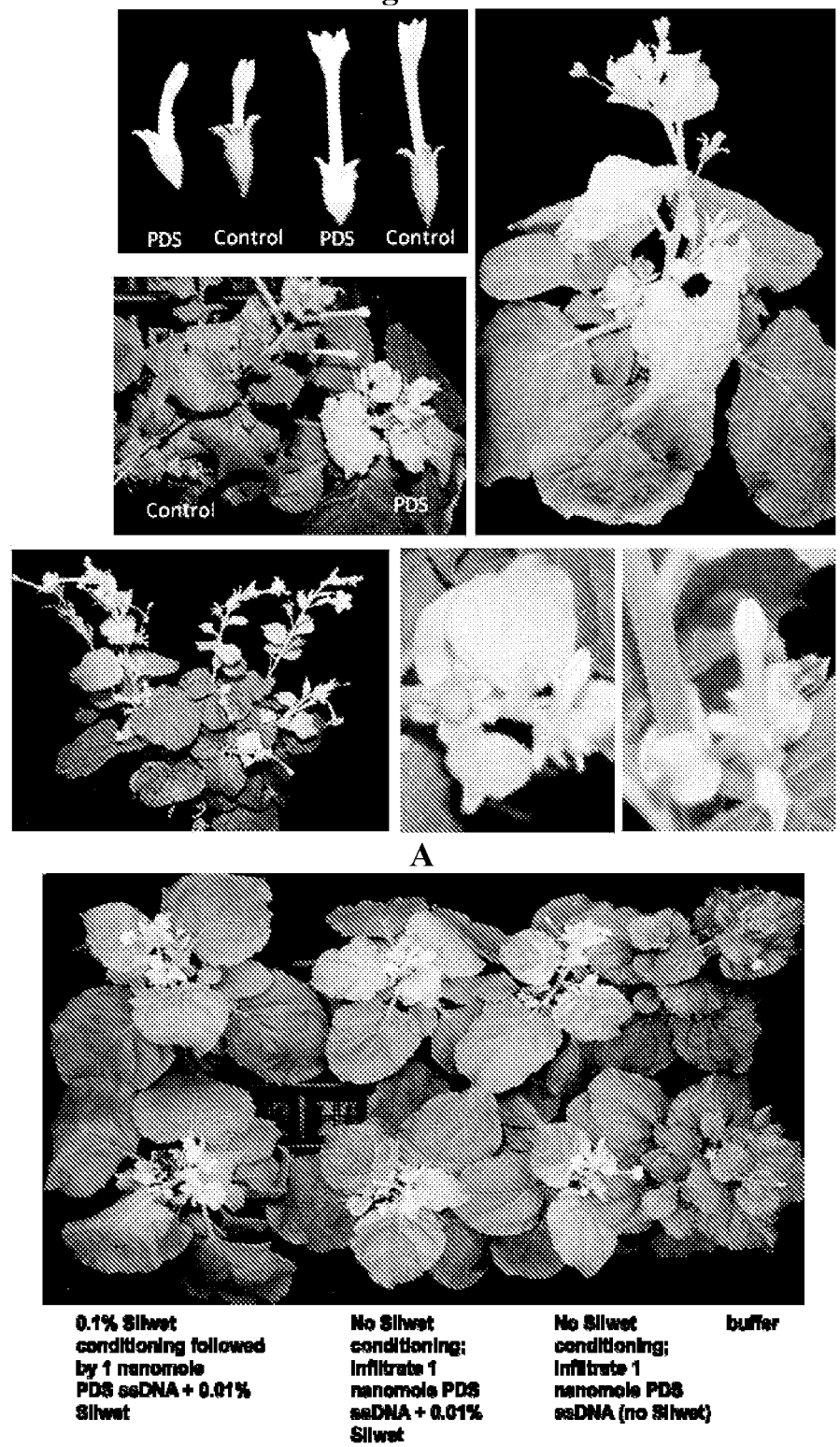
FIG. 18A illustrates bleaching of apical leaves, stems, and flowers of *Nicotiana benthamiana* plants topically treated first with a surfactant solution and then with an ssDNA PDS oligonucleotide to induce systemic silencing of phytoene desaturase as described in Example 12.
FIG. 18B illustrates bleaching of apical leaves, stems, and flowers of *Nicotiana benthamiana* plants topically treated with an ssDNA PDS oligonucleotide to induce systemic silencing of phytoene desaturase, with or without conditioning with a surfactant solution, as described in Example 12.

Four-week old tobacco (*Nicotiana benthamiana*) plants were used in all treatments. Two fully expanded leaves (one cotyledon, one true leaf) were conditioned by dipping into freshly made surfactant solution (0.1% SILWET L-77 in double-distilled water) for a few seconds and allowed to dry for 15-30 minutes. Twenty microliters of a single-stranded DNA (ssDNA) 22-mer oligonucleotide with the sequence GGCAGTACAATTAAAGGAGATG (SEQ ID NO:39), corresponding to the nucleotides at positions 1099-1120 of *Nicotiana benthamiana* phytoene desaturase (SEQ ID NO:2) was applied as a 25 micromolar solution in 0.01% SILWET L-77 in 5 millimolar sodium phosphate buffer, pH 6.8 to the top surface of each conditioned leaf for a total of 40 microliters (1 nanomole oligonucleotide) per plant. Control plants were treated with the SILWET solution without the DNA oligonucleotide. Plants were observed for bleaching 3 days post-treatment. Apical leaves, stems, and flowers of plants treated with the ssDNA oligonucleotide all displayed bleaching indicating systemic silencing of PDS (FIG. 18A).

Flowers of both control and ssDNA-treated plants were allowed to set seed. Seeds were collected from mature fruits, weighed, and allowed to germinate. Seed weights were identical (about 11 mg per 100 seeds) and seed morphology appeared similar between the ssDNA-treated and the control plants. A reduced amount of seed produced per fruit and a reduction in germination rate (4 out of 100 seeds germinated) was observed in seeds from the ssDNA-treated plants, compared to the amount of seed per fruit and germination rate (95 out of 100 seeds germinated) of seeds from control plants.

In a separate assay using a similar procedure, tobacco plants were conditioned by dipping in 0.1% SILWET L-77 in double-distilled water, allowed to dry for 15-30 minutes, and treated with the PDS ssDNA 22-mer (SEQ ID NO:39) applied as a 25 micromolar solution in 0.01% SILWET L-77 in 5 millimolar sodium phosphate buffer, pH 6.8 to the top surface of each conditioned leaf for a total of 40 microliters (1 nanomole oligonucleotide) per plant. Other plants were not conditioned with a surfactant treatment, but were treated only with 1 nanomole of the PDS ssDNA 22-mer (SEQ ID NO:39) applied either by infiltration with a needleless syringe (shown in FIG. 18B) or by hand application of drops to the leaf surface (not shown in FIG. 18B), and either as a 25 micromolar solution in 0.01% SILWET L-77 in 5 millimolar sodium phosphate buffer, pH 6.8 or as a 25 micromolar solution in 5 millimolar sodium phosphate buffer, pH 6.8 (without surfactant). Negative control plants were treated with the SILWET buffer solution without the DNA oligonucleotide. Results are depicted in FIG. 18B. All plants treated only with direct application of the PDS ssDNA (without conditioning by SILWET L-77 surfactant treatment), whether applied by infiltration or by hand application of drops, displayed bleaching of apical leaves, stems, and flowers, indicating systemic silencing of PDS.

Example 13

This example illustrates methods and topically applied compositions for inducing systemic silencing including the use of agents for conditioning of a plant to permeation by polynucleotides. More specifically, this example describes use of polynucleotides of the invention to control herbicide-resistant Palmer amaranth.

Palmer amaranth plants having lower (fewer than 30) copy numbers of 5-enolpyruvylshikimate-3-phosphate synthase (EPSPS) are susceptible to treatment with dsRNA designed to silence EPSPS followed by treatment with glyphosate (see details in Example 1). However, Palmer amaranth plants having high copy numbers of EPSPS (i.e., 30 or more copies of EPSPS) are resistant to glyphosate treatment and are a challenge for weed resistance management. For example, in one assay (results not shown) on glyphosate resistant high-copy Palmer amaranth using treatments similar to those described in Example 1 but where either dose of dsRNA was increased up to ten-fold (i.e., 8 nanomoles of short dsRNAs described in Example 1 per plant) or where a proprietary glyphosate formulation ("Roundup® WeatherMAX® brand herbicide") combined with a tallowamine surfactant was used, glyphosate activity was improved (estimated by observing plant growth measured as plant height) but the resistant plants were not killed.

Three different glyphosate resistant high-copy Palmer amaranth lines (3 plants per replicate) were treated with dsRNA using the treatment conditions listed in Table 6, where the dsRNA delivery vehicle, permeabilization or conditioning agent, and order of steps were varied. Results are depicted in FIG. 19. Treatment with "4X" glyphosate (i.e., treatment with 3360 g acid equivalent per hectare of Roundup® WeatherMAX® brand herbicide which is four-fold the standard rate of application of 840 g acid equivalent per hectare) alone did not kill 35-copy (experiment 3) or 57-copy (experiment 6) Palmer amaranth.

In one set of experiments (1-3, Table 6), including 2% ammonium sulfate in an aqueous dsRNA delivery vehicle comprising 0.1% tallowamine surfactant and 10% glycerol (experiment 2) improved the efficacy of a 10-fold dose of dsRNA followed by a 4× glyphosate application. Improved efficacy of a 10-fold dose of dsRNA followed by glyphosate application was also observed when ammonium sulfate was included in a dsRNA delivery vehicle without a tallowamine surfactant (experiment 8).

In another set of experiments (4-6, Table 6), applying the SILWET L-77 surfactant prior to applying the dsRNA in a delivery vehicle containing ammonium sulfate was effective, whereas combining the SILWET L-77 surfactant with the dsRNA in the dsRNA delivery vehicle containing ammonium sulfate was not effective. Applying glyphosate ("Roundup® WeatherMAX® brand herbicide") at 72 hours (experiment 7) was less effective than applying glyphosate at 48 hours (experiment 2) after treatment with dsRNA.

TABLE 6

| Palmer amaranth line | EPSPS Copy number | Experiment number | Step 1 | | | Step 2 | Step 3* |
|---|---|---|---|---|---|---|---|
| | | | EPSPS dsRNA relative concentration | dsRNA delivery vehicle | | | |
| R31 | 35 | 1 | 10X | 0.1% tallowamine surfactant + 10% glycerol | | 1% Silwet L-77 | 4× WeatherMAX (48 h) |

TABLE 6-continued

| | | | | | | |
|---|---|---|---|---|---|---|
| | 2 | | 10X | 2% ammonium sulfate + 0.1% tallowamine surfactant + 10% glycerol | 1% Silwet L-77 | 4× WeatherMAX (48 h) |
| | 3 | | Buffer only (control) | 2% ammonium sulfate + 0.1% tallowamine surfactant + 10% glycerol | 1% Silwet L-77 | 4× WeatherMAX (48 h) |

| | | | | Step 2 | | |
|---|---|---|---|---|---|---|
| Palmer amaranth line | EPSPS Copy number | Experiment number | Step 1 | EPSPS dsRNA relative concentration | dsRNA delivery vehicle | Step 3* |
| R34 | 57 | 4 | — | 10X | 1% Silwet L-77 + 2% ammonium sulfate | 4× WeatherMAX (48 h) |
| | | 5 | 1% Silwet L-77 | 10X | 2% ammonium sulfate | 4× WeatherMAX (48 h) |
| | | 6 | 1% Silwet L-77 | Buffer only (control) | 2% ammonium sulfate | 4× WeatherMAX (48 h) |

| | | | Step 1 | | | |
|---|---|---|---|---|---|---|
| Palmer amaranth line | EPSPS Copy number | Experiment number | EPSPS dsRNA relative concentration | dsRNA delivery vehicle | Step 2 | Step 3* |
| R28 | 87 | 7 | 10X | 2% ammonium sulfate + 0.1% tallowamine surfactant + 10% glycerol | 1% Silwet L-77 | 4× WeatherMAX (72 h) |

| | | | | Step 2 | | |
|---|---|---|---|---|---|---|
| Palmer amaranth line | EPSPS Copy number | Experiment number | Step 1 | EPSPS dsRNA relative concentration | dsRNA delivery vehicle | Step 3* |
| R28 | 87 | 8 | 1% Silwet L-77 | 10X | 2% ammonium sulfate | 4× WeatherMAX (72 h) |
| | | 9 | 1% Silwet L-77 | Buffer only (control) | 2% ammonium sulfate | 4× WeatherMAX (72 h) |

*glyphosate (as the commercial formulation "Roundup ® WeatherMAX ® brand herbicide", which contains 660 g/L glyphosate K+ salt in a carrier including the MON56151 tallowamine surfactant blend of tallowamine (16-18C) and cocoamine (12-14C) in the ratio of 55:45) is listed at the amount used (where 1X = 840 g acid equivalent per hectare of Roundup ® WeatherMAX ® brand herbicide, 4X = 3360 g acid equivalent per hectare of Roundup ® WeatherMAX ® brand herbicide) and hours after application of dsRNA Example 14

This example illustrates methods and topically applied compositions for inducing systemic silencing including the use of agents for conditioning of a plant to permeation by polynucleotides.

Two small RNAs identified through small RNA sequencing were found to be abundant in and unique to Palmer amaranth plants that had been treated with four oligonucleotide-size "short" EPSPS dsRNA molecules as described in Example 1. These two small RNAs were respectively mapped to nucleotide positions 743-764 and 566-585 of the full-length EPSPS having the sequence shown in FIG. 20 (SEQ ID NO:40). Two 25 nucleotide long oligonucleotide-size "short" dsRNA molecules were designed with an antisense strand that is capable of hybridizing to the mRNA transcribed from the Palmer amaranth EPSPS gene at nucleotide positions 743-767 ("short dsRNA-5") and 564-588 ("short dsRNA-6"), as indicated by the italicized underlined nucleotides in SEQ ID NO:40 shown in FIG. 20, which also shows the four oligonucleotide-size "short" EPSPS dsRNA molecules (underlined, non-italicized text) and the three "long" double-stranded RNA polynucleotides (bolded text as described in Example 1.

Application of a mixture of the four oligonucleotide-size "short" EPSPS dsRNA molecules (described in Example 1) followed by application of glyphosate replicating the treatment procedure described in Example 1 resulted in 4 out of 4 Palmer amaranth plants with 16 copies of EPSPS being killed. Using the same treatment procedure but applying short dsRNA-5 and short dsRNA-6 together resulted in 0 out of 4 Palmer amaranth plants being killed. Adding either or both short dsRNA-5 and short dsRNA-6 to the mixture of the four oligonucleotide-size "short" EPSPS dsRNA molecules (described in Example 1) resulted in 4 out of 4 Palmer amaranth plants being killed, i. e., no antagonistic effect of short dsRNA-5 and short dsRNA-6 was observed.

Example 15

This example illustrates methods and topically applied compositions for inducing systemic silencing including the use of agents for conditioning of a plant to permeation by polynucleotides. More specifically, this example describes use of salicylic acid and polynucleotides.

Salicylic acid (SA) induces virus resistance in tobacco; see, e. g., Chivasa et al. (1997) *Plant Cell*, 19:547-557. Glyphosate-resistant Palmer amaranth plants having 49 or 63 copies EPSPS were pretreated with 15 millimolar SA. A solution of the four oligonucleotide-size "short" EPSPS dsRNA molecules (described in Example 1) was applied by hand at 1, 5, or 24 hours after treatment with SA, followed 72 hours later by spraying with glyphosate (1682 g acid equivalent per hectare of Roundup® WeatherMAX® brand herbicide). No improvement of the effects of the dsRNAs and glyphosate activity (estimated by observing plant growth measured as plant height) was observed for any of the SA treatments at 7 days after glyphosate treatment.

Example 16

This example illustrates methods and topically applied compositions for inducing systemic silencing including the use of agents for conditioning of a plant to permeation by polynucleotides. More specifically, this example describes variations in the order and timing of application of polynucleotides and surfactant solution.

These assays were conducted on Palmer amaranth plants with high copy numbers (56, 63, or 100 copies) of EPSPS, using a protocol including the following steps: (1) application of dsRNA (a solution of the four oligonucleotide-size "short" EPSPS dsRNA molecules described in Example 1) in a solution containing tallowamine surfactant and glycerol; (2) application of 1% SILWET L-77 silicone surfactant; and (3) application of glyphosate (1682 g acid equivalent per hectare of Roundup® WeatherMAX® brand herbicide). Spacing of the timing of the application of the polynucleotides and application of SILWET was assessed, with the SILWET spray applied at 30 minutes, 1 hour, or 2 hours after application of the dsRNA solution. In this set of assays, the three different times of the SILWET solution application all produced similar results, i. e., stunting of growth of most of the high copy plants that were treated with the dsRNA solution, as compared to control high copy plants which were treated with a control solution containing only tallowamine surfactant and glycerol.

Example 17

This example illustrates methods and topically applied compositions for inducing systemic silencing including the use of agents for conditioning of a plant to permeation by polynucleotides. More specifically, this example describes application of polynucleotides of the invention by low-volume spray and the use of a silicone surfactant and ammonium sulfate.

A solution of dsRNA (a solution of the four oligonucleotide-size "short" EPSPS dsRNA molecules described in Example 1) in a solution containing 2% ammonium sulfate was applied by low-volume spray to Palmer amaranth having 16 copies of EPSPS, followed by spraying with glyphosate (1682 g acid equivalent per hectare of Roundup® WeatherMAX® brand herbicide), resulting in the Palmer amaranth plants being killed.

Six Palmer amaranth plants per treatment were treated with a three-step procedure using low-volume spray: (1) spraying 1% SILWET L-77; (2) spraying 2 milliliters of a dsRNA solution containing equal amounts of the four oligonucleotide-size "short" EPSPS dsRNA molecules described in Example 1 at one of 3 doses (1× or 0.8 nanomoles per plant, 2× or 1.6 nanomoles per plant, or 4× or 3.2 nanomoles per plant); and (3) spraying glyphosate (1682 g acid equivalent per hectare of Roundup® WeatherMAX® brand herbicide) at a rate of 159 liters/acre. Nine days after the glyphosate spray, all six plants sprayed with 4× (3.2 nanomoles per plant) dsRNA were killed, and the plants sprayed with 2× (1.6 nanomoles per plant) dsRNA or 1× (0.8 nanomoles per plant) dsRNA were stunted (FIG. 21A).

Several assays were carried out on glyphosate-resistant Palmer amaranth grown from field-collected seeds. Plants were treated with various protocols described below, with some plants being treated topically with a dsRNA solution and control plants being treated with the buffer (dsRNA vehicle); application was by low-volume spray. Unless otherwise noted, the dsRNA solution contained equal amounts of the four oligonucleotide-size "short" EPSPS dsRNA molecules described in Example 1 in buffer at a "4X" dose (3.2 nanomoles per plant); the buffer consisted of 10 millimolar sodium phosphate and 0.01% (v/v) SILWET L-77 organosilicone surfactant in diethylpyrocarbonate (DEPC) water (Omega Bio-Tek) and adjusted to pH 6.8; and herbicide was a glyphosate herbicide applied at 840 g acid equivalent per hectare of Roundup® WeatherMAX® brand herbicide at a rate of 159 liters/acre. Results are provided in Table 7.

Assays 1 and 2: These assays were carried out on glyphosate-resistant Palmer amaranth grown from seeds obtained from a soil sample from a farm location with known glyphosate-resistant Palmer amaranth stands. For assay 1, ten plants per treatment were treated as follows: (1) spraying 1% SILWET L-77; (2) spraying 2 milliliters of the dsRNA solution; and (3) spraying glyphosate. For assay 2, eighteen plants per treatment were treated using the same procedure as in assay 1.

Assay 3: This assay compared treatments applied at different developmental stages and used seedlings grown from Palmer amaranth seeds from a Macon County, GA site and selected for glyphosate resistance. The buffer included 2% ammonium sulfate. Twelve small (3-leaf stage) or twelve large (5-leaf stage) seedlings per treatment were treated as follows: (1) spraying 1% SILWET L-77; (2) spraying 2 milliliters of the dsRNA solution; and (3) spraying glyphosate. This treatment provided better control (killed more plants) on small seedlings as compared to the larger seedlings. The dsRNA treatment killed or stunted more glyphosate-resistant plants than treatment with buffer and herbicide achieved, although at 16 days after treatment not all dsRNA-treated plants were killed.

Assays 4 and 5: These assays used Palmer amaranth plants grown from seeds in soil from a Pemiscot, MO farm. The buffer included 2% ammonium sulfate. Eleven small (3-leaf stage) seedlings per treatment were treated as follows: (1) spraying 1% SILWET L-77; (2) spraying 2 milliliters of the dsRNA solution; and (3) spraying glyphosate. For assay 5, twelve plants per treatment were treated using the same procedure as in assay 4.

Assay 6: This assay used Palmer amaranth plants grown from seeds in soil from the "Ivy2" farm. The buffer included 2% ammonium sulfate. Eighteen small (3-leaf stage) seedlings per treatment were treated as follows: (1) spraying 1% SILWET L-77; (2) applying 2 milliliters of the dsRNA solution, either by hand or by spraying; and (3) spraying glyphosate. In this assay the method of application (hand drop or spraying) provided similar results.

Assay 7: This assay used 3- to 4-leaf stage Palmer amaranth seedlings grown from F3 seeds selected for glyphosate resistance and more resistant to glyphosate than plants in assays 1-6. The buffer included 2% ammonium sulfate. Eighteen plants per treatment were treated as follows: (1) spraying 1% SILWET L-77; (2) spraying 2 milliliters of the dsRNA solution; and (3) spraying glyphosate.

TABLE 7

| Assay Number | killed plants/total plants | | Comments |
| --- | --- | --- | --- |
| | dsRNA-treated | control | |
| 1 | 2/10 | 0/10 | dsRNA-treated survivors stunted compared to controls (FIG. 21B) |
| 2 | 7/18 | 4/18 | dsRNA-treated survivors stunted at 8 and 30 days after treatment, compared to controls |
| 3 (large seedlings) | 5/12 | 3/12 | dsRNA/ammonium sulfate-treated survivors more stunted after treatment, compared to controls |
| 3 (small seedlings) | 9/12 | 6/12 | |
| 4 | 7/11 | 2/11 | dsRNA/ammonium sulfate-treated survivors more stunted after treatment, compared to controls |
| 5 | 8/12 | 3/12 | |
| 6 (hand drop) | 14/18 | — | |
| 6 (spray) | 13/18 | 9/18 | |
| 7 | 8/18 | 2/18 | |

Example 18

This example illustrates methods and topically applied compositions for inducing systemic silencing including the use of agents for conditioning of a plant to permeation by polynucleotides.

Figure 22:
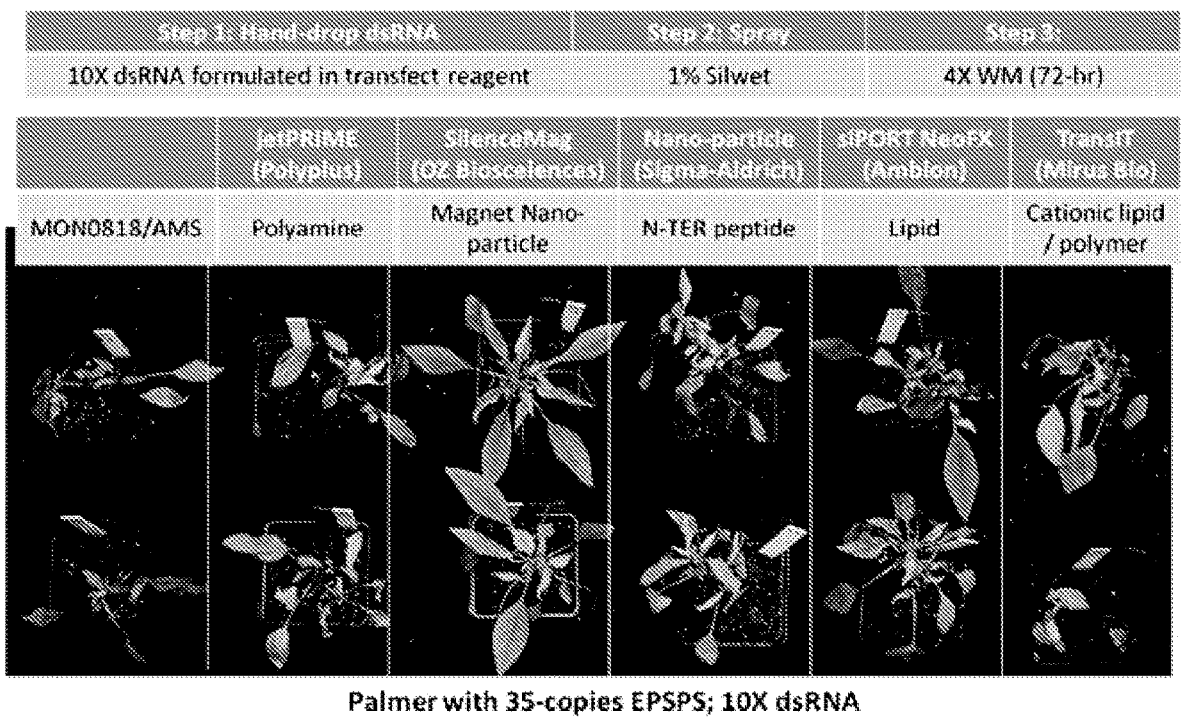
FIG. 22 illustrates results obtained from treating Palmer amaranth with tallowamine surfactant and ammonium sulfate or with transfection reagents, as described in Example 18.

In these assays, the dsRNA solution contained equal amounts of the four oligonucleotide-size "short" EPSPS dsRNA molecules described in Example 1 at a "10×" dose (8 nanomoles per plant) in a solution containing either 0.2% tallowamine surfactant and 2% ammonium sulfate (identified in FIG. 22 as "tallowamine/AMS"), or one of the following transfection reagents: (a) a polyamine (JetPRIME™, Polyplus-transfection SA, Illkirch, France), (b) a magnetic nanoparticle (SilenceMag, OZ Biosciences, Marseille, France), (c) a peptide (N-TER™ Nanoparticle, Sigma-Aldrich, St. Louis, MO), (d) a lipid (siPORT™ NeoFX™, Ambion, Foster City, CA), or (e) a cationic lipid/polymer (TransIT®, Mirus Bio, Madison, WI). Plants were treated as follows: (1) hand-applying dsRNA solution; (2) spraying 1% SILWET L-77; and (3) spraying with glyphosate applied at 840 g acid equivalent per hectare of Roundup® WeatherMAX® brand herbicide at a rate of 159 liters/acre. This protocol when used with dsRNA in the tallowamine surfactant/ammonium sulfate solution kills glyphosate-resistant Palmer amaranth having 35 copies EPSPS. Results are depicted in FIG. 22. Stunting or death of the plants was observed for plants treated with dsRNA in solutions containing polyamine (JetPRIME™), peptide (N-IER™ Nanoparticle), cationic lipid/polymer (TransIT®), or tallowamine surfactant/ammonium sulfate.

Example 19

This example illustrates methods using compositions including topically applied polynucleotides for inducing systemic silencing in a plant. More specifically, this example describes use of different types of polynucleotides for inducing systemic silencing.

Sense single-stranded DNAs (ssDNAs) and anti-sense single-stranded RNAs (ssRNAs) corresponding to the Palmer amaranth EPSPS gene at positions 14-38, positions 153-177, 345-369, and 1105-1129 (indicated by underlined nucleotides in FIG. 1) were purchased from Integrated DNA Technologies. The sense ssDNAs and anti-sense ssRNAs were annealed by heating equal moles of mixed ssDNAs and ssRNAs at 95 degrees Celsius for 5 minutes and slowly cooled over 1.5-2 hours to room temperature to yield the DNA/RNA hybrids.

16-copy glyphosate-resistant Palmer amaranth plants were used in the assays which used this procedure: (1) spraying 1% SILWET L-77; (2) hand-applying on four mature leaves of each plant a total of 0.8 nanomoles of either the Palmer EPSPS dsRNAs (as described in Example 1) or of the Palmer EPSPS DNA/RNA hybrids; and (3) spraying with glyphosate applied at 840 g acid equivalent per hectare of Roundup® WeatherMAX® brand herbicide at a rate of 159 liters/acre.

Results are depicted in FIG. 23. Seven days after the herbicide spraying, 4 out of 6 dsRNA-treated plants were dead and the remaining 2 were dying, whereas plants sprayed with the DNA/RNA hybrid were stunted in growth (glyphosate injury) compared to the control.

Example 20

This example illustrates methods using compositions including topically applied polynucleotides for inducing systemic silencing in a plant. More specifically, this example describes use of different types of polynucleotides for inducing systemic silencing.

Figure 24:
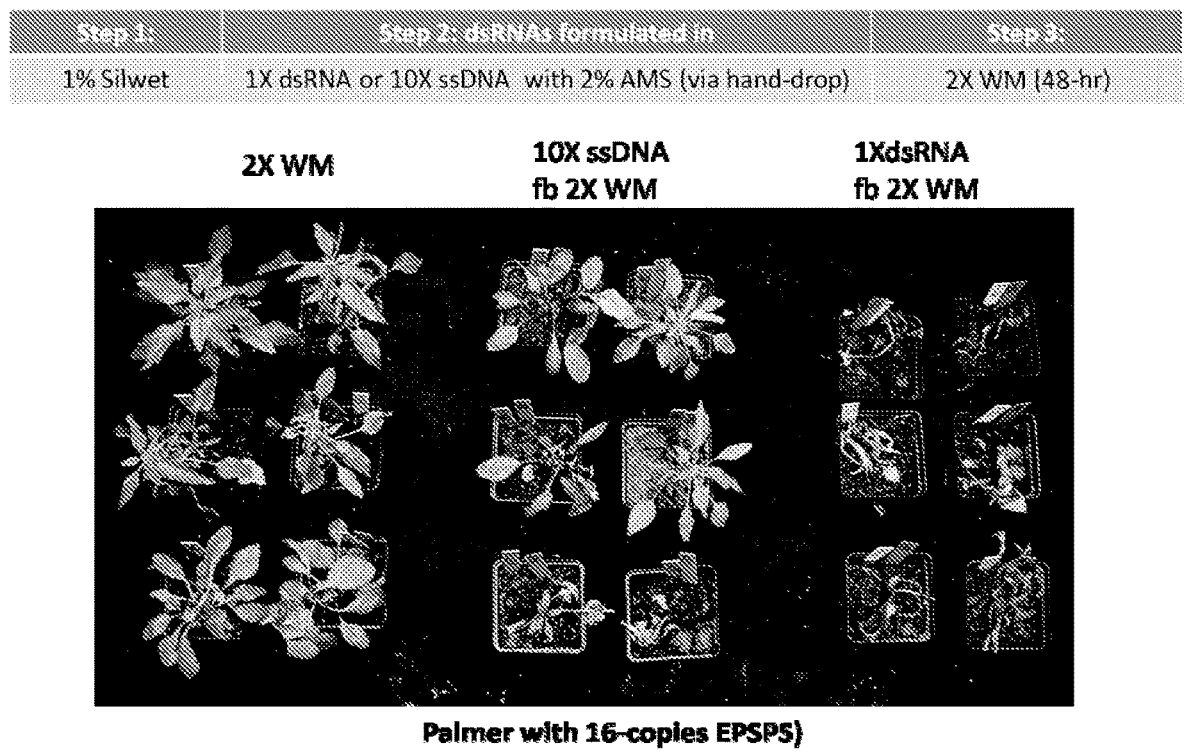
FIG. 24 illustrates results of treating glyphosate-resistant Palmer amaranth plants with either EPSPS dsRNA or EPSPS ssDNA polynucleotides, as described in Example 20. The upper photography was taken at 8 days after herbicide spray and the lower (bar) graph presents the results as a glyphosate injury (GI) scored 8 days after herbicide spray.

Six glyphosate-resistant Palmer amaranth plants having 16 copies of EPSPS were used per treatment in this assay. A 0.8 nanomoles ("1×") per plant treatment of dsRNA, a ten-fold greater amount (8 nanomoles per plant treatment, "10×") of ssDNA polynucleotides (described in Example 19) and buffer alone as a control, were applied to separate plants by hand in buffer containing 2% ammonium sulfate, followed 48 hours later by spraying with glyphosate applied at 840 g acid equivalent per hectare of Roundup® WeatherMAX® brand herbicide at a rate of 159 liters/acre. FIG. 24 depicts the results. Both polynucleotide treatments gave better control of the Palmer amaranth compared to plants treated only with buffer and herbicide. Of the plants treated with the 10×ssDNA treatment, two of six were killed, and the remaining four were stunted in growth by 30%. Of the plants treated with the 1×dsRNA treatment, all six plants were killed by 8 days after WM spray or 10-day after dsRNA treatment.

Example 21

This example illustrates methods using compositions including topically applied polynucleotides for inducing systemic silencing in a plant. More specifically, this example describes selection of a polynucleotide sequence for inducing systemic silencing in a plant.

Twelve dsRNAs of approximately 250 bp each and having one strand of the dsRNA corresponding to the EPSPS tiled DNA sequences of SEQ ID NOS:41-52 (Table 8) were designed to cover in a tiling fashion the full coding sequence and part of the 5' and 3' untranslated regions of the Palmer amaranth EPSPS gene, as depicted in FIG. 25A.

TABLE 8

| Tiling segment number (see FIG. 25A) | Sequence | SEQ ID NO. |
|---|---|---|
| 1 | CGCCAGGGCTGCAGACGCGTTACGTANTCGGATCCAGAATTCGTGATTAAC GTCACAGCATGTCATGTAAAACACGCGAATCAGACCGGTCCACTCTTGTTT TAATTTGAGACAATTTTGATGTTGAGTCATCCCACACCAACCCCAAAAAAT TCAACAACAAACTCTTATAATGATTCCCTCTACTCTACTAGAGTCTACACC AACCCACTTTCTCTTTGCCCACCAAAACTTTGGTTTGGTAAGAACT | 41 |
| 2 | CACCAACCCACTTTCTCTTTGCCCACCAAAACTTTGGTTTGGTAAGAACTA AGCCCTCTTCTTTCCCTTCTCTCTCTTAAAAGCCTAAAATCCACCTAACTTT TTCAGCCAACAAACAACGCCAAATTCAGAGGAAGAATAATGATGGCTCAA GCTACTACCATCAACAATGGTGTCCATACTGGTCAATTGCACCATACTTTA CCCAAAACCCAGTTACCCAAATCTTCAAAAACTCTTAATT | 42 |
| 3 | CCATACTTTACCCAAAACCCAGTTACCCAAATCTTCAAAAACTCTTAATTTT GGATCAAACTTGAGAATTTCTCCAAAGTTCATGTCTTTAACCAATAAAAGA GTTGGTGGGCAATCATCAATTGTTCCCAAGATTCAAGCTTCTGTTGCTGCT GCAGCTGAGAAACCTTCATCTGTCCCAGAAATTGTGTTACAACCCATCAAA GAGATCTCTGGTACTGTTCAATTGCCTGGGTCAAAGTCTTTATCC | 43 |
| 4 | TCAAAGAGATCTCTGGTACTGTTCAATTGCCTGGGTCAAAGTCTTTATCCA ATCGAATCCTTCTTTTAGCTGCTTTGTCTGAGGGCACAACAGTGGTCGACA ACTTGCTGTATAGTGATGATATTCTTTATATGTTGGACGCTCTCAGAACTCT TGGTTTAAAAGTGGAGGATGATAGTACAGCCAAAAGGGCAGTCGTAGAGG GTTGTGGTGGTCTGTTTCCTGTTGGTAAAGATGGAAAGGAAGAGAT | 44 |
| 5 | GAGGGTTGTGGTGGTCTGTTTCCTGTTGGTAAAGATGGAAAGGAAGAGATT CAACTTTTCCTTGGTAATGCAGGAACAGCGATGCGCCCATTGACAGCTGCG GTTGCCGTTGCTGGAGGAAATTCAAGTTATGTGCTTGATGGAGTACCAAGA ATGAGGGAGCGCCCCATTGGGGATCTGGTAGCAGGTCTAAAGCAACTTGG TTCAGATGTAGATTGTTTTCTTGGCACAAATTGCCCTCCTGTTCGGG | 45 |
| 6 | TGGTTCAGATGTAGATTGTTTTCTTGGCACAAATTGCCCTCCTGTTCGGGTC AATGCTAAAGGAGGCCTTCCAGGGGGCAAGGTCAAGCTCTCTGGATCGGT TAGTAGCCAATATTTAACTGCACTTCTCATGGCTACTCCTTTGGGTCTTGGA GACGTGGAGATTGAGATAGTTGATAAATTGATTTCTGTACCGTATGTTGAA ATGACAATAAAGTTGATGGAACGCTTTGGAGTATCCGTAGAACAT | 46 |
| 7 | TTGAAATGACAATAAAGTTGATGGAACGCTTTGGAGTATCCGTAGAACAT AGTGATAGTTGGGACAGGTTCTACATTCGAGGTGGTCAGAAATACAAATCT CCTGGAAAGGCATATGTTGAGGGTGATGCTTCAAGTGCTAGCTACTTCCTA GCCGGAGCCGCCGTCACTGGTGGGACTGTCACTGTCAAGGGTTGTGGAAC AAGCAGTTTACAGGGTGATGTAAAATTTGCCGAAGTTCTTGAGAAGAT | 47 |
| 8 | ACAAGCAGTTTACAGGGTGATGTAAAATTTGCCGAAGTTCTTGAGAAGAT GGGTTGCAAGGTCACCTGGACAGAGAATAGTGTAACTGTTACTGGACCAC CCAGGGATTCATCTGGAAAGAAACATCTGCGTGCTATCGACGTCAACATG AACAAAATGCCAGATGTTGCTATGACTCTTGCAGTTGTTGCCTTGTATGCA GATGGGCCCACCGCCATCAGAGATGTGGCTAGCTGGAGAGTGAAGGAAA | 48 |
| 9 | AGATGGGCCCACCGCCATCAGAGATGTGGCTAGCTGGAGAGTGAAGGAAA CCGAACGGATGATTGCCATTTGCACAGAACTGAGAAAGCTTGGGGCAACA GTTGAGGAAGGATCTGATTACTGTGTGATCACTCCGCCTGAAAAGCTAAAC CCCACCGCCATTGAAACTTATGACGATCACCGAATGGCCATGGCATTCTCT CTTGCTGCCTGTGCAGATGTTCCCGTCACTATCCTTGATCCGGGATGC | 49 |
| 10 | CTCTTGCTGCCTGTGCAGATGTTCCCGTCACTATCCTTGATCCGGGATGCAC CCGTAAAACCTTCCCGGACTACTTTGATGTTTTAGAAAAGTTCGCCAAGCA TTGATGAGTAGCTATATACGAGATCCTTAAATTGTACGCCGAAGGTTTTGA TTTGAGTCTAATAGTAGATAAAAGGCTATAAATAAACTGGCTTTCTGCTTG AGTAATTATGAAATTCTTTGTATTATGTTTGTGAGATTTGAAGTAGCTTATA | 50 |

TABLE 8-continued

| Tiling segment number (see FIG. 25A) | Sequence | SEQ ID NO. |
|---|---|---|
| 11 | TAATTATGAAATTCTTTGTATTATGTTTGTGAGATTTGAAGTAGCTTATAAA<br>TTACAATGTACTAAAGTCTAGAAATAAGTTATGTATCTTTTAAATCAATGA<br>GAAATGCATACTTGAAAGGCTTGACCTTGTATTTGTGACCTAAAGAGTACT<br>AACTTTGGAGTTTCCAACTCATTTGTTTATCTCATTTTTTTTAATTTTTGAT<br>TTAAATTGTTTATTTTTATGAGTAATCATGTATCTTTCTTATTCTAACCAAA<br>TGTAATACTCCTTC | 51 |
| 12 | TATGAGTAATCATGTATCTTTCTTATTCTAACCAAATGTAATACTCCTTCCA<br>ACTCTCTTTAAACGTCCACACTCTGGGCACAGAGTGTAATAGTGTGGTGGT<br>TGGAGTCTTTTAAGTGATTATAATAATTGTAAATGTGGTAGTTAGAATATT<br>TTAAGTAATGTAGGTGGGGTATTATGGTCTTGTTGAACATAGGATATTTAG<br>GTAAAAAATCTATGCAAAAAAAGGAAAGTAAGCAAATAAAGCGAATTGA<br>CCTGAAAAGAAAAGTGGACATGTATAGTGAGTTGGAGGAAGTATTTT | 52 |

The four oligonucleotide-size "short" EPSPS dsRNA molecules as described in Example 1 and FIG. 1 are located in the tiling segments 2, 3, 4, and 8 respectively, and are shown as light grey bars within those segments. The polynucleotides were synthesized in vitro transcription using a pBR322 vector with the EPSPS polynucleotides inserted at EcoRI and BamHI cloning sites; plasmid DNA was isolated with Qiagen Maxi prep kits and digested with EcoRI and BamHI restriction enzymes. The digested DNA solution was used in the treatment of the plants without further purification.

Glyphosate-resistant Palmer amaranth plants having 16 copies of EPSPS were treated as follows: spraying with 1% SILWET L-77; (2) hand application of a dsRNA solution (containing polynucleotides selected from the twelve tiling segments or the four "short" dsRNA molecules described in Example 1 at the rate of 0.01 nanomole DNA/plant) or buffer as a control; and (3) 48 hours later spraying with glyphosate applied at 840 g acid equivalent per hectare of Roundup® WeatherMAX® brand herbicide at a rate of 159 liters/acre. Above-ground height of the treated plants was observed 11 days after herbicide treatment; plants that were dead or dying were assigned a height of zero. Results are depicted in FIGS. 25B and 25C. The dsRNA polynucleotides combinations showing the greatest efficacy in this assay included the four "short" dsRNA molecules described in Example 1, the combination of tiling segments 2, 5, 8, and 11, and the combination of tiling segments 7, 8, and 9.

Example 22

This example illustrates methods using compositions including topically applied polynucleotides for inducing systemic silencing in a plant. More specifically, this example describes topical application of polynucleotides following application of herbicide to a plant.

Figure 26:
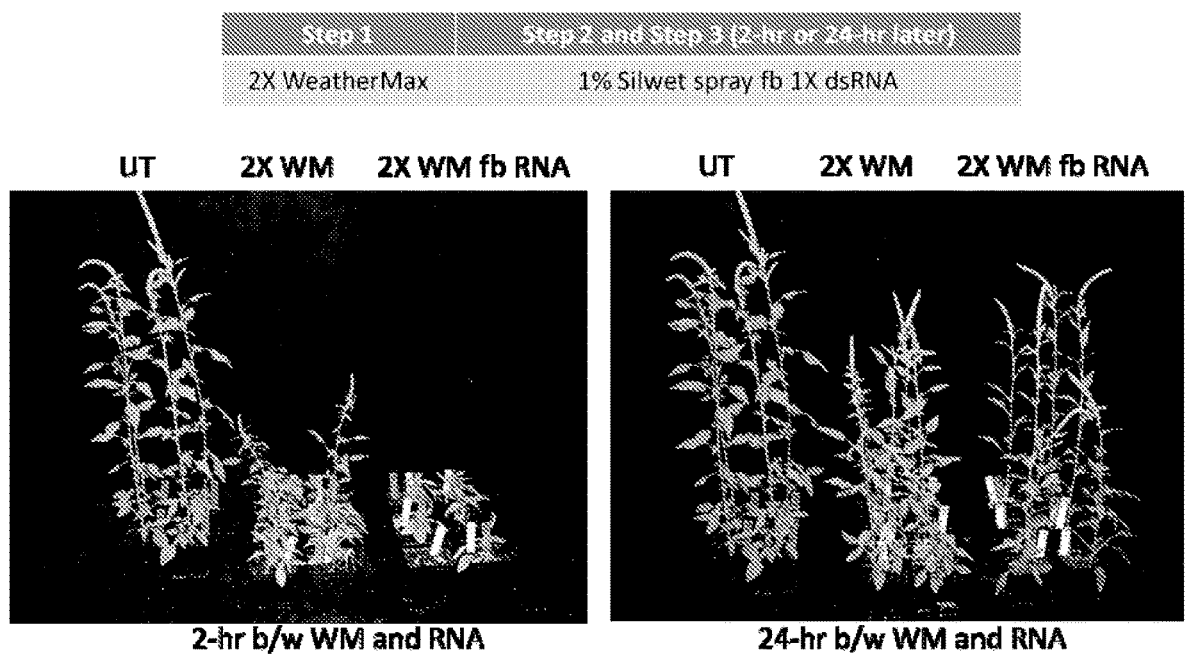
FIG. 26 illustrates results of treating glyphosate-resistant Palmer amaranth plants with glyphosate followed by spraying with 1% SILWET L-77 (Silicone Polyether Copolymer) followed by application of EPSPS dsRNA in buffer containing 2% ammonium sulfate, as described in Example 22. Untreated ("UT") control plants were treated only with the 1% SILWET L-77 spray but not with herbicide or dsRNA. Plants were photographed and rated at 16 days after treatment.

In one assay, glyphosate-resistant Palmer amaranth plants having 16 copies of EPSPS were sprayed with glyphosate applied at 840 g acid equivalent per hectare of Roundup® WeatherMAX® brand herbicide at a rate of 159 liters/acre. Two or 24 hours after herbicide application, the plants were treated by spraying with 1% SILWET L-77. Fifteen to 20 minutes after SILWET treatment, the plants were treated by hand application of either 0.8 nanomoles ("1×") per plant of the four oligonucleotide-size "short" EPSPS dsRNA molecules as described in Example 1 in buffer containing 2% ammonium sulfate or buffer containing 2% ammonium sulfate. In this assay, untreated ("UT") control plants were treated only with the 1% SILWET L-77 spray but not with herbicide or dsRNA. Results are depicted in FIG. 26. In this assay, application of 1% SILWET resulted in improved glyphosate activity by 60% when applied 2 hours after herbicide spraying and by 20% when applied 24 hours after herbicide spraying. In this assay, application of 1% SILWET followed by EPSPS dsRNA resulted in improved glyphosate activity by at least 80% when applied 2 hours after herbicide spraying and by 20% when applied 24 hours after herbicide spraying.

In another assay, Palmer amaranth plants grown from seeds in soil from a farm site in Macon, GA were sprayed with glyphosate applied at 840 g acid equivalent per hectare of Roundup® WeatherMAX® brand herbicide at a rate of 159 liters/acre. Three days after herbicide treatment, 9 of 40 plants were killed and 3 were severely stunted. Surviving plants were sprayed with 1% SILWET L-77, followed by topical application by hand of either 8 nanomoles ("10×") per plant of the four oligonucleotide-size "short" EPSPS dsRNA molecules as described in Example 1 or buffer as a control. Three days later, 3 more plants in the dsRNA-treated group were dead and 2 more plants in the buffer-treated group were dead. At this point (6 days after the original herbicide treatment and 3 days after the SILWET/dsRNA or buffer treatment), half of the surviving plants in each group were sprayed with a second application of glyphosate (applied at the same dose as in the first application). Two weeks after this second herbicide treatment, the remaining dsRNA-treated plants showed 80% injury and the remaining buffer-treated plants showed 40% injury.

Example 23

This example illustrates methods using compositions including topically applied polynucleotides for inducing systemic silencing in a plant. More specifically, this example describes a single-step topical application of a single composition including polynucleotides, surfactant, and herbicide for controlling herbicide-resistant weeds.

This assay was carried out on a field population of glyphosate-resistant Palmer amaranth plants that were known to have very high copy numbers of EPSPS (plants from this study site have been reported to have from 5 to more than 160 copies of EPSPS by Gaines et al. (2010) Proc. Natl. Acad. Sci. USA, 107:1029-1034). The polynucleotides used in this assay were an equimolar mixture of the four oligonucleotide-size "short" EPSPS dsRNA molecules as described in Example 1.

Four to six inch tall plants in a treatment area of 1 foot by 5 feet were sprayed in a single treatment with either 264 micrograms ("100X") or 52.8 micrograms ("20X") of the EPSPS dsRNAs in a solution that also contained 1% SILWET L-77 surfactant, 2% ammonium sulfate, and glyphosate (applied at 1682 g acid equivalent per hectare of Roundup® WeatherMAX® brand herbicide at a rate of 159 liters/acre). For comparison, other plants in treatment areas of 1 foot by 5 feet were sprayed with glyphosate (in a solution that also contained 1% SILWET L-77 surfactant and 2% ammonium sulfate) applied at the same rate.

Figure 27:
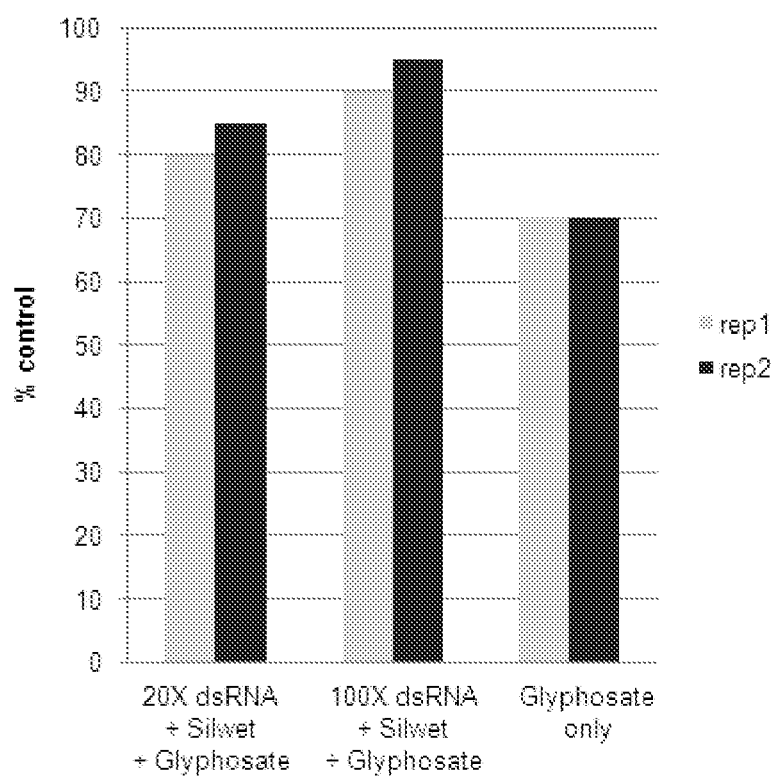
FIG. 27 illustrates results of treating a field population of high copy number glyphosate-resistant Palmer amaranth with a composition containing a 20× or 100× amount of EPSPS dsRNA polynucleotides, surfactant, ammonium sulfate, and herbicide or with a composition containing, surfactant, ammonium sulfate, and herbicide, as described in Example 23. For each treatment, two replicate 1 foot by 5 foot plots were treated.

Results are depicted in FIG. 27. Treating the plants with only glyphosate (applied at 1682 g acid equivalent per hectare of Roundup® WeatherMAX® brand herbicide at a rate of 159 liters/acre) in a solution that also contained SILWET L-77 and ammonium sulfate resulted in about 70% control (death of plants). The one-step treatment using a composition containing the 20×EPSPS dsRNA polynucleotides, surfactant, ammonium sulfate, and herbicide resulted in about 80-85% control of the glyphosate-resistant Palmer amaranth, which is the approximate control rate obtained by spraying with glyphosate applied at 6720 g acid equivalent per hectare of Roundup® WeatherMAX® brand herbicide at a rate of 159 liters/acre (i. e., at 8 times the standard application rate of about 840 g acid equivalent per hectare of Roundup® WeatherMAX® brand herbicide at a rate of 159 liters/acre). The one-step treatment using a composition containing the 100× EPSPS dsRNA polynucleotides, surfactant, ammonium sulfate, and herbicide resulted in about 90-95% control of the glyphosate-resistant Palmer amaranth, which is the approximate control rate obtained by spraying with glyphosate applied at 13440 g acid equivalent per hectare of Roundup® WeatherMAX® brand herbicide at a rate of 159 liters/acre (i. e., at 16 times the standard application rate of about 840 g acid equivalent per hectare of Roundup® WeatherMAX® brand herbicide at a rate of 159 liters/acre).

Example 24

This example illustrates a method for inducing systemic regulation of a target gene in a vegetable plant by topical application to the vegetable of a polynucleotide molecule including a segment with a nucleotide sequence essentially identical to, or essentially complementary to, a sequence of 18 or more contiguous nucleotides in either the target gene or RNA transcribed from the target gene, whereby the molecule permeates the interior of the vegetable plant and induces systemic regulation of the target gene. In this example, growing vegetable plants were treated with a topically applied composition for inducing systemic silencing of a target gene in a vegetable or fruit crop plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, this example demonstrates the use of topically applied polynucleotides to induce systemic silencing of a phytoene desaturase (PDS) gene in a vegetable crop plant, i. e., lettuce (*Lactuca sativa*).

Lettuce PDS has the sequence

```
                                              (SEQ ID NO: 53)
ATGTCTCTGTTTGGAAATGTTTCTGCCATTAACTCAAGTGGAAAGTGTAT
AGTAATGAATCTTTCAAGCACACAAATCACTTCAAGAGATTGTTTCAAGA
TTACCTCAGGGCAAAAAGATGTTTTGTCATTTGGATGCTGTGATGCTATG
GGTAACAGATTGCAATTCCCAAGTGCTCGTTCTTTTACACCAAGATCAAA
GAAGAATGTCTCCCCTCTAAAGGTAGTTTGTGTTGATTATCCAAGACCAG
ATCTTGATAACACATCTAATTTCTTGGAAGCTGCTCACTTGTCTTCAACC
TTCAGAACTTCCCCACGCCCATCTAAGCCATTGAAGATTGTAATTGCTGG
TGCAGGTTTAGCTGGTTTATCAACTGCTAAGTATTTAGCTGATGCAGGTC
ACAAGCCAATTTTACTAGAAGCAAGAGATGTTCTTGGTGGAAAGGTGGCA
GCTTGGAAAGATGATGATGGAGATTGGTATGAGACAGGTTTACACATATT
CTTTGGAGCTTACCCAAATGTACAAAATTTATTTGGAGAGCTAGGAATTA
ATGATAGATTACAGTGGAAGGAGCATTCTATGATATTTGCAATGCCAAAT
AAGCCTGGAGAATTTAGTAGGTTTGACTTCCCAGATGTTTTACCTGCACC
ATTGAATGGAATTTTTGCTATATTGAGGAACAATGAAATGCTGACGTGGC
CTGAGAAAGTGAAGTTTGCAATTGGGCTGTTGCCTGCAATGTTAGGTGGA
CAGGCTTATGTTGAGGCCCAAGATGGGCTTAGTGTTCAGGACTGGATGAG
AAAGCAAGGTATACCTGATCGAGTTACTACTGAAGTGTTTATTGCAATGT
CAAAAGCATTAAACTTTATAAATCCAGATGAACTTTCAATGCAATGTATT
CTCATTGCTCTAAACCGTTTTCTTCAGGAAAAGCATGGTTCCAAGATGGC
ATTTTTAGATGGGAGCCCACCAGAAAGACTTTGCAAGCCAATTGTTGACC
ACATCGAGTCACTCGGTGGCCAAGTCAGAGTCAACTCACGAATACAAAAA
ATTGAGTTAAACAAAGACGGAACTGTCCGGAACTTTCTATTGAGTGATGG
GAATGTTCTAGAAGCTGATGCTTATGTTTTCGCTACCCCTGTTGACATTC
TCAAGCTTCTTTTACCCGAAGAATGGAAACCAATTCCATATTTCAAAAAA
TTAGAGAAGTTAGTCGGTGTTCCTGTTATAAACGTTCATATATGGTTTGA
CAGAAAGCTGAAAAACACATATGATCACTTACTTTTCAGTAGGTCACCTC
TGCTGAGTGTGTATGCTGACATGTCAGTGACATGTAAGGAATATTATGAT
CCGAATAAGTCAATGTTGGAGTTGGTTCTTGCTCCAGCTGAGGAATGGAT
TTCAAGAAGTGACACTGATATTATTGATGCAACAATGAGTGAACTTTCAA
GGCTTTTTCCTGATGAAATTGCAGCTGATCAAAGTAAAGCAAAAATCTTG
AAATATAAAGTTGTTAAAACACCAAGGTCTGTTTATAAAACTGTTCCAGA
TTGTGAACCATGTCGACCCCTACAAAGATCTCCAATTCAAGGATTTTATT
TATCTGGTGATTATACTAAACAAAAGTATTTGGCTTCAATGGGGGGTGCT
GTTTTATCTGGAAAAATTTGTGCACAAGCTATTTTACAAGATTATGAGAT
GCTTGCTACA.
```

Polynucleotide single-stranded DNAs of 21-45 nucleotides in length with the following sequences were synthesized: taatacgactcactatagggtttggagcttacccaaATGtac ("HL286", sense orientation, SEQ ID NO:54), taatacgactcactatagg-gaggccacgtcagcatttcattgttc ("HL287", anti-sense orientation, SEQ ID NO:55), ccattcaATGgtgcaggtaaaac ("HL288", anti-sense orientation, SEQ ID NO:56), catagaATGctccttccactg ("HL289", anti-sense orientation, SEQ ID NO:57), and caaataaattttgtacatttgggtaagctccaa ("HL290", anti-sense orientation, SEQ ID NO:58). An ssDNA solution was made with an equal mixture of all five polynucleotides in 0.01% SILWET L-77 in 5 millimolar sodium phosphate buffer, pH 6.8.

Figure 28:
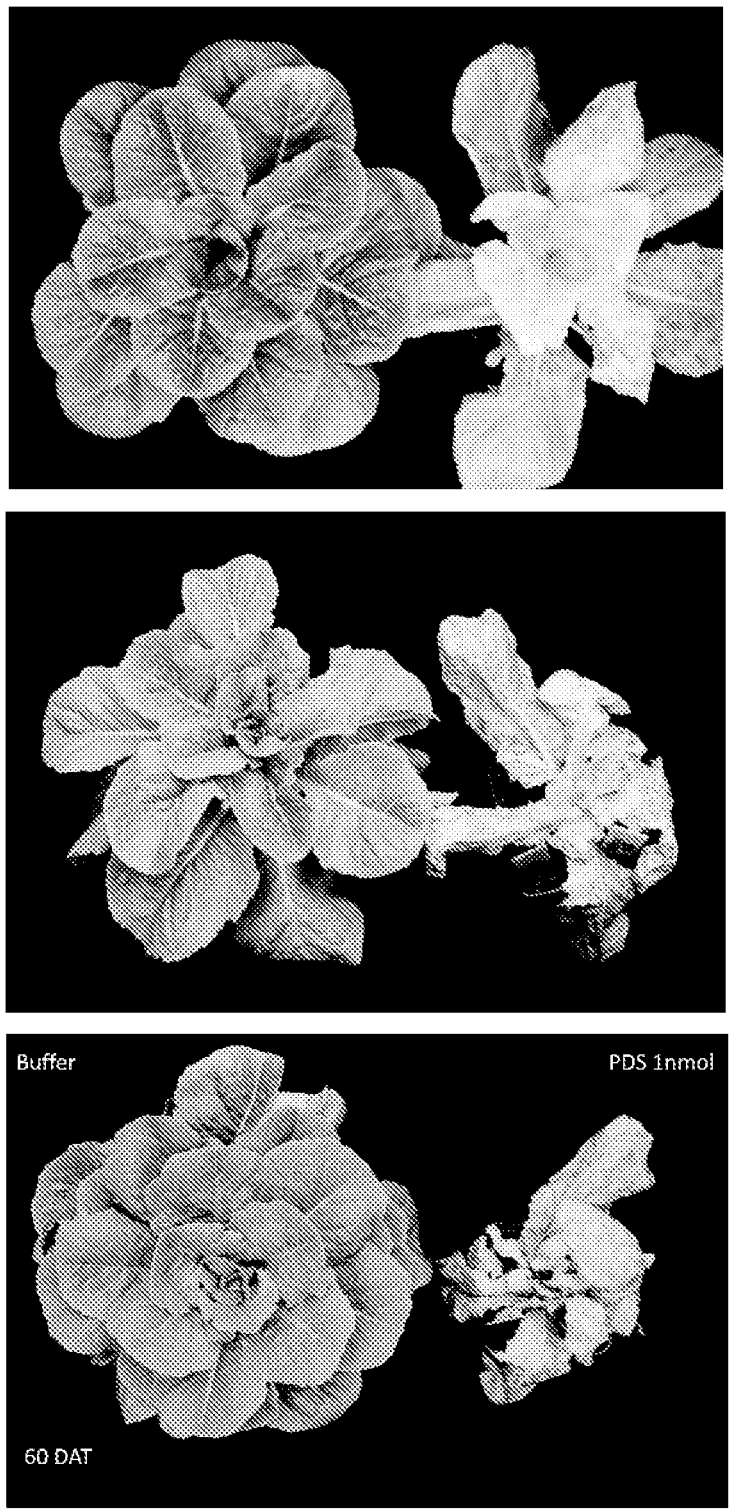
FIG. 28 depicts the progression of bleaching and death of the lettuce plants treated with 1 nanomole ssDNA per plant at (from top to bottom) 37, 46, and 60 days after treatment, as described in Example 24.

Lettuce variety LS49 "Green Tower" was used in the assays. Two fully expanded leaves of each plant were dipped into a freshly made 0.1% SILWET L-77 in double-distilled water solution for a few seconds. The leaves were allowed to dry for 15-30 minutes. Each plant was then treated by applying 20 microliters ssDNA solution to the top surface of two SILWET-treated leaves (total 40 microliters per plant). Table 9 lists the assay conditions used and the observed bleaching of plants topically treated with ssDNA polynucleotides. FIG. 28 depicts the progression of bleaching and death of the lettuce plants treated with 1 nanomole ssDNA per plant at (from top to bottom) 37, 46, and 60 days after treatment.

TABLE 9

| Developmental stage | Amount of each ssDNA applied (nanomoles/plant) | Earliest observation of bleaching |
| --- | --- | --- |
| 4 weeks post-germination, plants have 2 fully expanded leaves | 1 | 3 weeks post-treatment |
| 5 weeks post-germination, plants have 4 fully expanded leaves | 4 | 4 days post-treatment |

The assays were repeated with 2 or 4 nanomoles ssDNA applied per plant. FIG. 29A depicts the systemic silencing evidenced by bleaching observed at 4 or 12 days after topical treatment with the polynucleotides.

The assays were repeated using each individual anti-sense ssDNAs ("HL287", SEQ ID NO:55; "HL288", SEQ ID NO:56; "HL289", SEQ ID NO:57; and "HL290", SEQ ID NO:58) with 8 nanomoles polynucleotide applied per plant; positive control plants were treated with a mixture of the four individual anti-sense ssDNAs at 2 nanomoles each (for a total of 8 nanomoles polynucleotide applied per plant) and negative control plants were treated only with buffer. FIG. 29B depicts the systemic silencing evidenced by bleaching observed at 4 after topical treatment with the anti-sense ssDNAs.

Example 25

This example illustrates an aspect of the invention. In this example, growing plants were treated with a topically applied composition for inducing systemic silencing of a target gene in a plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, this example demonstrates the use of topically applied polynucleotides to induce systemic silencing of a phytoene desaturase (PDS) gene in a vegetable crop, i. e., tomato (*Solanum lycopersicum*).

Tomato PDS has the sequence (SEQ ID NO: 59)
GGGTTTATCTCGCAAGTGTGGCTATGGTGGGACGTGTCAAATTTTGGATT

GTAGCCAAACATGAGATTTGATTTAAAGGGAATTGGCCAAATCACCGAAA

GCAGGCATCTTCATCATAAATTAGTTTGTTTATTTATACAGAATTATACG

CTTTTACTAGTTATAGCATTCGGTATCTTTTTCTGGGTAACTGCCAAACC

ACCACAAATTTCAAGTTTCCATTTAACTCTTCAACTTCAACCCAACCAAA

TTTATTTGCTTAATTGTGCAGAACCACTCCCTATATCTTCTAGGTGCTTT

CATTCGTTCCGAGTAAAATGCCTCAAATTGGACTTGTTTCTGCTGTTAAC

TTGAGAGTCCAAGGTAGTTCAGCTTATCTTTGGAGCTCGAGGTCGTCTTC

TTTGGGAACTGAAAGTCGAGATGGTTGCTTGCAAAGGAATTCGTTATGTT

TTGCTGGTAGCGAATCAATGGGTCATAAGTTAAAGATTCGTACTCCCCAT

GCCACGACCAGAAGATTGGTTAAGGACTTGGGGCCTTTAAAGGTCGTATG

CATTGATTATCCAAGACCAGAGCTGGACAATACAGTTAACTATTTGGAGG

CTGCATTTTTATCATCAACGTTCCGTGCTTCTCCGCGCCCAACTAAACCA

TTGGAGATTGTTATTGCTGGTGCAGGTTTGGGTGGTTTGTCTACAGCAAA

ATATTTGGCAGATGCTGGTCACAAACCGATACTGCTGGAGGCAAGGGATG

TTCTAGGTGGAAAGGTAGCTGCATGGAAAGATGATGATGGAGATTGGTAC

GAGACTGGTTTGCATATATTCTTTGGGGCTTACCCAAATATTCAGAACCT

GTTTGGAGAATTAGGGATTAACGATCGATTGCAATGGAAGGAACATTCAA

TGATATTTGCAATGCCAAGCAAGCCAGGAGAATTCAGCCGCTTTGATTTC

TCCGAAGCTTTACCCGCTCCTTTAAATGGAATTTTAGCCATCTTAAAGAA

TAACGAAATGCTTACATGGCCAGAGAAAGTCAAATTTGCAATTGGACTCT

TGCCAGCAATGCTTGGAGGGCAATCTTATGTTGAAGCTCAAGATGGGATA

AGTGTTAAGGACTGGATGAGAAAGCAAGGTGTGCCGGACAGGGTGACAGA

TGAGGTGTTCATTGCTATGTCAAAGGCACTCAACTTTATAAACCCTGACG

AACTTTCAATGCAGTGCATTTTGATCGCATTGAACAGGTTTCTTCAGGAG

AAACATGGTTCAAAAATGGCCTTTTTAGATGGTAATCCTCCTGAGAGACT

TTGCATGCCGATTGTTGAACACATTGAGTCAAAAGGTGGCCAAGTCAGAC

TGAACTCACGAATAAAAAAGATTGAGCTGAATGAGGATGGAAGTGTCAAG

AGTTTTATACTGAGTGACGGTAGTGCAATCGAGGGAGATGCTTTTGTGTT

TGCCGCTCCAGTGGATATTTTCAAGCTTCTATTGCCTGAAGACTGGAAAG

AGATTCCATATTTCCAAAAGTTGGAGAAGTTAGTCGGAGTACCTGTGATA

AATGTACATATATGGTTTGACAGAAAACTGAAGAACACATATGATCATTT

GCTCTTCAGCAGAAGCTCACTGCTCAGTGTGTATGCTGACATGTCTGTTA

CATGTAAGGAATATTACAACCCCAATCAGTCTATGTTGGAATTGGTTTTT

GCACCTGCAGAAGAGTGGATATCTCGCAGCGACTCAGAAATTATTGATGC

AACGATGAAGGAACTAGCAACGCTTTTTCCTGATGAAATTTCAGCAGATC

AAAGCAAAGCAAAAATATTGAAGTACCATGTGTCAAAACTCCGAGGTCT

GTTTATAAAACTGTGCCAGGTTGTGAACCCTGTCGGCCTTTACAAAGATC

CCCAATAGAGGGGTTTTATTTAGCCGGTGACTACACGAAACAGAAATACT

-continued

```
TGGCTTCAATGGAAGGCGCTGTCTTATCAGGAAAGCTTTGTGCTCAAGCT

ATTGTACAGGATTATGAGTTACTTGTTGGACGTAGCCAAAAGAAGTTGTC

GGAAGCAAGCGTAGTTTAGCTTTGTGGTTATTATTTAGCTTCTGTACACT

AAATTTATGATGCAAGAAGCGTTGTACACAACATATAGAAGAAGAGTGCG

AGGTGAAGCAAGTAGGAGAAATGTTAGGAAAGCTCCTATACAAAAGGATG

GCATGTTGAAGATTAGCATCTTTTTAATCCCAAGTTTAAATATAAAGCAT

ATTTTATGTACCACTTTCTTTATCTGGGGTTTGTAATCCCTTTATATCTT

TATGCAATCTTTACGTTAGTTAAAAAAAAAAAAAAAAAAAAAAACTCGA.
```

A 201 nucleotide dsRNA polynucleotide with an antisense strand capable of hybridizing to the RNA encoded by the sequence

```
                                        (SEQ ID NO: 60)
TCGCAGCGACTCAGAAATTATTGATGCAACGATGAAGGAACTAGCAACGC

TTTTTCCTGATGAAATTTCAGCAGATCAAAGCAAAGCAAAAATATTGAAG

TACCATGTTGTCAAAACTCCGAGGTCTGTTTATAAAACTGTGCCAGGTTG

TGAACCCTGTCGGCCTTTACAAAGATCCCCAATAGAGGGGTTTTATTTAG
``` which correspond to the nucleotides at positions 1724-1923 of the mRNA transcribed from the tomato PDS gene sequence (SEQ ID NO:59) was synthesized by RT PCR using oligonucleotide primers with the sequences TAATACGACTCACTATAGGGTCGCAGCGACTCAGAAATTATTG (SEQ ID NO:61, sense primer) and TAATACGACTCACTATAGGGGTAAAGGCCGACAGGGTTCACAACC (SEQ ID NO:62, antisense primer). A 2.5 micromolar dsRNA solution was made with the 201 nucleotide dsRNA polynucleotide (SEQ ID NO:60) in 0.01% SILWET L-77 in 5 millimolar sodium phosphate buffer, pH 6.8.

Figure 30:
FIG. 30 illustrates bleaching of leaves (right top panel) and flowers (right middle panel) of tomato plants treated with tomato phytoene desaturase polynucleotides, as described in Example 25.

Three-week old tomato seedlings were treated as follows. Two fully expanded leaves were dipped into a freshly made 0.1% SILWET L-77 solution in double-distilled water for a few seconds. The leaves were allowed to dry for 30 minutes to 1 hour. Each plant was then treated by applying 20 microliters dsRNA solution to the top surface of two SILWET-treated leaves (total 40 microliters per plant). Control plants were treated with buffer. The plants were kept in a growth chamber for observation. FIG. 30 depicts the systemic silencing of the target gene PDS as evidenced by bleaching of the dsRNA-treated plants 30 days after topical treatment. The dsRNA-treated plants were severely stunted, compared to control plants.

Example 26

This example illustrates an improvement to herbicidal compositions adapted for topical coating onto the exterior surface of a growing plant where the plant lethal agent includes polynucleotides having a sequence essentially identical or complementary to sequences of one or more plant genes or sequence of transcribed DNA from the plant genes. The polynucleotides effect systemic suppression of the plant gene in plant organs or tissues other than those that received the topical polynucleotide application. More specifically this example illustrates an herbicidal composition adapted for topical coating onto the exterior surface of a growing plant comprising surfactant and at least one plant lethal agent including combinations of polynucleotides having sequence targeting the 5-enolpyruvylshikimate-3-phosphate synthase (EPSPS) gene, a transcription initiation factor (TIF), and DNA-dependent ATPase (ddATPase) in Palmer amaranth.

The herbicidal composition includes at least one of the following 21-base-pair double-stranded RNA polynucleotides:

(1) nDsRNA1:
sense strand
(SEQ ID NO: 63)
CUACCAUCAACAAUGGUGUCC
and anti-sense strand
(SEQ ID NO: 64)
GGACACCAUUGUUGAUGGUAG (2) nDsRNA3:
sense strand
(SEQ ID NO: 65)
GUCGACAACUUGCUGUAUAGU
and anti-sense strand
(SEQ ID NO: 66)
ACUAUACAGCAAGUUGUCGAC (3) nDsRNA4:
sense strand
(SEQ ID NO: 67)
GGUCACCUGGACAGAGAAUAG
and anti-sense strand
(SEQ ID NO: 68)
CUAUUCUCUGUCCAGGUGACC (4) nDsNA5:
sense strand
(SEQ ID NO: 69)
AAUGCCAGAUGUUGCUAUGAC
and anti-sense strand
(SEQ ID NO: 70)
GUCAUAGCAACAUCUGGCAUU A mixture of multiple polynucleotides is advantageous for preventing selection of resistance in the treated plants. In an embodiment, the herbicidal composition includes a mixture of all four of the above dsRNA polynucleotides having SEQ ID NOS: 63-70. In another embodiment, the herbicidal composition includes single-stranded DNA polynucleotides with deoxyribonucleotide sequences corresponding to one or more of the dsRNA sequences SEQ ID NOS: 63-70. In another embodiment, the herbicidal composition includes RNA/DNA hybrids with nucleotide sequences corresponding to one or more of the dsRNA sequences SEQ ID NOS: 63-70. In another embodiment, the herbicidal composition includes dsRNA polynucleotides where the 2' hydroxyls are methylated for stability.

The herbicidal composition includes a surfactant such as SILWET L-77 (or other effective surfactants such as those provided in Example 36). Optionally, the herbicidal composition can include one or more additives such as a salt, chelating agent, or a humectant (such as those provided in Example 35) to improve herbicidal performance, e. g., by enhancing transfer of the polynucleotide into the interior of the plant, enhancing efficacy of the polynucleotides, or potentiating the herbicidal activity of the non-polynucleotide herbicide.

Optionally the herbicidal composition includes polynucleotides designed to regulate multiple genes in the plant. In an embodiment, the herbicidal composition includes polynucleotides having sequence essentially identical or complementary to the sequence of a second gene or to the sequence of RNA transcribed from the second gene, wherein the regulation of the second gene provides a synergistic enhancement of the herbicidal activity of the composition.

In an embodiment, the herbicidal composition includes polynucleotides having sequence essentially identical or complementary to the sequence of the endogenous Palmer amaranth 5-enolpyruvylshikimate-3-phosphate synthase (EPSPS) gene or to the sequence of RNA transcribed from the endogenous EPSPS gene as well as polynucleotides having sequence essentially identical or complementary to the sequence of the endogenous Palmer translation initiation factor (TIF) gene or to the sequence of RNA transcribed from the endogenous TIF gene. Translation initiation factor (TIF) is a nuclear-encoded chloroplast protein that is essential for initiating protein synthesis and is expressed throughout a plant. *Arabidopsis thaliana* has an orthologue named AT1G17220.1 (described on the publicly available database The *Arabidopsis* Information Resource found online at www.arabidopsis.org/servlets/ TairObject?type=locus&name=AT1G17220) and assigned GenBank accession number GI:186478573, which has been identified as a chloroplast localized protein with similarity to bacterial translation initiation factor 2; see also Miura et al. (2007) *Plant Cell,* 19:1313-1328 for a description of this gene. TIF sequences were identified from Palmer amaranth (*Amaranthus palmeri*); one TIF gene was identified to have the sequence of SEQ ID NO:71. Examples of polynucleotides for suppression of this TIF gene in *Amaranthus palmeri* are listed in Table 10.

TABLE 10

| Poly-nucleotide | Position in TIF sequence | Sequence | SEQ ID NO. |
|---|---|---|---|
| Palmer amaranth TIF | Entire sequence of SEQ ID NO: 71 | ATGGCAACAATGGCTTCCCTAGTGAGTTTGGGAAGCTCTGGAG CAACTTGCTCAGGGCAATTGGAGGTTTCCTTTTCATTGGTTAAG AAAATTACATTGCCTAGAAGAAATTGTAGTTGCAATTTTAGGCA ATTAGGAGGGGGGAGGAGATGGCGTTACGTTTCGGTGTGTAGA CTTTCTGTCACTACTGATTATGTTTCTGAGCAAGGAAATGCTGT TTCTCTTGAAAATGCATATAGTGAGAGTAAAGAAGAGGGTCTC ATCTTGAAGCCTTCTCCTAAGCCGGTTTTGAAATCCGGGTCTGA TGGAAATCGGAAATTTGGGGAGAGTTCGGTGGCGTTTTCGAGT AATGGGAAATTGGATAATGTAGAGGAGAGGAAGAAGGTTATTG ATTCATTGGATGAGGTATTAGAAAAGGCCGAGAGATTAGAAAC GGCGAACTTACAAGCAGATAATAGAAAGGATAGCACAAATGTA AATAAACCGTCTCCGAGTGTAAGTAGTTCAACCAATGGTAAAC CTGTAAATAATTTGAACAAAGGGAAGCCTAAAGCTGCGAAGAG CGTTTGGAGAAAGGGAAATCCAGTTTCTACTGTGCAAAAAGTA GTGCAAGAATCTCCGAAGATTGAAAAGGTTGAGAGAGTGGAAG CTCGAACGACCAGCCAATCGTCTGAAACGATAAGACCCCCAGT GCCACTACAGAGGCCTGAGATTAAGTTGCAGGCAAAGCCTTCT ACTGCTCCTCCACCCATGCCTAAGAAGCCGGTTTTGAAGGATGT GGGGATGTCCTCCAGAGCTGATGGGAAGGACCAGTCTGTGAAA TCTAAAGAGAGGAAGCCTATTCTAGTGGACAAATTTGCCACCA AGAAGGCATCAGTTGATCCGTCGATTGCTCAAGCAGTAATTGC CCCACCAAAACCTGCTAAATTTCCTTCTGGAAAGTTTAAAGATG ATTATCGGAAGAAGGGTCTTGCAGCTGGTGGGCCGAAGAGGCG TATGGTCAATGATGATGATATTGAAATGCATGAAGACACTTCA GAGCTCGGTCTTTCTATTCCTGGTGCTGCTACGGCTCGGAAAGG CAGGAAATGGAGTAAGGCAAGTCGCAAGGCTGCCAGACGCCA AGCAGCTAGAGATGCCGCTCCTGTTAAAGTGGAAATCTTAGAG GTTGAAGAAAAGGGCATGTCGACCGAAGAATTAGCATACAACT TGGCTATTAGCGAAGGTGAAATTCTTGGGTACCTGTATTCTAAG GGGATAAAACCAGATGGTGTGCAAACTCTTGACAAGGCAATGG TAAAGATGATATGTGAAAGATATGACGTGGAGGTTTTGGACGC ACTTTCTGAACAAATGGAAGAAATGGCTCGAAAGAAGGAAATT TTCGACGAAGATGACCTTGACAAGCTTGAAGATAGGCCTCCTG TGCTTACTATAATGGGTCATGTAGATCATGGCAAGACGACCCTT CTGGATTATATACGGAAGAGCAAGGTTGCTGCTTCTGAAGCTG GTGGGATTACACAAGGTATTGGTGCTTATAAAGTGGAAGTACC GGTTGATGGCAAGTTGCTGCCTTGTGTCTTTCTTGACACTCCCG GACACGAGGCGTTCGGGGCAATGAGGGCTCGTGGAGCAAGAGT GACAGATATTGCTATTATAGTTGTAGCTGCTGACGATGGGATCC GTCCTCAAACAAATGAAGCCATAGCACATGCAAAAGCAGCTGG TGTACCTATTGTGGTTGCAATTAATAAGATTGACAAGGATGGG GCTAATCCGGACCGTGTGATGCAAGAGCTTTCATCAATTGGTCT AATGCCAGAGGATTGGGGTGGTGATACCCCAATGGTCAAGATA AGTGCTCTAAAAGGTGAAAATGTGGACGAGTTACTCGAGACAG CCATGCTTGTCGCCGAGTTGCAAGAGTTAAAGGCTAATCCTCAG AGGAACGCTAAGGGCACTGTAATTGAGGCTGGTCTTCATAAAT CAAAAGGACCCATTGCCACTTTTATTGTGCAGAATGGTACCCTC AAACAAGGGGATACTGTAGTTTGTGGGGAAGCATTTGGGAAGG TTCGTGCCCTATTTGATCACGGAGGGAATCGCGTTGATGAAGCT GGTCCATCTATTCCCGTGCAGGTTATTGGATTGAATAATGTTCC TTTTGCCGGTGATGAGTTCGAGGTAGTGAGTTCCCTTGATATAG CTCGTGAAAAGGCAGAGGTCCGTGCAGAGTCTTTACGAAATGA GCGTATAGCTGCTAAGGCCGGAGACGGAAAGGTTACGCTGTCA TCCTTGGCATCGGCTGTTTCTTCAGGGAAGATGGCTGGTTTGGA TTTGCACCAGTTAAATATCATTTTGAAGGTTGATGTTCAGGGAT | 71 |

TABLE 10-continued

| Poly-nucleotide | Position in TIF sequence | Sequence | SEQ ID NO. |
|---|---|---|---|
| | | CAATCGAGGCATTGAGGCAAGCTCTAGAAGTTCTTCCTCAAGA<br>TAACGTCACTTTGAAGTTTCTCTTACAAGCGACCGGAGATGTTA<br>CTACAAGTGATGTTGATCTTGCAGTTGCTAGTAAAGCTATTATC<br>TTGGGGTTCAATGTGAAGGCACCAGGTTCTGTCGAAAAATTAG<br>CAGATAACAAAGGTGTTGAAATTCGGCTTTATAAAGTCATTTAT<br>GATCTAATTGACGACATGCGGAGTGCAATGGAAGGAATGCTAG<br>ATCCCGTTGAGGAACAAGTTGCAATTGGTTCAGCCGAAGTGCG<br>GGCTACATTCAGTAGTGGTAGTGGCCGTGTCGCTGGATGCATG<br>GTGACCGAGGGAAAGATTACCAAAGGCTGTGGGATTCGAGTGA<br>TACGGAAGGGAAAAACTGTCCACGTTGGAGTTCTTGATTCGTTG<br>CGTCGAGTAA | |
| 200 bp DNA | 341-541 | TTTCGAGTAATGGGAAATTGGATAATGTAGAGGAGAGGAAGAA<br>GGTTATTGATTCATTGGATGAGGTATTAGAAAAGGCCGAGAGA<br>TTAGAAACGGCGAACTTACAAGCAGATAATAGAAAGGATAGCA<br>CAAATGTAAATAAACCGTCTCCGAGTGTAAGTAGTTCAACCAA<br>TGGTAAACCTGTAAATAATTTGAACAAA | 72 |
| 160 bp dsRNA | 342-501 | Sense:<br>UUCGAGUAAUGGGAAAUUGGAUAAUGUAGAGGAGAGGAAGA<br>AGGUUAUUGAUUCAUUGGAUGAGGUAUUAGAAAAGGCCGAG<br>AGAUUAGAAACGGCGAACUUACAAGCAGAUAAUAGAAAGGA<br>UAGCACAAAUGUAAAUAAACCGUCUCCGAGUGUAAGU | 73 |
| | | Anti-sense:<br>ACUUACACUCGGAGACGGUUUAUUUACAUUUGUGCUAUCCUU<br>UCUAUUAUCUGCUUGUAAGUUCGCCGUUUCUAAUCUCUCGGC<br>CUUUUCUAAUACCUCAUCCAAUGAAUCAAUAACCUUCUUCCU<br>CUCCUCUACAUUAUCCAAUUUCCCAUUACUCGAA | 74 |
| anti-sense DNA TIF_AS1 | 555-576 | ATTTCTCCAAACGCTCTTCGCA | 75 |
| anti-sense DNA TIF_AS2 | 342-363 | ATCCAATTTCCCATTACTCGAA | 76 |
| anti-sense DNA TIF_AS3 | 412-433 | GTTTCTAATCTCTCGGCCTTTT | 77 |
| anti-sense DNA TIF_AS4 | 488-509 | TTGAACTACTTACACTCGGAG | 78 |
| anti-sense DNA TIF_AS5 | 368-389 | TAACCTTCTTCCTCTCCTCTA | 79 |
| anti-sense DNA TIF_AS6 | 790-811 | GTCCTTCCCATCAGCTCTGGA | 80 |
| anti-sense DNA TIF_AS7 | 1052-1073 | CGTAGCAGCACCAGGAATAG | 81 |
| anti-sense DNA TIF_AS8 | 1655-1676 | CAGCAGCTACAACTATAATAG | 82 |

In an embodiment, the herbicidal composition includes a mixture of at least two of the above EPSPS dsRNA polynucleotides having SEQ ID NOS: 63-70 and also at least one polynucleotide having sequence essentially identical or complementary to the sequence of the endogenous Palmer translation initiation factor (TIF) gene or to the sequence of RNA transcribed from the endogenous TIF gene, such as those provided in Table 10. In a specific embodiment, the herbicidal composition includes a mixture of the four EPSPS dsRNA polynucleotides having SEQ ID NOS: 63-70 and a 160 base-pair TIF double-stranded RNA polynucleotide having the sense sequence of (SEQ ID NO. 73)
UUCGAGUAAUGGGAAAUUGGAUAAUGUAGAGGAGAGGAAGAAGGUUAUUG

AUUCAUUGGAUGAGGUAUUAGAAAAGGCCGAGAGAUUAGAAACGGCGAAC

UUACAAGCAGAUAAUAGAAAGGAUAGCACAAAUGUAAAUAAACCGUCUCC

GAGUGUAAGU and the anti-sense sequence of (SEQ ID NO. 74)
ACUUACACUCGGAGACGGUUUAUUUACAUUUGUGCUAUCCUUUCUAUUAU

CUGCUUGUAAGUUCGCCGUUUCUAAUCUCUCGGCCUUUUCUAAUACCUCA

UCCAAUGAAUCAAUAACCUUCUUCCUCUCCUCUACAUUAUCCAAUUUCCC

AUUACUCGAA.

In some embodiments, the polynucleotides are designed to regulate multiple target genes, resulting in a synergistic effect on herbicide activity. For example, a synergistic effect on herbicide activity was obtained by treatment of a plant with polynucleotides designed to suppress a translation initiation factor (TIF) and 5-enolpyruvylshikimate-3-phosphate synthase (EPSPS) followed by treatment with the non-polynucleotide herbicide glyphosate.

The polynucleotides listed in Table 11 were produced by synthesis or by in vitro transcription.

TABLE 11

| Name | Comments | Nucleotide sequences |
|---|---|---|
| IDT [1] | Palmer/EPSPS dsRNA with two 2-deoxyribonucleotides (in bold underlined text) at 3' end of sense strand (25-mer) and a 2-nucleotide overhang at 3' end of anti-sense strand (27-mer); chemically synthesized by IDT | Sense: CUACCAUCAACAAUGGUGUCCAUAC (SEQ ID NO. 83)<br>Anti-sense: GUAUGGACACCAUUGUUGAUGGUAGUA (SEQ ID NO. 84) |
| IDT [2] | | Sense: AGUUGGUGGGCAAUCAUCAAUUGTT (SEQ ID NO. 85)<br>Anti-sense: AACAAUUGAUGAUUGCCCACCAACUCU (SEQ ID NO. 86) |
| IDT [3] | | Sense: GGUCGACAACUUGCUGUAUAGUGAT (SEQ ID NO. 87)<br>Anti-sense: AUCACUAUACAGCAAGUUGUCGACCUC (SEQ ID NO. 88) |
| IDT [4] | | Sense: UGCAAGGUCACCUGGACAGAGAATA (SEQ ID NO. 89)<br>Anti-sense: UAUUCUCUGUCCAGGUGACCUUGCAAC (SEQ ID NO. 90) |
| IDT [5] | Palmer/EPSPS dsRNA (21-mer) with blunt ends; chemically synthesized by IDT | Sense: AACAUGAACAAAAUGCCAGAU (SEQ ID NO. 91)<br>Anti-sense: AUCUGGCAUUUUGUUCAUGUU (SEQ ID NO. 92) |
| IDT blunt[1] | Palmer/EPSPS dsRNA (27-mer) with blunt ends; synthesized via in vitro T7 transcription | 1S-Anti-sense GUAUGGACACCAUUGUUGAUGGUAGUA (SEQ ID NO. 93)<br>1S-Sense UACUACCAUCAACAAUGGUGUCCAUAC (SEQ ID NO. 94) |
| IDT blunt [2] | | 2S-Anti-sense AAUAAUUGAUGAUUGCCCACCAACUCU (SEQ ID NO. 95)<br>2S-Sense AGAGUUGGUGGGCAAUCAUCAAUUAUU (SEQ ID NO. 96) |
| IDT blunt [3] | | 3S-Anti-sense AUCACUAUACAGCAAGUUGUCGACCAC (SEQ ID NO. 97)<br>3S-Sense GUGGUCGACAACUUGCUGUAUAGUGAU (SEQ ID NO. 98) |
| IDT blunt [4] | | 4S-Anti-sense UAUUCUCUGUCCAGGUGACCUUGCAAC (SEQ ID NO. 99)<br>4S-Sense GUUGCAAGGUCACCUGGACAGAGAAUA (SEQ ID NO. 100) |
| 3OH [1] | Palmer/EP SPS dsRNA (27-mer) with 3'-overhangs; synthesized via in vitro T7 transcription | 1S-Anti-sense gGUAUGGACACCAUUGUUGAUGGUAGUAC (SEQ ID NO. 101)<br>1S-Sense GCUACCAUCAACAAUGGUGUCCAUACCAC (SEQ ID NO. 102) |
| 3OH [2] | | 2S-Anti-sense gAAGAAUUGAUGAUUGCCCACCAACUCAC (SEQ ID NO. 03)<br>2S-Sense GAGUUGGUGGGCAAUCAUCAAUUAUUCAC (SEQ ID NO. 104) |
| 3OH [3] | | 3S-Anti-sense gAUCACUAUACAGCAAGUUGUCGACAC (SEQ ID NO. 105)<br>3S-Sense GUCGACAACUUGCUGUAUAGUAUCAC (SEQ ID NO. 106) |
| 3OH [4] | | 4S-Anti-sense gUAUUCUCUGUCCAGGUGACCUUGCACAC (SEQ ID NO. 107)<br>4S-Sense GUGCAAGGUCACCUGGACAGAGAAUACAC (SEQ ID NO. 108) |
| IDT HP [1] | Palmer/EPSPS single strand of RNA designed to self-hybridize into a hairpin, containing anti-sense sequence on the 5' arm and anti-sense sequence on the 3' arm, with an intermediate GAAA tetranucleotide loop; chemically synthesized by IDT | 1S-GUAUGGACACCAUUGUUGAUGGUAGUAGAAAUACUACCAUCAACAAUGGUGUCCAUAC (SEQ ID NO. 109) |
| IDT HP [2] | | 2S-AUAAUUGAUGAUUGCCCACCAACUCUGAAAAGAGUUGGUGGGCAAUCUCAAUUAUU (SEQ ID NO. 110) |
| IDT HP [3] | | 3S-AUCACUAUACAGCAAGUUGUCGACCACGAAAGUGGUCGACAACUUGCUGUAUAGUGAU (SEQ ID NO. 111) |
| IDT HP [4] | | 4S-UAUUCUCUGUCCAGGUGACCUUGCAACGAAAGUUGCAAGGUCACCUGGACAGAGAAUA (SEQ ID NO. 112) |

TABLE 11-continued

| Name | Comments | Nucleotide sequences |
|---|---|---|
| [TIF] | Palmer/translation initiation factor (TIF) dsRNA (160-mer) synthesized via in vitro T7 transcription | Sense:<br>UUCGAGUAAUGGGAAAUUGGAUAAUGUAGAGGAGAGGAAGAAGGUU<br>AUUGAUUCAUUGGAUGAGGUAUUAGAAAAGGCCGAGAGAUUAGAAA<br>CGGCGAACUUACAAGCAGAUAAUAGAAAGGAUAGCACAAAUGUAAAU<br>AAACCGUCUCCGAGUGUAAGU (SEQ ID NO. 73)<br>Anti-sense:<br>ACUUACACUCGGAGACGGUUUAUUUACAUUUGUGCUAUCCUUUCUAU<br>UAUCUGCUUGUAAGUUCGCCGUUUCUAAUCUCUCGGCCUUUUCUAAU<br>ACCUCAUCCAAUGAAUCAAUAACCUUCUUCCUCUCCUCUACAUUAUC<br>CAAUUUCCCAUUACUCGAA (SEQ ID NO. 74) |
| [ddATPase] | Palmer/DNA-dependent ATPase (ddATPase) dsRNA (168-mer) synthesized via in vitro T7 transcription | Sense:<br>GAUCACAAAUUUGCCGGUUUAUGAUCAAAUACGGAACAUAAGACAGA<br>UACACUUGAACACCAUGAUUCGCAUUGGGGGUGUGGUUACUCGUCGU<br>UCUGGAGUAUUCCUCAGUUGAUGCAGGUGAAGUAUGACUGCAAUAA<br>AUGUGGGGCUAUCCUGGGUCCCUUUUU (SEQ ID NO. 113)<br>Anti-sense:<br>AAAAAGGGACCCAGGAUAGCCCCACAUUUAUUGCAGUCAUACUUCAC<br>CUGCAUCAACUGAGGGAAUACUCCAGAACGACGAGUAACCACACCCC<br>CAAUGCGAAUCAUGGUGUUCAAGUGUAUCUGUCUUAUGUUCCGUAUU<br>UGAUCAUAAACCGGCAAAUUUGUGAUC (SEQ ID NO. 114) |

Solutions of the polynucleotides were prepared and applied to the leaves of Palmer amaranth using the protocols described in Table 12.

TABLE 12

| Protocol number (description) | Protocol |
|---|---|
| 1 (1-step hand) | 1. Apply mixture of polynucleotides in 1% Silwet L-77, 2% ammonium sulfate in 10 millimolar sodium phosphate buffer, pH 6.8 (or control buffer solution of 1% Silwet L-77, 2% ammonium sulfate in 10 millimolar sodium phosphate buffer, pH 6.8) by hand pipetting<br>2. 48 or 72 hours later, spray glyphosate ("2X Wmax" or 1682 g acid equivalent per hectare of Roundup ® WeatherMAX ® brand herbicide) by regular sprayer (10 gallons/acre) |
| 2 (1-step sprayer) | 1. Spray mixture of polynucleotides in 1% Silwet L-77, 2% ammonium sulfate in 10 millimolar sodium phosphate buffer, pH 6.8 (or control buffer solution of 1% Silwet L-77, 2% ammonium sulfate in 10 millimolar sodium phosphate buffer, pH 6.8) by Milli sprayer<br>2. 48 or 72 hours later, spray glyphosate ("2X Wmax" or 1682 g acid equivalent per hectare of Roundup ® WeatherMAX ® brand herbicide) by regular sprayer (10 gallons/acre) |
| 3 (2-step hand) | 1. Spray 1% Silwet as $1^{st}$ step by regular sprayer or Milli sprayer;<br>2. Apply mixture of polynucleotides in 1% Silwet L-77, 2% ammonium sulfate in 10 millimolar sodium phosphate buffer, pH 6.8 (or control buffer solution of 1% Silwet L-77, 2% ammonium sulfate in 10 millimolar sodium phosphate buffer, pH 6.8) by hand pipetting<br>3. 48 or 72 hours later, spray glyphosate ("2X Wmax" or 1682 g acid equivalent per hectare of Roundup ® WeatherMAX ® brand herbicide) by regular sprayer (10 gallons/acre) |
| 4 (2-step sprayer) | 1. Spray 1% Silwet as $1^{st}$ step by regular sprayer or Milli sprayer;<br>2. Spray mixture of polynucleotides in 1% Silwet L-77, 2% ammonium sulfate in 10 millimolar sodium phosphate buffer, pH 6.8 (or control buffer solution of 1% Silwet L-77, 2% ammonium sulfate in 10 millimolar sodium phosphate buffer, pH 6.8) by Milli sprayer<br>3. 48 or 72 hours later, spray glyphosate ("2X Wmax" or 1682 g acid equivalent per hectare of Roundup ® WeatherMAX ® brand herbicide) by regular sprayer (10 gallons/acre) |
| 5 (tank mix) | Spray mixture of polynucleotides in 1% Silwet L-77, 2% ammonium sulfate in 10 millimolar sodium phosphate buffer, pH 6.8 containing glyphosate at 1682 g acid equivalent per hectare of Roundup ® WeatherMAX ® brand herbicide (or control buffer solution of 1% Silwet L-77, 2% ammonium sulfate in 10 millimolar sodium phosphate buffer, pH 6.8 containing glyphosate at 1682 g acid equivalent per hectare of Roundup ® WeatherMAX ® brand herbicide) by Milli sprayer. |

Combinations of polynucleotides were tested as indicated in Table 13.

TABLE 13

| Polynucleotides applied in combination | SEQ ID NO. | Protocol | Amount applied of each polynucleotide (g/acre) | Total polynucleotide applied (g/acre) | EPSPS copy number* | Results** |
|---|---|---|---|---|---|---|
| IDT [1] | 83, 84, | 1 | 0.29 | 0.87 | 112 | 75% killed |
| IDT [3] | 87, 88 | | 0.29 | | | (27 DAT) |
| IDT [4] | 89, 90 | | 0.29 | | | |
| IDT [1] | 83, 84, | 1 | 0.29 | 1.4 | 112 | 100% killed |
| IDT [3] | 87, 88 | | 0.29 | | | (27 DAT) |
| IDT [4] | 89, 90 | | 0.29 | | | |
| [TIF] | 73, 74 | | 0.50 | | | |
| IDT [1] | 83, 84, | 1 | 0.29 | 1.37 | 112 | 11.2% |
| IDT [3] | 87, 88 | | 0.29 | | | stunted |
| IDT [4] | 89,90 | | 0.29 | | | (27 DAT) |
| [ddATPase] | 113, 114 | | 0.50 | | | |
| IDT [1] | 83, 84, | 1 | 0.29 | 1.87 | 112 | 100% killed |
| IDT [3] | 87, 88 | | 0.29 | | | (27 DAT) |
| IDT [4] | 89, 90 | | 0.29 | | | |
| [TIF] | 73, 74 | | 0.50 | | | |
| [ddATPase] | 114, 114 | | 0.50 | | | |
| IDT [1] | 83, 84, | 1 | 0.29 | 1.2 | 112, 36 | 0% control |
| IDT [2] | 85, 86 | | 0.29 | | | (11 DAT); |
| IDT [3] | 87, 88 | | 0.29 | | | 0% control |
| IDT [4] | 89, 90 | | 0.29 | | | (31 DAT) |
| IDT [1] | 83, 84, | 1 | 1.4 | 5.8 | 112, 36 | 0% control |
| IDT [2] | 85, 86 | | 1.4 | | | (11 DAT); |
| IDT [3] | 87, 88 | | 1.4 | | | 15% stunted |
| IDT [4] | 89, 90 | | 1.4 | | | (31 DAT) |
| IDT [1] | 83, 84, | 1 | 2.9 | 12 | 112, 36 | 0% control |
| IDT [2] | 85, 86 | | 2.9 | | | (11 DAT); |
| IDT [3] | 87, 88 | | 2.9 | | | 35% stunted |
| IDT [4] | 89, 90 | | 2.9 | | | (31 DAT) |
| IDT [1] | 83, 84, | 1 | 5.8 | 23 | 112, 36 | 51% stunted |
| IDT [2] | 85, 86 | | 5.8 | | | (11 DAT); |
| IDT [3] | 87, 88 | | 5.8 | | | 100% |
| IDT [4] | 89, 90 | | 5.8 | | | stunted (31 DAT) |
| IDT [1] | 83, 84, | 2 | 0.29 | 1.2 | 33, 54 | 9% stunted |
| IDT [2] | 85, 86 | | 0.29 | | | (6 DAT) |
| IDT [3] | 87, 88 | | 0.29 | | | |
| IDT [4] | 89, 90 | | 0.29 | | | |
| IDT [1] | 83, 84, | 2 | 5.8 | 23 | 33, 54 | 100% killed |
| IDT [2] | 85, 86 | | 5.8 | | | (6 DAT) |
| IDT [3] | 87, 88 | | 5.8 | | | |
| IDT [4] | 89, 90 | | 5.8 | | | |
| IDT [1] | 83, 84, | 2 | 0.29 | 0.87 | 33, 54 | 20% stunted |
| IDT [3] | 87, 88 | | 0.29 | | | (6 DAT) |
| IDT [4] | 89, 90 | | 0.29 | | | |
| IDT [1] | 83, 84, | 2 | 5.8 | 17 | 33, 54 | 100% killed |
| IDT [3] | 87, 88 | | 5.8 | | | (6 DAT) |
| IDT [4] | 89, 90 | | 5.8 | | | |
| IDT [5] | 91, 92 | 1 | 0.29 | 0.29 | 34, 36, 54 | 14.1% stunted (22 DAT) |
| IDT [5] | 91, 92 | 1 | 2.9 | 2.9 | 34, 36, 54 | 100% kill (22 DAT) |
| IDT [1] | 83, 84, | 1 | 2.9 | 12 | 34, 36, 54 | 100% killed |
| IDT [2] | 85, 86 | | 2.9 | | | (22 DAT) |
| IDT [3] | 87, 88 | | 2.9 | | | |
| IDT [4] | 89, 90 | | 2.9 | | | |
| IDT [1] | 83, 84, | 1 | 2.9 | 14 | 34, 36, 54 | 100% killed |
| IDT [2] | 85, 86 | | 2.9 | | | (22 DAT) |
| IDT [3] | 87, 88 | | 2.9 | | | |
| IDT [4] | 89, 90 | | 2.9 | | | |
| IDT [5] | 91, 92 | | 2.9 | | | |
| IDT [1] | 83, 84, | 1 | 2.9 | 8.7 | 34, 36, 54 | 100% killed |
| IDT [3] | 87, 88 | | 2.9 | | | (22 DAT) |
| IDT [4] | 89, 90 | | 2.9 | | | |
| IDT [1] | 83, 84, | 1 | 2.9 | 12 | 34, 36, 54 | 100% killed |
| IDT [3] | 87, 88 | | 2.9 | | | (22 DAT) |
| IDT [4] | 89, 90 | | 2.9 | | | |
| IDT [5] | 91, 92 | | 2.9 | | | |

TABLE 13-continued

| Polynucleotides applied in combination | SEQ ID NO. | Protocol | Amount applied of each polynucleotide (g/acre) | Total polynucleotide applied (g/acre) | EPSPS copy number* | Results** |
|---|---|---|---|---|---|---|
| IDT [5] | 91, 92 | 1 | 0.29 | 0.29 | 33, 54, 55 | 71% stunted (18 DAT) |
| IDT [5] | 91, 92 | 1 | 2.9 | 2.9 | 33, 54, 55 | 100% killed (18 DAT) |
| IDT [1] | 83, 84, | 1 | 0.29 | 1.4 | 33, 54, 55 | 100% killed (18 DAT) |
| IDT [2] | 85, 86 | | 0.29 | | | |
| IDT [3] | 87, 88 | | 0.29 | | | |
| IDT [4] | 89, 90 | | 0.29 | | | |
| IDT [5] | 91, 92 | | 0.29 | | | |
| IDT [1] | 83, 84, | 1 | 0.29 | 1.2 | 33, 54, 55 | 100% killed (18 DAT) |
| IDT [2] | 85, 86 | | 0.29 | | | |
| IDT [3] | 87, 88 | | 0.29 | | | |
| IDT [4] | 89, 90 | | 0.29 | | | |
| IDT HP [1] | 109 | 3 | 0.29 | 1.2 | 16, 33 | 100% killed (18 DAT) |
| IDT HP [2] | 110 | | 0.29 | | | |
| IDT HP [3] | 111 | | 0.29 | | | |
| IDT HP [4] | 112 | | 0.29 | | | |
| IDT [1] | 83, 84, | 3 | 0.29 | 1.2 | 16, 33 | 100% killed (18 DAT) |
| IDT [2] | 85, 86 | | 0.29 | | | |
| IDT [3] | 87, 88 | | 0.29 | | | |
| IDT [4] | 89, 90 | | 0.29 | | | |
| IDT [1] | 83, 84, | 3 | 0.29 | 0.87 | 16, 36 | 100% killed (18 DAT) |
| IDT [3] | 87, 88 | | 0.29 | | | |
| IDT [4] | 89, 90 | | 0.29 | | | |
| IDT [1] | 83, 84, | 3 | 5.8 | 17 | 16, 36 | 100% killed (18 DAT) |
| IDT [3] | 87, 88 | | 5.8 | | | |
| IDT [4] | 89, 90 | | 5.8 | | | |
| IDT [1] | 83, 84, | 3 | 29 | 87 | 16, 36 | 100% killed (18 DAT) |
| IDT [3] | 87, 88 | | 29 | | | |
| IDT [4] | 89, 90 | | 29 | | | |
| IDT [1] | 83, 84, | 3 | 0.29 | 1.1 | 16, 36 | 100% killed (18 DAT) |
| IDT [2] | 85, 86 | | 0.29 | | | |
| IDT [3] | 87, 88 | | 0.29 | | | |
| IDT [4] | 89, 90 | | 0.29 | | | |
| 3'-OH [1] | 101, 102 | 3 | Not applicable | 22-26 microliters (by volume) | 16 | 100% killed (10 DAT) |
| 3'-OH [2] | 103, 104 | | | | | |
| 3'-OH [3] | 105, 106 | | | | | |
| 3'-OH [4] | 107, 108 | | | | | |
| IDT Blunt [1] | 93, 94 | 3 | 0.29 | 1.1 | 16 | 75% killed (10 DAT) |
| IDT Blunt [2] | 95, 96 | | 0.29 | | | |
| IDT Blunt [3] | 97, 98 | | 0.29 | | | |
| IDT Blunt [4] | 99, 100 | | 0.29 | | | |
| IDT Blunt [1] | 93, 94 | 3 | 5.8 | 23 | 16 | 100% killed (10 DAT) |
| IDT Blunt [2] | 95, 96 | | 5.8 | | | |
| IDT Blunt [3] | 97, 98 | | 5.8 | | | |
| IDT Blunt [4] | 99, 100 | | 5.8 | | | |
| IDT [1] | 83, 84, | 3 | 29 | 87 | 16 | 34% stunted (14 DAT) |
| IDT [2] | 85, 86 | | 29 | | | |
| IDT [3] | 87, 88 | | 29 | | | |
| IDT [2] | 85, 86 | 3 | 29 | 87 | 16 | 48% stunted (14 DAT) |
| IDT [3] | 87, 88 | | 29 | | | |
| IDT [4] | 89, 90 | | 29 | | | |
| IDT [1] | 83, 84, | 3 | 29 | 87 | 16 | 25% stunted (14 DAT) |
| IDT [2] | 85, 86 | | 29 | | | |
| IDT [4] | 89, 90 | | 29 | | | |
| IDT [1] | 83, 84, | 3 | 29 | 58 | 16 | 44% stunted (14 DAT) |
| IDT [4] | 89, 90 | | 29 | | | |
| IDT [3] | 87, 88 | 3 | 29 | 58 | 16 | 41% stunted (14 DAT) |
| IDT [4] | 89, 90 | | 29 | | | |
| IDT [2] | 85, 86 | 3 | 29 | 58 | 16 | 40% stunted (14 DAT) |
| IDT [4] | 89, 90 | | 29 | | | |
| IDT [1] | 83, 84 | 3 | 29 | 29 | 16 | 51% stunted (13 DAT) |
| IDT [2] | 85, 86 | 3 | 29 | 29 | 16 | 0% control (13 DAT) |
| IDT [3] | 87, 88 | 3 | 29 | 29 | 16 | 51% stunted (13 DAT) |
| IDT [4] | 89, 90 | 3 | 29 | 29 | 16 | 51% stunted (13 DAT) |

TABLE 13-continued

| Polynucleotides applied in combination | SEQ ID NO. | Protocol | Amount applied of each polynucleotide (g/acre) | Total polynucleotide applied (g/acre) | EPSPS copy number* | Results** |
|---|---|---|---|---|---|---|
| IDT [1] | 83, 84, | 3 | 29 | 116 | 16 | 75% killed (13 DAT) |
| IDT [2] | 85, 86 | | 29 | | | |
| IDT [3] | 87, 88 | | 29 | | | |
| IDT [4] | 89, 90 | | 29 | | | |

*where more than one copy number is listed, the treated plants were a mixture of copy numbers
**DAT = days after treatment; "0% control" means no difference between treated and control plants was observed; stunting % is calculated as [100 - (average height of the test plants/average height of control plants) * 100]

Double-stranded 25-mer RNA polynucleotide sequences for suppression of the TIF gene in *Amaranthus palmeri* were designed as listed in Table 14.

TABLE 14

| Name | Sequence | SEQ ID NO: |
|---|---|---|
| TIF_dsRNA1 | antisense:<br>5'-UUUUCUAAUACCUCAUCCAAUGAAU-3'| 115 |
| | sense:<br>5'-AUUCAUUGGAUGAGGUAUUAGAAAA-3' | 116 |
| TIF_dsRNA2 | antisense:<br>5'-UAUCUGCUUGUAAGUUCGCCGUUUC-3' | 117 |
| | sense:<br>5'-GAAACGGCGAACUUACAAGCAGAUA-3' | 118 |
| TIF_dsRNA3 | antisense:<br>5'-GGAGACGGUUUAUUUACAUUUGUGC-3' | 119 |
| | sense:<br>5'-GCACAAAUGUAAAUAAACCGUCUCC-3' | 120 |
| TIF_dsRNA4 | antisense:<br>5'-UAUUUACAGGUUUACCAUUGGUUGA-3' | 121 |
| | sense:<br>5'-UCAACCAAUGGUAAACCUGUAAAUA-3' | 122 |

The TIF 25-mer dsRNA polynucleotides were tested on both high (112) copy and low (16) copy EPSPS glyphosate-resistant Palmer amaranth.

High-copy plants were treated with a mixture of 4 short EPSPS dsRNAs (short dsRNA-1, short dsRNA-3, short dsRNA-4, as described in Example 1 and IDT [5] (SEQ ID NOS:91-92 as described in Table 11) at 11.5 grams/acre and one individual TIF dsRNA at 5.8 grams/acre, or with each individual TIF 25-mer dsRNA at 5.8 grams/acre; polynucleotide solutions were formulated in 10 millimolar sodium phosphate buffer (pH 6.8) containing 2% ammonium sulfate and 1% SILWET L-77. Thirty minutes after polynucleotide treatment, plants were either sprayed with glyphosate (1682 g acid equivalent per hectare of Roundup® WeatherMAX® brand herbicide) or not.

Low-copy plants were treated with a mixture of 4 short EPSPS dsRNAs (short dsRNA-1, short dsRNA-3, short dsRNA-4, as described in Example 1, and IDT [5] (SEQ ID NOS:91-92 as described in Table 11)) at 0.23 grams/acre and one individual TIF dsRNA at 5.8 grams/acre, or with each individual TIF 25-mer dsRNA at 5.8 grams/acre; polynucleotide solutions were formulated in 10 millimolar sodium phosphate buffer (pH 6.8) containing 2% ammonium sulfate and 1% SILWET L-77. Thirty minutes after polynucleotide treatment, plants were either sprayed with glyphosate (1682 g acid equivalent per hectare of Roundup® WeatherMAX® brand herbicide) or not.

Figure 31:
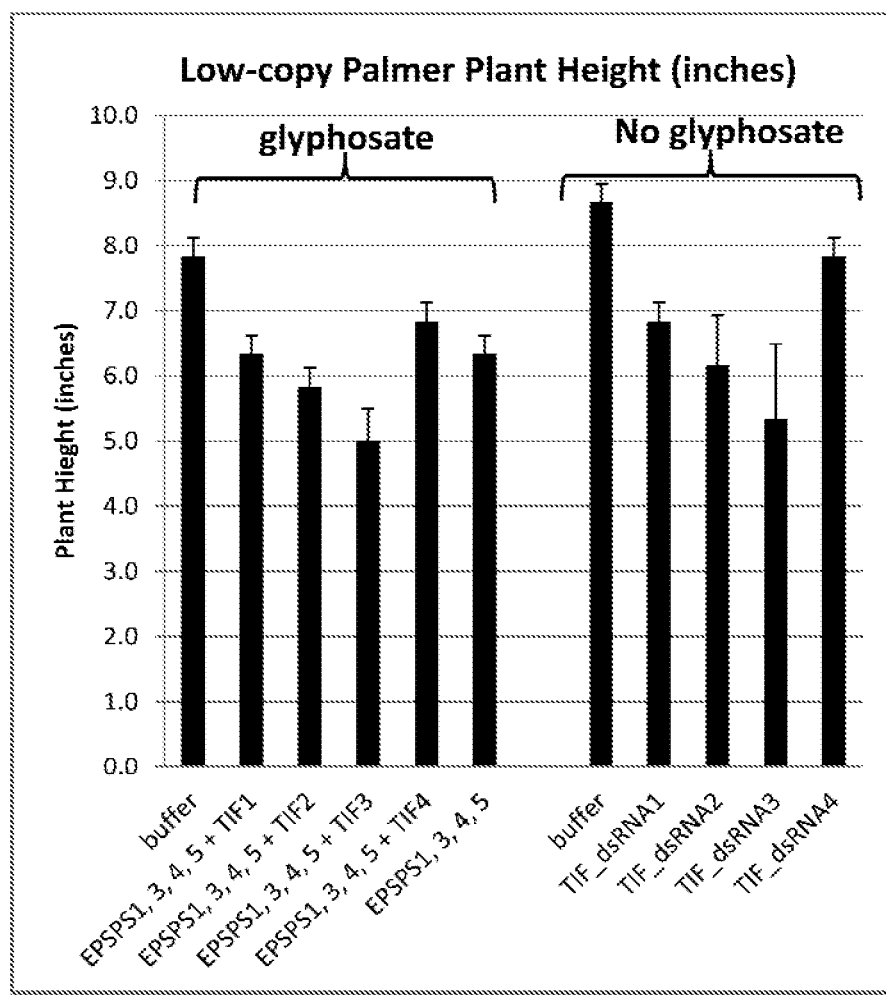
FIG. 31 illustrates enhancement of glyphosate herbicidal activity in low-copy number Palmer amaranth of the EPSPS polynucleotides by TIF polynucleotides and that the TIF polynucleotides have herbicidal activity on their own, as described in Example 26. EPSPS polynucleotides "1, 3, 4" refer to "short" dsRNAs having an anti-sense strand that is capable of hybridizing to the mRNA transcribed from the Palmer amaranth EPSPS gene (SEQ ID NO:1) at positions 14-38 (short dsRNA-1), 345-369 (short dsRNA-3), and 1105-1129 (short dsRNA-4), respectively as indicated by underlined nucleotides in FIG. 1 (see Example 1). EPSPS "5" refers to IDT [5] (SEQ ID NOS:91-92 as described in Table 11).
Figure 32:
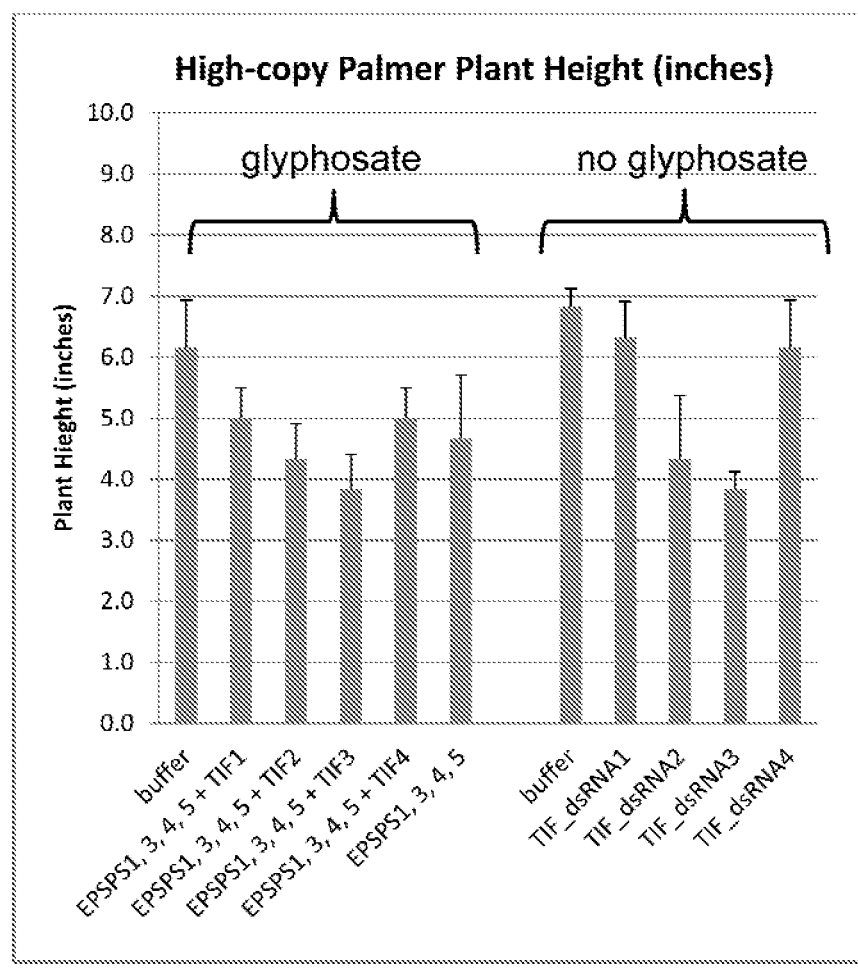
FIG. 32 illustrates enhancement of glyphosate herbicidal activity in high-copy number Palmer amaranth of the EPSPS polynucleotides by TIF polynucleotides and that the TIF polynucleotides have herbicidal activity on their own, as described in Example 26. EPSPS polynucleotides "1, 3, 4" refer to "short" dsRNAs having an anti-sense strand that is capable of hybridizing to the mRNA transcribed from the Palmer amaranth EPSPS gene (SEQ ID NO:1) at positions 14-38 (short dsRNA-1), 345-369 (short dsRNA-3), and 1105-1129 (short dsRNA-4), respectively as indicated by underlined nucleotides in FIG. 1 (see Example 1). EPSPS "5" refers to IDT [5] (SEQ ID NOS:91-92 as described in Table 11).

Results are depicted in FIGS. 31 and 32 and show that the TIF polynucleotides enhance the activity of the EPSPS polynucleotides and that the TIF polynucleotides have herbicidal activity on their own.

Example 27

Aspects of the invention include polynucleotide compositions and methods of use for potentiating the activity of a non-polynucleotide herbicide in a plant. For example, a polynucleotide composition designed to regulate an herbicide target gene, or an herbicide deactivation gene, or a stress response gene, or a combination of such target genes, is applied to a weed or to a volunteer plant, concurrently or followed or preceded by application of a non-polynucleotide herbicide (typically a conventional chemical herbicide), resulting in potentiation of the activity of the non-polynucleotide herbicide. The combination of a polynucleotide composition with a non-polynucleotide herbicide (e. g., a conventional chemical herbicide) provides a synergistic effect, i. e., the herbicidal effect of the combination is greater than the sum of the herbicidal effect of the polynucleotide composition and the herbicidal effect of the non-polynucleotide herbicide.

Examples of conventional chemical herbicides and their corresponding herbicide target genes are provided in Table 15.

TABLE 15

| Herbicide examples | Target gene (herbicide target gene) |
|---|---|
| glyphosate | 5-enolpyruvylshikimate-3-phosphate synthase (EPSPS) |
| Lactofen, flumioxazin, etc | protoporphyrinogen oxidase (PPO) |
| Mesotrione, isoxaflutole | 4-hydroxyphenyl-pyruvate-dioxygenase (HPPD) |
| Quizalofop, clethodim | acetyl coenzyme A carboxylase (ACCase) |
| Norflurazone, clomazone | phytoene desaturase (PDS) |
| glufosinate | glutamine synthase (GS) |
| Rimsulfuron, chlorsulfuron | acetolactate synthase (ALS) |
| Atrazine, diuron, bromoxynil, metribuzin | D1 protein of photosystem II (PSII) |
| Dinitroaniline, pendimethalin | tubulin |
| Dichlobenil, isoxaben | Cellulose synthase |

Examples of conventional chemical herbicides and their corresponding herbicide deactivation genes are provided in Table 16.

TABLE 16

| Herbicide examples | Target gene (herbicide deactivation gene) |
|---|---|
| Acetochlor, metolachlor | glutathione S-transferase (GST) |
| Many including SU herbicides | Mono-oxygenases including cytochromes P450 (see, e.g., a cytochrome P450 for conferring resistance to HPPD inhibitors, benzothiadiazinones, sulfonylureas, and other classes of herbicides, described in U.S. Patent Application Publication 2009/0011936) |
| Thiazopyr | esterases (e.g., esterases involved in apoptosis or senescence) |
| 2,4-D, metribuzin, | glucosyl transferases; malonyl transferases |
| Glyphosate, paraquat | Cellular compartmentation and sequestration genes (e.g., ABC transporters) |

Example 28

This example illustrates a method for inducing systemic regulation of a target endogenous gene in a growing plant including topically coating onto leaves of the growing plant polynucleotides having sequence essentially identical to, or essentially complementary to, a sequence of 18 or more contiguous nucleotides in either the target endogenous gene or messenger RNA transcribed from the target endogenous gene, whereby the polynucleotides permeate the interior of the growing plant and induce systemic regulation of the target endogenous gene.

Double-stranded RNA or anti-sense ssDNA polynucleotides were designed for the herbicide targetted genes 5-enolpyruvylshikimate-3-phosphate synthase (EPSPS), phytoene desaturase (PDS), protoporphyrin IX oxygenase (PPO), phenylalanine ammonia lyase (PAL), hydroxyphenylpyruvate dioxygenase (HPPD), acetyl-coenzyme A carboxylase (ACCase), acetolactate synthase (ALS), and glutamine synthase (GS). For each herbicide targetted gene, a solution containing a mixture of 8 anti-sense ssDNA polynucleotides in 2% ammonium sulfate in 10 millimolar sodium phosphate buffer, pH 6.8, was applied at a rate of 2.32 g/acre following application of 0.5% SILWET L-77 spray (10 gallons/acre). The tested polynucleotides and resulting phenotype observations are listed in Table 17.

TABLE 17

| Gene | Name | Size (nt) | Sequence | SEQ ID NO: | Phenotype |
|---|---|---|---|---|---|
| EPSPS | | | (See sequences provided in working Examples 1, 9, 13, 14, 21, 26) | — | Topical dsRNA followed by glyphosate killed glyphosate-resistant Palmer (up to 60 copies of EPSPS) within 7-10 days |
| PDS | PDS sense | 185 | GACGGAAACCCUCCAGAGAGGCUGU GCAUGCCUAUUGUUAAACACAUCGA GUCACUAGGUGGUGAAGUUAAACUU AACUCUCGUAUACAAAAGAUUCAGU UGGACCAGAGUGGAAGCGUGAAGAG UUUUUUGCUAAAUAACGGGAGGGAA AUACGAGGAGAUGCCUAUGUUUUUG CCACCCCAGU | 123 | Topical dsRNA caused bleaching and stunting phenotype, and is systemic. |
| | PDS anti-sense | 185 | ACUGGGGUGGCAAAAACAUAGGCAU CUCCUCGUAUUUCCCUCCCGUUAUUU AGCAAAAAACUCUUCACGCUUCCAC UCUGGUCCAACUGAAUCUUUUGUAU ACGAGAGUUAAGUUUAACUUCACCA CCUAGUGACUCGAUGUGUUUAACAA UAGGCAUGCACAGCCUCUCUGGAGG GUUUCCGUC | 124 | |
| PPO | PPO_OLIG01 | 21 | GTGATATTACCTCCAACACGAT | 125 | Topical anti-sense |
| | PPO_OLIG02 | 21 | ATAGTAAGCACAGGATCGGAG | 126 | DNAs caused |
| | PPO_OLIG03 | 21 | CTTTCAATCCACTGTCAACCG | 127 | stunting of plant |
| | PPO_OLIG04 | 21 | ATCAAGCGTTCGAAGACCTCAT | 128 | growth. |
| | PPO_OLIG05 | 21 | CAGCAATGGCGGTAGGTAACA | 129 | |
| | PPO_OLIG06 | 21 | GCAATTGCCCGAATCCTTTTA | 130 | |
| | PPO_OLIG07 | 21 | TAGCTCAATATCAAGGTCCTA | 131 | |
| | PPO_OLIG08 | 21 | TCATAAGCACCCTCTATACAC | 132 | |
| PAL | PAL_OLIG01 | 21 | TTCTTAACCTCGTCGAGATG | 133 | Topical anti-sense |
| | PAL_OLIG02 | 21 | ATACCCGAGTATCCTTGCAAA | 134 | DNAs caused |
| | PAL_OLIG03 | 21 | TAGGGCCCACGGCCTTGGAGT | 135 | stunting of plant |
| | PAL_OLIG04 | 21 | AGCGGATATAACCTCAGCTAG | 136 | growth. |
| | PAL_OLIG05 | 21 | CTTCGTGGCCCAACGAATGAC | 137 | |
| | PAL_OLIG06 | 21 | CAAGCTCGGGTCCCTGCTTGC | 138 | |
| | PAL_OLIG07 | 21 | GGAAGGTAGATGACATGAGTT | 139 | |
| | PAL_OLIG08 | 21 | GATGGCATAGTTACCACTGTC | 140 | |
| HPPD | HPPD_OLIG01 | 21 | TCCGTAGCTTACATACCGAAG | 141 | Topical anti-sense |
| | HPPD_OLIG02 | 21 | TCCAAGTGAATAGGAGAAACA | 142 | DNAs caused |
| | HPPD_OLIG03 | 21 | AGCAGCTTCTGCGTCTTCTAC | 143 | stunting of plant |
| | HPPD_OLIG04 | 21 | ACAGCACGCACGCCAAGACCG | 144 | growth. |
| | HPPD_OLIG05 | 21 | CGATGTAAGGAATTTGGTAAA | 145 | |

TABLE 17-continued

| Gene | Name | Size (nt) | Sequence | SEQ ID NO: | Phenotype |
|---|---|---|---|---|---|
| | HPPD_OLIG06 | 21 | CGAGGGGATTGCAGCAGAAGA | 146 | |
| | HPPD_OLIG07 | 21 | GTAGGAGAATACGGTGAAGTA | 147 | |
| | HPPD_OLIG08 | 21 | GACCCCAAGAAAATCGTCTGC | 148 | |
| ACCase | ACCA_OLIG01 | 20 | GTCTTACAAGGGTTCTCAA | 149 | Topical anti-sense |
| | ACCA_OLIG02 | 21 | ATCTATGTTCACCTCCCTGTG | 150 | DNA caused |
| | ACCA_OLIG03 | 21 | ATAAACCATTAGCTTTCCCGG | 151 | stunting of plant |
| | ACCA_OLIG04 | 21 | TTTATTGGAACAAGCGGAGTT | 152 | growth. |
| | ACCA_OLIG05 | 21 | TATAGCACCACTTCCCGATAG | 153 | |
| | ACCA_OLIG06 | 21 | GCACCACGAGGATCACAAGAA | 154 | |
| | ACCA_OLIG07 | 21 | CCACCCGAGAAACCTCTCCAA | 155 | |
| | ACCA_OLIG08 | 21 | CAGTCTTGACGAGTGATTCCT | 156 | |
| ALS | ALS-OLIGO1 | 22 | GTTCTTCAGGGCTAAATCGGGA | 157 | No significant |
| | ALS-OLIGO2 | 22 | GTTCAAGAGCTTCAACGAGAAC | 158 | phenotype |
| | ALS-OLIGO3 | 22 | ATACAAACTCCAACGCGTCCAG | 159 | |
| | ALS-OLIGO4 | 22 | CTCTTGGAAAGCATCAGTACCA | 160 | |
| | ALS-OLIGO5 | 22 | CTAGAAAGATACCCACCCAATT | 161 | |
| | ALS-OLIGO6 | 22 | ACTAGAATTCAAACACCCACCC | 162 | |
| | ALS-OLIGO7 | 22 | TTTCTGCTCATTCAACTCCTCC | 163 | |
| | ALS-OLIGO8 | 22 | TATGTATGTGCCCGGTTAGCTT | 164 | |
| GS (glutamine synthase) | GS_OLIG01 | 21 | TCATATCCAAGCCAGATCCTC | 165 | No significant |
| | GS_OLIG02 | 21 | TGCATCACACATCACCAAGAT | 166 | phenotype |
| | GS_OLIG03 | 21 | GTACTCCTGTTCAATGCCATA | 167 | |
| | GS_OLIG04 | 21 | ATTGATACCAGCATAGAGACA | 168 | |
| | GS_OLIG05 | 21 | AGCAATTCTCTCTAGAATGTA | 169 | |
| | GS_OLIG06 | 21 | CATCATTCCTCATCGACTTAG | 170 | |
| | GS_OLIG07 | 21 | CTCTCGTTGCCCTCTCCATAA | 171 | |
| | GS_OLIG08 | 21 | CAACGCCCCAGGAGAAAGTTC | 172 | |

The herbicidal activity of ssDNA polynucleotides that target the enzymes 4-hydroxyphenylpyruvate (HPPD) and protoporphyrinogen oxidase (PPO), and a transcription initiation factor (TIF), and their effect on the herbicide activity when used in combination with the herbicides mesotrione, fomesafen, and atrazine in Palmer amaranth was investigated. The polynucleotides used in this experiment were 8 HPPD anti-sense ssDNA oligonucleotides (SEQ ID NOS: 141-148), 8 PPO anti-sense oligonucleotides (SEQ ID NOS: 125-132), and 8 TIF anti-sense ssDNA oligonucleotides (SEQ ID NOS:75-82, see Example 26).

Glyphosate-sensitive Palmer amaranth (*Amaranthus palmeri*) plants were grown in 4-inch square pots with Sun Gro® Redi-Earth seedling mix containing 3.5 kg/cubic meter Osmocote® 14-14-14 fertilizer in a greenhouse with 14 h photoperiod and a daytime temperature of 30 degrees Celsius and night temperature of 20 degrees Celsius. The plants were sub-irrigated as necessary.

Plants at 10 to 15 cm height were pre-treated manually with 40 microliters (4 fully expanded mature leaves were treated with 10 microliters of solution per leaf on each plant) of a buffer-surfactant solution (as a control; 0.5% SILWET L-77 and 2% ammonium sulfate), or a buffer-surfactant-ssDNA polynucleotide mixture of the anti-sense oligonucleotides targeting HPPD PPO, or TIF. Some plants were left untreated and were used as controls. Twenty-four hours later, untreated plants, buffer-surfactant treated plants, and buffer-surfactant-ssDNA treated plants were treated using a track-sprayer equipped with a 9501E nozzle and calibrated to deliver 93 liters of solution per hectare with a HPPD inhibitor, mesotrione (4 pounds active ingredient per gallon), or with a PPO inhibitor, fomesafen (2 pounds active ingredient per gallon), or with a Photosystem II inhibitor, atrazine (90% active ingredient) as indicated in Table 18. Crop oil concentrate (COC) at 1% was added to all herbicide treatments. A low rate of each herbicide (mesotrione: 13 g per acre, equivalent to 1/8× of the recommended field rate; fomesafen: 16 g per acre, equivalent to 1/22× of the recommended field rate; and atrazine: 170 g per acre, equivalent to 1/8× of the recommended field rate) was used to be able to detect any improvement of herbicide activity by the oligonucleotide mixture.

TABLE 18

| Treatment number | Pre-treatment | Active Ingredient | Rate (grams per hectare of active ingredient) |
|---|---|---|---|
| 0 | Buffer-surfactant | — | |
| 1 | Untreated | Mesotrione | 13 |
| 2 | Buffer-surfactant | Mesotrione | 13 |
| 3 | Buffer-surfactant-ssDNA-HPPD | | |
| 4 | Buffer-surfactant-ssDNA-HPPD | Mesotrione | 13 |
| 5 | Untreated | Fomesafen | 16 |
| 6 | Buffer-surfactant | Fomesafen | 16 |
| 7 | Buffer-surfactant-ssDNA-PPO | | |
| 8 | Buffer-surfactant-ssDNA-PPO | Fomesafen | 16 |
| 9 | Untreated | Atrazine | 170 |
| 10 | Buffer-surfactant-ssDNA-TIF | | |
| 11 | Buffer-surfactant-ssDNA-TIF | Atrazine | 170 |

Figure 33:
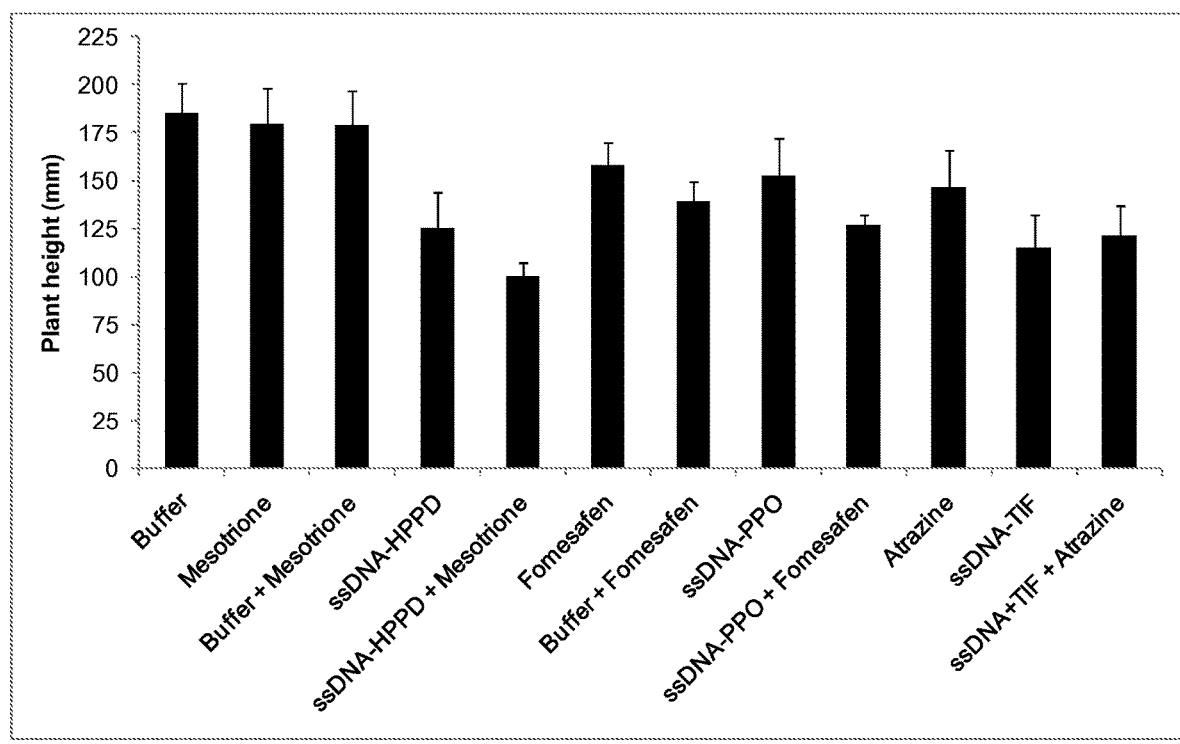
FIG. 33 illustrates the herbicidal effect on Palmer amaranth after treatment with the indicated combinations of non-polynucleotide herbicides and polynucleotides, as described in Example 28.

Plant height was determined at four days after herbicide treatment. Data were collected from one experiment with four replications per treatment. Results (expressed as Palmer amaranth plant height as affected by the buffer-surfactant solution, ssDNA, and herbicide treatment combinations) are presented in Table 19 and FIG. 33. Plants treated with HPPD anti-sense ssDNA oligonucleotides, PPO anti-sense ssDNA oligonucleotides, and TIF anti-sense ssDNA oligonucleotides showed growth stunting, measuring 125, 153, and 115 mm, respectively, while the plants treated with buffer-surfactant (control) measured 185 mm (FIG. 33). Treatment with HPPD anti-sense ssDNA oligonucleotides, PPO anti-sense ssDNA oligonucleotides, and TIF anti-sense ssDNA oligonucleotides respectively caused a 32%, 18%, and 38% growth reduction relative to the buffer-surfactant control.

No major differences in plant height were observed between plants treated with buffer-surfactant followed by herbicide, and plants treated with herbicide only. The plants treated with HPPD anti-sense ssDNA oligonucleotides followed by mesotrione showed the greatest reduction in plant growth, measuring 100 mm, a 46% reduction compared to the buffer-surfactant treated plants. The plants treated with PPO anti-sense ssDNA oligonucleotides followed by fomesafen measured 126 mm, a 32% reduction compared to the buffer-surfactant treated plants. The plants treated with TIF anti-sense ssDNA oligonucleotides followed by atrazine measured 121 mm, a 34% reduction compared to the buffer-surfactant treated plants.

TABLE 19

| Treatment number | Pre-treatment | Active Ingredient | Rate (grams per hectare of active ingredient) | Plant height (mm) | Standard Error |
|---|---|---|---|---|---|
| 0 | Buffer | — | — | 185 | 15 |
| 1 | Untreated | Mesotrione | 13 | 180 | 18 |
| 2 | Buffer | Mesotrione | 13 | 179 | 18 |
| 3 | ssDNA-HPPD | | | 125 | 19 |
| 4 | ssDNA-HPPD | Mesotrione | 13 | 100 | 7 |
| 5 | Untreated | Fomesafen | 23 | 158 | 12 |
| 6 | Buffer | Fomesafen | 23 | 139 | 10 |
| 7 | ssDNA-PPO | | | 153 | 20 |
| 8 | ssDNA-PPO | Fomesafen | 23 | 126 | 6 |
| 9 | Untreated | Atrazine | 170 | 146 | 19 |
| 10 | ssDNA-TIF | | | 115 | 17 |
| 11 | ssDNA-TIF | Atrazine | 170 | 121 | 16 |

Example 29

This example illustrates tested sequences of double-stranded RNA polynucleotides designed for different essential genes to ascertain the effect of the tested sequence on observable phenotype. For each essential gene, a solution containing the dsRNA polynucleotide in 2% ammonium sulfate in 10 millimolar sodium phosphate buffer, pH 6.8, was applied to Palmer amaranth at a rate of 240 picomole per plant following application of 0.5% SILWET L-77 spray (10 gallons/acre). The tested polynucleotides and resulting phenotype observations are listed in Table 20.

TABLE 20

| Gene | Name | Size (nt) | Sequence | SEQ ID NO: | Phenotype |
|---|---|---|---|---|---|
| Translation initiation factor (TIF) | sense | 160 | UUCGAGUAAUGGGAAAUUGGAUAAUGUA GAGGAGAGGAAGAAGGUUAUUGAUUCAU UGGAUGAGGUAUUAGAAAAGGCCGAGAG AUUAGAAACGGCGAACUUACAAGCAGAU AAUAGAAAGGAUAGCACAAAUGUAAAUA AACCGUCUCCGAGUGUAAGU | 73 | Topical dsRNA caused stunting of plant growth. |
| | anti-sense | 160 | ACUUACACUCGGAGACGGUUUAUUUACA UUUGUGCUAUCCUUUCUAUUAUCUGCUU GUAAGUUCGCCGUUUCUAAUCUCUCGGCC UUUUCUAAUACCUCAUCCAAUGAAUCAA UAACCUUCUUCCUCUCCUCUACAUUAUCC AAUUUCCCAUUACUCGAA | 74 | |
| DNA-dependent ATPase (ddATPase) | sense | 168 | GAUCACAAAUUUGCCGGUUUAUGAUCAA AUACGGAACAUAAGACAGAUACACUUGA ACACCAUGAUUCGCAUUGGGGGUGUGGU UACUCGUCGUUCUGGAGUAUUCCCUCAGU UGAUGCAGGUGAAGUAUGACUGCAAUAA AUGUGGGGCUAUCCUGGGUCCCUUUUU | 113 | Topical dsRNA caused stunting of plant growth. |
| | anti-sense | 168 | AAAAAGGGACCCAGGAUAGCCCCACAUUU AUUGCAGUCAUACUUCACCUGCAUCAACU GAGGGAAUACUCCAGAACGACGAGUAAC CACACCCCAAUGCGAAUCAUGGUGUUCA AGUGUAUCUGUCUUAUGUUCCGUAUUUG AUCAUAAACCGGCAAAUUUGUGAUC | 114 | |
| Hydroxy-3-Methylbut-2-enyl diphophate synthase (HMEDS) | sense | 200 | CUGAAGCUGGUGAAGGUGAAGAUGGACG AAUGAAAUCUGCGAUUGGAAUUGGGACC CUUCUUCAGGAUGGCUUGGGAGAUACGA UCAGGGUGUCUCUAACAGAACCACCAGAA GAGGAGAUAGACCCUUGCAGAAGGUUGG CAAAUCUUGGAACAAAAGCAGCUGAAAU UCAGCAAGGAGUGGCACCAUUUGAAG | 173 | No significant phenotype. |
| | anti-sense | 200 | CUUCAAAUGGUGCCACUCCUUGCUGAAUU UCAGCUGCUUUUGUUCCAAGAUUUGCCA ACCUUCUGCAAGGGUCUAUCUCCUCUUCU GGUGGUUCUGUUAGAGACACCCUGAUCG UAUCUCCCAAGCCAUCCUGAAGAAGGGUC CCAAUUCCAAUCGCAGAUUUCAUUCGUCC AUCUUCACCUUCACCAGCUUCAG | 174 | |

TABLE 20-continued

| Gene | Name | Size (nt) | Sequence | SEQ ID NO: | Phenotype |
|---|---|---|---|---|---|
| Fertilization independent endosperm / TF (FIE) | sense | 183 | UCCCAUCAAAGUUCCCUACAAAAUAUGUG CAGUUUCCUAUCUUCCUUGCCGCCAUUCA UACAAACUAUGUUGAUUGUACAAGGUGG CUUGGUGAUUUUGUUCUUUCUAAGAGUG UUGACAAUGAGAUUGUACUGUGGGAGCC AAUUAUGAAGGAGCAAUCUCCUGGAGAG GGUUCAGUUGACA | 175 | No significant phenotype. |
| | anti-sense | 183 | UGUCAACUGAACCCUCUCCAGGAGAUUGC UCCUUCAUAAUUGGCUCCCACAGUACAAU CUCAUUGUCAACACUCUUAGAAAGAACA AAAUCACCAAGCCACCUUGUACAAUCAAC AUAGUUUGUAUGAAUGGCGGCAAGGAAG AUAGGAAACUGCACAUAUUUUGUAGGGA ACUUUGAUGGGA | 176 | |
| 26S proteasome ATPase subunit RPT5B (RPTB) | sense | 143 | UUGUGCUUAAAACAUCGACCAGACAGAC AAUAUUUCUUCCUGUUGUUGGACUAGUU GAUCCUGAUACGCUGAAACCUGGUGAUU UAGUUGGUGUCAACAAAGAUAGUUAUCU UAUCCUGGACACUCUGCCGUCGGAUAUG AU | 177 | No significant phenotype. |
| | anti-sense | 143 | AUCAUAUUCCGACGGCAGAGUGUCCAGG AUAAGAUAACUAUCUUUGUUGACACCAA CUAAAUCACCAGGUUUCAGCGUAUCAGG AUCAACUAGUCCAACAACAGGAAGAAAU AUUGUCUGUCUGGUCGAUGUUUUAAGCA CAA | 178 | |
| ligase 1 (LIG1) | sense | 159 | CGCUGCAGUUGGUGAAGUAGAUCCCGGC AAGGGGAUUUCACUCCGGUUUCCACGUCU GGUUCGUAUCCGAGAGGAUAAAUCUCCA GAGGACGCCACAUCAUCUGAGCAGGUGGC GGAUAUGUACAGAUCUCAAGCAAACAAU CCACACCGCAAAAAGAG | 179 | No significant phenotype. |
| | anti-sense | 159 | CUCUUUUUGCGGUGUGGAUUGUUUGCUU GAGAUCUGUACAUAUCCGCCACCUGCUCA GAUGAUGUGGCGUCCUCUGGAGAUUUAU CCUCUCGGAUACGAACCAGACUGGGAAAC CGGAGUGAAAUCCCCUUGCCGGGAUCUAC UUCACCAACUGCAGCG | 180 | |
| tRNA synthetase (tS) | sense | 159 | UAAAGAUGGCGGAAAAAUCGACUAUGAU AAAUUGAUUGACAAAUUCGGCUGUCAGC GACUUGAUUUAUCGCUCAUUCAGAGAAU UGAGCGCAUCACUGCUCGUCCUGCUCAUG UAUUUCUUCGCCGCAACGUUUUCUUCGCU CACCGUGAUUUGAAUGA | 181 | No significant phenotype. |
| | anti-sense | 159 | UCAUUCAAAUCACGGUGAGCGAAGAAAA CGUUGCGGCGAAGAAAUACAUGAGCAGG ACGAGCAGUGAUGCGCUCAAUUCUCUGA AUGAGCGAUAAAUCAAGUCGCUGACAGC CGAAUUUGUCAAUCAAUUUAUCAUAGUC GAUUUUUCCGCCAUCUUUA | 182 | |
| Ubiquitin specific protease 14 (UBP) | sense | 150 | UGAAGCUGAUGCUGAAGGAAAGGAUAUU GAUGCUAGUGAAGUAGUUCGCCCAAGGG UGCCAUUAGAAGCUUGCCUAGCUAGCUAC UCAGCUCCGGAGGAGGUGAUGGACUUCU ACAGCACUGCAUUGAAGGCAAAGGCAAC UGCUACAAA | 183 | No significant phenotype. |
| | anti-sense | 150 | UUUGUAGCAGUUGCCUUUGCCUUCAAUG CAGUGCUGUAGAAGUCCAUCACCUCCUCC GGAGCUGAGUAGCUAGCUAGGCAAGCUU CUAAUGGCACCCUUGGGCGAACUACUUCA CUAGCAUCAAUAUCCUUUCCUUCAGCAUC AGCUUCA | 184 | |
| Serine hydroxymethyl transferase 2 (SHMT) | sense | 155 | ACACCUGCCCUAACAUCUCGGGGUUUUCU CGAAGAAGAUUUUGUUAAAGUGGCCGAG UAUUUUGAUGCUGCUGUUAAGCUGGCUC UAAAAAUCAAGGCUGACACAAAAGGAAC AAAGUUGAAGGACUUCGUUGCCACCUUG CAGUCUGGUGUUUU | 185 | No significant phenotype. |

TABLE 20-continued

| Gene | Name | Size (nt) | Sequence | SEQ ID NO: | Phenotype |
|---|---|---|---|---|---|
| | anti-sense | 155 | AAAACACCAGACUGCAAGGUGGCAACGA AGUCCUUCAACUUUGUUCCUUUUGUGUC AGCCUUGAUUUUUAGAGCCAGCUUAACA GCAGCAUCAAAAUACUCGGCCACUUUAAC AAAAUCUUCUUCGAGAAAACCCCGAGAU GUUAGGGCAGGUGU | 186 | |
| Methionine-tRNA ligase/synthase (MtS) | sense | 159 | UGAACUACGAAGCAGGCAAAUUCUCCAA AAGUAAAGGCAUUGGAGUUUUUGGGAAU GACGCCAAGAAUUCUAAUAUACCUGUAG AAGUGUGGAGAUACUAUCUGCUAACAAA CAGGCCUGAGGUAUCAGACACAUUGUUC ACUUGGGCGGAUCUUCAAG | 187 | No significant phenotype. |
| | anti-sense | 159 | CUUGAAGAUCCGCCCAAGUGAACAAUGU GUCUGAUACCUCAGGCCUGUUUGUUAGC AGAUAGUAUCUCCACACUUCUACAGGUA UAUUAGAAUUCUUGGCGUCAUUCCCAAA AACUCCAAUGCCUUUACUUUUGGAGAAU UUGCCUGCUUCGUAGUUCA | 188 | |

Example 30

This example illustrates polynucleotides which are designed to target a particular low sequence homology region and are useful e. g., for selecting a specific allele of a target gene or a gene of a specific species. Polynucleotides designed to target non-coding sequence are useful in regulating non-coding RNAs that are involved in gene regulations, e. g., regulating non-coding RNAs that are processed to siRNAs in an RNAi-regulated pathway. FIG. 34 depicts an alignment of the Nicotiana benthamiana PDS locus 1 promoter (SEQ ID NO:319) and PDS locus 2 promoter (SEQ ID NO:320); in the case of locus 1 which contains multiple transcription start sites, the promoter sequence used in this alignment is the one with the most 5' transcription start site. The Nicotiana benthamiana PDS1 and PDS2 genes were found to have low sequence homology in the promoter region but high sequence homology in the coding region.

Polynucleotides designed to target different parts of the PDS1 and PDS2 promoters are listed in Table 21.

TABLE 21

| Poly-nucleo-tide Mixture | | promoter target | Sequence | SEQ ID NO. | position/dir |
|---|---|---|---|---|---|
| 2 | HL419 | PDS promoter 1 motif target | TCCCATCTCCCACATGGGTTACTG | 189 | 590-567 |
| 2 | HL420 | PDS promoter 1 motif target | CAGTAACCCATGTGGGAGATGGGA | 190 | 567-590 |
| 2 | HL421 | PDS promoter 1 motif target | GGCTGATGAAATTCAAGTGCTA | 191 | 557-536 |
| 2 | HL422 | PDS promoter 1 motif target | AAACTGAGCTTGGAAATAATC | 192 | 517-497 |
| 2 | HL423 | PDS promoter 1 motif target | GAACCCAAAATTGTCACTTTTT | 193 | 448-427 |
| 3 | HL424 | PDS promoter 1 motif target | ATGCACTTGTTTATACTCTTGTCA | 194 | 403-438 |
| 3 | HL425 | PDS promoter 1 motif target | ATTTATTAGTGTTCTAAAGAA | 195 | 357-337 |
| 3 | HL426 | PDS promoter 1 motif target | TGTAGTAGCTTATAAGATTAGCTT | 196 | 287-264 |
| 3 | HL427 | PDS promoter 1 motif target | GTTGTCCCTTTTATGGGTCTTT | 197 | 240-183 |
| 3 | HL428 | PDS promoter 1 motif target | CCCGTGCAATTTCTGGGAAGC | 198 | 86-66 |
| 5 | HL429 | PDS promoter 2 motif target | ATTAGTTTTTATACACGAAAGAT | 199 | 1313-1336 |

TABLE 21-continued

| Poly-nucleo-Mixtide | promoter target | Sequence | SEQ ID NO. | position/dir |
|---|---|---|---|---|
| 5 HL430 | PDS promoter 2motif target | ATCTTTCGTGTATAAAAAACTAAT | 200 | 1336-1313 |
| 5 HL431 | PDS promoter 2motif target | TTGGTGGTTTGGCCACTTCCGT | 201 | 1291-1270 |
| 5 HL432 | PDS promoter 2motif target | TTTGTTTGCTATTTAGCTGGA | 202 | 1256-1236 |
| 5 HL433 | PDS promoter 2motif target | CAATTTGCAGCAACTCGCACTGGA | 203 | 1205-1182 |
| 6 HL434 | PDS promoter 2motif target | TCCCACCATTGGCTATTCCGAC | 204 | 1156-1135 |
| 6 HL435 | PDS promoter 2motif target | CTGTCTCTCTTTTTAATTTCT | 205 | 1105-1085 |
| 6 HL436 | PDS promoter 2motif target | CCACTTTGCACACATCTCCCACTT | 206 | 1056-1033 |
| 6 HL437 | PDS promoter 2motif target | GAGGATCCACGTATAGTAGTAG | 207 | 1016-995 |
| 6 HL438 | PDS promoter 2motif target | TTTAAATAAAGAAATTATTTA | 208 | 889-869 |
| 1 HL439 | PDS promoter1 | TAATACGACTCACTATAGGGCTTGAGTTTATAACGAAGCT | 209 | |
| 1 HL440 | PDS promoter1 | TAATACGACTCACTATAGGGCTTCTAATTTTCAAGGACG | 210 | |
| 1 HL441 | PDS promoter1 | AGCTTCTAATTTTCAAGGACGATA | 211 | Anti-sense |
| 1 HL442 | PDS promoter1 | GTCATGTGACTCCACTTTGATTTTG | 212 | Anti-sense |
| 1 HL443 | PDS promoter1 | CTCAATTCCGATAAATTTAAGAAAT | 213 | Anti-sense |
| 1 HL444 | PDS promoter1 | CGAAGCTATTGGACCGACCTAATTTC | 214 | Sense |
| 1 HL445 | PDS promoter1 | GGAATTGAGGGCTTCCCAGAAATTGC | 215 | Sense |
| 1 HL446 | PDS promoter1 | ATGACTTTTTGATTGGTGAAACTAA | 216 | Sense |
| 4 HL447 | PDS promoter2 | TAATACGACTCACTATAGGTGGAACTCCAACACACAAAAATTTC | 217 | Sense |
| 4 HL448 | PDS promoter2 | TAATACGACTCACTATAGGTTGAAAAATAATCATAATTTTA | 218 | Anti-sense |
| 4 HL449 | PDS promoter2 | GCATAATATATTGATCCGGTAT | 219 | Anti-sense |
| 4 HL450 | PDS promoter2 | CTGAAAGTTCATACATAGGTACTC | 220 | Anti-sense |
| 4 HL451 | PDS promoter2 | GGTACTCCAATTTTCAGTATAT | 221 | Anti-sense |
| 4 HL452 | PDS promoter2 | CTGAAAATTGGAGTACCTATGTAT | 222 | Sense |
| 4 HL453 | PDS promoter2 | ATGTATGAACTTTCAGAATATTATACC | 223 | Sense |
| 4 HL454 | PDS promoter2 | TACCGGATCAATATATTATGCT | 224 | Sense |

Figure 35:
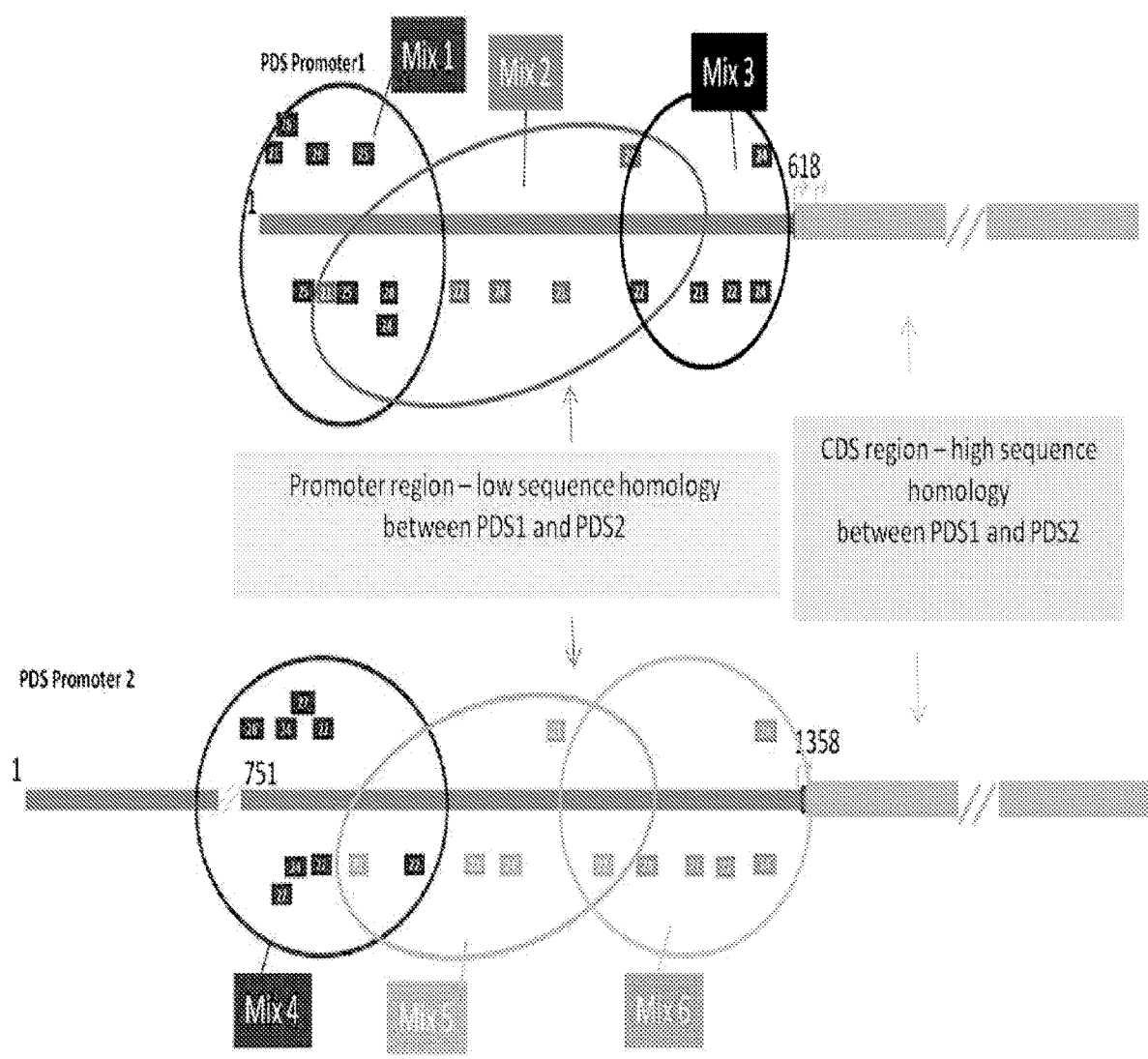
FIG. 35 schematically illustrates the *Nicotiana benthamiana* PDS locus 1 and locus 2 promoters and the regions targetted by mixtures of polynucleotides, as described in Example 30.

Six different combinations of polynucleotides (1 nanomole/plant of each applied polynucleotide) as listed in Table 21 and illustrated in FIG. 35 were tested on 4-week-old *Nicotiana benthamiana* plants using a procedure similar to that described in Example 12. Polynucleotide solutions were prepared in 0.01% (v/v) SILWET L-77 and 2% (w/v) ammonium sulfate in 5 millimolar sodium phosphate, pH 6.8. Two fully expanded leaves per plant were dipped into 0.1% SILWET L-77 solution freshly made with ddH2O for a few seconds, and allowed to dry. About 30 minutes later, 20 microliters of polynucleotide solution was applied to each of the two pre-treated leaves. Positive control plants were similarly treated with a DNA oligonucleotide targetting a conserved segment of the coding region of PDS1 and PDS2; negative control plants were similarly treated with a DNA oligonucleotide designed to silence green fluorescent protein (GFP). All six combinations of polynucleotides designed to target the PDS1 or PDS2 promoter regions induced systemic silencing in the treated plants as evidenced by bleaching. Treatment with either dsRNA or dsDNA polynucleotides of approximately 200 bp and targetting the PDS1 or PDS2 promoter regions also induced systemic silencing in the treated plants as evidenced by bleaching.

The following additional genomic sequences (including promoter and transcribed intron and exon sequence) listed in Table 22 were identified for *Amaranthus palmeri* genes for use in designing polynucleotides for topical application:

TABLE 22

| Gene Name | Sequence | SEQ ID NO. |
|---|---|---|
| ACC1 | TTCAAAATGAATTTAAAATTATATAAAAATCAATATGGACACAAGACCGGAT<br>ATCAATCCGACCCGAAATAGTTGACTTGAAATCAACCTGATGACCCGAATGA<br>ACACCTCTAGTTATCACTAACAAGGGTCAGATTGCGTACATCAAACCCCTCA<br>AATCCTGCTTAGGTGGGAGCTTGTCAATGGCTTAGGGGTAACGGGAATGTGT<br>GTGCTATGTACATTGTGCATCTATTCTTATGCTTATTTATGTTGAGTTAGTTTT<br>TTTTTTGGATCAAATATAAAGAGCTTAACTTTTGTATTTTCTTGATGTGGTGT<br>AGTGGTGATGAAGATCAGGCTGAGAGAATCTAAATTGGCCAAAATTCTGAG<br>AGAACAAGAAGTGAGTTCAGCCCTTCGTGCTGCTGGTGTTGGTGTGATTAGT<br>TGCATCATACAGAGAGATGAAGGGCGAACTCCGATGAGGCATTCATTCTATT<br>GGTCAGCAGAAAAACAATATTATAGTGAGGAGCCTTTACTACGTCATTTGGA<br>ACCCCCTCTATCTATGTATCTCGAGCTGGTACTAGTCTCTGAACCGATTGCCT<br>TTCTTCTGCTTTGTTATTTTGTGTGATATTTCGACTTAAGTCTAATTTACATCG<br>TTTTGTACATTTGTTATC | 225 |
| ACC3 | TTTTGCTTTTTTACTATTATTTCCTTCTTTTCAAGGATTTGAGTTGTTTATTGCT<br>GACTGCTTCCTATGTATTACCCATATGTCTCTGTATAGGCATTACGGGAGCTG<br>TACCTACATCTAACTCCTATACAACGTGTGAATATTGCCCGGCATCCTAATCG<br>CCCCACTTTTCTTGACCACGTATTCAGCATCACAGAAAAGGTTTCTGATTTAT<br>TATAATTTTTGTCATTTGTATTCACTCTTCAATAAAGTACATCCATTATCAAT<br>CTTTACGGAGGTTGTTCACACAACTTCTTGTTTCATTTTGCATAATTAGTTTGT<br>GGAACTACATGGAGATCGTGCTGGTTATGATGACCCTGCTATAGTTACTGGC<br>CTTGGTACGATAGATGGTAGGCGTTATATGTTCATTGGTCATCAAAAGGGAA<br>GAAATACGAAGGAAAATATTGCACGGAATTTCGGGATGCCTACTCCTCATGG<br>GTAAATGCTTTACTATAATGTTTTACTTTAATTTAATTACCTATGTTATTTAGG<br>ATGAAAATGAATACTTTTCTTATTACTATTACTTAGGTTCCTAATGCACAAAA<br>ACCGTAATTATTAATGTACCCTAATGGAATTAACACATGGTAATTAAGCTCT<br>CCGCTTTGTGTAATTAATCCAATTTTTTAGAGAGTCAAATAGTTCAGGTTAAA<br>CTAGAGCTTTTCATACCCAAATAATAAAACCAAGGGTAAATTTCCAAAA | 226 |
| ACC4 | ATGTGATCAATTAAAGAAAAAGTCTAATTATATGAGCCCGTCTCACAGTGAC<br>GGAGCTATCATAGAGCCCATGGGGTCACGTGCCCTTCGGGGTTTTTAGAAAA<br>AATTCAAAGTATACTTTTCTATTAATAAGAGTAAAAATGTAAAATTAATATT<br>AAACTCTTTTGATAATAAATACTCTCTCACTTTAGTAATTTTGTCTTATTTATT<br>TATTTTATCTCATGTGTTTAATAAGGTCAGTTGACTTATTTTGTTCCATTTTCT<br>TTTATGGTATGCCGTATTTAAAATTTTAGCAAGTAAAGATAAAATAGTTGTT<br>AATCTTACAAATAAAACTCTATCGAAATTTCATCCATTAGTTAATGTCCCCAA<br>AAAGTCCGAACTACAAATCGACCACTGTCATCACATGGTGAGATAGTCTCAT<br>ATAAAACGAGTTCAGTTATTAAAGGAAAATAGGAAACACGAAACAGTTAAT<br>TTAGGCGGGGCCTATGTATTATCCAAATGTGATACTCCAGTCCACATTACTC<br>AGTCCTTCCAATTGAACAGTTGGCTTAATCTACCAAGCGCGTGGCCATAAAT<br>GCCTCTAACACTTTTCAATCTCTCAGATAACTCTCACACCACTTATCATCACA<br>ATTCACAATTACTCTAATTCTTTTTATTCCTTTCCATGTCGCTAATTTTCTACT<br>GATTCAGGTTTTATTCTCAGCTTTTATCAATTTTATTTCATGCTTTTTATGTCA<br>ATTTCTTGTTTCGCATTTTGTCTTCCACTTGCTGTCTGTTTTATTAATCAATTTT<br>GTATGATTGTTGGAATAATTGTATGTATTTTTCATGATTTTCCTCTTATGGAG<br>GTTCATAATGTATTGCTAGATTTGTTTACTTTCAC | 227 |
| ACC5 | AATTTGAGCGGGAAAATTTTAATATCATTAAATAGTCTTTGCTTTAGTATATA<br>GAATAGTTAAAATTAATAGTCAAACTTATTGTAATAGCATGCACTAATCTAT<br>AATAATCTTATCCTGAAAGCTATAATAAAATTATAAAAAAATATATGTGAAA<br>AACTAATTTGAGCGGGAAAATTTTAACCAAGGGCTAACACGTATCATTAAAT<br>AGTCTTTACTTTAGTATATAGAATGATAATTAACGATCATAAAACAAAATTG<br>TCACTTTCAGTAGCAAACTTACAAAATGAGCAGAGTACCTCATATCATAAAA<br>TTGCTTCTTTCTCATTTGTTGTGTTGCTCTCATTTTAGGAGTTCATCGTTTATA<br>TCGTCGTCTTACCACTCAATCACTTTTAGATTTATTAGTAGCACTTCCTCAAT<br>CTACAGCAGCAATTTCTACAGTTCAACAACCTC | 228 |
| ACC6 | GGAAAATTTACCTAGAATAATCCAATTTATTCGTGATTTTTCTACAAATTCCA<br>ACTTCAAGGGGTATTTGCCTAAAGTAATTAAACTTGGATACCCCGATGACCT<br>GCTATAGTAGATAATTTACCAGAAAATTAAAAATGAAAATTAATTTAAAATT<br>AGAGAAAAATTTTGAAATTTCATATAAAAAATTTTAAATAATAAAAAAAATA<br>TAAATTTTTTTGAACATTTTATTTTAATCTATCTTTTTTGAAAAAATAAAACTT<br>AGTTATAGCAAGTGATCTGGTCACCGGGTTTACTCTAGGAAAATATCCCTCA | 229 |

TABLE 22-continued

| Gene Name | Sequence | SEQ ID NO. |
|---|---|---|
| | AAGTTGAGATTATTCATGGTTAATAAATAGGTGAGATTATTATAGAAAAATT ACGAATAAATTGGATTATTGTTGGTAATTTTTTTTTCAAAACTATCCCTAGGA AGGACCTTATTAGTGATTCTCCCTCTACTTTGGAGGAGTATATTGTGGACTTC CCATCTTCCTTAATTGTATTGTAACTTTTAACTATTGATTCTTTAAAAAAAAG AACTTATAAAATTGTAGGGTTAATAAAAATCTAAGATTTTATCTAATTTCACTT TGATTATTCCGATTTTGTATTCACATTATTTTAAATGACATTCGTCAAATAAA AAAAAATAGTTTCATTGCATTCCAATTTTGTTGACTAGGGGGATTAAAGAAA GAATAGTATCAATAATCGTAATGTAGCAAGTAGTACAAAAGAAGTATATTTC AATATGTCAAACTTTGATCTCGTTGTAACTTGTAATTTGTACGATGCGGTGTG AATGACATACTTCACCTTTTTCATTATTTTATACTGGTAGTGACATGGGATTA TTATTGCGATATTTGCAGTAATGAAATTTTTTGGTTGTTGCTTTTACAAAC AAAAATTCTACCGAATTTTTTATTAATTTAATTCAACACGTTGGTGTTACCCA TGATTTATAGGTCTGGGTCCGCCACTGCTAGCTAACATTAAACAATTTAACA AACTCAATACACCAACCTAAAAATAAAATTTTTTGGCCATAATTTTTAGAA TTTTAGTTTTTAAACATTATATTTGGGAATTTTTTTCCTTTTATATATATAAA ATAAAAAAAAATCCAAAAAGGGGACACACATTAATACACACTTGAAAGCA TCGATGATATCGAAGAAAACCAGATGGGGTGCCCAATTATCTTCGTCTCCT TCGATATTATCGAATTCATTAACAACATTATATCAAAAACCAACCAAATTAC CAACTTTCGAAACCAATATTCGCCGTATTTTCTCTATTCAACAATCCCTACA ATGGCGGCATTGCCAGCTTCTTCTTCTCCTGCAATTTCGGAATCACCCACTTG CAATTTTCTTCCTATTCAAAAAATCACTACCACTCGCTTTCTAAGGTTTCATT CGGTTTTACTCCCAAGCCTAAATTTGGCCTTTTCTCCAAGGTTTATTTTCTATC TCTTTTTTAATTGGTTAATCAATTGGATTGTTGAATTTTTCAGGGTTTAACGG TATAATATTTGTGGGTTTTTTCGAGTACATTCTGGGTTTGTAGTATTGGATTT GGCATTGCTTTTAATTTTTGAGATTGGGTTTTTGGGTTTTATTTGGTTCTTGT GATTCAAGGTTATTGATTTGCTGCATTAAACTGTATTTATGGAATGATGTCAA TTAACTGTTACATTACATTGCTTTATGGTTTTCATCATGCTGATTAGTGATTA CTGTGTTTGAATCTCTTGCTTCTCTATGTACTATTTAATCTGATACAACAAGT ACAACCTAGAAAACAGGTTAAAGGGAAATCTATAAGCTTAGTAAATTAACA CTTGAAAGAAGCTAATGACGGAGAGAGGGGTCTTTTTGGAGAAGGCAGTTTT CATATTATTGCTCAGTTCTCTAGTGCAGCTTTACTTCACTTAGACACTCTTAA GTAGAGGTCATAGGTGTTCAGAATAGATCCAAAGACCCGATATTTACCGGAC TTTGTAAACAACTTAACCCGACTTCAAAATGAATTTACAATCATATAAAAGC AATATGGACTTAAACCGATTTTGAACCGACCTTGACCGGTTGATCCGAATGA ATGCCTCTACTCTTAAGCATGTCAACTGTAATATGAAATAGAATTATAATAT AAACTAAGTTCATGTTTTCTTCAACTACAAATGAAATTTTATGACCCAAATA ATGTGTGAATACCCCCAGCAATAGGTTGAATGGCATTTAGTTCAGTTGATTTT AGCAGACCACATCTGCCCTCATATTCCATTGTTCAGTTTAGTTGTTAGTAGCT GTACATAATAGACTAATTAAGTTGTCATTTTGATCCATGTTATGGTTGTCTGG GATAAACGGATTGGAATTGTATAATAAAAGTTTGGGTTAGTTTATTTTGCTCT AGGAGGGGTTATGTCATATGTGCACTCTGTTGGCAACCCGACAATGCAAAAC ATTTTCATACTTGGTACGTTGTTGCGTGTTTTGTGCCCTTCGTATTTTGTAACT GTTGATGAATGTGTAAAAATATACTACATGATCATATGCTAGTAGGTCTTCTT CACCTAGTAAAGAAATTTTTCTAACACGAGAAGTTCAAAACATATTCCCATT ACCATTATCCAACATCAGTACCCGAGTCCAAGTAACATAGGGTGTCCCTTTA TGATAGTATAAGAATTGGTGCATGAAAAACGCGTGATTGTAGCGAGGATAG TAGGCGGGAGAGGTACAGGATTTGAAAATTTTGAATTGCTAAAACGCTATCA GGATCTTGTTTTTCTTACTTTGATGTTGCTTTTTTGAAATTTGATCCAAATTGT TAAATTATTGAGACTAATTCCTGTTGATCCTGTCGTGAACTTTGTAGAATCTT TCAGGCCGCATTCTCACAGTGAAGGCTCAATTAAACAAGGTGAGTCTTTTTT TGTCTTAACTCTTATGCAGTTCATTATCTCTTCTACTGATGAGAAACCACTA TTTTGGCCTAATTCTAATTTCCTTCTAGGTTGCTTTGGATGGTTCAAATCATGC TCCATCACCTTCGCACGAAAAATCTGGGCTACCAGCCCAAGAAAAGAAGAA CGATGAGCCGTCTAGTGAATCTTCTCCTGCAGCATCAGTGTCTGAAGAACGA GTCTCCGAATTCTTGAGCCAAGTTGCCGGTCTTGTCAAGTATGTAACATTCTT TATTTTCATTCTTCCACACACTCGCAATTTGGATAACGAGATGTCTTTAGAGA CGTCTGGGGAACAAGGGAGAAATGAGTCTAGAGGTTGCTAGAGAGAACGAG ATAAATACTAATATATATGAATATTTCATAATCCACATTAAAAAAATACAAT TGAATTTGCATTATGGTGAACTACCAAAGAATCGAATATTTTTTAATACTCCA TGTTTTGTGGTCTAGACTTGTGGATTCTAGAGACATTGTAGAGTTGCAATTAA AACAACTGGACTGTGAGATATTGATCCGCAAGCAGGAAGCTATTCCTCAACC ACAAATTCCTAATCCTACACATGTCGTTGCAATGCAACCACCACCACCTGCT GTAGCGTCTGCCCCAGCTCCCGTCTCTTCACCAGCCACTCCTCGTCCTGCGTT ACCTGCCCCAGCGCCTGCTGCCACGTCAGCTAAGCCATCACTTCCACCTCTC AAGAGCCCTATGTCAGGCACATTCTACCGTAGTCCAGCTCCTGGCGAGCCGC CTTTCGTGAAGGTAAGTGTATACCCCTTTTTAGTGTTGTATTTCTGTGTTATA TCAATTTTTGCATTTTGTGAAGCTGAAAATAAATCTTTCATTTTCCATAGGTT GGGAGATAAAGTTAAGAAAGGACAAGTCATATGCATTATCGAGGCTATGAAG TTGATGAATGAAATCGAGGTACGTATGTTATTGCTTTAAACTTCATGCCTTAG GCCGTGAAGTT | |
| ALS1 | ACAAAAAGCACAAATTCAATAATATACTCTTTAAGTTTGTTTATCTTCTAATT AGTTCGGTTAAAACGGTTCCCCACTTTCTTCTCCGACTCTCACAATTATCTTC CCCTATTCATTTTTCTTCCACCCTCTCTAATGGCGGCTGTTTCCTTCAATATCA ATGGTGGAAAGATTGGAACTTTATGTTCAAGACACGAATTCGTTTGTGGGTT TGTAAGAAAATTTCATTTTAGAACTCATACTTCTATATTTGAAAAACATATGC | 230 |

TABLE 22-continued

| Gene Name | Sequence | SEQ ID NO. |
|---|---|---|
| | CAAAAACTTCAAGGTTTAAAGCAATGGAAGTTTCTGCAAATGCAACAGTAA<br>ATATAGTTCCTGTTTCAGCTCATTCTAGGTAATTTTATTTCTCGAAAATTTCC<br>GATTTACAATTAAATTAATCTTGTTTTGTAGGTAATGAATTGCAGAAGAAAT<br>AGATGGATTCTTATTTGTTTATTGGTATTTGTTTATAAATTTTTGTTTATATTA<br>GTTTCTGAATTGTGATTATTCTGATTGTATGTCAAGGTTTAGGTTGTTATTAA<br>TAAATGTAAATTGGATTGATTGAAGTTGCAATAAGGTGATGGCGTGATGCTG<br>ATTGTTGTAAATTTT | |
| ALS2 | CAACAATGAGAATTTAGAATCCATATCAATCTTGATATTCAAGGGTATTTAA<br>GTAATTAAAGAACAACCATTGTTAAGCGCCTCCACTATCTTCTTCCTTCTCAT<br>TCTCCATTCTCGCTTAGCTTTCCTCTCGCACTAATTACCTCCATTTGCAACCTT<br>TCAAGCTTTCAACAATGGCGTCCACTTCTTCAAACCCACCATTTTCCTCTTTT<br>ACTAAACCTAACAAAATCCCTAATCTGCAATCATCCATTTACGCTATCCCTTT<br>GTCCAATTCTCTTAAACCCACTTCTTCTTCTTCAATCCTCCGCCGCCCCCTTCA<br>AATCTCATCATCTTCTTCTCAATCACCTAAACCTAAACCTCCTTCCGCTACTA<br>TAACTCAATCACCTTCATCTCTCACCGATGATAAACCCTCTTCTTTTGTTTCCC<br>GATTTAGCCCTGAAGAACCCAGAAAAGGTTGCGATGTTCTCGTTGAAGCTCT<br>TGAACGTGAAGGTGTTACCGATGTTTTTGCTTACCCTGGTGGAGCATCCATG<br>GAAATCCATCAAGCTCTTACTCGTTCTAATATCATTAGAAATGTTCTTCCTCG<br>ACATGAACAAGGTGGGGTTTTCGCTGCTGAAGGCTACGCTCGTGCTACTGGA<br>CGCGTTGGAGTTTGTATTGCCACTTCTGGTCC | 231 |
| EPSPS1 | ATTTGGATAACTTTTTCCTTTGATTCGAATCGGATTATTTTTAATACAGTATT<br>ATGAACTGATTTAATGAAAGTGGAGGAAGTTTCAATTTTTAAAGTTGTAGGT<br>GTAATGTTTTCTCATTTTGGATATGAAAGTGGAGGAAGTTTCAATTTCGAATC<br>ATGTTTGCCAGTTGATTCAATGAATGCTCTTGGAAATGACCAAGAGTTCAAG<br>GCTCTTGTTATAAAACATTTCAATTTTGATCTAAGAATGAACTATTTAGAAC<br>TTAAAGTAATTAAATTATTAGTTATAACTTATAAAAAAATTCAATTTTAACCT<br>TAAATTTATAAATTATGACCTTAAAAAGATCAAGTATTGAACGCATATTTAG<br>AAAAATTATAATTCGGTTATCAGTCTCATATTGAGACGGTCTCGTCCAAGA<br>CAAGTTGTATCATTTATATAATCAAATATAATTATGAGTGTATTCATGTAGGT<br>TTCAACTTTAAAGCCTAGGTGAAAGATATGTTGTAGCATCTTTGTGAAAGTC<br>AGCCTATAACTTGGTTCTAAAATTTTGAAGCATAACCATATAGTCCCTCGAA<br>TTCATTCAAGTTGTCCAATTTACTTTTTTATACTTGCCGAGACAACATTTAAA<br>CCCTTAATATTTCTAATTAATCTTAATTAAAAATTATGAAAATTTGATATTAA<br>TAATCTTTGTATTGAAACGAATTTAACAAGATCTCACATGACTATGTTTTAAC<br>TTATAGATTAAAAAAAAATACAAATTAAGAGTGATAAGTGAATAGTGCCCC<br>AAAACAAATGGGACAACTTAGATGAATTGGAGGTAATATTAGGTAGCAAGT<br>GATCACTTTAACATCAAAATTGATCACTTATAGGTTCAAATTGAAACTTTTAC<br>TTTAATTGATATGTTTAAATACTACTTTAAATTGAAATTGATATTTTTAAGGT<br>CAAAATTGAAACCTTTAAGATTATAATTGAAAATTGGCAGAAGAAAAACAA<br>AGAGAAAGAATATAAGCACGCAAATTGTACCGATCTACTCTTATTTCAATT<br>TGAGACGGTCTCGCCCAAGACTAGATGTTCGGTCATCCTACACCAACCCCAA<br>AAAATTCAACAACAAAGTCTTATAATGATTCCCTCTAATCTACTACAGTCTA<br>CACCAACCCACTTTCTCTTTGCCCACCAAAACTTTGGTTTGGTAAGAACTAAG<br>CCCTCTTCTTTCCCTTCTCTCTCTTAAAAGCCTGAAAAATCCACCTAACCTT<br>TTTTTAAGCCAACAAACAACGCCAAATTCAGAGAAAGAATAATGGCTCAAG<br>CTACTACCATCAACAATGGTGTCCAAACTGGTCAATTGCACCATACTTTACC<br>CAAATCCCAGTTACCCAAATCTTCAAAAACTCTTAATTTTGGATCAAACTTG<br>AGAATTTCTCCAAAGTTCATGTCTTTAACCAATAAAAAAGAGTTGGTGGGCA<br>ATCATTCAATTGTTCCCAAGATTCAAGCTTCTGTTGCTGCTGCAGCTGAGAAA<br>CCTTCATCTGTCCCAGAAATTGTGTTACAACCCATCAAAGAGATCTCTGGTA<br>CTGTTCAATTGCCTGGGTCAAAGTCTTTATCCAATCGAATCCTTCTTTTAGCT<br>GCTTTGTCTGAGGTATTTATTTCTCAACTGCGAAAACAATCTCTATTTGATAT<br>TGGAATTTATATTACATACTCCATCTTGTTGTAATTGCATTAGTAGATACTTA<br>TGTTTTGACCTTTGTTCATTTGTTTGTTGAATTGGTAGTGTTGAGAATTTGAAT<br>GTAATTATTTGTTTTTCCATGTGAATTTAATCTGATTAAATCCACTTCTTATTT<br>ATGTTAAGTTGCAATGATGTTTGCCAAATGGTTATCATTGAAGGATAAGTTT<br>GCCTACTTTTGACCCTCCCAACTTCGCGGTGGTAGAGCCATTTTATGTTATTG<br>GGGGAAATTAGAAAGATTTATTTGTTTTGCCTTTCGAAATAGTAGCGTTCGT<br>GATTCTGATTTGGGTGTCTTTATAGATATGATATATGGGTTATTCATGTAATG<br>TGTAGGTTATGCATTATGTTGGATGCATGTCTGGTGTTATTGCTGTAAATGG<br>ATGAATGTTGTTATTTGGAGACATTTTTTCATTCATTTTTTCCCTTTTTAATTG<br>GAACTGGAAGAGGGAAAGTTATTGGGAGTAATTAAAAGGTTGTGAGTTCGA<br>TACACTGCATCAAAGACGAAGAACTTGACATAGATGTTGAAGGCTAATCCTT<br>ATCACTGCTTGAATTCAATATGTATCTGAAAATTTTACCCCTCTATATGCATC<br>TGTTTTTGCTAATAAAGTGTTTTTGGACTATCATGTTTTGTGATGCTTAAGAG<br>GGTGATATTACTGAGATAAATGGAAATATCAAAATAACATCTATTGTGAAGT | 232 |
| EPSPS2 | CAAGCTTCAATTATCGTTTTCAAAATAAGTATTTCAAAGTCTATAAAGATATT<br>GTATAAGTTTTAGTTCAAATTTAATAAGTTTTTTTTTTTTTTTTTTTTTTTTT<br>TGAAAATCCAAATTGAATAAGTTAATARTTAAATTATGACATATAATTATGA<br>CATATAATTTGACCATGATATTTTACAATCTAACTTAATTTTGAACTTATTAT<br>TTCTAATATTCAATTATCGTTCTAAAAATAAGTATTTAAATTGTATAGATATA<br>TTGTATAACATTTAGTTCAAATTTAATTATTGATAGTTTTATTGACTATTTATT<br>TGGKGTTTGAAATTCATCCATAGAATGATAGAATAACACCATTTTTTATATA | 233 |

TABLE 22-continued

| Gene Name | Sequence | SEQ ID NO. |
|---|---|---|
| | ACTTCGTTCTAAAATTTTGAAGCATAACCATATACTCCCTCCAATTCATCCAA GTTGTCCAATTTACTTTTTCATACTTGCCGAGGCAACATTTAAACCCTTAATA TTTCTAATTAATGTTAATTAAAAATTATGAAAATTTGATATTAATAATCCTTG TATTGAAACAAATCTAACAAGATCCCACATGACTATGTTTTAACTTATAGAT TAAGAATAAAATACAAATTAAGAGTAATAAGTGAATAGTGTCCCAAAACAA ATAGGACAACTTGGATGAATTGGAGGTAGTATTAGGTAGCAAGTGATCACTT TAACATCAAAATTGATCAGTTACAGGTTCAAATTGAAACTTTTACTTTAATTG ATATGTTTAAATACTACTTTAAATTGAAATTGATATTCTTAAGGTCAAAATTG AAAAACTTTAAGATTATAATTGAAAAATGCCCAGAAGATGAAAAAACAGAGA GAAAGCATGTAAGACACGCAAATTGAACCAGTCTACTCTTGTTTCAATTTGA GACGGTCTCGCCCAAGACCAGATGTTCAGTCATCCTACACCAACCCCAAAAA ATTCAACAACAAACTCTTATAATGATTCCCTCTAATCTACTAGAGTCTACACC AACCCCACTTTCTCTTTGCCCACCAAAACTTTGGTTTGGTGAGAACTAAGCCCT CTTCTTTCCCTTCTCTCTCTTAAAAGCCTAAAACCCACCAACTTTTTCAGCCA AGAACAACGCGAAATTCAGAGGAAGAATAATGGCTCAAGCTACTACCATC AACAATGGTGTCCATACTGGTCAATTGCACCATACTTTACCCAAAACCCAGT TACCCAAATCTTCAAAAACTCTTAATTTTGGATCAAACTTGAGAATTTCTCCA AAGTTCATGTCTTTAACCAATAAAAGAGTTGGTGGGCAATCATCAATTGTTC CCAAGATTCAAGCTTCTGTTGCTGCTGCAGCTGAGAAACCTTCATCTGTCCCA GAAATTGTGTTACAACCCATCAAAGAGATCTCTGGTACTGTTCAATTGCCTG GGTCAAAGTCTTTATCCAATCGAATCCTTCTTTTAGCTGCTTTGTCTGAGGGC ACAACAGTGGTCGACAACTTGCTGTATAGTGATGATATTCTTTATATGTTGG ACGCTCTCAGAACTCTTGGTTTAAAAGTGGAGGATGATAGTACAGCCAAAAG GGCAGTCGTAGAGGGTTGTGGTGGTCTGTTTCCTGTTGGTAAAGATGGAAAG GAAGAGATTCAACTTTTCCTTGGTAATGCAGGAACAGCGATGCGCCCATTGA CAGCTGCGGTTGCCGTTGCTGGAGGAAATTCAAGTTATGTGCTTGATGGAGT ACCAAGAATGAGGGAGCGCCCCATTGGGGATCTGGTAGCAGGTCTAAAGCA ACTTGGTTCAGATGTAGATTGTTTCTTGGCACAAATTGCCCTCCTGTTCGGG TCAATGCTAAAGGAGGCCTTCCAGGGGGCAAGGTCAAGCTCTCTGGATCGGT TAGTAGCCAATATTTAACTGCACTTCTCATGGCTACTCCTTTGGGTCTTGGAG ACGTGGAGATTGAGATAGTTGATAAATTGATTTCTGTACCGTATGTTGAAAT GACAATAAAGTTGATGGAACGCTTTGGAGTATCCGTAGAACATAGTGATAGT TGGGACAGGTTCTACATTCGAGGTGGTCAGAAATACAAATCTCCTGGAAAGG CATATGTTGAGGGTGATGCTTCAAGTGCTAGCTACTTCCTAGCCGGAGCCGC CGTCACTGGTGGGACTGTCACTGTCAAGGGTTGTGGAACAAGCAGTTTACAG GTATAATGTTAACCCTTACCCTTCACATTGTTCTGCTAAATTCTAGAGGACCC TTTCAATTCTGGGTGGGATAAGCACGGCAATTTGACCGCAAAAAAATTGCAA AATTATTCTGCTGATAGAACATCTCGAGATGAGATCATATTGAGTTTTGGCG TCAACATAAACCTAATCAAATAATGAAAATACAAACATCATATGGTTTCTT TTGTCTTTATGACTAGACACTCTCTATTATTCCTTGATTGGGATCTTATTTGAA ATTGCTGTGTAGCCTACACCTCATGTTCAGATTTTGTTCGTATACCAGACTTT TCTTGATTGGGATCTTATTTGTCCCCTGGATTTTGCATAGGGTGATGTAAAAT TTGCCGAAGTTCTTGAGAAGATGGGTTGCAAGGTCACCTGGACAGAGAATA GTGTAACTGTTACTGGACCACCCAGGGATTCATCTGGAAAGAAACATCTGCG TGCTATCGACGTCAACATGAACAAAATGCCAGATGTTGCTATGACTCTTGCA GTTGTTGCCTTGTATGCAGATGGGCCCACCGCCATCAGAGATGTGGCTAGCT GGAGAGTGAAGGAAACCGAACGGATGATTGCCATTTGCACAGAACTGAGAA AGCTTGGGCAACAGTTGAGGAAGGATCTGATTACTGTGTGATCACTCCGCC TGAAAAGCTAAACCCCACCGCCATTGAAACTTATGACGATCACCGAATGGCC ATGGCATTCTCTCTTGCTGCCTGTGCAGATGTTCCCGTCACTATCCTTGATCC GGGATGCACCCGTAAAACCTTCCCGGACTACTTTGATGTTTTAGAAAAGTTC GCCAAGCATTGA | |
| GS3 | TCTTAATTTGTATTTATTATTAATCTATAAGTTAAAACATAGTCAAGTGAGA TCTTGTTTGATTCGTCTCTATGCAAGGATTTTCATATCAACTTTTCATAATTTT TGATTATACACAATTACAAATATTAACGAACGAATAAGTGCATTAAAAAGA GTGCAAAAAGCAAATGGGACACTTGTGTTGAATAGGAGGGAGTATACATTA AGATGAATCTAACGAGATCTCACATGGATATAATTTGTCTTCTATATATGTCT AAAAAAATCTTGATCAAATTTCTCTTTCCAAAATAGAATATTCTAAATGGGAA GAACATTAAGAAACGGAGGGAGTACTTATAAGTTAAGATAGTTGGGGGTAT TTAGGTAAAAAAATCTATGCCAAAAGTAGAAAGTGGACAATTAGAGTGACT TTACTAAATAAGGAAAGTGGACATTTAAAATGAATCGGAGGGAGCATATTA ACTTTATTTTCAAAGTGTGAAACATAATCATATTTAGGTAAAAAAATTATCA ATTTAACGTCAAAATTGATCACAAATAGGTTAAAATTGAAATTTTTTATGTTA ATTGATCTATTGTTCACTTTAAATTGAATTGATATCCTTTAAGGTTAAAATT AATACCTCTAAAATTAAAATTATTAAAGGCCCAGAAAATAAAAAAAAAAGA AGACAGGCTATTAGTAAAATTATTAAGTATGTAAGGTTGATACACGCGCGAA TTGAGCCGGCCCACTTTTAGTTTCAATTTGAAACAGTCTCAATCAAGACCAA TTATTTATTATTTTATTATTTTATTGTTTAAGCTCAATGGGTTGGACTTGATA AATTATATTTTGAGGAGACGGGCTATTAGTAAAATTAATAGTTGGAATCTTT TTTGATATACTATAAAAAGAGGTATCTGGTGGAGCCTTAAATCTGCGCAATT GAAGTCCTCAATACACATCTCGCTCTTCTTATTCTCTTTCATCTATTTCCTCCT TTGATCAAACTACGCCATGTCTCTCTTAAATGATCTCGTTAACCTTAATCTCT CTGAAACTACCGATAAGATTATCGCTGAATACATATGGTAATACAACAATCC TTCCTCTTTTTCATTT | 234 |

TABLE 22-continued

| Gene Name | Sequence | SEQ ID NO. |
|---|---|---|
| GS5 | AAAAAACCGTCTTATTTGTAGAAAATAAAAAACTAAAAAGTAGTATCAACTT<br>TTAGACTAGTCATAAGTGAGTGGCATCAAACTTGTTCTATAAAAGGGAAGA<br>GTTCCTCAACTTGAGATTCATATTTTTTGTGATTTCTAAATAGAAGAACATAC<br>TCATCTTCCACTTCTCTTATTCATCAAATTTTATTTGTTCCCAAAAAAAACAT<br>GTCTCTTCTTACAGATCTCATCAATCTTAATCTTTCTGACTCCACTGAGAAGA<br>TCATTGCTGAATACATATGGTCAGTTTTCATCCCTTTTTTTTACCTTTAATCCC<br>ACTTTTTGTTTTTACCCACCATTTTTTTCATCTATTTTCTCTTAAAGATTTTAA<br>CTTTTTACTTTTTTGTGTATATAACATTCATTTTTTCAATTGGGTAGGTTAGAA<br>AATTTCTATAAATAAATAAATAAATNNNNNNNNNTACCTTAATCCCACTTTT<br>TGTTTCTACCCACCATTTTTTTCATCAATTTTTCTTAAAGATTTTAACTTTTTTT<br>AACTTTTTCTTGGTTTTTGTGTATATACCAATCATTTATTTTCACTAGTGTAGG<br>TTAAAAAATATCTAAAAATAAATAAAATAGAATAAAAATGTAATCACTAGA<br>TTAACCCATGAATTATTTCCCTTGTTTTTACTCAAACTTTTTACCCTTGTTAAA<br>AAAATAATGATATAAATAAATTTTTGAGGGTTTGTTAAACCCATATGTAATC<br>TATATCGAAAAAATTAGATAGCGGGTTTTGTTGTGGACAAACTAAATAACAA<br>ATTTAGGAATAAACTTTTGAGGGTTTATTGAAAAAATAACCCCATATTTAATC<br>TATATCGAAAAAATGATAGCGAGCTTTGTATAGAT | 235 |
| HPPD | CGTCGAAGTAGAAGACGCGGAAGCTGCTTTTAACATCAGCGTTTCGCATGGG<br>GCTATTCCCTGTGTTTCTCCTATTCAATTGGAAAACGGTGTCGTTTTATCTGA<br>GGTTCATTTATATGGGGATGTTGTGCTTCGGTATGTAAGCTACGGAAATGAA<br>TGTGGGGATGTGTTTTTTCTTCCTGGGTTTGAGGAAATGCCGGAGGAATCAT<br>CGTTTAGAGGACTTGATTTTGGCATTCGAAGGTTGGATCATGCTGTAGGGAA<br>TGTCCCTGAGTTGGCTCCTGCAATTGCTTATTTGAAGAAGTTTACTGGGTTTC<br>ATGAGTTTGCTGAGTTTACAGCTGAAGATGTTGGGACGAGTGAAAGTGGATT<br>GAATTCAGCCGTATTGGCAAACAATGATGAAATGGTGTTGTTTCCGATGAAT<br>GAACCTGTGTATGGGACAAAAAGGAAGAGCCAAATTCAAACTTATTTGGAG<br>CATAATGAAGGGCTGGTGTACAGCATTTGGCTTTGATGAGTGAAGACATAT<br>TTTGGACTTTAAGGGAGATGAGGAAGAGAAGTGTTCTTGGTGGGTTTGAGTT<br>TATGCCGTCGCCGCCTCCGACTTATTACCGGAATTTGAGGAACAGAGCTGCT<br>GATGTATTGAGTGAGGAGCAGATGAAGGAGTGTGAAGAGTTGGGGATTTTG<br>GTGGATAAAGATGATCAGGGCACTTTGCTTCAAATCTTCACCAAACCTATTG<br>GAGACAGGTAAATTTTAATCTTGCTTTCAATTGCTTTTGCTTGATGGATTGAC<br>TAGCAAATTTGATCGCATTTTGTTGCTTATATGACTTGATGATACTTCCTCTG<br>TTTCGAAATACTCGCTACATTCGCTACATTTTGTTTTGTGCACTATTCATCGTT<br>CAAGCTTATTTTACATATTGCGACTAATGTGTAACTAAAAATATAGTCAAGT<br>GGGATCTTGTTTGAATCGTCTAATGGCATACTTTCATCATATTAAATTTTTAT<br>AATTTTTAGATTAGTGTAGTTTAAGATATTAATGCTCAAAATTGTGCATTGGA<br>TTGCGTAAAAAAGTGAAATGTAGCAAGTATTATGAAA | 236 |
| PDS | AAAACCAAAGGAAATAAGTTATAGGTAGGAAAAATTGTTATTGAAGTTAAT<br>GTAGTAAACTAGTAACTTAAACTGTGATACCCCGGATTTAGCTTAAAAAGAG<br>ATTGATAGACTACTCATATCAACAAGGTGCATCTTCTTTTCTAGGGAGCCCAT<br>TTGCTAAGAACTCTACAGTTAAGCGTGCTTGGTGGGAGCAATCTTAGGATG<br>GGTGACCTCCTGGGAAGTTTTCCTGGGTGCGCACGGGTGAGGCCAAAGTGCG<br>TTAAAAAGACTTGTGTTGGTCTGTGGGGCTTGTCTACAGTCTCCATGAGTAGT<br>CACCGGCGGTACGAGAGGCCGGGGTGTTACATAAACAGACTCAAAGGCGCT<br>AAGCCAAGTAGCCAATAGCAACATGTGTGGCCTGCGGACAGTCACAAAAC<br>ACACAATTTCTTATTTTTACTCTCTTTTATCTCTTTTAGGCTTTAGCCATCAAC<br>AATAAAACAACATGATAAAGCAATTCATTTACTGCTAAATTCCAACAATTTG<br>GTCCCTTTTTCCTGTTCTTTCAGTTTCACATACCCTCTTATCAATCTATATCCA<br>AAACCTATTTCATTTTCCAAACTCTTTTAAACCCAAAAATCAAAACTTTTGATT<br>GAAGAACAAACTTTGGGGGTTTTGGAAAATGAGTCATTTTGGATATGCTTGT<br>GCTACTCAATCCACATCAAGATATGTTCTTTTAGGAAATTCAAATAACCCCA<br>CTTCAATTTCATCTATTGGAAGTGATTTTTTGGGTCATTCTGTGAGAAATTTC<br>AGT | 237 |
| PPOX | TGGTACCTACCCTGTTTACATTTTCAATTTCCCCCTTTTTTCTCTACTACTCCT<br>ACTTTATTGATTCTTATCCATGTGTGTTCTATGGGAATTGACATTAATTGTTC<br>AGGTGTGTATGCTGGTGATCCTTCTAAGTTGAGTATGAAAGCTGCATTTGGA<br>AAGGTCTGGACCTTAGAGCAAAAGGGTGGTAGTATCATTGCCGGTACACTCA<br>AAACTATTCAGGAAAGGAAGAATAATCCTCCACCGCCTCGAGACCCGTCCGT<br>AATCACCATTACTCATTGCTTTCCTTCACCTTGTATCTTACCTTAATATACATG<br>TATTTAATTGATAATGTCACATTGCCTCATTTGCAGCCGCCTTCCTAAACCTA<br>AGGGCCAGACTGTTGGATCCTTTAGGAAAGGGCTCATTATGTTACCTACCGC<br>CATTGCTGCTAGGTATCTTTTGACTCTCAAATCTTAAATATTTCTCATCTTCTC<br>CTTCTGCTAATACTAGTATGTTTACCATCTTTTTATTTTTTAGGCTTGGCAGT<br>AAAGTCAAACTATCGTGGACACTTTCTAATATTGATAAGTCGCTCAATGGTG<br>AATACAATCTCACTTATCAAACACCCGATGGACCGGTTTCTGTTAGGACCAA<br>AGCGGTTGTCATGACTGTCCCTTCATACATTGCAAGTAGCCTGCTTCGTCCGC<br>TCTCAGTGAGTATCATTCCTTCCTTCATTTCTTTTCGTTTATTGTTGTCCAATG<br>TCTTGTTAAACACCAGTTTGGCCTTGTGCTCGTGAATTATGGCTACAATGTTA<br>ACTGATTCAGGCACTGTGGGAGATGCCTAAGTTTCTAAAACCTCTGCGCATA<br>ATGTTTGTTTGGATGTTAGGAATTGCATTGAAAAATTGCTTTTGTGATGTTGA<br>TGTTAATACCAATTACAAGTGTGTTCTTCAACTTCTGCAATACCTTGTTCGAG<br>TGAGCTTGAGGGGGTTTAGATTAGTGTCCAATGTGAAACTAGCAAATGAACT | 238 |

TABLE 22-continued

| Gene Name | Sequence | SEQ ID NO. |
|---|---|---|
| | CCAAGCGCTGGGATAGGTCCTTGGGATGGAGCCCCTGATACCCAAGACAGT<br>ATTCAAACCCTCTAAGTAGAGTGAGAGATCAAGGAAAGAAACTGGGTGGTT<br>CCTCAAATCGTAAAAAATGAATACAGTGTCATGATTGCTAATCTTATCACAA<br>ATCGTAAAAAATGAATTATGGTCGATTTTGGACTATTTTTGGGTCATTTTGAG<br>TGAATCTCGAACTTAAAAAGCGAGTCTTCTAGCAGTTCTTGTTACAGCGGGG<br>CATACATAGGTAGGAATTTGGTTTTTTACTATTTGAGCCTTTTGACTGTTGTG<br>GCCGGTAATATGGAATAGTCTAGCACTTCTGCGTGTGTACAACTAGTATTTA<br>TTGTAATTATGTGATCGCACTTAACTCTCAGATAAAACCTTAAGCACTAACA<br>TTTTGTTTTGGTTGAAGGAATCAGGAGGAAAGAAAATTGAGGGATTTGTTGG<br>TATATAGATTCCTTTGTTTGGATAACAAAATTGGAGTGGAGAGATTTGGAAG<br>GAAGAATTTTATAGGGATTAGTTCCCATTACACTTATGTTGATTACAAAATTT<br>CTCCAAAAGTGGAAAGATTTTGAGTGAAAATGTTTTTTATTTCTCTTCCTCTC<br>CCTTTCTTTCCCTCTTAAACAAACAAGGAAAGTTAATCTTATCATTCCGTACC<br>TTCCCCTTCTGTTCTTTTTTTTCTCTCCAAAATTCTTATCCTAACGTAGTGTTA<br>TTGTCACTGTCTTATGAACGAGAATTCTTTTCTTCCTAATACTGCTTGTGTTGC<br>ACAGTCAATGATTTAGCTAGATCATCTTTGGTTAGCTACTCAAATATTTACA<br>TAAAATACTTGTAGAAATAAATACCAATAGGTCTTGTCAAGAAGTAGTTTCA<br>ATGCTATAAGTTTTAACCAATCCTCAAAATTTACACCATGGAGATATCTGCG<br>GATAAGAACTAGTAACTGTAGCAGCTGTAACTGTTGCAATCAGTTTTATGGT<br>TTGCCTTGCAAATCAAACTTTGGATGTTGTTTGCCTTACAATTTGTTACTATT<br>ACGTGAAGTTTAGTGTTCGCCCTTCACATTGTACTTTGGTTTTTGTTTTCCTTG<br>CAATTTGCTCTTTGAAGTATAAAGTGCTGAGTGCTGAGTGCTGAGTGCTGAC<br>CTTTCCTGCTCAGGATGTTGCTGCAGATTCTCTTTCTCAATTTTACTATCCACC<br>AGTCGCAGCAGTGTCCCTTTCTTATCCCAAAGAAGCAATTAGACCAGAATGC<br>TTGATCGATGGAGAACTAAAAGGATTCGGGCAATTGCATCCTCGCAGCCAGG<br>GTGTGGAAACCTTGGGTATATGCTCCCATTCAACTATATCTCAATTTTTATGA<br>GTATTTTTCTTTCTCTGAATTATTCAATTTGGTGACGTTAAATTTTGATTGTAC<br>TCGACAGGAACAATTTATAGTTCATCTCTTTTCCCTGGTCGAGCACCACCTGG<br>TAGGACCTTGATCTTGAGCTACATTGGAGGTGCTACAAATGTTGGCATATTA<br>CAAAAGGCAAGTCATTTATACAATTATATCTGTTGTATCCTCAAATAAGTGG<br>GTATCAATCCTGACGACATGCTTGCTTGTATCGATGCAGAGTGAAGATGA | |

Example 31

This example illustrates a polynucleotide sequence that regulates gene expression in more than one plant species. Two highly conserved regions in EPSPS sequences from different weed species were identified and shown as the "Region 1" and "Region 2" sequences in Table 23.

TABLE 23

| Species/gene or consensus sequence | Region 1 | SEQ ID NO: | Region 2 | SEQ ID NO: |
|---|---|---|---|---|
| Euphorbia_heterophylla_1Contig1 | AGTTTACAGGGAGATGTAAAGTT | 239 | TCGATGTGAACATGAACAAAATGCCAGATGTCGCTATGACATTGGCTGTGGTTG | 251 |
| Euphorbia_heterophylla_2Contig1 | AGTTTGCAGGGAGATGTGAAATT | 240 | TCGATGTGAATATGAACAAAATGCCAGATGTTGCTATGACATTAGCTGTGGTTGC | 252 |
| Ambrosia_trifida_1Contig1 | AGTTTACAGGGGGATGTAAAGTT | 241 | TCGATGTTAACATGAACAAAATGCCAGATGTTGCCATGACGCTTGCAGTCGTTGC | 253 |
| velvetleaf_1Contig1 | AGTTTGCAGGGTGATGTAAAATT | 242 | TTGATGTCAACATGAACAAAATGCCAGATGTTGCCATGACTCTCGCTGTTGTTGC | 254 |
| Xanthium_strumarium_2Contig1 | AGTTTGCAGGGTGATGTGAAATT | 243 | TTGATGTCAACATGAACAAAATGCCTGATGTCGCAATGACTCTTGCTGTGGTTGC | 255 |
| Ipomoea_hederacea_1Contig1 | AGTTTACAGGGGGATGTTAAGTT | 244 | TTGATGTCAACATGAACAAAATGCCAGATGTTGCCATGACTCTTGCTGTAGTTGC | 256 |
| Chenopodium_album_1Contig1 | AGTTTACAGGGTGATGTAAAATT | 245 | TTGATGTCAACATGAACAAAATGCCAGATGTCGCAATGACTCTTGCTGTTGTTGC | 257 |

TABLE 23-continued

| Species/gene or consensus sequence | Region 1 | SEQ ID NO: | Region 2 | SEQ ID NO: |
|---|---|---|---|---|
| Digitaria_sanguinalis_1Contig1 | AGTTTGCAGGGTGATGTGAAATT | 246 | TTGACGTCAACATGAACAAAATGCCTGATGTCGCAATGACTCTTGCTGTGGTTGC | 258 |
| Senna_obtusifolia_1Contig3 | AGTTTACAGGGAGATGTAAAATT | 247 | TTGATGTCAACATGAACAAGATGCCAGATGTTGCCATGACGCTTGCTGTAGTTGC | 259 |
| Waterhemp_EPSPS | AGTTTACAGGGTGATGTAAAATT | 248 | TCGACGTCAACATGAATAAAATGCCAGATGTTGCTATGACTCTTGCAGTTGTTGC | 260 |
| Palmer_EPSPS | AGTTTACAGGGTGATGTAAAATT | 249 | TCGACGTCAACATGAACAAATGCCAGATGTTGCTATGACTCTTGCAGTTGTTGC | 261 |
| palmer_1Contig1 | AGTTTACAGGGTGATGTAAAATT | 250 | TCGACGTCAACATGAACAAATGCCAGATGTTGCTATGACTCTTGCAGTTGTTGC | 262 |

Table 24 lists 21-, 22-, 24-, 35-, 45-, and 55-mer dsRNA polynucleotide sequences designed based on the EPSPS consensus sequence for region 2, TNGANGTcAAcAT-GAAcAAaATGCCaGATGTNGCNATGACNcTtGCN GTNGTTGC (SEQ ID NO:263).

TABLE 24

| Name | Sequence | SEQ ID NO: |
|---|---|---|
| Consensus_21 mer dsRNA | Sense: AACAUGAACAAAAUGCCAGAU | 264 |
| | Anti-sense: AUCUGGCAUUUUGUUCAUGUU | 265 |
| Consensus_22 mer dsRNA | Sense: AACAUGAACAAAAUGCCAGAUG | 266 |
| | Anti-sense: CAUCUGGCAUUUUGUUCAUGUU | 267 |
| Consensus_24 mer dsRNA | Sense: CAACAUGAACAAAAUGCCAGAUGU | 268 |
| | Anti-sense: ACAUCUGGCAUUUUGUUCAUGUUG | 269 |
| Consensus_35 mer dsRNA | Sense: UCGACGUCAACAUGAACAAAAUGCCAGAUGUUGCU | 270 |
| | Anti-sense: AGCAACAUCUGGCAUUUUGUUCAUGUUGACGUCGA | 271 |
| Consensus_45 mer dsRNA | Sense: UCGACGUCAACAUGAACAAAAUGCCAGAUGUUGCUAUGACUCUUG | 272 |
| | Anti-sense: CAAGAGUCAUAGCAACAUCUGGCAUUUUGUUCAUGUUGACGUCGA | 273 |
| Consensus_55 mer dsRNA | Sense: UCGACGUCAACAUGAACAAAAUGCCAGAUGUUGCUAUGACUCUUGCAGUUGUUGC | 274 |
| | Anti-sense: GCAACAACUGCAAGAGUCAUAGCAACAUCUGGCAUUUUGUUCAUGUUGACGUCGA | 275 |

The EPSPS consensus dsRNA polynucleotides were synthesized by in vitro transcription and topically applied as crude RNA preparations. Gly (horseweed, sicklepod, crabgrass, morning glory, lambsquarter, *euphorbia*) tested.

Example 32

This example illustrates use of a topical polynucleotide treatment for transiently silencing a gene in a plant to effect a desired phenotype. Silencing polyphenol oxidase in plant tissues inhibits browning of cut or damaged plant tissues, a valuable trait for fruits and vegetables where resistance to browning is a desirable trait.

Anti-sense DNA oligonucleotides with the sequences shown in Table 25 were designed to target three polyphenol oxidase genes (PPO1, PPO2, and PPO3) from lettuce; the underlined text indicates T7 sequence that was included in the anti-sense polynucleotides.

TABLE 25

| Anti-sense oligo-nucleotide | Sequence (5'-3') | SEQ ID NO. | Length |
|---|---|---|---|
| HH07 | TAATACGACTCACTATAGGGCTTTATTGAATTTAGCTATGTAATC | 276 | 45 |
| HH09 | TAATACGACTCACTATAGGGTTTATCAACCAAATGTGCAGC | 277 | 41 |
| HH11 | TAATACGACTCACTATAGGGTTGTCTGTACATAATTGTGAGATTTGTGG | 278 | 49 |

Three-week old lettuce plants (variety SVR3603 L4) were treated as follows. Two source leaves (leaves that are older and are ~60% of their mature size) on each plant were pre-treated with 0.1% (v/v) SILWET L-77 and allowed to dry (~15 minutes). To each leaf 20 microliters of a mixture of the polyphenol oxidase anti-sense polynucleotides in a solution of 0.01% (v/v) SILWET L-77 and 2% (w/v) ammonium sulfate in 5 millimolar sodium phosphate, pH 6.8, were applied as small droplets; each plant was treated with 6.7 nanomoles of each of the three polynucleotides HH07, HH09, and HH11 (for a total of 20 nanomoles per plant). Control plants were treated either with an unrelated polynucleotide HH02-05 (anti-sense to phytoene desaturase) or with buffer (0.01% (v/v) SILWET L-77 and 2% (w/v) ammonium sulfate in 5 millimolar sodium phosphate, pH 6.8) alone.

Approximately 3 weeks after the topical polynucleotide treatment, "untreated" lettuce leaves (i. e., not those treated with the topical polynucleotides) were cut from the lettuce head under water and incubated in a cup with 1.33 millimolar methyl jasmonate in 5% ethanol. Leaves were inspected for central rib browning and photographed every 24 hours. Samples were taken from the remaining plants and frozen for small RNA and mRNA analysis Plants treated with the polyphenol oxidase anti-sense polynucleotides HH07, HH09, and HH11 showed significant reduction in central rib browning after treatment with methyl jasmonate. Plants treated with HH02-05 (anti-sense to phytoene desaturase) as a control showed a small reduction in central rib browning compared to the buffer-treated control.

Example 33

This example illustrates an herbicidal composition adapted for topical coating onto the exterior surface of a growing plant comprising surfactant and at least one plant lethal agent, the improvement wherein the plant lethal agent includes polynucleotides having a sequence essentially identical or complementary to sequence of a plant gene or sequence of the plant gene's transcribed RNA, the polynucleotides effecting systemic suppression of the plant gene. More specifically this example illustrates an herbicidal composition adapted for topical coating onto the exterior surface of a growing plant comprising surfactant and at least one plant lethal agent, the improvement wherein the plant lethal agent includes polynucleotides effecting suppression of the endogenous phytoene desaturase (PDS), 5-enolpyruvylshikimate-3-phosphate synthase (EPSPS), or ribulose-1,5-bisphosphate carboxylase oxygenase (RuBisCO) genes from *Nicotiana benthamiana*. This example also illustrates the use of topically applied polynucleotides to suppress a very highly expressed gene (ribulose-1,5-bisphosphate carboxylase oxygenase) in a plant.

An anti-sense polynucleotide with the sequence CATCTCCTTTAATTGTACTGC (SEQ ID NO:34) was designed for the endogenous *Nicotiana benthamiana* phytoene desaturase (PDS) gene, which has the cDNA sequence fragments

```
                                             (SEQ ID NO: 38)
ATGCCCCAAATCGGACTTGTATCTGCTGTTAATTTGAGAGTCCAAGGTAA

TTCAGCTTATCTTTGGAGCTCGAGGTCTTCGTTGGGAACTGAAAGTCAAG

ATGTTTGCTTGCAAAGGAATTTGTTATGTTTTGGTAGTAGCGACTCCATG

GGGCATAAGTTAAGGATTCGTACTCCAAGTGCCACGACCCGAAGATTGAC

AAAGGACTTTAATCCTTTAAAGGTAGTCTGCATTGATTATCCAAGACCAG

AGCTAGACAATACAGTTAACTATTTGGAGGCGGCGTTATTATCATCATCG

TTTCGTACTTCCTCACGCCCAACTAAACCATTGGAGATTGTTATTGCTGG

TGCAGGTTTGGGTGGTTTGTCTACAGCAAAATATCTGGCAGATGCTGGTC

ACAAACCGATATTGCTGGAGGCAAGAGATGTCCTAGGTGGGAAGGTAGCT

GCATGGAAAGATGATGATGGAGATTGGTACGAGACTGGGTTGCACATATT

CTTTGGGGCTTACCCAAATATGCAGAACCTGTTTGGAGAACTAGGGATTG

ATGATCGGTTGCAGTGGAAGGAACATTCAATGATATTTGCGATGCCTAAC

AAGCCAGGGGAGTTCAGCCGCTTTGATTTTCCTGAAGCTCTTCCTGCGCC

ATTAAATGGAATTTTGGCCATACTAAAGAACAACGAAATGCTTACGTGGC

CCGAGAAAGTCAAATTTGCTATTGGACTCTTGCCAGCAATGCTTGGAGGG

CAATCTTATGTTGAAGCTCAAGACGGTTTAAGTGTTAAGGACTGGATGAG

AAAGCAAGGTGTGCCTGATAGGGTGACAGATGAGGTGTTCATTGCCATGT

CAAAGGCACTTAACTTCATAAACCCTGACGAGCTTTCGATGCAGTGCATT

TTGATTGCTTTGAACAGATTTCTTCAGGAGAAACATGGTTCAAAAATGGC
```

-continued

```
CTTTTTAGATGGTAACCCTCCTGAGAGACTTTGCATGCCGATTGTGGAAC
ATATTGAGTCAAAAGGTGGCCAAGTCAGACTAAACTCACGAATAAAAAAG
ATCGAGCTGAATGAGGATGGAAGTGTCAAATGTTTTATACTGAATAATGG
CAGTACAATTAAAGGAGATGCTTTTGTGTTTGCCACTCCAGTGGATATCT
TGAAGCTTCTTTTGCCTGAAGACTGGAAAGAGATCCCATATTTCCAAAAG
TTGGAGAAGCTAGTGGGAGTTCCTGTGATAAATGTCCATATATGGTTTGA
CAGAAAACTGAAGAACACATCTGATAATCTGCTCTTCAGCAGAAGCCCGT
TGCTCAGTGTGTACGCTGACATGTCTGTTACATGTAAGGAATATTACAAC
CCCAATCAGTCTATGTTGGAATTGGTATTTGCACCCGCAGAAGAGTGGAT
AAATCGTAGTGACTCAGAAATTATTGATGCTACAATGAAGGAACTAGCGA
AGCTTTTCCCTGATGAAATTTCGGCAGATCAGAGCAAAGCAAAAATATTG
AAGTATCATGTTGTCAAAACCCCAAGGTCTGTTTATAAAACTGTGCCAGG
TTGTGAACCCTGTCGGCCCTTGCAAAGATCCCCTATAGAGGGTTTTTATT
TAGCTGGTGACTACACGAAACAGAAGTACTTGGCTTCAATGGAAGGTGCT
GTCTTATCAGGAAAGCTTTGTGCACAAGCTATTGTACAGGATTACGAGTT
ACTTCTTGGCCGGAGCCAGAAGATGTTGGCAGAAGCAAGCGTAGTTAGCA
TAGTGAACTAA.
```

Anti-sense polynucleotides with the sequences CTGTGATCAT-CATATGTATCA (SEQ ID NO:279), CCTTAACTCTCCAGCTAGCAA (SEQ ID NO:280), CAGCCCGCAAATGTTTCATTC (SEQ ID NO:281), GCCGTCAATGGCCGCATTGCT (SEQ ID NO:282), TCCTTCCCTCAGAAAGGGCAG (SEQ ID NO:283), and TTGCCT-CATGCTGCTAATCTG (SEQ ID NO:284) were designed for the endogenous *Nicotiana benthamiana* 5-enolpyruvylshikimate-3-phosphate synthase (EPSPS) gene, based on the *Nicotiana benthamiana* EPSPS cDNA sequence

```
                                            (SEQ ID NO: 285)
CTTATATGTGCTTAAGCCTAACGTGCACCCGGCCCCTTAACCCCAGCAGT
TTTCAATCTACCTACCGTCTCTACCATTTTCTTCTAGTTGGTGAAAATTT
CTAACTTTGAGAAAACAAGCCAAAGTTTTGTTTCTAAGAACGCAAAATG
AGTGAAATTTTTTGCAGCAATGGCACAGATTAGCAGCATGAGGCAAGGA
TACAGACCCCTAATCTTAATTCCTATTTTCCTAAAACCCAAAAGGTTCCT
CTTTTTTCGCATTCTATCTTCTTTGGATCAAAGAAAATAACCCAAAATTC
AGCAAAATCTTTGTGGGTGTGTAAGAAAGATTCAGTTTTGAGGGTGGCAA
AGTCACCTTTTAGGATTTGTGCATCAGTGGCCACTGCACAGAAGCCCAAC
GAGATTGTGCTGCAACCCATCAAAGATATATCAGGCACTGTTAAATTGCC
TGGTTCTAAATCCCTTTCCAACCGTATTCTCCTTCTTGCTGCCCTTTCTG
AGGGAAGGACTGTTGTTGACAATTTACTGAGTAGTGATGACATTCATTAC
ATGCTTGGTGCGTTGAAAACACTTGGACTTCATGTAGAAGATGACAATGA
AAACCAACGAGCAATTGTGGAAGGTTGTGGTGGGCAGTTTCCTGTCGGCG
AGAAGTCTGAGGAAGAAATCCAACTATTCCTTGGAAATGCAGGAACAGCA
ATGCGGCCATTGACGGCAGCAGTTACTGTAGCTGGAGGACATTCAAGATA
TGTACTTGATGGAGTTCCTAGGATGAGAGAGAGACCGAT,
```

```
                                            (SEQ ID NO: 286)
CACTGACGTTGGATTAGAGGTAGGCTCCTTATATGTGCTTAAGCCTAACG
TGCAGCCGGCCCCCAACCCCAGCAGTTTTCAATCTACCTACCGTCTCTAC
CATTTTCTTATAGTAGTTGAAAATTTCTAACTTTGAGAAAACAAGCCAAA
GTTTTGTTTCTAAGAACACAAAGGGAGTGAAATTTTTTGCAGCAATGGCA
CAGATTAGCAGCATGAGGCAAGGGATACAGACCCCTAATCTTAATTCCTA
TTTTCCTAAAACCCAAAAGGTTCCTCTTTTTTCGCATTCTATCTTCATTG
GATCAAAGAAAATAACCCAAAATTCAGCAAAATCTTTGTGGGTGTGTAAG
AAAGATTCAGTTTTGAGGGTGGCAAAGTCACCTTTTAGGATTTGTGCATC
AGTGGCCACTGCACAGAAGCCTAACGAGATTGTGCTGCAACCTATCAAAG
ATATATCAGGCACTGTTAAATTACCTGGTTCTAAATCCCTTTCCAATCGT
ATTCTCCTTCTTGCTGCCCTTTCTGAGGGAAGGACTGTTGTTGACAATTT
ACTGAGTAGTGATGACATTCATTACATGCTTGGTGCATTGAAAACACTTG
GACTTCATGTAGAAGATGACAATGAAAACCAACGAGCAATCGTAGAAGGT
TGTGGTGGGCAGTTTCCTGTCGGCAAGAAGTCTGAGGAAGAAATCCAACT
ATTCCTTGGAAATGCAGGAACAGCAATGCGGCCATTGACGGCAGCAGTTA
CTGTAGCTGGTGGACATTCTAGATATGTACTTGATGGAGTTCCTAGGAT,
and
```

```
                                            (SEQ ID NO: 287)
AAATTCTTGGTTCGAGGAGGTCAGAAGTACAAGTCTCCTGGAAAAGCATA
TGTTGAAGGAGATGCCTCAAGTGCTAGCTACTTTTTGGCGGGTGCAGCTG
TCACAGGTGGAACTGTCACTGTTGAAGGTTGTGGAACAAGCAGTTTACAG
GGGGATGTTAAGTTTGCTGAGGTCCTCGAAAAGATGGGGCAGAAGTTAC
ATGGACAGAGAACAGTGTCACGGTTAAAGGACCTCCAAGGAACTCTTCTG
GAATGAAACATTTGCGGGCTGTTGACGTTAACATGAACAAAATGCCAGAT
GTTGCCATGACTCTTGCTGTAGTTGCACTTTTTGCTGATAGTCCTACTGC
CATAAGAGATGTTGCTAGCTGGAGAGTTAAGGAAACTGAGCGGATGATTG
CCATATGCACAGAACTTAGGAAGTTGGGTGCAACAGTTGTAGAAGGGCCA
GACTACTGCATAATCACTCCACCTGAAAAGTTAAAAGTAGCGGAAATTGA
TACATATGATGATCACAGAATGGCCATGGCTTTCTCTCTTGCGGCTTGTG
CTGATGTTCCAGTCACCATTAAGGACCCCGGTTGTACTCGCAAAACCTTC
CCCAACTACTTTGACGTTCTCCAGCAGTATTCCAAGCATTAAACCACTTT
CCATTAAGAATTTTGAAAAAGAGAGACTTTGACAACAATGGTGTCATACC
GGAAGAGAAAAGCTTTGATCCAAGCTTTCAACTCCTTTTCATTTGTCATG
TGATGATCATTGTATTTGTTGAAGTTGAGCTGCTTTTCTTTTGTCCAGAA
GACATGTATGGATACTATTACTATATAGTTAAGGTGAACTCAGCA.
```

Anti-sense polynucleotides with the sequences CCA-CATGGTCCAGTATCTGCC (AK195, RBCS_1-2-3-4, SEQ ID NO:288), CAAGCAAGGAACCCATCCATT (AK196, RBCS_1-2-3-4, SEQ ID NO:289), GGCCACACCTGCATGCATTGC (AK197, RBCS_1-2-3-4, SEQ ID NO:290), GTGTTCACGGTAGACAAATCC (AK198, RBCS_1-2, SEQ ID NO:291), TGCACTGCACTTGACGCACGT (AK199, RBCS_1-2, SEQ ID NO:292), AACTGATGCATTGCACTTGAC (AK200, RBCS_3-4, SEQ ID NO:293), CAAATCAGGAAGGTATGAGAG (AK201, RBCS_3-4, SEQ ID NO:294), and TGTCAAGGTTTTGTTTCCTGG (AK202, RBCS_3-4, SEQ ID NO:295) were designed for the endogenous *Nicotiana benthamiana* ribulose-1,5-bisphosphate carboxylase oxygenase (RuBisCO) gene, based on the *Nicotiana benthamiana* chloroplastic RuBisCO small chain 2A cDNA sequence fragments (SEQ ID NO: 296)
GCAATGGCTTCCTCAGTTCTTTCCTCAGCAGCAGTTGCCACCCGCAGCAA

TGTTGCTCAAGCTAACATGGTTGCACCTTTCACAGGTCTTAAGTCTGCTG

CCTCATTCCCTGTTTCAAGAAAGCAAAACCTTGACATCACTTCCATTGCC

AGCAACGGCGGAAGAGTGCAATGCATGCAGGTGTGGCCACCAATTAACAT

GAAGAAGTATGAGACTCTCTCATACCTTCCCGATTTGAGCCAGGAGCAAT

TGCTCTCCGAAATTGAGTACCTTTTGAAGAATGGATGGGTTCCTTGCTTG

GAATTCGAGACTGAGAAAGGATTTGTCTACCGTGAACACCACAAGTCACC

AGGATACTATGATGGCAGATACTGGACCATGTGGAAGCTACCTATGTTCG

GATGCACTGATGCCACCCAAGTGTTGGCTGAGGTGGGAGAGGCGAAGAAG

GAATACCCACAGGCCTGGGTCCGTATCATTGGATTTGACAACGTGCGTCA

AGTGCAGTGCATCAGTTTCATTGCCTCCAAGCCTGACGGCTAC, (SEQ ID NO: 297)
ACAATGGCTTCCTCAGTTCTTTCCTCAGCAGCAGTTGCCACCCGCAGCAA

TGTTGCTCAAGCTAACATGGTTGCACCTTTCACTGGTCTTAAGTCAGCTG

CCTTTTTCCCTGTTTCAAGGAAGCAAAACCTTGACATCACTTCCATTGCC

AGCAACGGCGGAAGAGTGCAATGCATGCAGGTGTGGCCACCAATTAACAA

GAAGAAGTACGAGACTCTCTCATACCTTCCTGATCTGAGCGTGGAGCAAT

TGCTTAGCGAAATTGAGTACCTCTTGAAAAATGGATGGGTTCCTTGCTTG

GAATTCGAGACTGAGCGCGGATTTGTCTACCGTGAACACCACAAGTCACC

GGGATACTATGACGGCAGATACTGGACCATGTGGAAGTTGCCTATGTTCG

GATGCACTGATGCCACCCAAGTGTTGGCCGAGGTGGAAGAGGCGAAGAAG

GCATACCCACAGGCCTGGATCCGTATTATTGGATTCGACAACGTGCGTCA

AGTGCAGTGCATCAGTTTCATTGCCTACAAGCCAGAAGGCTAC, (SEQ ID NO: 298)
CAAGCCAACATGGTTGCACCCTTCACTGGCCTCAAGTCCGCCTCCTCCTT

CCCTGTTACCAGGAAACAAAACCTTGACATTACCTCCATTGCTAGCAATG

GTGGAAGAGTTCAATGCATGCAGGTGTGGCCACCAATTAACATGAAGAAG

TACGAGACACTCTCATACCTTCCTGATTTGAGCCAGGAGCAATTGCTTAG

TGAAGTTGAGTACCTTTTGAAAAATGGATGGGTTCCTTGCTTGGAATTCG

AGACTGAGCGTGGATTCGTCTACCGTGAACACCACAACTCACCAGGATAC

TACGATGGCAGATACTGGACCATGTGGAAGTTGCCCATGTTCGGGTGCAC

TGATGCCACTCAGGTGTTGGCTGAGGTCGAGGAGGCAAAGAAGGCTTACC

CACAAGCCTGGGTTAGAATCATTGGATTCGACAACGTCCGTCAAGTGCAA

TGCATCAGTTTTATCGCCTCCAAGCCAGAAGGCTAC, and (SEQ ID NO: 299)
GGCTCAGTTATGTCCTCAGCTGCCGCTGTTTCCACCGGCGCCAATGCTGT

TCAAGCCAGCATGGTCGCACCCTTCACTGGCCTCAAGGCCGCCTCCTCCT

TCCCGGTTTCCAGGAAACAAAACCTTGACATTACTTCCATTGCTAGAAAT

GGTGGAAGAGTCCAATGCATGCAGGTGTGGCCGCCAATTAACAAGAAGAA

GTACGAGACACTCTCATACCTTCCTGATTTGAGCGTGGAGCAATTGCTTA

GCGAAATTGAGTACCTTTTGAAAAATGGATGGGTTCCTTGCTTGGAATTC

GAGACTGAGCATGGATTCGTCTACCGTGAACACCACCACTCACCAGGATA

CTACGATGGCAGATACTGGACGATGTGGAAGTTGCCCATGTTCGGGTGCA

CCGATGCCACTCAGGTCTTGGCTGAGGTAGAGGAGGCCAAGAAGGCTTAC

CCACAAGCCTGGGTCAGAATCATTGGATTCGACAACGTCCGTCAAGTGCA

ATGCATCAGTTTCATCGCCTACAAGCCCGAAGGCTAT.

Figure 36:
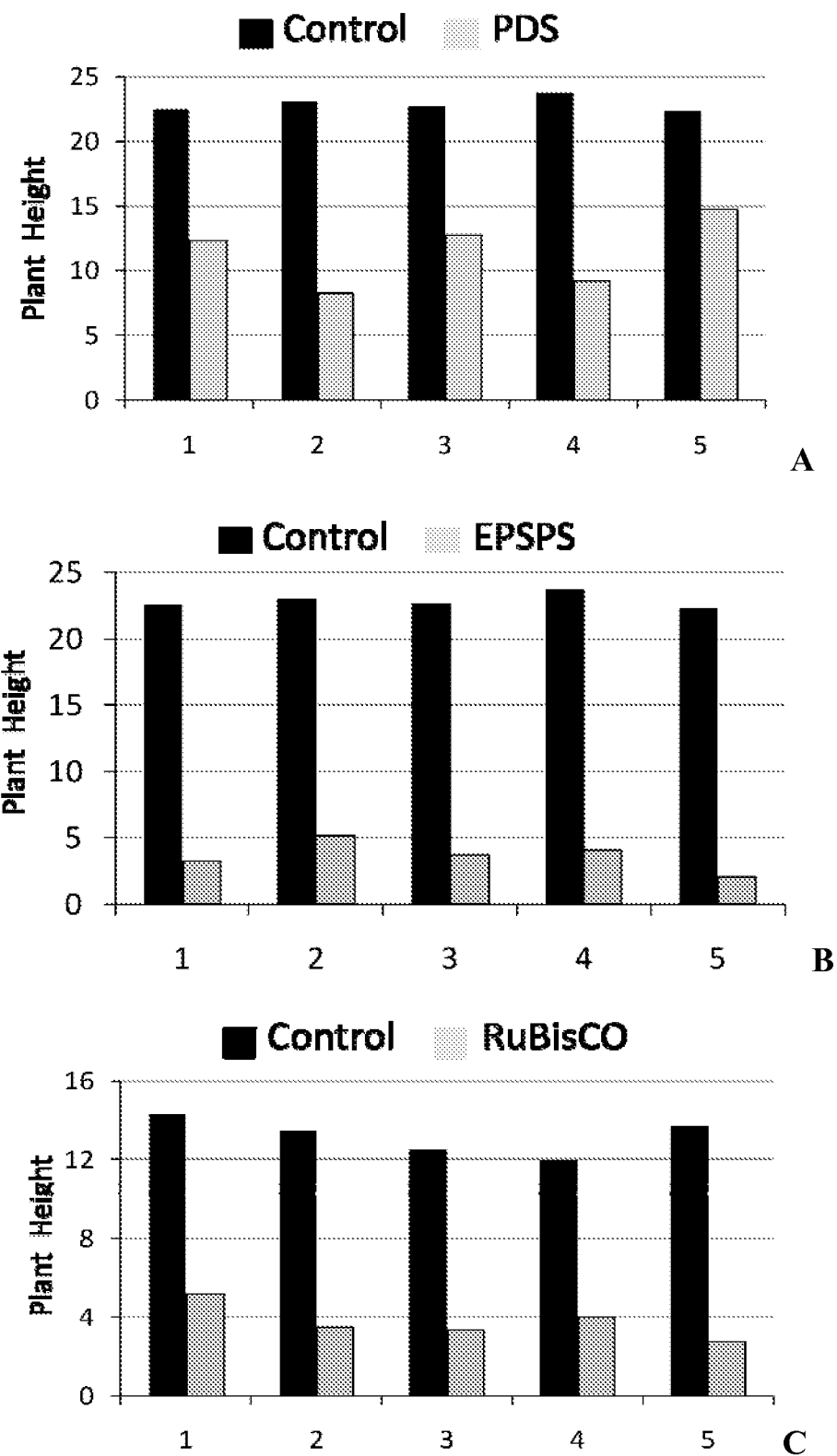
FIG. 36 illustrates the effect on plant height in *Nicotiana benthamiana* in plants treated with a PDS anti-sense polynucleotide (FIG. 36A), EPSPS anti-sense polynucleotides (FIG. 36B), or RuBisCO anti-sense polynucleotides (FIG. 36C), as described in Example 33.
Figure 37:
FIG. 37 illustrates the effect on *Zea mays* (Gaspe) monocot plants by topical treatment with dsRNA polynucleotides ("EPSPS DNA oligo") targetting the endogenous EPSPS gene, or with buffer alone as a control, as described in Example 34.

*Nicotiana benthamiana* plants were treated using a procedure similar to that described in Example 12. Polynucleotide solution (or mixed polynucleotides in the case of EPSPS and RuBisCO) were prepared in 0.01% (v/v) SILWET L-77 and 2% (w/v) ammonium sulfate in 5 millimolar sodium phosphate, pH 6.8. Two fully expanded leaves per plant were dipped into 0.1% SILWET L-77 solution freshly made with ddH2O for a few seconds, and allowed to dry. About 30 minutes later, 20 microliters of polynucleotide solution, was applied to each of the two pre-treated leaves. For PDS, each of 5 plants received 25 nanomoles of the PDS anti-sense polynucleotide (SEQ ID NO:34); for EPSPS, each of 5 plants received 50 nanomoles of each EPSPS anti-sense polynucleotide (SEQ ID NOS:279-284); and for RuBisCO, each of 5 plants received 50 nanomoles of each RuBisCO anti-sense polynucleotide (SEQ ID NOS:288-295). Paired control plants were treated with buffer (0.01% (v/v) SILWET L-77 and 2% (w/v) ammonium sulfate in 5 millimolar sodium phosphate, pH 6.8). The results measured as plant height at 12 days (PDS and EPSPS) or 10 days (RuBisCO) after treatment, are shown in FIGS. 36A-36B. Plants treated with the PDS anti-sense polynucleotide displayed severe stunting (FIG. 36A) and bleaching. Plants treated with the EPSPS anti-sense polynucleotides displayed severe stunting (FIG. 36B) and severe damage to the meristem and stem tissues. Plants treated with the RuBisCO anti-sense polynucleotides displayed severe stunting (FIG. 36C) and malformed apical tissues.

A second set of experiments was designed to investigate the effects of silencing a component of the endogenous RNAi silencing pathway in a plant. Argonaute (AGO) proteins are components of the RNA-induced silencing complex (RISC) which binds small RNAs in the RNAi silencing process. Suppression of Argonaute would be expected to reduce the observed phenotypic effect caused by an RNAi silencing process. AGO1 anti-sense polynucleotides with the sequences GGAGGCAAAATACGAGCCTCA (HL510, SEQ ID NO:300), CACTAATCTTAATACCAAACT (HL511, SEQ ID NO:301), TATGGGTCATTAGCATAGGCATTAT (HL512, SEQ ID NO:302), TCTCAAGAATATCACGCTCCC (HL513, SEQ ID NO:303), CCCTTGGGGACGCTGGCAGGTCAC (HL514, SEQ ID NO:304), TAATACGACTCACTATAGGGGGAGAGAGCTAGATCTTTTG (HL515, SEQ ID NO:305), TAATACGACTCACTATAGGCACAGTATTTCTTCCTCCAACC (HL516, SEQ ID NO:306), TTGCTCATCTTAAATACATGT (HL517, SEQ ID NO:307), TCATCTTAAATACATGTTTTGTCA (HL518, SEQ ID NO:308), TTATCTTCAGGGATACATTAGC (HL519, SEQ ID NO:309), AATACTGCTTGCTCATCTTAAATA (HL520, SEQ ID NO:310), GACAATTCCAAGTTCAGTTTC (HL521, SEQ ID NO:311), CCGTTTTAGATCACCATAAAGAGA (HL522, SEQ ID NO:312), TTGTCTGGTAATATCACAATC (HL523, SEQ ID NO:313) were designed for the endogenous *Nicotiana benthamiana* Argonaute-1 (AGO1) gene, based on two *Nicotiana benthamiana* AGO1-2 partial cDNA sequences, (SEQ ID NO: 314)
ATGGTGAGGAAGAGGAGAACTGAGTTACCTGGTTCTGGTGAGAGCTCTGGGTCTCAAGAAACTGGCG
GACAGGGTCGTGGCCAGCATCCACAGCAGCTGCACCAAGCTACCTCCCAGACTCCATATCAAACTGCA
ATGACTACTCAGCCAATACCTTATGCAAGACCAACTGAAACATCCTCCGAAGCTGGTTCCTCATCTCA
GCCACCTGAGCAGGCAGCTCTACAAGTGACACAACAGTTCCAGCAACTTGCTTTGCAACAAGAAGCGG
CTACAACGCAAGCAGTTCCACCTGCATCAAGCAAATTACTAAGGTTTCCCCTGCGTCCAGGGAAGGGG
AGCAATGGTATGAGATGCATAGTCAAAGCCAATCACTTCTTCGCAGAGCTGCCTGACAAAGACTTGCA
CCAGTATGATGTCACAATTTCTCCAGAGGTGTCATCACGTGGCGTCAACCGTGCTGTCATGGCGCAACT
GGTGAAGCTGTACCAAGAATCTCATCTTGGGAAGAGACTTCCAGCATATGATGGAAGGAAAAGTCTAT
ACACTGCAGGGCCCCTTCCATTTGTTCAAAAAGACTTCAAAATAACTCTTATTGATGATGAGGATGGG
CCTGGTGGTGCTAGAAGGGAAAGGGAATTTAAAGTTGTGATCAAATTGGCTGCCCGTGCTGATCTTCA
TCACTTGGGAATGTTTTTAGAAGGGAAACAGGCTGATGCACCTCAAGAGGCGCTTCAAGTTCTGGATA
TTGTTCTGCGTGAGTTGCCAACATCTAGGTTTTGTCCTGTGGGTCGTTCTTTCTATTCCCGTGATTTAGG
GCGAAAGCAACCATTGGGTGAAGGTTTAGAAAGTTGGCGTGGGTTCTATCAAAGCATTCGCCCCACAC
AAATGGGCTTATCACTGAACATCGATATGTCTTCCACTGCATTCATTGAGCCACTGCCAGTCATTGATT
TTGTGACACAGCTTCTGAACCGAGATGTGCCATCTAGACCACTGTCTGATGCTGGCCGTGTAAAGATA
AAAAAAGCTCTGAGAGGTGTGAAGGTGGAGGTTACTCATCGTGGAAATATGCGGAGGAAGTACCGCA
TTTCGGGTTTAACATCTCAAGCAACAAGAGAGTTGACCTTCCCTGTTGATGAAAATGGTACAGTGAAA
TCTGTAATTGAGTATTTTCGAGAAACATATGGGTTTGTAATTCAGCATACTCAGTGGCCTTGTCTACAA
GTTGGAAATCAGCAGAGACCTAATTACTTGCCAATGGAAGTCTGCAAGATTGTGGAGGGACAAAGGT
ACTCAAAGCGCTTGAATGAGAGACAGATTACTGCACTTCTGAAAGTGACCTGCCAGCGTCCCCAAGGG
AGGGAGCGTGATATTCTTGAGACCGTACATCATAATGCCTATGCTAATGACCCATATGCCAAGGAGTT
TGGTATTAAGATTAGTGACAAGTTGGCACAAGTTGAGGCTCGTATTTTGCCTCCACCTCGGCTTAAATA
TCATGATAACGGTCGAGAAAAGGACTGCCTGCCACAAGTTGGCCAATGGAATATGATGAATAAGAAA
ATGGTAAATGGAGGGACGGTGAACAATTGGATCTGCATAAACTTCTCTCGCAATGTGCAAGATAGTGT
TGCTCATGGGTTTTGCTCTGAGCTTGCACAAATGTGCCAGATATCTGGCATGAATTTCAATCCAAATCC
TGTTCTGCCACCTTCGAGTGCACGCCCTGATCAGGTCGAAAGAGTATTGAAAACTCGATTTCATGATGC
TATGACTAAGTTGCAGCTGCATGGGAGAGAGCTTGATTTGCTAGTTGTCATCTTGCCAGACAATAATG
GATCTCTTTATGGTGATCTGAAGCGCATTTGTGAGACTGAACTAGGAGTCGTCTCACAGTGCTGTTTGA
CAAAACATGTATTTAAGATGAGCAAACAGTATCTAGCCAATGTAGCGCTGAAAATCAATGTGAAGGTG
GGAGGGAGAAACACTGTGCTTGTTGATGCAATATCGAGGCGAATTCCTCTTGTCAGCGACCGGCCTAC
CATCATTTTGGTGCAGATGTCACCCACCCTCACCCTGGGGAGGACTCTAGCCCATCCATTGCCGCGGT
GGTTGCTTCTCAAGATTGGCCTGAGATTACAAAGTATGCTGGTCTAGTTTCTGCTCAAGCCCATAGGCA
AGAGCTTATTCAGGATCTGTACACGACTAGGCAAGATCCTGTTAAGGGGACAGTTGCTGGTGGAATGA
TTAAGGACTTACTTATATCCTTCCGAAGAGCTACTGGACAAAAGCCCCAGAGAATAATTTTCTATAGG
GATGGTGTTAGTGAAGGACAATTTTATCAAGTGCTTCTGTTCGAACTTGATGCGATCCGCAAAGCATGT
GCGTCTTTGGAGCCAAATTATCAGCCCCCAGTCACATTTGTTGTGGTTCAGAAACGACATCACACAAG
GCTTTTTGCCAATAACCACCGTGACAGAAATGCAGTTGACAGGAGCGGGAACATTATACCTGGTACTG
TTGTAGATTCAAAGATATGCCACCCGACAGAGTTTGATTTCTATCTTTGTAGCCATGCCGGCATACAGG
GTACGAGCCGTCCAGCTCACTACCATGTTCTATGGGACGAGAACAAATTCACAGCCGATGCGCTGCAG
TCTTTGACCAACAACCTCTGCTATACATATGCAAGGTGCACGCGTTCCGTCTCCATCGTTCCCCCTGCA -continued

TATTATGCACATTTGGCAGCTTTCCGTGCTCGATTTTATATGGAGCCGGAGACATCTGACGGTGGTTCA

GTAACAAGTGGGGCTGCTGGTGGCAGAGGGGGTGGTGCAGGAGCTGCTGGAAGGAACACCCGAGCCC

CAAGTGCTGGTGCTGCTGTTAGACCTCTTCCTGCGCTCAAGGATAATGTGAAGAGGGTTATGTTCTACT

GC and (SEQ ID NO: 315)
CACCTATCACTCTCTTTCTCTCTACAAACATATCGTGCCGTTTCTCTCTCGGCCTCTCTTCGTGTTTTA

GGGCACCGTGGTGGTTGGTATCCAGGCGGCGGTTTTGAGTTATTACCATGGTGCGGAAGAAGAGGACT

GATGTTCCTGGTGGTGCTGAGAGTTTTGAGTCCCATGAAACTGGAGGGGCACGAGGTGGTGCCCAACG

CCCATCACAGCAGCAGCAACATCAGCATCAGCAAGGCGGAGGAAGAGGCTGGGCACCTCAGCATGGA

GGACATGGTGGCCGTGGTGGTGGGGGAGCTCCACGTGGTGGAATGGCCCCTCAACAATCCTATGGTGG

ACCTCCTGAATACTACCAACAGGGCAGGGGAACTCAACAGTATCAACGAGGTGGAGGACAACCCCAG

CGCCGTGGTGGCATGGGGGGCCGTGGGGCACGGCCACCAGTACCCGAGCTGCACCAAGCAACCCAGA

CTCCACATCAGCCTGTACCATATGGAAGACCATCAGAAACATACTCAGAGGCTGGTTCCTCGTCTCAG

CCACCTGAACCAACGACACAGCAAGTGACTCAGCAATTCCAGCAACTTGTTGTGCAGCCAGAAGCAGC

TGCAACCCAAGCAATACAACCAGCATCGAGCAAGTCGATGAGGTTTCCACTCCGGCCAGGAAAGGGT

AGTACTGGTATTAGATGCATAGTTAAGGCCAATCACTTCTTTGCCGAGTTACCTGACAAAGATCTGCAC

CAGTATGATGTTTCAATTACTCCTGAGGTCGCCTCTCGGGGTGTCAACCGGGCCGTCATGGAGCAGCT

GGTGAAGCTTTATAGAGAATCCCATCTTGGGAAGAGGCTTCCAGCCTATGACGGAAGAAAAGTCTAT

ACACAGCAGGGCCCCTCCCTTTTGTTCAAAAGGATTTTAAAATCACTCTAATTGATGATGATGATGGAC

CTGGTGGTGCTAGGAGGGAAAGAGAGTTTAAAGTTGTGATCAAGCTGGCGGCTCGTGCTGATCTTCAT

CACTTGGGGATGTTCTTACAAGGGAGACAGGCTGATGCACCGCAAGAAGCACTTCAGGTGCTGGATAT

TGTGCTACGTGAGTTGCCAACATCTAGGTATTGTCCTGTGGGCCGCTCTTTCTATTCCCCTCATTTAGGA

CGAAGACAACCACTGGGTGAAGGTTTAGAGAGCTGGCGTGGCTTCTATCAAAGTATTCGTCCTACACA

GATGGGATTATCCCTGAATATTGATATGTCTTCCACGGCTTTCATTGAGCCACTGCCGATTATTGACTT

CGTGAGCCAGCTTCTGAATCGGGATATCTCTTCTAGACCACTGTCTGATGCTGACCGCGTTAAGATAAA

GAAGGCACTGAGAGGTGTAAAGGTGGGGGTCACTCATCGTGGAAATATGCGGAGGAAGTATCGCATT

TCTGGCTTGACGTCTCAAGCAACAAGAGAGTTGACTTTTCCTGTCGATGAAAGGGGTACGATGAAAGC

TGTTGTGGAATATTTTCGGGAAACCTATGGTTTTGTCATTCGGCATACCCAGTGGCCTTGTCTTCAAGT

TGGAAATACGCAGAGGCCAAATTACTTGCCAATGGAAGTATGTAAGATTGTAGAGGGACAGAGATAC

TCAAAGCGCTTGAATGAGAGGCAGATAACAGCACTTCTAAAAGTGACCTGCCAACGTCCTCAAGAGA

GAGAACGTGATATTCTTCAGACTGTTCATCACAATGCTTATGCTGATGACCCATATGCGAAGGAGTTTG

GTATTAAGATCAGTGAGGAGCTTGCTCAAGTTGAGGCTCGCGTTTTGCCTGCACCTTGGCTTAAATACC

ATGATACAGGTCGAGAGAAAGACTGTCTGCCACAAGTGGGCCAGTGGAATATGATGAATAAGAAAAT

GGTTAATGGAGGAACAGTGAACAACTGGATCTGTGTAAACTTTTCTCGCAATGTGCAAGACACAGTTG

CACGTGGATTTTGTTCCGAGCTTGCACAAATGTGCATGATATCCGGAATGAACTTCAATCCCAATCCTG

TTCTACCACCAGTGAGTGCTCGCCCTGATCAAGTTGAGAGAGTCTTGAAAACTCGATTTCACGATGCTA

TGACAAAGTTGCAGCCAAATGGGAGAGAGCTAGATCTTTTGATTGTGATATTACCAGACAATAACGGC

TCTCTTTATGGTGATCTAAAACGGATTTGTGAAACTGAACTTGGAATTGTCTCACAATGCTGCTTGACA

AAACATGTATTTAAGATGAGCAAGCAGTATTTAGCTAATGTATCCCTGAAGATAAATGTGAAGGTTGG

AGGAAGAAATACTGTGCTGGTTGATGCGCTCTCTAGACGAATTCCCCTTGTCAGCGACCGCCCAACTA

TCATTTTTGGTGCAGATGTCACCCATCCCCACCCTGGGGAGGATTCTAGCCCGTCAATTGCTGCGGTGG

-continued

```
TTGCTTCTCAAGATTGGCCTGAAATTACAAAGTATGCTGGTTTGGTTTCTGCTCAAGCGCATAGGCAAG

AGCTTATACAAGATCTGTACAAGACTTGGCAAGATCCAGTTAGAGGACCTGTGACTGGTGGCATGATA

AAGGAATTACTTATTTCCTTCCGTCGAGCAACTGGACAGAAGCCGCAGAGAATTATATTCTACAGAGA

TGGTGTTAGTGAAGGACAATTTTACCAAGTTCTTCTTTTTGAACTTGATGCAATCCGCAAGGCATGTGC

ATCTTTAGAACCCAACTATCAGCCCCCGGTTACGTTTGTTGTGGTCCAGAAACGGCATCATACTAGGTT

GTTTGCCAATAACCACCACGACAGAAATGCAGTTGATCGGAGTGGGAACATTTTGCCTGGTACCGTTG

TAGATTCAAAGATATGCCACCCTACTGAATTTGATTTCTATCTCTGTAGCCATGCCGGCATACAGGGTA

CTAGCCGCCCAGCTCATTATCATGTTCTGTGGGATGAGAACAATTTTACTGCTGACGCCCTGCAGTCTT

TGACTAACAATCTTTGCTATACATATGCTAGGTGTACTCGTTCTGTCTCCATTGTTCCACCAGCATATTA

TGCACATTTGGCAGCTTTCCGTGCTCGGTTTTACATGGAGCCAGAGACATCTGATAATGGATCAGTCAC

AAGCGCAGCTGCTTCAAACAGAGGAGGTTTAGGAGCTATGGGAAGGAGCACGCGAGCACCAGGTGCT

GGTGCTGCTGTAAGGCCCCTTCCTGCTCTCAAGGAGAATGTTAAGAGGGTTATGTTTTATTGT.
```

*Nicotiana benthamiana* plants were treated using a procedure similar to that described in Example 12. Polynucleotide solution (or mixed polynucleotides in the case of AGO1) were prepared in 0.01% (v/v) SILWET L-77 and 2% (w/v) ammonium sulfate in 5 millimolar sodium phosphate, pH 6.8. Two fully expanded leaves per plant were dipped into 0.1% SILWET L-77 solution freshly made with ddH2O for a few seconds, and allowed to dry. About 30 minutes later, 20 microliters of polynucleotide solution was applied to each of the two pre-treated leaves. For PDS, each of 5 plants received 25 nanomoles of the PDS anti-sense polynucleotide (SEQ ID NO:34); for AGO1, each of 5 plants received 50 nanomoles of each of the 14 AGO1 anti-sense polynucleotides (SEQ ID NOS:300-313); for PDS and AGO combined treatments, each of 5 plants received 25 nanomoles of the PDS anti-sense polynucleotide (SEQ ID NO:34) and 50 nanomoles of each of the 14 AGO1 antisense polynucleotides (SEQ ID NOS:300-313) applied on separate leaves. Paired control plants were treated with buffer (0.01% (v/v) SILWET L-77 and 2% (w/v) ammonium sulfate in 5 millimolar sodium phosphate, pH 6.8). No difference was observed between plants treated with the AGO1 anti-sense polynucleotides and the plants treated with buffer alone. Plants treated with the PDS anti-sense polynucleotide displayed systemic bleaching. Plants treated with both the PDS anti-sense polynucleotide and the separately applied AGO1 anti-sense polynucleotides did not display systemic bleaching, indicating that suppression of AGO1 blocked the systemic spread of the silencing signal.

Example 34

This example illustrates a method for inducing systemic regulation of a target endogenous gene in a growing plant comprising topically coating onto leaves of said growing plant polynucleotides having sequence essentially identical to, or essentially complementary to, a sequence of 18 or more contiguous nucleotides in either said target endogenous gene or messenger RNA transcribed from said target endogenous gene, whereby said polynucleotides permeate the interior of said growing plant and induce systemic regulation of said target endogenous gene. More specifically this example illustrates use of a composition comprising surfactant and polynucleotides to at least transiently induce systemic regulation of the endogenous *Zea mays* 5-enolpyruvylshikimate-3-phosphate synthase (EPSPS) gene.

A genomic sequence of the endogenous *Zea mays* 5-enolpyruvylshikimate-3-phosphate synthase (EPSPS) gene was identified as (SEQ ID NO: 316)
```
ACCTACTTCCCCCTCGCCCCTCTCATGGTCTCTCTCGCGCCCAGATCTGC

TACTAGACGGCACCGCTGCAGCGCGTCGTGTCGCGGGGGTTGGTGGCAGG

CAGCGAGAGCTTGCCGTTCCTCTCTCTCAGTTGTCAGGTCCTAGGCTCAC

CTCACCGGCTCCCAGCCCGCTTCTATTTCTTCCTCCCCGACCCCGTGCAG

GTGGCAGTCCAGTCCACGCCACCAACCGCGAGGCGAACCAAACCAACCCA

CTCTCCCCAACCCCGCGCGCCCAGGCCGCCCGCCCTACCAACCATCGGCG

TCGGCAATGGCGGCCATGGCGACCAAGGCCGCCGCGGGCACCGTGTCGCT

GGACCTCGCCGCGCCGCCGGCGGCGGCAGCGGCGGCGGCGGTGCAGGCGG

GTGCCGAGGAGATCGTGCTGCAGCCCATCAAGGAGATCTCCGGCACCGTC

AAGCTGCCGGGGTCCAAGTCGCTTTCCAACCGGATCCTCCTGCTCGCCGC

CCTGTCCGAGGTGAGCGATTTTGGTGCTTGCTGCGCTGCCCTGTCTCACT

GCTACCTAAATGTTTTGCCTGTCGAATACCATGGATTCTCGGTGTAATCC

ATCTCACGATCAGATGCACCGCATGTCGCATGCCTAGCTCTCTCTAATTT

GTCTAGTAGTTTGTATACGGATTAATATTGATAAATCGGTACCGCAAAAG

CTAGGTGTAAATAAACACTAGAAAATTGGATGTTCCCCTATCGGCCTGTA

CTCGGCTACTCGTTCTTGTGATGGCATGCTGTCTCTTCTTGGTGTTTGGT

GAACAACCTTATGAAATTTGGGCGCAAAGAACTCGCCCTCAAGGGTTGAT

CTTATGCCATCGTCATGATAAACAGTGGAGCACGGACGATCCTTTACGTT

GTTTTTAACAAACTTTGTCAGAAAACTAGCATCATTAACTTCTTAATGAC

GATTTCACAACAAAAAAGGTAACCTCGCTACTAACATAACAAAATACTT

GTTGCTTATTAATTATATGTTTTTTAATCTTTGATCAGGGGACAACAGTG

GTTGATAACCTGTTGAACAGTGAGGATGTCCACTACATGCTCGGGGCCTT

GAGGACTCTTGGTCTCTCTGTCGAAGCGGACAAAGCTGCCAAAAGAGCTG

TAGTTGTTGGCTGTGGTGGAAAGTTCCCAGTTGAGGATTCTAAAGAGGAA
```

```
GTGCAGCTCTTCTTGGGGAATGCTGGAACTGCAATGCGGCCATTGACAGC
AGCTGTTACTGCTGCTGGTGGAAATGCAACGTATGTTTCCTCTCTTTCTC
TCTACAATACTTGCTGGAGTTAGTATGAAACCCATGGGTATGTCTAGTGG
CTTATGGTGTATTGGTTTTGAACTTCAGTTACGTGCTTGATGGAGTACC
AAGAATGAGGGAGAGACCCATTGGCGACTTGGTTGTCGGATTGAAGCAGC
TTGGTGCAGATGTTGATTGTTTCCTTGGCACTGACTGCCCACCTGTTCGT
GTCAATGGAATCGGAGGGCTACCTGGTGGCAAGGTTAGCTACTAAGGGCC
ACATGTTACATTCTTCTGTAAATGGTACAACTATTGTCGAGCTTTTGCAT
TTGTAAGGAAAGCATTGATTGATCTGAATTTGATGCTACACCACAAAATA
TCCTACAAATGGTCATCCCTAACTAGCAAACAATGAAGTAATACTTGGCA
TGTGTTTATCAAATTAATTTCCATCTTCTGGGGCATTGCCTGTTTTCTAG
TCTAATAGCATTTGTTTTTAGCATTAATTAGCTCTTACAATTGTTATGTT
CTACAGGTCAAGCTGTCTGGCTCCATCAGCAGTCAGTACTTGAGTGCCTT
GCTGATGGCTGCTCCTTTGGCTCTTGGGGATGTGGAGATTGAAATCATTG
ATAAATTAATCTCCATTCCCTACGTCGAAATGACATTGAGATTGATGGAG
CGTTTTGGTGTGAAAGCAGAGCATTCTGATAGCTGGGACAGATTCTACAT
TAAGGGAGGTCAAAAATACAAGTAAGCTCTGTAATGTATTTCACTACTTT
GATGCCAATGTTTCAGTTTTCAGTTTTCCAAACAGTCGCATCAATATTTG
AATAGATGCACTGTAGAAAAAAAATCATTGCAGGGAAAAACTAGTACTGA
GTATTTTGACTGTAAATTATTTTACCAGTCGGAATATAGTCAGTCTATTG
GAGTCAAGAGCGTGAACCGAAATAGCCAGTTAATTATCCCATTATACAGA
GGACAACCATGTATACTATTGAAACTTGGTTTATAAGAGAATCTAGGTAG
CTGGACTCGTAGCTGCTTGGCATGGATACCTTCTTATCTTTAGGAAAAGA
CACTTGATTTTTTTTTCTGTGGCCCTCTATGATGTGTGAACCTGCTTCT
CTATTGCTTTAGAAGGATATATCTATGTCGTTATGCAACATGCTTCCCTT
AGCCATTTGTACTGAAATCAGTTTCATAAGTTCGTTAGTGGTTCCCTAAA
CGAAACCTTGTTTTTCTTTGCAATCAACAGGTCCCCTAAAAATGCCTATG
TTGAAGGTGATGCCTCAAGCGCAAGCTATTTCTTGGCTGGTGCTGCAATT
ACTGGAGGGACTGTGACTGTGGAAGGTTGTGGCACCACCAGTTTGCAGGT
AAAGATTTCTTGGCTGGTGCTACAATAACTGCTTTTGTCTTTTTGGTTTC
AGCATTGTTCTCAGAGTCACTAAATAACATTATCATCTGCAAATGTCAAA
TAGACATACTTAGGTGAATTCATGTAACCGTTTCCTTACAAATTTGCTGA
AACCTCAGGGTGATGTGAAGTTTGCTGAGGTACTGGAGATGATGGGAGCG
AAGGTTACATGGACCGAGACTAGCGTAACTGTTACTGGCCCACCGCGGGA
GCCATTTGGGAGGAAACACCTCAAGGCGATTGATGTCAACATGAACAAGA
TGCCTGATGTCGCCATGACTCTTGCTGTGGTTGCCCTCTTTGCCGATGGC
CCGACAGCCATCAGAGACGGTAAAACATTCTCAGCCCTACAACCATGCCT
CTTCTACATCACTACTTGACAAGACTAAAAACTATTGGCTCGTTGGCAGT
GGCTTCCTGGAGAGTAAAGGAGACCGAGAGGATGGTTGCGATCCGGACGG
AGCTAACCAAGGTAAGGCTACATACTTCACATGTCTCACGTCGTCTTTCC
ATAGCTCGCTGCCTCTTAGCGGCTTGCCTGCGGTCGCTCCATCCTCGGTT
GCTGTCTGTGTTTTCCACAGCTGGGAGCATCTGTTGAGGAAGGGCCGGAC
TACTGCATCATCACGCCGCCGGAGAAGCTGAACGTGACGGCGATCGACAC
GTACGACGACCACAGGATGGCCATGGCCTTCTCCCTTGCCGCCTGTGCCG
AGGTCCCCGTGACCATCCGGGACCCTGGGTGCACCCGGAAGACCTTCCCC
GACTACTTCGATGTGCTGAGCACTTTCGTCAAGAATTAATAAAGCGTGCG
ATACTACCACGCAGCTTGATTGAAGTGATAGGCTTGTGCTGAGGAAATAC
ATTTCTTTTGTTCTGTTTTTTCTCTTTCACGGGATTAAGTTTTGAGTCTG
TAACGTTAGTTGTTTGTAGCAAGTTTCTATTTCGGATCTTAAGTTTGTGC
ACTGTAAGCCAAATTTCATTTCAAGAGTGGTTCGTTGGAATAATAAGAAT
AATAAATTACGTTTCAGTGGCTGTCAAGCCTGCTGCTACGTTTTAGGAGA
TGGCATTAGACATTCATCATCAACAACAATAAAACCTTTTAGCCTCAAAC
AATAATAGTGAAGTTATTTTTTAGTCCTAAACAAGTTGCATTAGGATATA
GTTAAAACACAAAAGAAGCTAAAGTTAGGGTTTAGACATGTGGATATTGT
TTTCCAT,
``` with a 5' untranslated region located at nucleotide positions 1-306 and a 3' untranslated region located at nucleotide positions 3490-3907. A EPSPS cDNA sequence was identified as (SEQ ID NO: 317)
```
ACCTACTTCCCCCTCGCCCCTCTCATGGTCTCTCTCGCGCCCAGATCTGC
TACTAGACGGCACCGCTGCAGCGCGTCGTGTCGCGGGGGTTGGTGGCAGG
CAGCGAGAGCTTGCCGTTCCTCTCTCTCAGTTGTCAGGTCCTAGGCTCAC
CTCACCGGCTCCCAGCCCGCTTCTATTTCTTCCTCCCCGACCCCGTGCAG
GTGGCAGTCCAGTCCACGCCACCAACCGCGAGGCGAACCAAACCAACCCA
CTCTCCCCAACCCCGCGCGCCCAGGCCGCCCGCCCTACCAACCATCGGCG
TCGGCAATGGCGGCCATGGCGACCAAGGCCGCCGCGGGCACCGTGTCGCT
GGACCTCGCCGCGCCGCCGGCGGCGCAGCGGCGGCGGCGGTGCAGGCGG
GTGCCGAGGAGATCGTGCTGCAGCCCATCAAGGAGATCTCCGGCACCGTC
AAGCTGCCGGGGTCCAAGTCGCTTTCCAACCGGATCCTCCTGCTCGCCGC
CCTGTCCGAGGGGACAACAGTGGTTGATAACCTGTTGAACAGTGAGGATG
TCCACTACATGCTCGGGGCCTTGAGGACTCTTGGTCTCTCTGTCGAAGCG
GACAAAGCTGCCAAAAGAGCTGTAGTTGTTGGCTGTGGTGGAAAGTTCCC
AGTTGAGGATTCTAAAGAGGAAGTGCAGCTCTTCTTGGGGAATGCTGGAA
CTGCAATGCGGCCATTGACAGCAGCTGTTACTGCTGCTGGTGGAAATGCA
ACTTACGTGCTTGATGGAGTACCAAGAATGAGGGAGAGACCCATTGGCGA
CTTGGTTGTCGGATTGAAGCAGCTTGGTGCAGATGTTGATTGTTTCCTTG
GCACTGACTGCCCACCTGTTCGTGTCAATGGAATCGGAGGGCTACCTGGT
GGCAAGGTCAAGCTGTCTGGCTCCATCAGCAGTCAGTACTTGAGTGCCTT
GCTGATGGCTGCTCCTTTGGCTCTTGGGGATGTGGAGATTGAAATCATTG
ATAAATTAATCTCCATTCCCTACGTCGAAATGACATTGAGATTGATGGAG
CGTTTTGGTGTGAAAGCAGAGCATTCTGATAGCTGGGACAGATTCTACAT
```

-continued
```
TAAGGGAGGTCAAAAATACAAGTCCCCTAAAAATGCCTATGTTGAAGGTG

ATGCCTCAAGCGCAAGCTATTTCTTGGCTGGTGCTGCAATTACTGGAGGG

ACTGTGACTGTGGAAGGTTGTGGCACCACCAGTTTGCAGGGTGATGTGAA

GTTTGCTGAGGTACTGGAGATGATGGGAGCGAAGGTTACATGGACCGAGA

CTAGCGTAACTGTTACTGGCCCACCGCGGGAGCCATTTGGGAGGAAACAC

CTCAAGGCGATTGATGTCAACATGAACAAGATGCCTGATGTCGCCATGAC

TCTTGCTGTGGTTGCCCTCTTTGCCGATGGCCCGACAGCCATCAGAGACG

TGGCTTCCTGGAGAGTAAAGGAGACCGAGAGGATGGTTGCGATCCGGACG

GAGCTAACCAAGCTGGGAGCATCTGTTGAGGAAGGGCCGGACTACTGCAT

CATCACGCCGCCGGAGAAGCTGAACGTGACGGCGATCGACACGTACGACG

ACCACAGGATGGCCATGGCCTTCTCCCTTGCCGCCTGTGCCGAGGTCCCC

GTGACCATCCGGGACCCTGGGTGCACCCGGAAGACCTTCCCCGACTACTT

CGATGTGCTGAGCACTTTCGTCAAGAATTAATAAAGCGTGCGATACTACC

ACGCAGCTTGATTGAAGTGATAGGCTTGTGCTGAGGAAATACATTTCTTT

TGTTCTGTTTTTTCTCTTTCACGGGATTAAGTTTTGAGTCTGTAACGTTA

GTTGTTTGTAGCAAGTTTCTATTTCGGATCTTAAGTTTGTGCACTGTAAG

CCAAATTTCATTTCAAGAGTGGTTCGTTGGAATAATAAGAATAATAAATT

ACGTTTCAGTGGCTGTCAAGCCTGCTGCTACGTTTTAGGAGATGGCATTA

GACATTCATCATCAACAACAATAAAACCTTTTAGCCTCAAACAATAATAG

TGAAGTTATTTTTTAGTCCTAAACAAGTTGCATTAGGATATAGTTAAAAC

ACAAAAGAAGCTAAAGTTAGGGTTTAGACATGTGGATATTGTTTTCCAT.
```

A 240 base pair double-stranded RNA polynucleotide was designed with one strand corresponding to the DNA sequence

```
                                          (SEQ ID NO: 318)
TACTTGAGTGCCTTGCTGATGGCTGCTCCTTTGGCTCTTGGGGATGTGGA

GATTGAAATCATTGATAAATTAATCTCCATTCCGTACGTCGAAATGACAT

TGAGATTGATGGAGCGTTTTGGTGTGAAAGCAGAGCATTCTGATAGCTGG

GACAGATTCTACATTAAGGGAGGTCAAAAATACAAGTCCCCTAAAAATGC

CTATGTTGAAGGTGATGCCTCAAGCGCAAGCTATTTCTTG
``` which corresponds to a 240 nucleotide segment located at nucleotide positions 937-1176 of the EPSPS cDNA sequence.

*Zea mays* (Gaspe) seeds were germinated on germination paper. Seedlings were transferred to 4 inch pots and plants were grown in a growth chamber. Three 17-day-old plants were topically treated with polynucleotides and three plants were used as controls. Two lower leaves of each plant were marked and then pre-treated by dipping in a solution of 0.1% SILWET L-77. About 30 minutes after the surfactant pre-treatment, 20 microliters of treatment solution was applied to the upper side of each of the two pre-treated leaves. Treatment solution consisted of a mixture of 100 microliters of 2× buffer solution, 90 microliters water, 10 microliters of a 4.6 micrograms/microliter solution of the EPSPS dsRNA (with one strand corresponding to SEQ ID NO:318); the 2X buffer solution was a mixture of 200 microliters of 0.1% SILWET L-77, 200 microliters 50 millimolar sodium phosphate, 146 microliters 34% ammonium phosphate, and 454 microliters water. At 8 days after treatment, two of the three polynucleotide-treated plants were stunted with damaged or dead apical leaves (similar to the phenotype observed in similarly EPSPS polynucleotide-treated *Nicotiana benthamiana* plants), whereas all three of the control plants had normal growth and morphology (FIG. 37).

Example 35

The efficacy of different substances (including salts, a chelating agent, a humectant, and polyamines) as polynucleotide transferring agents or as enhancers of a known polynucleotide transferring agent was investigated. Ammonium sulfate had previously been shown to enhance permeability of plants to polynucleotides (see, e. g., Example 13). Table 26 lists the effect on herbicidal activity (presented as percent of weed control/kill, and as plant height) of ammonium sulfate and EDTA as additives to 1% SILWET L-77 spray solutions of topically applied polynucleotides (RNA) on glyphosate-resistant Palmer amaranth plants. In this particular experiment, ethylenediaminetetraacetic acid (EDTA) at 0.004% was found to act similarly to 2% ammonium sulfate in the spray solution, enhancing the efficacy of the polynucleotides and potentiating the herbicidal activity of glyphosate.

TABLE 26

| Treatment | Palmer control (%) | Palmer height (cm) |
|---|---|---|
| No addition + | 0 | 7.5 |
| 2% ammonium sulfate + | 43 | 1.8 |
| 0.004% EDTA | 45 | 1.0 |

Table 27 lists the effect on herbicidal activity (presented as percent of weed control/kill, and as plant height) of various salts including inorganic salts (sodium chloride, sodium sulfate, ammonium sulfate, ammonium chloride) and organic salts (tetramethylammonium chloride, tetraethylammonium chloride, tetrapropylammonium bromide, and tetrabutylphosphonium bromide) as additives to 1% SILWET L-77 spray solutions of topically applied polynucleotides (RNA) on glyphosate-resistant Palmer amaranth plants. In this particular experiment, ammonium chloride and tetrabutylphosphonium bromide were found to act similarly to ammonium sulfate in the spray solution, enhancing the efficacy of the polynucleotides and potentiating the herbicidal activity of glyphosate.

TABLE 27

| Treatment | Palmer control (%) | Palmer height (cm) |
|---|---|---|
| No addition + | 0 | 16.0 |
| 2% sodium chloride + | 15 | 15.0 |
| 2% sodium sulfate + | 7 | 17.0 |
| 2% ammonium sulfate + | 54 | 9.3 |
| 2% ammonium chloride + | 52 | 10.3 |
| 2% tetramethylammonium chloride + | 19 | 15.0 |
| 2% tetraethylammonium chloride + | 27 | 12.0 |
| 2% tetrapropylammonium bromide + | 34 | 11.0 |
| 2% tetrabutylphosphonium bromide + | 19 | 13.3 |
| 2% tetrabutylphosphonium bromide | 55 | 5.3 |

Table 28 lists the effect of the humectant glycerin on herbicidal activity (presented as percent of weed control/kill, and as plant height) of topically applied polynucleotides (RNA) on glyphosate-resistant Palmer amaranth plants. Glycerin was found to enhance the efficacy of the polynucleotides, potentiating the herbicidal activity of glyphosate.

TABLE 28

| Treatment | Palmer control (%) | Palmer height (cm) |
|---|---|---|
| No addition | 0 | 16.0 |
| Silwet L-77/AMS (no glycerin) | 54 | 9.3 |
| Silwet L-77/AMS + 0.5% glycerin | 57 | 6.3 |

Figure 38:
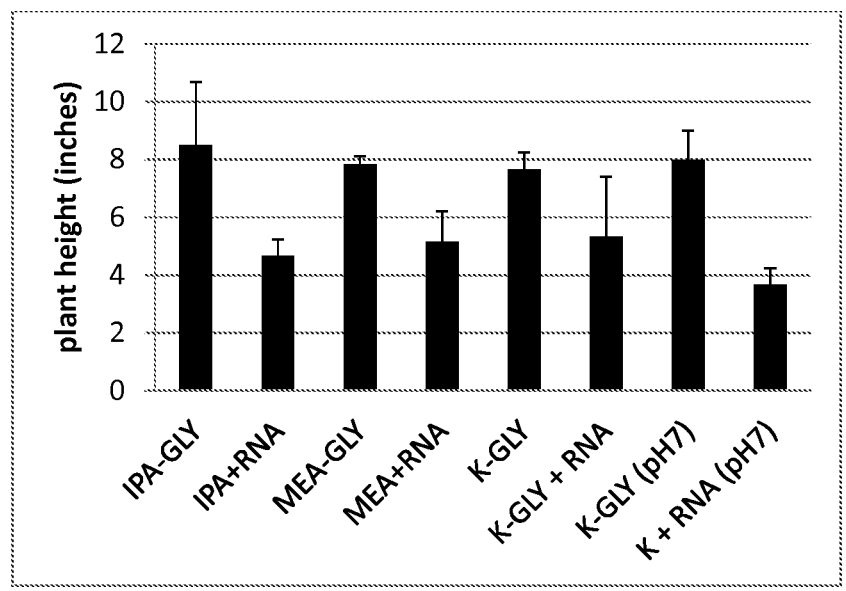
FIG. 38 illustrates the effect of varying glyphosate counter-ions on herbicidal activity on glyphosate-resistant Palmer amaranth plants, as described in Example 35.

FIG. 38 depicts the effect of varying glyphosate counterions on herbicidal activity (presented as percent of weed control/kill, and as plant height) of topically applied polynucleotides (RNA) on glyphosate-resistant Palmer amaranth plants. A mixture of EPSPS polynucleotides (IDT [1] (SEQ ID NO:83-84), IDT [2] (SEQ ID NO:85-86), IDT [3] (SEQ ID NO:87-88), and IDT [4] (SEQ ID NO:89-90)) in 0.5% SILWET L-77, 2% ammonium sulfate in 10 millimolar sodium phosphate buffer, pH 6.8 with 0.2% Roundup® WeatherMax® carrier (MON56151 tallowamine surfactant blend of tallowamine (16-18C) and cocoamine (12-14C) in the ratio of 55:45) and 1682 g acid equivalent per hectare of one of the glyphosate salts; K+glyphosate, isopropylammonium+glyphosate or monoethanolammonium+glyphosate at 215 liters/acre by Milli spray on 3 replicates of 4-6 inch glyphosate-resistant Palmer amaranth containing 16 copies of EPSPS. Plant height was scored at 21 days after glyphosate treatment. Results (presented as percent of weed control/kill, and as plant height) are given in Table 29. The isopropylammonium and monoethanolammonium salts of glyphosate provided better herbicidal activity compared to the potassium salt.

TABLE 29

| Treatment | Palmer control (%) | Palmer height (cm) |
|---|---|---|
| No addition | 0 | 16 |
| K + glyphosate | 23 | 12.3 |
| K + glyphosate + EPSPS polynucleotides | 32 | 10.8 |
| IPA + glyphosate | 9 | 14.5 |
| IPA + glyphosate + EPSPS polynucleotides | 66 | 5.5 |
| MEA + glyphosate | 9 | 14.5 |
| MEA + glyphosate + EPSPS polynucleotides | 66 | 5.5 |

Figure 39:
FIG. 39 illustrates the effect of the polyamines spermine ("SPM") and spermidine ("SPMD") or ammonium sulfate ("AMS") on glyphosate-resistant Palmer amaranth containing 33, 36, or 57 copies of EPSPS, as described in Example 35. "fb 4X WM" means "followed by treatment with glyphosate (3360 g acid equivalent per hectare of Roundup® WeatherMAX® brand herbicide)".

The effect of the polyamine cations spermine (N,N'-bis (3-aminopropyl)butane-1,4-diamine) and spermidine (N-(3-aminopropyl)butane-1,4-diamine) on herbicidal activity of topically applied polynucleotides (RNA) on glyphosate-resistant Palmer amaranth plants was investigated. Polynucleotide solutions were prepared using a mixture of equal amounts of the four oligonucleotide-size "short" dsRNA molecules described in Example 1, which have an anti-sense strand designed to hybridize to the mRNA transcribed from the Palmer amaranth EPSPS gene (SEQ ID NO:1) at positions 14-38 (short dsRNA-1), positions 153-177 (short dsRNA-2), 345-369 (short dsRNA-3), and 1105-1129 (short dsRNA-4), as indicated by underlined nucleotides in FIG. 1; the dsRNAs had a two nucleotide overhang at the 3' end of the anti-sense strand, and had two deoxynucleotides as the terminal nucleotides at the 3' end of the sense strand. The dsRNA polynucleotide solutions were prepared with either 1 or 10 millimolar spermine or spermidine or 2% ammonium sulfate, in a 10 millimolar sodium phosphate (pH 6.8) buffer. Control solutions (without polynucleotides) were prepared with either 1 or 10 millimolar spermine or spermidine or 2% ammonium sulfate, in a 10 millimolar sodium phosphate (pH 6.8) buffer. Glyphosate-resistant Palmer amaranth plants (33, 36, or 57 copies EPSPS) were pre-sprayed with 1% SILWET L-77. The dsRNA polynucleotide solutions (11.6 grams/acre) or buffer solutions were applied as drops on four lower fully expanded leaves of glyphosate resistant Palmer amaranth by pipetting. Two days following polynucleotide treatment the plants were sprayed with glyphosate (3360 g acid equivalent per hectare of Roundup® WeatherMAX® brand herbicide). Plants were photographed at 14 days after glyphosate treatment; results are shown in FIG. 39. Treatment with dsRNA and 10 millimolar spermine followed by glyphosate treatment killed glyphosate-resistant Palmer amaranth with 33-copy EPSPS and severely injured and stunted glyphosate-resistant Palmer amaranth with 36-copy EPSPS. Treatment with 10 mM spermidine alone stunted 33-copy glyphosate-resistant Palmer amaranth. In this particular experiment, neither spermine nor spermidine at 1 or 10 millimolar performed as well as 2% ammonium sulfate.

Example 36

The efficacy of different surfactants as polynucleotide transferring agents was tested in polynucleotide spray solutions applied to glyphosate-resistant Palmer amaranth. Break-Thru surfactants were obtained from Evonik Industries; SILWET surfactants were obtained from Momentive. Spray solutions were prepared the same day as spraying. A mixture of EPSPS polynucleotides (IDT [1] (SEQ ID NO:83-84), IDT [3] (SEQ ID NO:87-88), and IDT [4] (SEQ ID NO:89-90)) was added to spray solutions 15 to 50 minutes before spraying and 1- to 2-milliliters applied using a custom low-dead-volume ("milli") sprayer to one-to-four inch glyphosate-resistant (R-22) Palmer amaranth plants grown from cuttings. Between 10 and 225 micrograms total polynucleotides were applied to each plant, depending on the experiment; typically 23 micrograms total polynucleotides were applied per plant. Treated plants were placed in a greenhouse set for either a 26.7/21.1 degrees Celsius or 29.4/21.1 degrees Celsius 14/10 hour temperature and supplemental light schedule. After 2 to 3 days, the plants were sprayed with glyphosate ("2xWmax" or 1682 g acid equivalent per hectare of Roundup® WeatherMAX® brand herbicide) by regular sprayer (10 gallons/acre) and returned to the greenhouse. The amount of control (visual injury) relative to unsprayed treatments, plant height and pictures of Palmer amaranth were collected at different time intervals up to 21 days after glyphosate treatment. Fresh weight of above-soil plant material was collected at the last time point. An overall plant injury score between 0 and 3 was given each treatment based on the combined analysis of Control, Height, Fresh Weight and Visual Plant Phenotype, where "3" "is strong herbicidal activity, "2" is moderate activity, "1" is mild activity and "0" is no activity observed after correction for any observed injury caused by treatment with glyphosate alone; results are shown in Table 30.

Physical properties of the different surfactants were also investigated and listed in Table 30. Seventy milliliters of surfactant solution (0.5% surfactant in aqueous solution containing 2% ammonium sulfate, buffer (20 millimolar potassium phosphate, pH 6.8), with or without an EPSPS polynucleotide (IDT [2] (SEQ ID NO:85-86), 0.09 milligrams/milliliter) added, were prepared on the same day as measurement. Dynamic surface tension was measured at ambient room temperature (22 to 23 degrees Celsius) on a Kruss BP100 tensiometer using the maximum bubble pressure method plotting surface tension versus surface age. The instrument was set to automatically detect the surface and immerse the capillary to a depth of 10 mm. Surface tension measurements for three surface ages (approximately 20, 500 and 1250 ms) were recorded. Surface tension in dynes per cm was reported at the 1250 ms interval as an approximation of static surface tension and the change between 20 and 500 ms was reported as an estimate of the dynamic surface tension. Hydrophile-lipophile balance (HLP) values for the surfactants were obtained from surfactant references and product information.

TABLE 30

| Surfactant name | CAS number | Chemistry | Surfactant Type | Surfactant Class | Palmer injury score | Surface tension literature | Surface tension 1250 ms | delta 20- 500 ms | HLB |
|---|---|---|---|---|---|---|---|---|---|
| Break-Thru S 321 | na | polyether-modified polysiloxane | organosilicone | nonionic | 3 | na | 22.7 | 27.1 | 40.0 |
| Break-Thru S 200 | 67674-67-3 | polyether-modified polysiloxane | organosilicone | nonionic | 3 | 22 | 26.9 | 23.0 | |
| Break-Thru OE 441 | 68937-55-3 | polyether-modified polysiloxane | organosilicone | nonionic | 1 | na | 43.8 | 2.9 | 40.0 |
| Break-Thru S 278 | 27306-78-1 | polyether-modified polysiloxane | organosilicone | nonionic | 2 | 21 | 24.2 | 23.4 | |
| Break-Thru S 243 | na | polyether-modified polysiloxane | organosilicone | nonionic | 2 | 47 | 50.3 | 7.7 | 16.7 |
| Silwet L-77 | 27306-78-1 | trisiloxane; polyalkylene oxide-modified polymethylsiloxane | organosilicone | nonionic | 3 | 20.5 | 26.4 | 23.4 | 13.5 |
| Silwet HS 429 | na | hydrolytically stable silicone | organosilicone | nonionic | 3 | 32-40 | 40.1 | 12.1 | |
| Silwet HS 312 | na | silicone | organosilicone | nonionic | 3 | 26.7 | 29.5 | 11.3 | |
| Break-Thru S 233 | 134180-760-0 | trisiloxane | organosilicone | nonionic | 3 | 23 | 26.1 | 10.0 | |

What is claimed is:

1. A liquid, herbicidal composition adapted for topical coating onto an exterior surface of a plant comprising: an organosilicone surfactant and at least one non-transcribable RNA polynucleotide,
wherein the organosilicone surfactant allows permeation of the non-transcribable RNA polynucleotide from the exterior surface of the plant into cells of the plant without the aid of a physical abrasive,
wherein the composition does not comprise a physical abrasive,
wherein the non-transcribable RNA polynucleotide comprises a nucleotide sequence that is identical or complementary to at least 21 contiguous nucleotides of an endogenous gene or a transcribed RNA of a plant, and
wherein the endogenous gene is an essential gene of the plant or encodes a protein that provides herbicide resistance to the plant.

2. The liquid, herbicidal composition of claim 1, wherein the endogenous gene or transcribed RNA encodes a 5-enolpyruvylshikimate-3-phosphate synthase (EPSPS), an acetohydroxyacid synthase, an acetolactate synthase (ALS), an acetyl-coenzyme A carboxylase (ACCase), a dihydropteroate synthase, a phytoene desaturase (PDS), a protoporphyrin IX oxygenase (PPO), a hydroxyphenylpyruvate dioxygenase (HPPD), a para-aminobenzoate synthase, a glutamine synthase (GS), a glufosinate-tolerant glutamine synthase, a 1-deoxy-D-xylulose 5-phosphate (DOXP) synthase, a dihydropteroate (DHP) synthase, a phenylalanine ammonia lyase (PAL), a glutathione S-transferase (GST), a D1 protein of photosystem II, a mono-oxygenase, a cytochrome P450, a cellulose synthase, a beta-tubulin, or a serine hydroxymethyltransferase.

3. The liquid, herbicidal composition of claim 1, wherein the endogenous gene is a native gene or a recombinant transgene.

4. The liquid, herbicidal composition of claim 1, wherein the organosilicone surfactant is a silicone polyether copolymer.

5. The liquid, herbicidal composition of claim 4, wherein the silicone polyether copolymer is a copolymer of polyalkylene oxide modified heptamethyl trisiloxane and allyloxypolypropylene glycol methylether.

6. The liquid, herbicidal composition of claim 1, wherein the liquid, herbicidal composition further comprises a non-polynucleotide herbicidal molecule.

7. The liquid, herbicidal composition of claim 6, wherein the non-polynucleotide herbicidal molecule is selected from the group consisting of glyphosate, dicamba, phosphinothricin, bromoxynil, ioxynil and chlorsulfuron.

8. The liquid, herbicidal composition of claim 1, wherein the liquid, herbicidal composition further comprises a humectant or a chelating agent.

9. The liquid, herbicidal composition of claim 1, wherein said at least one non-transcribable RNA polynucleotide is selected from the group consisting of ssRNA, dsRNA and RNA/DNA hybrids.

10. The liquid, herbicidal composition of claim 1, wherein the liquid, herbicidal composition comprises a first RNA polynucleotide and a second RNA polynucleotide, and wherein the first RNA polynucleotide comprises a nucleotide sequence that is identical or complementary to 21 or more contiguous nucleotides of an endogenous gene or a transcribed RNA of a plant and the second polynucleotide comprises a nucleotide sequence that is identical or complementary to 21 or more contiguous nucleotides of a different endogenous gene or transcribed RNA of a plant.

11. The liquid, herbicidal composition of claim 1, wherein the liquid, herbicidal composition comprises a first RNA polynucleotide and a second RNA polynucleotide, wherein the first and second RNA polynucleotides have different sequences, and wherein the first RNA polynucleotide comprises a nucleotide sequence that is identical or complementary to 21 or more contiguous nucleotides of an endogenous gene or a transcribed RNA of a plant and the second RNA polynucleotide comprises a nucleotide sequence that is identical or complementary to 21 or more contiguous nucleotides of the same endogenous gene or transcribed RNA of a plant.

12. The liquid, herbicidal composition of claim 1, wherein the organosilicone surfactant is at a concentration of about 0.015% to about 2.0% by weight.

13. The liquid, herbicidal composition of claim 4, wherein the silicone polyether copolymer is at a concentration of about 0.015% to about 2.0% by weight.

14. The liquid, herbicidal composition of claim 1, wherein the organosilicone surfactant is at a concentration of about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, or about 2% by weight.

15. The liquid, herbicidal composition of claim 4, wherein the silicone polyether copolymer is at a concentration of about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, or about 2% by weight.

* * * * *